US007626080B2

(12) United States Patent
Frohberg

(10) Patent No.: US 7,626,080 B2
(45) Date of Patent: Dec. 1, 2009

(54) PLANTS WITH REDUCED ACTIVITY OF A CLASS 3 BRANCHING ENZYME

(75) Inventor: Claus Frohberg, Kleinmachnow (DE)

(73) Assignee: Bayer Cropscience AG, Monheim am Rhein (DE)

( * ) Notice: Subject to any disclaimer, the term of this patent is extended or adjusted under 35 U.S.C. 154(b) by 0 days.

(21) Appl. No.: 10/573,998

(22) PCT Filed: Sep. 29, 2004

(86) PCT No.: PCT/EP2004/010985

§ 371 (c)(1), (2), (4) Date: Mar. 30, 2006

(87) PCT Pub. No.: WO2005/030942

PCT Pub. Date: Apr. 7, 2005

(65) Prior Publication Data

US 2006/0253929 A1 Nov. 9, 2006

(30) Foreign Application Priority Data

Sep. 30, 2003 (EP) ................................. 03090325

(51) Int. Cl.

*C12N 15/82* (2006.01)
*C12N 15/55* (2006.01)
*C12N 15/63* (2006.01)
*C12N 15/29* (2006.01)
*A01H 5/00* (2006.01)

(52) U.S. Cl. ....................... 800/285; 800/286; 800/295; 800/298; 435/320.1; 435/468; 435/200; 435/201; 536/23.1; 536/23.2; 536/23.6; 536/24.5

(58) Field of Classification Search ....................... None
See application file for complete search history.

(56) References Cited

FOREIGN PATENT DOCUMENTS

| | | | |
|---|---|---|---|
| WO | WO 96/34968 | | 11/1996 |
| WO | WO9634968 | * | 11/1996 |
| WO | WO 01/70942 | | 9/2001 |
| WO | WO0170942 | * | 9/2001 |

OTHER PUBLICATIONS

Tetlow et al 2004 Journal of Experimental Botany 55(406):2131-2145.*

Der Hoeven et al 2001 GenBank Accession BG886850.*

Blauth et al. (Mar. 2001) "Identification of *Mutator* Insertional Mutants of Starch-Branching Enzyme 2a in Corn." *Plant Physiology* 125: 1396-1405.

Blauth et al. (2002) "Identification of *Mutator* insertional mutants of starch-branching enzyme 1 (*sbe1*) in *Zea mays* L." *Plant Molecular Biology* 48: 287-297.

Flipse et al. (1996) "Introduction of sense and antisense cDNA for branching enzyme in the amylose-free potato mutant leads to physico-chemical changes in the starch." *Planta* 198: 340-347.

Jobling et al. (1999) "A minor form of starch branching enzyme in potato (*Solanum turberosum* L.) tubers has a major effect on starch structure: cloning and characterisation of multiple forms of *SBE A.*" *The Plant Journal* 18(2): 163-171.

Khoshnoodi et al. (1996) "The multiple forms of starch-branching enzyme I in *Solanum tuberosum." Eur. J. Biochem* 242: 148-155.

Larsson et al. (1998) "Molecular Cloning and characterization of starch-branching enzyme II from potato." *Plant Molecular Biology* 37: 505-511.

Mizuno et al. (Sep. 5, 1993) "Alteration of the Structural Properties of Starch Components by the Lack of an Isoform of Starch Branching Enzyme in Rice Seeds." *The Journal of Biological Chemistry* 268(25): 19084-19091.

Rydberg et al. (2001) "Comparison of starch branching enzyme I and II from potato." *Eur. J. Biochem.* 268: 6140-6145.

GenBank Accession No. BG886850 (Jun. 8, 2001).

GenBank Accession No. Q8GWK4 (Mar. 1, 2003).

GenBank Accession No. AK118785 (Dec. 13, 2002).

EPO Communication issued Feb. 16, 2009 in EPO Application No. 04 787 074.6.

UniProtKB/Swiss-Prot Q8U8L4 (GLGB_AGRT5) downloaded from http://www.uniprot.org/uniprot/Q8U8L4, 8 pgs, dated Jun. 23, 2009.

UniProtKB/TrEMBL Q82AS4 (Q82AS4_STRAW) downloaded from http://www.uniprot.org/uniprot/Q82AS, 9 pgs, dated Jun. 23, 2009.

* cited by examiner

*Primary Examiner*—Anne Marie Grunberg
*Assistant Examiner*—Brent Page
(74) *Attorney, Agent, or Firm*—Hunton & Williams LLP

(57) ABSTRACT

The present invention relates to plant cells and plants, which are genetically modified, wherein the genetic modification leads to the reduction of the activity of a Class 3 vegetable branching enzyme in comparison with corresponding wild type plant cells or wild type plants that have not been genetically modified. Furthermore, the present invention relates to means and methods for the manufacture of such plant cells and plants. Plant cells and plants of this type synthesise a modified starch. The present invention therefore also relates to the starch synthesised by the plant cells and plants according to the invention as well as to methods for the manufacture of the starch and to the manufacture of starch derivatives of this starch. Furthermore, the present invention relates to nucleic acids coding a Class 3 branching enzyme, vectors, host cells, plant cells and plants containing such nucleic acid molecules.

52 Claims, 67 Drawing Sheets

| SwissProt Acc No. or Entry Name | Amino acid No. | SwissProt Acc No. or Entry Name | Amino acid No. |
|---|---|---|---|
| APU_THETU | 1251-1331 | Q9XED2 | 101-191 |
| GLGB_SYNY3 | 22-110 | Q08131 | 137-227 |
| P71095 | 39-130 | GLGB_HUMAN | 73-168 |
| Q9RXB0 | 181-274 | Q9V6K7 | 52-144 |
| PULA_KLEPN | 301-395 | Q22137 | 53-147 |
| P70983 | 1143-1238 | Q9RM63 | 25-149 |
| Q41386 | 205-298 | ISOA_FLASP | 36-163 |
| O64454 | 202-295 | ISOA_PSEAY | 30-155 |
| O69008 | 105-191 | P73608 | 22-122 |
| O34587 | 104-189 | O04196 | 74-177 |
| Q9XDB5 | 231-319 | Q9SPT7 | 8-110 |
| PULA_THEMA | 223-311 | Q41742 | 114-218 |
| Q59319 | 206-300 | GLGX_HAEIN | 10-101 |
| YIEL_ECOLI | 41-123 | Q9RNH5 | 20-117 |
| Q9RX51 | 22-100 | GLGX_ECOLI | 9-104 |
| O66936 | 24-116 | Q9RXP5 | 13-108 |
| Q59832 | 141-233 | GLGX_MYCTU | 24-119 |
| GLGB_STRAU | 160-252 | Q9X947 | 18-113 |
| GLGB_BUTFI | 24-116 | P72691 | 19-120 |
| GLGB_AGRTU | 130-223 | P95868 | 17-117 |
| Q9RQI5 | 134-226 | O84046 | 11-108 |
| GLGB_ECOLI | 122-214 | Q9Z8F5 | 11-108 |
| GLGB_HAEIN | 122-214 | Q9ZVT2 | 232-335 |
| GLGB_SYNY3 | 126-217 | Q44528 | 2-83 |
| GLGB_MYCTU | 127-223 | Q9X2G0 | 276-357 |
| Q9RTB7 | 26-115 | Q9X2G0 | 15-98 |
| GLGB_BACSU | 23-115 | Q45643 | 46-114 |
| Q59242 | 23-115 | Q9X2G0 | 126-217 |
| O84874 | 117-209 | TREZ_ARTSQ | 5-90 |
| O49185 | 62-153 | TREZ_MYCTU | 2-68 |
| GLGB_YEAST | 59-153 | Q55088 | 1-79 |
| Q9Y8H3 | 47-147 | Q53641 | 1-79 |

Table 1 Amino acid sequences, contained in the "seed alignment", that are used for producing the HMM for the Pfam isoamylase domain (PF 02922). The table gives the "accession" number (Acc No) or the name (Entry Name), under which the corresponding amino acid sequences are entered in the SwissProt database. Those sections of the amino acid sequences of the corresponding SwissProt entry, which are part of the "seed alignment" (amino acid No.), are also given.

FIG. 1

| SwissProt Acc No. or Entry Name | Amino acid No. | SwissProt Acc No. or Entry Name | Amino acid No. |
|---|---|---|---|
| AMYM_BACLI | 137-479 | CDG1_PAEMA | 46-426 |
| MALZ_ECOLI | 128-522 | CDGT_BACOH | 44-420 |
| APU_THESA | 393-821 | AMYB_PAEPO | 751-1107 |
| APU_THEET | 390-820 | AMYA_ASPOR | 34-390 |
| CDAS_THEET | 136-494 | AMY1_DEBOC | 49-405 |
| NEPU_BACST | 139-497 | AMY1_SACFI | 40-396 |
| AMYM_BACAD | 139-497 | AMY1_ECOLI | 193-611 |
| AMY2_DICTH | 138-470 | ISOA_PSEAY | 209-652 |
| MALT_AEDAE | 29-425 | AMY_BUTFI | 126-520 |
| MAL2_DROME | 30-432 | AMY_BACSU | 41-383 |
| MAL3_DROME | 31-428 | AMY_THECU | 40-392 |
| MAL1_DROME | 35-420 | AMY_STRHY | 37-360 |
| MAXS_YEAST | 17-441 | AMY_STRGR | 35-372 |
| MAYS_YEAST | 22-446 | AMY_ALTHA | 28-373 |
| MA3S_YEAST | 21-443 | AMYA_AERHY | 26-369 |
| TREC_ECOLI | 15-414 | AMYC_HUMAN | 26-413 |
| TREC_BACSU | 16-418 | AMYA_DROME | 29-396 |
| O16G_BACSP | 11-420 | AMY1_AERHY | 22-379 |
| O16G_BACCE | 13-419 | AMT4_PSESA | 38-387 |
| DEXB_STRMU | 13-394 | AMY2_ECOLI | 12-402 |
| AMY_BACME | 44-406 | AMY_BACLI | 34-420 |
| AMY3_DICTH | 39-381 | AMY_BACAM | 34-422 |
| AMY_STRLI | 77-520 | AMT6_BACS7 | 40-426 |
| CDGT_KLEPN | 47-463 | AMY3_WHEAT | 26-348 |
| AMYM_BACST | 46-430 | AM3A_ORYSA | 29-367 |
| CDGT_BACST | 47-425 | AMYA_VIGMU | 24-361 |
| AMYR_BACS8 | 46-425 | AM2A_ORYSA | 23-366 |

Table 2 Amino acid sequences, contained in the "seed alignment", that are used for producing the HMM for the Pfam alpha-amylase domain (PF 00128). The table gives the "accession" number (Acc No) or the name (Entry Name), under which the corresponding amino acid sequences are entered in the SwissProt database. Those sections of the amino acid sequences of the corresponding SwissProt entry, which are part of the "seed alignment" (amino acid No.), are also given.

FIG. 2

Table 3 Information for producing the HMM for the Pfam isoamylase domain (PF 02922)

```
HMMERR2.0 [2.3.1]
NAME  isoamylase_N
ACC   PF02922
DESC  Isoamylase N-term
LENG  121
ALPH  Amino
RF    no
CS    no
MAP   yes
COM   hmmbuild -F HMM_ls.ann SEED.ann
COM   hmmcalibrate --seed 0 HMM_ls.ann
NSEQ  65
DATE
CKSUM 3012
GA    2.3 2.3
TC    2.3 2.3
NC    2.1 2.1
XT          -8455     -4  -1000  -1000  -8455     -4  -8455     -4
NULT           -4  -8455
NULE          595  -1558     85    338   -294    453  -1158    197    249    902  -1085   -142    -21   -313     45    531    201    384  -1998   -644
EVD   -56.839790 0.222419
HMM             A      C      D      E      F      G      H      I      K      L      M      N      P      Q      R      S      T      V      W      Y
             m->m   m->i   m->d   i->m   i->i   d->m   d->d   b->m   m->e
              -32      *  -5527
      1       433  -2912  -5203  -4583    312  -4575  -3427  -2412  -4218  -2763    739  -4157   2303  -3877  -1058   -777    159  -2330   1852   3373     1
      -      -149   -500    233     43   -381    399    106   -626    210   -466   -720    275    394     45     96    359    117   -369   -294   -249
```

FIG. 3

| | | | | | | | | | | | | | | | | | | | | | |
|---|---|---|---|---|---|---|---|---|---|---|---|---|---|---|---|---|---|---|---|---|---|
| - | -1 | -10660 | -11703 | -894 | -1115 | -701 | -1378 | -32 | * | | | | | | | | | | | | |
| 2 | -503 | -4276 | -455 | 1534 | 635 | 1339 | -2632 | -1609 | 373 | 78 | 463 | -1115 | -680 | 241 | -2737 | -924 | -593 | -1619 | 43 | 316 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10857 | -11899 | -894 | -1115 | -701 | -1378 | * | * | | | | | | | | | | | | |
| 3 | -806 | -4386 | -2899 | -88 | -1199 | -4001 | -313 | -1878 | 1255 | -1032 | -3486 | -2653 | 2668 | -172 | 105 | 545 | 387 | -400 | -4594 | -3936 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10916 | -11958 | -894 | -1115 | -701 | -1378 | * | * | | | | | | | | | | | | |
| 4 | -1972 | -3101 | -5615 | -1806 | 2143 | -2106 | -3692 | -829 | -4575 | 2525 | 1112 | -4465 | -4871 | -4199 | -4376 | -1753 | -1159 | -2514 | -3558 | 1139 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10916 | -11958 | -894 | -1115 | -701 | -1378 | * | * | | | | | | | | | | | | |
| 5 | -1026 | -6327 | -1172 | -753 | -6643 | 3551 | -4321 | -471 | -1174 | -6434 | -5732 | -3689 | -5515 | -3996 | -5049 | -4652 | -4943 | -6008 | 166 | -5877 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10941 | -11983 | -894 | -1115 | -701 | -1378 | * | * | | | | | | | | | | | | |
| 6 | 2712 | 446 | -5632 | -1558 | 482 | -1817 | -3713 | -635 | -4593 | -29 | -2327 | -4485 | 109 | -4218 | -4397 | -260 | -3237 | 343 | -3582 | 161 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10941 | -11983 | -894 | -1115 | -701 | -1378 | * | * | | | | | | | | | | | | |
| 7 | -1172 | -4458 | -2893 | 183 | -1229 | -4010 | 3316 | -580 | -1 | -4467 | -169 | 1206 | -4102 | -102 | -67 | 428 | 1327 | 312 | -4653 | -3981 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10941 | -11983 | -894 | -1115 | -701 | -1378 | * | * | | | | | | | | | | | | |
| 8 | -427 | -3201 | -5058 | -841 | 1372 | -4749 | -3587 | 346 | -159 | -603 | -2400 | -4198 | 1637 | -1158 | 168 | -1606 | -1672 | 834 | 1850 | 2394 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -335 | -10941 | -2276 | -894 | -1115 | -701 | -1378 | * | * | | | | | | | | | | | | |
| 9 | -554 | 121 | 1665 | 593 | -4483 | -1316 | 276 | 7 | -1953 | 322 | -3267 | 244 | -1346 | 1174 | -268 | 144 | -340 | -577 | -4365 | 380 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -365 | -10608 | -2164 | -894 | -1115 | -3823 | -106 | * | * | | | | | | | | | | | | |
| 10 | 797 | -3873 | 616 | 858 | -4188 | 1176 | -2048 | -3935 | -458 | -1843 | -2963 | -2026 | 1626 | -1590 | 99 | 164 | -514 | -1189 | 683 | -15 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -46 | -10244 | -5043 | -894 | -1115 | -4637 | -59 | * | * | | | | | | | | | | | | |

FIG. 4

| | | | | | | | | | | | | | | | | | | | | | |
|---|---|---|---|---|---|---|---|---|---|---|---|---|---|---|---|---|---|---|---|---|---|
| 1 1 | -14 | -3841 | 1826 | 1314 | -810 | 836 | -2009 | -1276 | 467 | -1532 | -2931 | 448 | 230 | 775 | -2097 | -2257 | -855 | -888 | -4026 | -3345 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1075 | -10201 | -931 | -894 | -1115 | -1364 | -709 | * | * | | | | | | | | | | | | |
| 1 2 | -847 | 832 | 1648 | -1300 | -3762 | -553 | 1139 | -810 | 389 | -1423 | 2049 | 1275 | -3064 | 738 | -253 | -621 | 912 | -3067 | -3637 | -2959 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -511 | -9739 | -1751 | -894 | -1115 | -5168 | -41 | * | * | | | | | | | | | | | | |
| 1 3 | -2797 | -4407 | -1367 | 2261 | -4735 | 892 | -2276 | -4550 | -2156 | -4468 | -3642 | 1207 | -3560 | 823 | -2778 | -2580 | 2401 | -4063 | -4646 | -3831 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -305 | -9232 | -2404 | -894 | -1115 | -5452 | -33 | * | * | | | | | | | | | | | | |
| 1 4 | -88 | 1322 | -3700 | 1196 | -1379 | -398 | 1869 | 1265 | -2718 | -141 | 1929 | -2663 | -3139 | -2380 | -2591 | -2162 | -1503 | 1517 | -1876 | -1529 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -90 | -8931 | -4097 | -894 | -1115 | -5563 | -31 | * | * | | | | | | | | | | | | |
| 1 5 | -1344 | -2813 | 2298 | 288 | 602 | -240 | 1306 | -2880 | 499 | -2828 | -1903 | 1507 | -2408 | 683 | -1068 | -1224 | -1284 | -289 | -2998 | -2315 | 15 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -139 | -8846 | -3483 | -894 | -1115 | -4086 | -88 | * | * | | | | | | | | | | | | |
| 1 6 | -1947 | -2556 | -4788 | -5046 | -5091 | 3282 | -4399 | -4858 | -4947 | -5141 | -4214 | -3556 | 477 | -4449 | -4699 | 816 | -2415 | 335 | -5331 | -5237 | 16 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1391 | -8903 | -698 | -894 | -1115 | -2384 | -307 | * | * | | | | | | | | | | | | |
| 1 7 | 1320 | -2772 | -1292 | 2128 | -3091 | -2427 | -1158 | -2783 | 864 | -2816 | -1944 | -1122 | 1166 | -729 | -1233 | -1401 | -1440 | 802 | -3046 | -2410 | 17 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8803 | -9845 | -894 | -1115 | -1304 | -749 | * | * | | | | | | | | | | | | |
| 1 8 | -165 | -3738 | 1692 | -454 | -4041 | -89 | -1948 | -3779 | 1272 | -1513 | -2833 | 353 | -3378 | -1495 | -2044 | -2196 | 459 | 2044 | -3933 | -3260 | 18 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10095 | -11137 | -894 | -1115 | -1909 | -447 | * | * | | | | | | | | | | | | |
| 1 9 | 500 | -3988 | 418 | 2 | -4310 | 1492 | -2148 | -4060 | 805 | -4005 | -3078 | 1770 | -1034 | 395 | -585 | 203 | -470 | -1409 | -4172 | -266 | 19 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -32 | -10365 | -5558 | -894 | -1115 | -138 | -3458 | * | * | | | | | | | | | | | | |
| 2 0 | -904 | -4476 | -607 | -506 | -1213 | 2552 | -196 | -696 | 627 | -4492 | -3565 | -12 | -360 | 186 | -434 | 81 | -490 | -4098 | -4659 | -771 | 20 |

FIG. 5

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10917 | -11959 | -894 | -1115 | -250 | -2654 | * | * | | | | | | | | | | | | |
| 2 1 | -903 | -3200 | -5719 | -5083 | -433 | -1893 | -3792 | 860 | -4678 | -1338 | -2403 | -4567 | -543 | -4301 | -4478 | -4006 | 2145 | 2518 | 1631 | 512 | 21 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 2 | -1902 | -4488 | -1380 | -132 | 190 | -4097 | -526 | 406 | -450 | -4488 | -3587 | 1974 | -4189 | -2312 | 1656 | -1028 | 1578 | 714 | -4694 | 444 | 22 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 3 | -1835 | -3207 | -5724 | -5089 | 3969 | -2056 | -3796 | -432 | -4684 | -325 | -2409 | -4572 | -4977 | -4306 | -1411 | -1974 | -3321 | -410 | -3659 | 1564 | 23 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 4 | 1377 | 1196 | -1346 | -2546 | -4550 | -4149 | -2821 | -1804 | 963 | -2327 | -3447 | -2834 | -1077 | -2403 | 2409 | 501 | 896 | -3897 | -4578 | 531 | 24 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 5 | -1482 | -3277 | -1253 | 931 | -116 | -5013 | -3887 | -1194 | -4761 | 1669 | -2465 | -4654 | -5058 | -4386 | -4568 | -4099 | -3396 | 2623 | -3750 | 265 | 25 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 6 | -7635 | -6573 | -7990 | -1924 | 2064 | -1893 | -4102 | -6546 | -7815 | -5859 | -5949 | -6513 | -7759 | -6639 | -1618 | -7150 | -7486 | -6697 | 5535 | 2570 | 26 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 7 | 2849 | -4354 | -5323 | -4910 | -5332 | -4813 | -4712 | -4952 | -1677 | -1991 | -4458 | -1206 | -5320 | -4560 | -4834 | 2037 | 97 | -4553 | 392 | -5256 | 27 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 8 | -464 | -4943 | -3578 | 156 | -5759 | -1752 | -3603 | -5508 | -1616 | -5465 | -4564 | -3477 | 3730 | -3175 | -1215 | 697 | -1675 | -4961 | -5617 | -4985 | 28 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 2 9 | -36 | -4571 | -945 | 163 | -4892 | 336 | 2269 | -2129 | -74 | -4587 | -3661 | 2138 | -4166 | 261 | -1460 | -822 | 1414 | -682 | -4755 | 700 | 29 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 6

| | | | | | | | | | | | | | | | | | | | | | |
|---|---|---|---|---|---|---|---|---|---|---|---|---|---|---|---|---|---|---|---|---|---|
| - | -1 | -11023 | -12065 | -894 | -1115 | -701 | -1378 | * | * | | | | | | | | | | | | |
| 3 0 | 3362 | -5060 | -3960 | -1527 | -6477 | -2136 | -4534 | -6257 | -4423 | -6303 | -5432 | -1004 | -811 | -1072 | -4921 | 178 | -4321 | -1832 | -6500 | -5893 | 30 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -18 | -11023 | -6420 | -894 | -1115 | -701 | -1378 | * | * | | | | | | | | | | | | |
| 3 1 | -1049 | -4555 | 148 | 1463 | -4875 | -4058 | -2716 | -993 | 1147 | -2673 | -863 | -983 | -4151 | 1892 | 1235 | -590 | 1202 | -788 | -4739 | -834 | 31 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11006 | -12048 | -894 | -1115 | -444 | -1916 | * | * | | | | | | | | | | | | |
| 3 2 | 331 | -4572 | 491 | 954 | -1179 | 489 | -470 | -4643 | 352 | -2337 | -3661 | 1027 | -1906 | -33 | 1510 | 470 | -638 | -1807 | 122 | -866 | 32 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 3 3 | 922 | 36 | -7042 | -6525 | -4477 | -6466 | -5600 | -626 | -6240 | -1110 | -433 | -6118 | -6412 | -5948 | -2134 | -5634 | -4511 | 3460 | -5365 | -4988 | 33 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 3 4 | 619 | -4558 | -156 | 758 | -499 | -4076 | -481 | -1791 | 587 | -2183 | -3649 | -2714 | -4169 | -413 | 962 | 1507 | 976 | -1017 | -4745 | 910 | 34 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 3 5 | -2161 | -4635 | -7592 | -7120 | -1252 | -1604 | -6387 | 540 | -6901 | 2467 | -3458 | -6804 | -6949 | -6529 | -6803 | -6367 | -5011 | 2356 | -5892 | -5607 | 35 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 3 6 | 557 | 2801 | -1721 | -4985 | -388 | -4905 | -248 | 1189 | 140 | 248 | -41 | -4518 | -4956 | -1129 | -1396 | -1302 | 194 | 1652 | -3666 | -218 | 36 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 3 7 | -924 | -3659 | -6262 | -5655 | -56 | 2370 | -4436 | -501 | -5277 | 1969 | -2773 | -5161 | -5523 | -4899 | -5089 | -4605 | -1925 | 945 | -4259 | -3925 | 37 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 3 8 | -3164 | -4080 | 2121 | -411 | 1807 | -919 | -2937 | -1027 | -2644 | -1377 | -3222 | -282 | -198 | -1254 | -3095 | 914 | -667 | -1060 | -4386 | 2201 | 38 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |

FIG. 7

| | | | | | | | | | | | | | | | | | | | | | |
|---|---|---|---|---|---|---|---|---|---|---|---|---|---|---|---|---|---|---|---|---|---|
| 3 9 | -1317 | -4571 | 1686 | -44 | 3174 | -452 | 570 | -4642 | 414 | -4587 | -3660 | -715 | -4166 | -2272 | -1098 | 55 | -637 | -1613 | -4755 | -4072 | 39 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 4 0 | 584 | -4574 | 362 | 369 | -4895 | -1946 | -2733 | -4646 | 367 | -1673 | -3664 | 3036 | 1201 | -2273 | -1400 | -914 | -302 | -4196 | -4758 | -4075 | 40 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -74 | -11023 | -4329 | -894 | -1115 | -701 | -1378 | * | * | | | | | | | | | | | | |
| 4 1 | -1777 | -4504 | 1404 | 142 | -4824 | 1166 | 1065 | -4574 | -2246 | -2300 | -3593 | 2273 | 194 | -772 | -215 | -398 | -459 | -678 | 189 | 96 | 41 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1080 | -10949 | -926 | -894 | -1115 | -2265 | -337 | * | * | | | | | | | | | | | | |
| 4 2 | 10 | -3574 | 1431 | 899 | -3894 | 1158 | -1734 | -3645 | -50 | -1313 | -2663 | 1007 | -267 | -1275 | -1822 | 504 | 735 | -3195 | -3757 | -263 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -258 | -9872 | -2622 | -894 | -1115 | -5207 | -40 | * | * | | | | | | | | | | | | |
| 4 3 | -1897 | -3368 | 980 | 558 | -3688 | 1508 | 642 | -3438 | -1111 | -100 | -2457 | 771 | -226 | 1860 | -284 | -1778 | -45 | -979 | -3552 | -2869 | 43 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -786 | -9617 | -1256 | -894 | -1115 | -5379 | -35 | * | * | | | | | | | | | | | | |
| 4 4 | -1320 | -2790 | 642 | -620 | -3110 | 845 | -953 | -2859 | 1750 | -2805 | -1880 | 897 | 64 | -494 | 447 | 644 | 269 | -338 | -2974 | -2292 | 44 |
| - | -145 | -500 | 232 | 43 | -381 | 398 | 105 | -627 | 210 | -466 | -721 | 275 | 393 | 48 | 95 | 359 | 117 | -370 | -295 | -246 | |
| - | -4000 | -1761 | -638 | -49 | -4913 | -5694 | -28 | * | * | | | | | | | | | | | | |
| 4 5 | -1645 | -3285 | 2437 | -36 | -3659 | -1761 | -1077 | -3545 | -1203 | -3463 | -2733 | 1962 | 2482 | -734 | -1954 | -1382 | -1715 | -3025 | -3646 | -2736 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -624 | -7357 | -1535 | -894 | -1115 | -407 | -2026 | * | * | | | | | | | | | | | | |
| 4 6 | -2743 | -4200 | -915 | 509 | -4517 | -3717 | 303 | -4263 | 689 | -1027 | -3291 | -2355 | -1213 | -385 | 645 | -2625 | -905 | -1471 | 5255 | -3708 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10608 | -11650 | -894 | -1115 | -3058 | -185 | * | * | | | | | | | | | | | | |
| 4 7 | -1155 | -4079 | 2253 | -120 | -880 | -3775 | 1342 | -615 | -2051 | -2023 | -3186 | 1492 | 960 | 383 | -2546 | -137 | -2712 | 495 | -4303 | 361 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10641 | -11683 | -894 | -1115 | -56 | -4726 | * | * | | | | | | | | | | | | |
| 4 8 | 656 | -4516 | -1114 | 731 | -1260 | 1230 | 465 | -242 | -98 | -1569 | -3612 | -2734 | 461 | 159 | -654 | -1260 | 819 | -242 | 1382 | 50 | 49 |

FIG. 8

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 4 9 | -3100 | -4560 | -1116 | 1388 | 96 | -908 | 885 | -119 | -725 | -1440 | 1409 | 536 | -4169 | 1003 | 1235 | 22 | 807 | -488 | -4746 | -4067 | 50 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 5 0 | 941 | -115 | -708 | 1773 | -4860 | -1149 | -2738 | -824 | -1301 | -2538 | 698 | -1344 | -4171 | -814 | 930 | 554 | 1279 | -254 | -4739 | -4062 | 51 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 5 1 | -420 | -3382 | -1879 | -4044 | 439 | -4712 | 3032 | 1305 | -703 | 332 | -2575 | 364 | -4775 | -722 | -67 | -3740 | 41 | 1148 | -3814 | 285 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 5 2 | -1952 | -4573 | -58 | 669 | -4895 | -4073 | -2732 | -4645 | -493 | -4589 | -3663 | -338 | 2995 | 1442 | 619 | -833 | -73 | -260 | -4757 | -4074 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 5 3 | -1019 | -3213 | -1623 | -1804 | -243 | -4921 | -3789 | -2702 | -1610 | 1632 | 4259 | -4550 | -4971 | -4279 | -4465 | -4004 | -3320 | -593 | -3668 | 798 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 5 4 | -1227 | -4571 | 654 | 1153 | -4892 | -1716 | 1453 | -1841 | 1364 | -4587 | -3661 | -2708 | 59 | -40 | 903 | -880 | 1286 | 260 | -4755 | 34 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -404 | -11023 | -2038 | -894 | -1115 | -701 | -1378 | * | * | | | | | | | | | | | | |
| 5 5 | -2745 | -4145 | -2622 | 504 | -415 | -3731 | 392 | -4166 | 1748 | -594 | -372 | -768 | 1315 | -1943 | 1913 | 493 | -1052 | -1625 | -4347 | 183 | 56 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1381 | -10620 | -700 | -894 | -1115 | -4109 | -86 | * | * | | | | | | | | | | | | |
| 5 6 | -1634 | -2867 | 129 | -1035 | -3099 | 918 | -1317 | -330 | 201 | 713 | -1982 | -1326 | -2738 | -894 | 930 | 1536 | 714 | -2441 | -3108 | -2486 | 57 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1723 | -9243 | -524 | -894 | -1115 | -4411 | -69 | * | * | | | | | | | | | | | | |
| 5 7 | -1133 | -2513 | -524 | 1978 | -2771 | 1477 | -678 | -2535 | 1066 | -2508 | -1648 | -560 | -2097 | -257 | -717 | -1002 | -1082 | -2134 | -2676 | 1915 | 58 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 9

| | | | | | | | | | | | | | | | | | | | | | |
|---|---|---|---|---|---|---|---|---|---|---|---|---|---|---|---|---|---|---|---|---|---|
| - | -1253 | -7810 | -796 | -894 | -1115 | -3061 | -184 | * | * | | | | | | | | | | | | |
| 58 | -994 | -1426 | 1440 | -1034 | -1461 | -2223 | -963 | -1010 | -885 | -66 | 1503 | -1180 | -2299 | -782 | 1512 | -1199 | 1429 | 886 | -1816 | -1370 | 59 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8190 | -9232 | -894 | -1115 | -906 | -1100 | * | * | | | | | | | | | | | | |
| 59 | -2441 | -3911 | 36 | 615 | -610 | -1517 | 1889 | -3980 | 1236 | -227 | -3000 | 1723 | 366 | -1615 | 1057 | -1067 | -2380 | 479 | -4095 | -3413 | 60 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -78 | -10278 | -4270 | -894 | -1115 | -1209 | -817 | * | * | | | | | | | | | | | | |
| 60 | -272 | -4175 | 1427 | -249 | -4496 | 825 | -235 | -923 | 391 | -577 | -3265 | 976 | -3770 | -602 | 1682 | 165 | -1303 | -978 | -4359 | -3676 | 61 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -81 | -10580 | -4214 | -894 | -1115 | -1882 | -456 | * | * | | | | | | | | | | | | |
| 61 | -713 | -4275 | 2377 | 1673 | -4595 | 133 | -2427 | -1328 | -1103 | -4291 | -3366 | -246 | -1321 | -1969 | -2526 | -881 | 1896 | -3897 | -4459 | -3773 | 62 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10626 | -11668 | -894 | -1115 | -373 | -2136 | * | * | | | | | | | | | | | | |
| 62 | -443 | -4504 | 216 | -81 | 1410 | 1699 | -313 | -4575 | -1074 | -4520 | -3593 | 1620 | -329 | 2 | -304 | 636 | -837 | -4126 | -4687 | -209 | 63 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10947 | -11990 | -894 | -1115 | -198 | -2966 | * | * | | | | | | | | | | | | |
| 63 | -1102 | -4838 | 403 | -2956 | -707 | 3185 | -502 | -4688 | -3155 | -4786 | -746 | 1368 | -4754 | -1258 | -3662 | -3660 | -3684 | -4391 | -4953 | 421 | 64 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 64 | -990 | -3200 | -5718 | -5082 | 406 | -4921 | -3792 | 1807 | -422 | -810 | -2403 | -1483 | -4971 | -4300 | -4477 | -4005 | 105 | 2648 | 1942 | 674 | 65 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 65 | -7684 | -6590 | -8044 | -8406 | 1262 | -7926 | -4105 | -6567 | -7962 | -5868 | -5967 | -6534 | -7780 | -6676 | -7320 | -7179 | -7532 | -6724 | 6021 | 1346 | 66 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -24 | -11023 | -5937 | -894 | -1115 | -701 | -1378 | * | * | | | | | | | | | | | | |
| 66 | -1081 | -39 | -645 | 2092 | -4866 | -2001 | 3120 | -4613 | -2304 | -4563 | -3640 | -2697 | -4153 | -2262 | -312 | 1595 | 956 | -1784 | -4735 | -4055 | 67 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10999 | -12041 | -894 | -1115 | -387 | -2088 | * | * | | | | | | | | | | | | |

FIG. 10

| | | | | | | | | | | | | | | | | | | | | | |
|---|---|---|---|---|---|---|---|---|---|---|---|---|---|---|---|---|---|---|---|---|---|
| 67 | 1191 | 1498 | -5739 | -5104 | -3173 | -675 | -3816 | 1715 | -4700 | 1112 | -209 | -4589 | -4992 | -4323 | -4500 | -4028 | -68 | 1675 | 1543 | -3338 | 68 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 68 | -607 | -4400 | -3047 | 467 | 2483 | -4124 | -415 | -4347 | -571 | -2213 | -3509 | -1371 | -4215 | -707 | -22 | -411 | 1595 | 1122 | -4629 | 1250 | 69 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 69 | -1125 | -3258 | -5787 | -5155 | -3223 | -430 | -3875 | 1839 | -1620 | 1905 | -2463 | -4642 | -5043 | -4379 | -4556 | -4083 | -1271 | 2065 | 163 | -3395 | 70 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 70 | -1005 | -4574 | 94 | 1232 | -1268 | -949 | 305 | -4645 | -597 | -4590 | -3663 | -423 | 3130 | -2273 | -1334 | -922 | 664 | -4196 | -4757 | -4074 | 71 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -799 | -11023 | -1236 | -894 | -1115 | -701 | -1378 | * | * | | | | | | | | | | | | |
| 71 | -1035 | -3869 | 42 | -553 | -4190 | 2429 | -2028 | -3940 | 383 | -1291 | -2958 | 754 | 531 | 23 | 131 | -774 | -203 | -1418 | -4052 | -3369 | 72 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1736 | -10226 | -517 | -894 | -1115 | -3087 | -181 | * | * | | | | | | | | | | | | |
| 72 | 727 | -2766 | 1622 | -596 | -3081 | -2270 | 1180 | -2828 | 1226 | -563 | -1858 | 1347 | -2368 | -480 | -1030 | 1120 | -1245 | -2385 | -2953 | -2272 | 73 |
| - | -148 | -501 | 232 | 48 | -382 | 397 | 104 | -627 | 211 | -467 | -722 | 277 | 395 | 47 | 95 | 359 | 116 | -368 | -296 | -250 | |
| - | -3941 | -523 | -2066 | -22 | -6038 | -5709 | -28 | * | * | | | | | | | | | | | | |
| 73 | -2095 | -3593 | 2287 | -826 | -4113 | 136 | -1685 | -3935 | -1635 | -3872 | -3056 | 2772 | 865 | -1307 | -2288 | -1905 | 989 | -3409 | -4061 | -3243 | 75 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8385 | -9427 | -894 | -1115 | -5796 | -26 | * | * | | | | | | | | | | | | |
| 74 | -3370 | -3802 | -3346 | -3527 | -5496 | 3620 | -3660 | -5604 | 777 | -5453 | -4841 | -3488 | -4255 | -3494 | -3154 | -3491 | -3663 | -4841 | -4854 | -5028 | 76 |
| - | -150 | -501 | 234 | 42 | -382 | 397 | 104 | -627 | 211 | -465 | -722 | 276 | 393 | 44 | 95 | 363 | 118 | -368 | -296 | -250 | |
| - | -3549 | -131 | -9427 | -22 | -6038 | -4725 | -56 | * | * | | | | | | | | | | | | |
| 75 | -1261 | 2000 | 664 | -2358 | 951 | -2717 | -1566 | -733 | -2084 | 267 | -424 | -2139 | 2442 | -1824 | -2112 | 228 | -1206 | 633 | -1672 | -1309 | 78 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8531 | -9573 | -894 | -1115 | -263 | -2585 | * | * | | | | | | | | | | | | |
| 76 | 892 | -4282 | 1991 | 467 | -4556 | 495 | -2583 | 504 | -1276 | -622 | -3384 | -162 | -482 | -2140 | -2683 | -213 | 284 | -489 | -4495 | -845 | 79 |

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10819 | -11861 | -894 | -1115 | -92 | -4010 | * | * | | | | | | | | | | | | |
| 77 | -874 | -3305 | -4976 | -1454 | 194 | -2338 | -3621 | 1526 | -963 | 1775 | -2502 | -1534 | -110 | -1436 | -945 | -1080 | -1758 | 820 | 2649 | -3384 | 80 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 78 | -357 | -4572 | 685 | 917 | -4893 | 291 | 1424 | -1497 | 1572 | -2482 | -3661 | -1041 | 1991 | -929 | -2819 | -661 | 172 | -4194 | -4755 | -1177 | 81 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -536 | -11023 | -1691 | -894 | -1115 | -701 | -1378 | * | * | | | | | | | | | | | | |
| 79 | -660 | 139 | 903 | 1067 | -4364 | 1116 | 2881 | -1448 | -444 | -1437 | -3153 | 877 | 1160 | -1812 | -2358 | -2514 | -2565 | -571 | -4253 | -3580 | 82 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -351 | -10488 | -2216 | -894 | -1115 | -3008 | -192 | * | * | | | | | | | | | | | | |
| 80 | -1185 | 335 | 497 | -1714 | -4146 | 2833 | -2042 | -3887 | -556 | -1696 | -2934 | 1660 | -3471 | -1588 | -450 | -830 | -926 | -3452 | -4032 | -3359 | 83 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -490 | -10207 | -1801 | -894 | -1115 | -4876 | -50 | * | * | | | | | | | | | | | | |
| 81 | 961 | -3448 | -1830 | -230 | -3765 | -909 | 654 | -3512 | -1203 | -3462 | -2539 | 47 | -3054 | 1533 | -1710 | 1907 | 1572 | -3068 | -3635 | -139 | 84 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2627 | -9720 | -257 | -894 | -1115 | -5316 | -37 | * | * | | | | | | | | | | | | |
| 82 | -1425 | -2189 | -1160 | -1096 | -3294 | 2933 | -1286 | -3062 | 1835 | -3036 | -2313 | -1209 | -2398 | -964 | -760 | -1448 | -1559 | -2556 | -2967 | -2661 | 85 |
| - | -150 | -501 | 232 | 42 | -381 | 402 | 105 | -621 | 209 | -465 | -721 | 274 | 393 | 44 | 95 | 358 | 120 | -370 | -295 | -250 | |
| - | -2273 | -761 | -2301 | -1549 | -603 | -1681 | -539 | * | * | | | | | | | | | | | | |
| 83 | 77 | -3267 | -66 | 57 | 205 | 2688 | -1433 | -3332 | -1020 | -3281 | -2359 | 196 | -2864 | 490 | 112 | -1682 | -253 | -2887 | -3453 | -2771 | 89 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9452 | -10494 | -894 | -1115 | -1361 | -711 | * | * | | | | | | | | | | | | |
| 84 | 627 | 582 | -868 | -3565 | -2609 | -4071 | 385 | -2156 | -731 | 530 | 1415 | -3416 | -4131 | 1816 | -3398 | -1179 | 229 | 1180 | 1903 | 1485 | 90 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10259 | -11301 | -894 | -1115 | -33 | -5486 | * | * | | | | | | | | | | | | |
| 85 | -998 | -272 | -1312 | 147 | 944 | -4088 | -2749 | -4547 | 636 | 767 | -3613 | -779 | -4180 | 238 | 1884 | -541 | -545 | -490 | -4716 | 1812 | 91 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 12

| | | | | | | | | | | | | | | | | | | | | | |
|---|---|---|---|---|---|---|---|---|---|---|---|---|---|---|---|---|---|---|---|---|---|
| - | -1 | -11023 | -12065 | -894 | -1115 | -701 | -1378 | * | * | | | | | | | | | | | | |
| 86 | -4871 | -522 | -7273 | -6801 | -4006 | -6725 | -5389 | 401 | -6490 | -2106 | -3511 | -6303 | -6634 | -298 | -6337 | -5905 | -4829 | 209 | -4919 | 4584 | 92 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 87 | 7 | -4545 | -2961 | 83 | -4853 | 1479 | -96 | -4595 | 2534 | -252 | -347 | -2720 | -4173 | -532 | -337 | -1539 | -525 | -1911 | -4736 | 5 | 93 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 88 | -1905 | -3714 | -6172 | -5598 | 2582 | -5424 | -3923 | 369 | -837 | -1692 | -2896 | -4990 | -5458 | -4757 | -4969 | -4518 | -3857 | -847 | 261 | 4039 | 94 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 89 | -491 | -44 | -3807 | 1600 | -142 | -4457 | -3193 | -179 | 356 | -893 | -442 | -1006 | -4533 | -1131 | 2679 | -2040 | -1632 | -273 | -4076 | 53 | 95 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 90 | -381 | 192 | -5979 | -5354 | 1663 | -5204 | -4093 | 2161 | -4960 | 280 | 1877 | -4850 | -5237 | -4582 | -4765 | -4296 | -3560 | 2082 | -3938 | 236 | 96 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 91 | -1360 | 856 | 1256 | -178 | -448 | -4116 | 2442 | -140 | 738 | -1771 | -3532 | -893 | -4207 | -601 | 1 | -1669 | 1115 | 658 | 2043 | -1166 | 97 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -52 | -11023 | -4840 | -894 | -1115 | -701 | -1378 | * | * | | | | | | | | | | | | |
| 92 | -1767 | -4492 | 391 | -332 | -4797 | 2082 | 1139 | -650 | -2283 | -2336 | -3585 | 798 | -1471 | -2241 | 342 | -592 | 898 | 872 | -4684 | -4011 | 98 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10972 | -12014 | -894 | -1115 | -256 | -2623 | * | * | | | | | | | | | | | | |
| 93 | -166 | -653 | 1178 | -302 | -1166 | 473 | 1013 | -1718 | -621 | -4575 | -3651 | 922 | 1911 | -938 | -89 | -2982 | -235 | -1085 | 9 | 1464 | 99 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -23 | -11023 | -6015 | -894 | -1115 | -701 | -1378 | * | * | | | | | | | | | | | | |
| 94 | -17 | -4552 | 1435 | -686 | 585 | 753 | 1661 | -4623 | -482 | -4568 | -3641 | 1595 | -510 | -798 | -1193 | 843 | -1359 | -4174 | 858 | 596 | 100 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1352 | -11001 | -718 | -894 | -1115 | -1381 | -699 | * | * | | | | | | | | | | | | |

FIG. 13

| | | | | | | | | | | | | | | | | | | | | | |
|---|---|---|---|---|---|---|---|---|---|---|---|---|---|---|---|---|---|---|---|---|---|
| 9 5 | 990 | -3393 | -409 | -208 | -3713 | -2897 | 1789 | -3462 | 1102 | -1191 | -2483 | 165 | 1197 | 777 | -1644 | -519 | -1862 | -3014 | 3290 | 326 | 101 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -154 | -9651 | -3326 | -894 | -1115 | -5359 | -36 | * | * | | | | | | | | | | | | |
| 9 6 | -2694 | -4027 | -1734 | 21 | 1263 | -3320 | 986 | -4084 | -2097 | -4097 | -3279 | 170 | 3097 | -1914 | -2648 | 1632 | -2688 | -3687 | -4239 | -3490 | 102 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -212 | -9501 | -2885 | -894 | -1115 | -5443 | -34 | * | * | | | | | | | | | | | | |
| 9 7 | 590 | -3111 | 230 | 1845 | 424 | -2623 | 751 | -3174 | 424 | -3125 | -2201 | -1260 | -2717 | 700 | -1372 | -1531 | 1287 | -2730 | -3297 | 1665 | 103 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1738 | -9292 | -517 | -894 | -1115 | -5540 | -31 | * | * | | | | | | | | | | | | |
| 9 8 | 763 | -3278 | 2505 | 1841 | -3526 | -1860 | -998 | -3362 | -969 | -3273 | -2473 | 1657 | -2265 | -619 | -1653 | -1329 | -1592 | -2876 | -3460 | -2597 | 104 |
| - | -143 | -505 | 238 | 38 | -376 | 401 | 100 | -629 | 210 | -470 | -726 | 274 | 388 | 42 | 90 | 364 | 117 | -364 | -269 | -255 | |
| - | -1546 | -1217 | -2137 | -4002 | -93 | -2398 | -303 | * | * | | | | | | | | | | | | |
| 9 9 | 924 | 1118 | -1238 | 1857 | -3128 | -2357 | -1016 | -2870 | 1001 | -799 | -1912 | 420 | -2450 | 1522 | 180 | -1265 | -1317 | -447 | -3010 | -2336 | 122 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -8916 | -9958 | -894 | -1115 | -776 | -1266 | * | * | | | | | | | | | | | | |
| 10 0 | -4244 | -5377 | -645 | -3281 | -6758 | 3521 | -4264 | -6619 | -4334 | -6569 | -5824 | -3559 | -5159 | -467 | -955 | -491 | -238 | -5843 | -6723 | -5952 | 123 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1366 | -10466 | -710 | -894 | -1115 | -4472 | -67 | * | * | | | | | | | | | | | | |
| 10 1 | -1545 | -2628 | -3 | -1022 | -2810 | -2587 | 3746 | -2470 | -928 | -66 | 1100 | 1005 | -2677 | 1275 | -1401 | 87 | -1485 | 40 | -2901 | -2314 | 124 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9104 | -10146 | -894 | -1115 | -4056 | -89 | * | * | | | | | | | | | | | | |
| 10 2 | -1738 | -3101 | 318 | -1072 | -3394 | -2715 | -1350 | -3113 | 293 | -902 | -2201 | -1366 | -2803 | 625 | 2944 | -213 | -1671 | -2712 | 1867 | 1672 | 125 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9260 | -10302 | -894 | -1115 | -3745 | -112 | * | * | | | | | | | | | | | | |
| 10 3 | -1830 | 1786 | -1979 | 181 | 3110 | -2914 | -1599 | -2494 | 187 | -2661 | -1872 | 348 | -2999 | 382 | -17 | -1850 | -1768 | -164 | -3033 | 1694 | 126 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9439 | -10481 | -894 | -1115 | -3895 | -100 | * | * | | | | | | | | | | | | |
| 10 4 | -486 | -3147 | 2145 | 605 | -3366 | -2937 | -1627 | 489 | -1269 | -3119 | -2267 | 2387 | -3039 | -1211 | -1759 | -421 | -1882 | 354 | -3396 | 422 | 127 |

FIG. 14

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9567 | -10609 | -894 | -1115 | -193 | -2999 | * | * | | | | | | | | | | | | |
| 10 5 | -1642 | -4357 | -2912 | 1666 | -1270 | -1006 | 1125 | -809 | -1170 | -1665 | -3460 | 317 | 1944 | 1076 | -1285 | -904 | -1341 | 651 | 1747 | -760 | 128 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -30 | -10913 | -5643 | -894 | -1115 | -2658 | -249 | * | * | | | | | | | | | | | | |
| 10 6 | -1173 | -4422 | 150 | 150 | -4731 | -3955 | -2614 | 874 | 758 | -114 | -3514 | 894 | -4047 | 971 | -224 | 68 | 369 | -36 | 2895 | -960 | 129 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10885 | -11927 | -894 | -1115 | -400 | -2047 | * | * | | | | | | | | | | | | |
| 10 7 | -3107 | -192 | -1522 | -578 | -1688 | -1620 | -372 | -949 | 1499 | -102 | -430 | 1040 | 942 | -2398 | 1137 | -958 | -317 | 885 | -4527 | 579 | 130 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10996 | -12038 | -894 | -1115 | -1491 | -634 | * | * | | | | | | | | | | | | |
| 10 8 | -3341 | -3194 | 1900 | 485 | 588 | -4869 | -297 | -72 | -4523 | 1289 | -2395 | -4458 | -4921 | -4178 | -1295 | -2068 | -1548 | 979 | 2426 | 1188 | 131 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -21 | -10996 | -6189 | -894 | -1115 | -363 | -2168 | * | * | | | | | | | | | | | | |
| 10 9 | -117 | -4097 | -3254 | -1038 | -4244 | -4216 | -2903 | -119 | 1662 | 837 | -3236 | -2962 | 385 | -851 | 1231 | -865 | 302 | 1173 | -4396 | -3839 | 132 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11003 | -12046 | -894 | -1115 | -420 | -1984 | * | * | | | | | | | | | | | | |
| 11 0 | 1344 | -4030 | -1481 | -678 | -4152 | -4269 | -2964 | 1060 | -984 | 1062 | -3176 | -1173 | 117 | -2623 | -546 | -280 | 815 | 530 | -4346 | -540 | 133 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 11 1 | -4562 | -5414 | 3854 | -4419 | -7555 | -1661 | -5445 | -7459 | -5967 | -7537 | -6744 | -4536 | 732 | -5224 | -6607 | 436 | -1693 | -6356 | -7702 | -7065 | 134 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 11 2 | 375 | -4583 | -3848 | -1187 | -4813 | -4730 | -3382 | -1424 | -2824 | -4555 | -3786 | -3528 | 3834 | -978 | 62 | -3761 | -1326 | -4174 | -4874 | -1076 | 135 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11023 | -12065 | -894 | -1115 | -701 | -1378 | * | * | | | | | | | | | | | | |
| 11 3 | -4784 | -428 | -6779 | -6355 | 582 | -1779 | -3987 | -4061 | -5937 | -2040 | 53 | 634 | -6164 | -5379 | -677 | -5268 | -4716 | -4009 | 3313 | 4259 | 136 |
| - | -149 | -500 | 233 | 43 | -381 | 399 | 106 | -626 | 210 | -466 | -720 | 275 | 394 | 45 | 96 | 359 | 117 | -369 | -294 | -249 | |

| | | | | | | | | | | | | | | | | | | | | | |
|---|---|---|---|---|---|---|---|---|---|---|---|---|---|---|---|---|---|---|---|---|---|
| - | -1 | -11023 | -12065 | -894 | -1115 | -701 | -1378 | * | * | | | | | | | | | | | | |
| 11 4 | 3042 | -4607 | -6209 | -6125 | -6739 | 540 | -5868 | 200 | -6057 | -6710 | -5828 | -1234 | -5611 | 733 | -6130 | 211 | -764 | -5531 | -6964 | -6720 | 137 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10994 | -12036 | -894 | -1115 | -701 | -1378 | * | * | | | | | | | | | | | | |
| 11 5 | -1554 | -4254 | -3118 | -2567 | 1616 | -4149 | -141 | -1803 | 2314 | -2413 | -3377 | -165 | 956 | -1065 | 1741 | -3071 | 1002 | -1581 | -4514 | -3916 | 138 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10994 | -12036 | -894 | -1115 | -701 | -1378 | * | * | | | | | | | | | | | | |
| 11 6 | 1683 | -4540 | 70 | 592 | 1140 | 57 | -2707 | -4608 | -453 | -2223 | -3630 | 225 | -4141 | -1025 | -156 | 165 | -3012 | -819 | -4725 | 1981 | 139 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10994 | -12036 | -894 | -1115 | -701 | -1378 | * | * | | | | | | | | | | | | |
| 11 7 | 435 | 976 | -5691 | -5055 | 1014 | 200 | -3764 | 1242 | -4650 | 303 | -37 | -4539 | -4943 | -323 | -4450 | -22 | -536 | 1867 | -3630 | 123 | 140 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10994 | -12036 | -894 | -1115 | -701 | -1378 | * | * | | | | | | | | | | | | |
| 11 8 | 116 | -4535 | 432 | 1251 | -4851 | -355 | 368 | -1120 | -2291 | -4549 | -3626 | -417 | -308 | -474 | -2798 | 926 | 847 | 1511 | -4721 | -101 | 141 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10731 | -11773 | -894 | -1115 | -701 | -1378 | * | * | | | | | | | | | | | | |
| 11 9 | 89 | 40 | 704 | -356 | -4621 | 997 | -259 | -4370 | 321 | -318 | -718 | -2448 | -399 | 482 | -193 | 844 | -1010 | 1049 | -4488 | -3807 | 142 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10731 | -11773 | -894 | -1115 | -701 | -1378 | * | * | | | | | | | | | | | | |
| 12 0 | -2839 | -4311 | 1556 | -525 | -4632 | -1454 | -2471 | -4383 | -368 | -1184 | -3401 | 2127 | 1394 | -2011 | 2020 | -74 | -1349 | -3933 | 793 | -3812 | 143 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10731 | -11773 | -894 | -1115 | -701 | -1378 | * | * | | | | | | | | | | | | |
| 12 1 | -2838 | -4293 | 113 | -626 | -544 | 1423 | -2474 | -4352 | -2058 | -2372 | -3384 | 22 | 2430 | 131 | -621 | 781 | -851 | 451 | -4481 | -3803 | 144 |
| - | * | * | * | * | * | * | * | * | * | * | * | * | * | * | * | * | * | * | * | * | |
| - | * | * | * | * | * | * | * | * | 0 | | | | | | | | | | | | |

FIG. 16

Table 4 Information for producing the HMM for the Pfam alpha-amylase domain (PF 00128)

```
HMMER   2.0 [2.3.1]
NAME    alpha-amylase
ACC     PF00128
DESC    Alpha amylase, catalytic domain
LENG
ALPH    Amino
RF      no
CS      no
MAP     yes
COM     hmmbuild -F HMM_ls.ann SEED.ann
COM     hmmcalibrate --seed 0 HMM_ls.ani
NSEQ    54
DATE
CKSUM   2797
GA      -82.0 -82.0
TC      -81.7 -81.7
NC      -82.7 -82.7
XT          -8455     -4  -1000  -1000  -8455     -4  -8455     -4
NULT           -4  -8455
NULE          595  -1558     85    338   -294    453  -1158    197    249    902  -1085   -142    -21   -313     45    531    201    384  -1998   -644
EVD     -218.894150  0.133020
HMM             A      C      D      E      F      G      H      I      K      L      M      N      P      Q      R      S      T      V      W      Y
             m->m   m->i   m->d   i->m   i->i   d->m   d->d   b->m   m->e
              -36      *  -5356
      1     -1605  -4092    285    925    969   -202    244  -4163  -1052  -4108  -3181  -2229  -3686   3256   -723   -566    423  -3713    766  -3593     1
      -      -149   -500    233     43   -381    399    106   -626    210   -466   -720    275    394     45     96    359    117   -369   -294   -249
```

FIG. 17

| | | | | | | | | | | | | | | | | | | | | | |
|---|---|---|---|---|---|---|---|---|---|---|---|---|---|---|---|---|---|---|---|---|---|
| - | -28 | -10485 | -5739 | -894 | -1115 | -701 | -1378 | -36 | * | | | | | | | | | | | | |
| 2 | -2887 | -2711 | -5230 | -4597 | -2673 | -1822 | -3316 | 3045 | -4195 | 522 | -1917 | -883 | -4488 | -3820 | -3998 | -1684 | -306 | 1681 | -3182 | -282 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10458 | -11500 | -894 | -1115 | -427 | -1963 | * | * | | | | | | | | | | | | |
| 3 | -1209 | -2710 | -5229 | -4593 | 2368 | -4432 | 278 | 1011 | -4188 | 444 | 1689 | -4078 | -4481 | -3811 | -3988 | -3516 | 516 | 317 | -3167 | 2755 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 4 | -275 | -2705 | -5221 | -4585 | 448 | -1450 | -3297 | -30 | -4181 | -155 | 899 | -4071 | 2650 | -3804 | -3982 | -1376 | 1224 | 1419 | -3163 | -2821 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 5 | -668 | -4093 | 2249 | 318 | -4414 | -1377 | 2291 | -4165 | -28 | -4109 | -3182 | -743 | -954 | 1554 | 1650 | -2500 | -348 | -1759 | -4276 | -3593 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 6 | -472 | -3803 | -3114 | -943 | -4039 | 851 | -2739 | -3669 | -2370 | 385 | -3045 | -2815 | -4109 | -2392 | 2651 | 1729 | -2901 | -3408 | -4184 | 328 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 7 | -1460 | -4497 | -7039 | -6833 | 4401 | -1492 | -4848 | -946 | -6493 | -1435 | -3124 | -5813 | -6017 | -5797 | -6161 | -4986 | -4659 | -3568 | -4250 | -3409 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 8 | 1015 | -4092 | -2467 | 1414 | -4412 | -3593 | 301 | -4163 | 1059 | -4107 | 425 | 1248 | -3686 | 544 | 382 | 119 | -68 | -1924 | -4275 | 1332 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -474 | -10485 | -1840 | -894 | -1115 | -701 | -1378 | * | * | | | | | | | | | | | | |
| 9 | -798 | -3710 | 1318 | 381 | -4030 | -3204 | -1867 | -3781 | -229 | -3725 | -2800 | 1805 | -3300 | -1408 | 1149 | -673 | -500 | -3332 | 4434 | -3210 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10013 | -11055 | -894 | -1115 | -3804 | -107 | * | * | | | | | | | | | | | | |
| 10 | -754 | -3691 | 95 | 139 | -4012 | 2378 | -1850 | -3763 | 799 | -3707 | -2780 | 504 | -3285 | 226 | 170 | -222 | -208 | -3313 | -3874 | 686 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -283 | -10013 | -2495 | -894 | -1115 | -323 | -2316 | * | * | | | | | | | | | | | | |

FIG. 18

| | | | | | | | | | | | | | | | | | | | | | |
|---|---|---|---|---|---|---|---|---|---|---|---|---|---|---|---|---|---|---|---|---|---|
| 11 | -2420 | -3619 | 3319 | -531 | -3837 | -1144 | -2112 | -3520 | -1746 | -919 | -489 | 654 | -3528 | -1695 | -2232 | -35 | -195 | -922 | -3868 | -169 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -87 | -10204 | -4120 | -894 | -1115 | -3240 | -161 | * | * | | | | | | | | | | | | |
| 12 | -1036 | -3694 | -489 | -1650 | -3978 | -3303 | -1966 | -873 | 862 | -3694 | -2794 | -232 | 2148 | -1519 | -889 | 1520 | 1384 | -893 | 1820 | -3242 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10119 | -11161 | -894 | -1115 | -3527 | -131 | * | * | | | | | | | | | | | | |
| 13 | -1310 | -3777 | 1225 | -400 | -4097 | -3280 | -1939 | -948 | 123 | -916 | -2866 | 1965 | -671 | -1479 | 669 | 1690 | 587 | -3398 | -3961 | -3279 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10119 | -11161 | -894 | -1115 | -3527 | -131 | * | * | | | | | | | | | | | | |
| 14 | -2309 | 669 | 102 | 248 | -4055 | 1478 | 544 | -181 | 276 | -1468 | -2841 | 2669 | -3381 | -463 | -2039 | -2195 | -130 | -963 | -3940 | -3266 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -166 | -10119 | -3211 | -894 | -1115 | -3527 | -131 | * | * | | | | | | | | | | | | |
| 15 | 507 | -4662 | 3087 | -356 | -4951 | -3666 | -2603 | -4742 | -2381 | -4670 | -3801 | 1868 | -3945 | 102 | -2969 | 458 | -3056 | -864 | -4846 | -4077 | 15 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -983 | -9955 | -1020 | -894 | -1115 | -3928 | -98 | * | * | | | | | | | | | | | | |
| 16 | -1432 | -2900 | -1279 | 454 | -3222 | -2404 | 849 | -2970 | 551 | -2915 | -1990 | 1351 | 2468 | 970 | 43 | -1313 | 329 | -2523 | -3081 | 822 | 16 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -224 | -8976 | -2818 | -894 | -1115 | -4922 | -48 | * | * | | | | | | | | | | | | |
| 17 | 347 | -2735 | 145 | 858 | -3055 | -1 | -898 | -2804 | -479 | -1002 | -1825 | -875 | 318 | 1050 | 656 | 1298 | 635 | -2356 | -2919 | -2237 | 17 |
| - | -150 | -501 | 237 | 45 | -381 | 400 | 105 | -627 | 212 | -467 | -721 | 276 | 393 | 44 | 95 | 358 | 116 | -370 | -295 | -250 | |
| - | -3921 | -996 | -1208 | -31 | -5562 | -5023 | -45 | * | * | | | | | | | | | | | | |
| 18 | -806 | -2136 | -672 | 725 | -2409 | -1787 | 2069 | -2122 | -79 | -2136 | -1251 | 1334 | -1889 | -31 | -576 | 1266 | 1192 | 187 | -2362 | -1714 | 19 |
| - | -149 | -500 | 232 | 42 | -381 | 398 | 105 | -623 | 211 | -464 | -721 | 275 | 393 | 45 | 97 | 359 | 117 | -367 | -295 | -247 | |
| - | -3106 | -442 | -2758 | -37 | -5313 | -5259 | -38 | * | * | | | | | | | | | | | | |
| 19 | -1101 | -1851 | -1203 | -809 | -1107 | -2079 | 2497 | -1776 | -717 | -1890 | -1184 | -983 | 2208 | -661 | -1099 | 1211 | -1094 | -1532 | -1558 | 2020 | 21 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -10 | -7715 | -8757 | -894 | -1115 | -3229 | -163 | * | * | | | | | | | | | | | | |
| 20 | 456 | -2091 | 880 | -981 | -1511 | -2393 | -977 | -1843 | -820 | -1991 | -1264 | -1188 | -2490 | -787 | 1164 | -1376 | -1276 | -1631 | 3621 | 2948 | 22 |

FIG. 19

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8293 | -9336 | -894 | -1115 | -1105 | -902 | * | * | | | | | | | | | | | | |
| 21 | -4548 | -5007 | -4752 | -4756 | -6164 | 3702 | 931 | -6660 | -3624 | -6413 | -5801 | -4630 | -5444 | -4302 | -411 | -4656 | -4785 | -5961 | -5743 | -5570 | 23 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -923 | -9690 | -1085 | -894 | -1115 | -4348 | -73 | * | * | | | | | | | | | | | | |
| 22 | 740 | -2742 | 752 | -578 | 1125 | -55 | 1540 | -2808 | 674 | -2756 | -1832 | 332 | -2345 | -452 | 691 | 1244 | -1216 | -2362 | -2927 | -2247 | 24 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -158 | -8772 | -3303 | -894 | -1115 | -5017 | -45 | * | * | | | | | | | | | | | | |
| 23 | 1093 | -1981 | 783 | -929 | 714 | -2349 | 1735 | -79 | -817 | -649 | -1134 | 774 | 455 | -742 | -1242 | -1294 | 1299 | -1479 | -2316 | -1803 | 25 |
| - | -148 | -501 | 232 | 42 | -374 | 397 | 104 | -628 | 211 | -465 | -722 | 276 | 395 | 44 | 95 | 360 | 119 | -371 | -296 | -248 | |
| - | -3784 | -111 | -9662 | -19 | -6287 | -5076 | -43 | * | * | | | | | | | | | | | | |
| 24 | 1491 | -2213 | 1203 | -932 | -2512 | 145 | -1141 | -177 | -842 | -2307 | -1499 | -1168 | 508 | -775 | -1296 | 1473 | -1252 | -226 | -2655 | -2101 | 27 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8620 | -9662 | -894 | -1115 | -5076 | -43 | * | * | | | | | | | | | | | | |
| 25 | -1203 | -2674 | 235 | 871 | -2992 | 1087 | -833 | -2742 | -420 | -2689 | -1765 | 853 | -2264 | 1628 | -929 | 525 | 1091 | -2295 | 2230 | -2175 | 28 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8620 | -9662 | -894 | -1115 | -5076 | -43 | * | * | | | | | | | | | | | | |
| 26 | -1213 | 2805 | 793 | 588 | 121 | 632 | -986 | -1897 | -694 | -2062 | 1632 | 794 | -2381 | -630 | -1146 | -1229 | 64 | -1647 | -2434 | 1661 | 29 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8620 | -9662 | -894 | -1115 | -5076 | -43 | * | * | | | | | | | | | | | | |
| 27 | 339 | 2653 | 576 | -652 | -2518 | -2231 | 1886 | 301 | -556 | -751 | -1446 | 1155 | -2320 | -504 | 1181 | 294 | -1135 | -1876 | -2586 | -1989 | 30 |
| - | -150 | -501 | 235 | 44 | -382 | 397 | 104 | -624 | 211 | -467 | -722 | 276 | 394 | 44 | 95 | 360 | 121 | -369 | -296 | -251 | |
| - | -3784 | -111 | -9662 | -19 | -6287 | -5076 | -43 | * | * | | | | | | | | | | | | |
| 28 | -39 | -2624 | 1833 | 352 | -2924 | -2171 | -840 | 315 | -433 | -360 | -1720 | 2015 | -2269 | 1105 | -939 | -43 | -1140 | -2235 | -2820 | -2149 | 32 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1468 | -8620 | -653 | -894 | -1115 | -5076 | -43 | * | * | | | | | | | | | | | | |
| 29 | -1168 | -1761 | -1657 | -1066 | -1714 | 1555 | -762 | -1800 | -73 | -1896 | -1201 | -1120 | -2243 | -520 | 2066 | -1254 | -1145 | -1562 | 4088 | -1308 | 33 |
| - | -150 | -501 | 239 | 44 | -382 | 397 | 104 | -627 | 209 | -465 | -722 | 276 | 395 | 44 | 95 | 358 | 116 | -370 | -282 | -247 | |

FIG. 20

| | | | | | | | | | | | | | | | | | | | | | |
|---|---|---|---|---|---|---|---|---|---|---|---|---|---|---|---|---|---|---|---|---|---|
| - | -2331 | -890 | -1933 | -1947 | -433 | -3740 | -112 | * | * | | | | | | | | | | | | |
| 30 | -1006 | -2546 | 1900 | 1847 | -2841 | -1663 | -540 | -2615 | -256 | -2550 | -1674 | -283 | 1442 | -116 | 1044 | -835 | -972 | -2160 | -2724 | -1985 | 38 |
| - | -149 | -500 | 234 | 44 | -381 | 398 | 105 | -627 | 211 | -466 | -721 | 278 | 393 | 45 | 95 | 359 | 117 | -367 | -295 | -250 | |
| - | -2612 | -263 | -8490 | -45 | -5016 | -4191 | -81 | * | * | | | | | | | | | | | | |
| 31 | -1276 | -1857 | -3073 | -3276 | -3951 | -2079 | -3114 | -3699 | -3291 | -3965 | -3211 | -2515 | 3791 | -3088 | -3258 | -1512 | 1591 | -2799 | -4068 | -3935 | 40 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -10 | -7741 | -8783 | -894 | -1115 | -5295 | -37 | * | * | | | | | | | | | | | | |
| 32 | 1795 | -2196 | -565 | 897 | -2705 | -1787 | -749 | -2424 | -444 | -2454 | -1592 | 1798 | -2035 | -339 | -950 | -891 | 1554 | -1990 | -2686 | -2033 | 41 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -567 | -7741 | -1643 | -894 | -1115 | -4278 | -76 | * | * | | | | | | | | | | | | |
| 33 | 1019 | -2549 | 1220 | 15 | -2866 | -1686 | -602 | -2639 | -347 | -2589 | -1721 | 1280 | -1948 | 2872 | -909 | -878 | -1019 | -2187 | -2775 | -2035 | 42 |
| - | -146 | -500 | 232 | 43 | -381 | 398 | 105 | -627 | 213 | -466 | -721 | 275 | 393 | 45 | 95 | 359 | 117 | -370 | -295 | -244 | |
| - | -2649 | -255 | -8527 | -44 | -5058 | -5334 | -36 | * | * | | | | | | | | | | | | |
| 34 | -842 | -2187 | 1083 | -73 | -2670 | 1600 | -538 | -2418 | -193 | -2392 | -1509 | -373 | -1867 | -113 | 1666 | 1096 | -836 | -1956 | -2579 | -1901 | 44 |
| - | -151 | -502 | 235 | 41 | -383 | 403 | 103 | -629 | 211 | -466 | -723 | 273 | 396 | 43 | 94 | 357 | 121 | -372 | -297 | -236 | |
| - | -2649 | -1232 | -1269 | -2921 | -204 | -4299 | -75 | * | * | | | | | | | | | | | | |
| 35 | -468 | -852 | -1748 | -1375 | -1367 | -1561 | -1139 | 2029 | -1215 | -1183 | -541 | -1214 | 1812 | -1077 | -1420 | 1463 | -613 | -493 | -1794 | -1390 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -15 | -7122 | -8164 | -894 | -1115 | -3735 | -113 | * | * | | | | | | | | | | | | |
| 36 | 844 | -2120 | -541 | 1228 | -2414 | -1688 | -358 | -2139 | 1304 | -2120 | -1225 | 1410 | -1794 | 86 | -407 | -628 | -674 | -1730 | 3129 | -1660 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -10 | -7701 | -8743 | -894 | -1115 | -1998 | -416 | * | * | | | | | | | | | | | | |
| 37 | 590 | -1848 | 1080 | -1680 | -1869 | -153 | -1528 | 902 | -1529 | 1445 | -1028 | -22 | -313 | -1404 | -1840 | -451 | -1448 | -1302 | 2063 | -1818 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -8953 | -9995 | -894 | -1115 | -3914 | -99 | * | * | | | | | | | | | | | | |
| 38 | -1473 | -2944 | 660 | -772 | -3266 | -2446 | 1929 | -3015 | 1777 | -635 | -2033 | 793 | -2539 | 543 | 1810 | 54 | -163 | -2566 | -3126 | -2445 | 56 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9047 | -10089 | -894 | -1115 | -3200 | -166 | * | * | | | | | | | | | | | | |

FIG. 21

| | | | | | | | | | | | | | | | | | | | | | |
|---|---|---|---|---|---|---|---|---|---|---|---|---|---|---|---|---|---|---|---|---|---|
| 39 | -1602 | -3045 | 1094 | 301 | 197 | -2580 | 1251 | -3095 | 1910 | -87 | 975 | 38 | -2673 | -785 | -1331 | 196 | 912 | -2660 | -3236 | -2561 | 57 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9230 | -10272 | -894 | -1115 | -4772 | -54 | * | * | | | | | | | | | | | | |
| 40 | -360 | -4540 | -6105 | -6279 | 3176 | -5925 | -2337 | -4407 | -18 | -3916 | -3879 | -4657 | -5814 | -4740 | -5283 | -5144 | -5247 | -4497 | 2202 | 3735 | 58 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9230 | -10272 | -894 | -1115 | -4772 | -54 | * | * | | | | | | | | | | | | |
| 41 | -2207 | 3448 | -4383 | -3804 | 2865 | -3703 | 2211 | -1531 | -3416 | -289 | -1230 | -3250 | -3744 | 415 | -3228 | -2791 | 56 | -1457 | 1995 | 950 | 59 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9230 | -10272 | -894 | -1115 | -1292 | -757 | * | * | | | | | | | | | | | | |
| 42 | -2335 | 1113 | -4673 | -4038 | -357 | 2872 | 413 | 1190 | -3635 | -2012 | -1368 | -3526 | -3932 | -3260 | -3439 | -2966 | -823 | 489 | 2156 | -2272 | 60 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9861 | -10903 | -894 | -1115 | -802 | -1230 | * | * | | | | | | | | | | | | |
| 43 | -5229 | -5553 | -6123 | -6490 | -6106 | 3663 | -6156 | -7798 | -6977 | -7616 | -7095 | -503 | -6308 | -6630 | -6847 | -5444 | -5649 | -6847 | 2842 | -5752 | 61 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10248 | -11290 | -894 | -1115 | -2023 | -408 | * | * | | | | | | | | | | | | |
| 44 | -2600 | -4083 | 3357 | -1838 | -4399 | -187 | 346 | -4154 | -488 | -1684 | -3178 | 745 | -3641 | -108 | -2336 | -92 | -85 | -3703 | -4266 | -3575 | 62 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10288 | -11330 | -894 | -1115 | -130 | -3539 | * | * | | | | | | | | | | | | |
| 45 | -7012 | -5986 | -7498 | -7818 | 1401 | -7363 | 936 | -5780 | -7378 | 2298 | -817 | -6000 | -7210 | -6118 | -6752 | -6607 | -6866 | -5998 | 4461 | 1549 | 63 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 46 | -940 | -4092 | 196 | -331 | -4412 | -3593 | -2252 | -1675 | 1546 | -4107 | -3181 | 1061 | -1010 | 2327 | 653 | -349 | -2558 | -915 | 1561 | 1599 | 64 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 47 | -3634 | -5231 | 826 | -129 | -757 | 3120 | -3144 | -5311 | -434 | -5236 | -4372 | 905 | -4479 | -2731 | -3537 | -788 | -1041 | -4841 | -5412 | -4633 | 65 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 48 | -1108 | -2725 | -5245 | -4610 | -1161 | -4452 | -3325 | 3058 | -4207 | 705 | -384 | -852 | -4500 | -3831 | -334 | -1907 | -2841 | 1462 | -3190 | -2848 | 66 |

FIG. 22

| | | | | | | | | | | | | | | | | | | | | | |
|---|---|---|---|---|---|---|---|---|---|---|---|---|---|---|---|---|---|---|---|---|---|
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 49 | 1260 | -2803 | -1772 | -3941 | -2771 | -1277 | -3144 | 2217 | -3664 | 539 | 730 | -1442 | -4369 | -3405 | -1052 | -1332 | 1925 | -2225 | -3248 | -2886 | 67 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 50 | -597 | -4092 | 1714 | 1104 | -4413 | -3593 | -2252 | -4164 | 197 | -494 | -694 | 1507 | -3686 | 1818 | -122 | 659 | -916 | -3714 | -4276 | -3593 | 68 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 51 | -886 | -4102 | -1336 | 653 | -4423 | -1236 | 1004 | -4174 | 3069 | -4117 | -3191 | 545 | -3694 | 291 | 394 | -607 | -2567 | -3724 | -4284 | -3602 | 69 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 52 | 78 | 2795 | -428 | -4242 | -2710 | -4369 | 145 | 695 | -1076 | 2295 | 273 | -3894 | -4423 | -49 | -3835 | -1877 | -2804 | -2167 | 866 | -2850 | 70 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 53 | 117 | -4092 | 2782 | 545 | -4413 | -1720 | -2252 | -1864 | -912 | -4108 | -3181 | 840 | 699 | -97 | -851 | -593 | 40 | -714 | -4275 | -3593 | 71 |
| . | -150 | -502 | 240 | 43 | -383 | 401 | 103 | -629 | 210 | -468 | -713 | 275 | 393 | 46 | 95 | 360 | 119 | -372 | -297 | -252 | |
| . | -583 | -1590 | -11527 | -327 | -2304 | -701 | -1378 | * | * | | | | | | | | | | | | |
| 54 | -2739 | -3261 | 702 | -1552 | -1049 | -1425 | -591 | -994 | -2540 | -1492 | -2430 | -1139 | -4014 | -872 | -2913 | -1575 | -171 | -1236 | -3633 | 4195 | 74 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 55 | -6061 | -5426 | -8423 | -7836 | 174 | -8240 | -6742 | 2396 | -7642 | 2680 | -2238 | -7944 | -7194 | -6330 | -7081 | -7629 | -5889 | -1773 | 897 | -5384 | 75 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 56 | 917 | -4094 | -2468 | -714 | -4414 | 570 | 830 | -4164 | 2745 | -4109 | -3183 | 74 | -3689 | 929 | -2342 | -1596 | 52 | -1108 | -4277 | -3595 | 76 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 57 | -680 | -4095 | 1980 | 794 | -4416 | 741 | -2254 | -4167 | 145 | -4111 | -3184 | 1061 | 1224 | 435 | -1051 | 378 | -386 | -3717 | -4278 | -3595 | 77 |
| . | -150 | -501 | 234 | 42 | -381 | 399 | 110 | -627 | 211 | -467 | -721 | 279 | 393 | 44 | 95 | 360 | 118 | -370 | -295 | -250 | |

FIG. 23

| | | | | | | | | | | | | | | | | | | | | | |
|---|---|---|---|---|---|---|---|---|---|---|---|---|---|---|---|---|---|---|---|---|---|
| - | -31 | -5599 | -11527 | -2807 | -223 | -701 | -1378 | * | * | | | | | | | | | | | | |
| 58 | 942 | -2775 | -1042 | -4088 | -2738 | -4341 | 560 | 891 | 225 | 2098 | 2191 | -1246 | -4397 | -3501 | -3763 | -3401 | -1516 | -2194 | 863 | -2867 | 86 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 59 | -4606 | -5401 | -3869 | -4255 | -7234 | 3748 | -5181 | -7338 | -5436 | -7311 | -6605 | -1046 | -5670 | -140 | -5877 | -4650 | -4961 | -6340 | -7108 | -6696 | 87 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 60 | -1029 | -2769 | -5299 | -1394 | 1996 | -4510 | -3389 | 2081 | -4267 | -2606 | -132 | -4156 | -4557 | -3893 | -4070 | -3598 | -472 | 2155 | -3252 | 2078 | 88 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 61 | -239 | -4233 | 1152 | -2113 | -4626 | 555 | -2487 | -4376 | -694 | -4333 | -466 | 1252 | -3879 | -2038 | -2610 | -250 | 2930 | -3919 | -4510 | -3828 | 89 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 62 | 2623 | -2941 | -4036 | -3461 | -2940 | 1140 | 1204 | -2494 | -3255 | -2818 | 176 | -3423 | -4268 | -533 | -3437 | -520 | -151 | 348 | -3379 | 69 | 90 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 63 | -4777 | -4256 | -7476 | -7167 | -4920 | -7349 | -7445 | 3081 | -7153 | 141 | -3597 | -7004 | -7060 | -7112 | -7338 | -6742 | -170 | 2423 | -6741 | -6228 | 91 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 64 | -6746 | -5975 | -6657 | -528 | -2190 | -7063 | -3585 | -5892 | -6009 | -1756 | -5291 | -5711 | -7002 | 1984 | -5787 | -6378 | -6602 | -6021 | 5623 | 2050 | 92 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 65 | -5029 | -4582 | -7496 | -6959 | 122 | -7061 | -6044 | 2298 | -6715 | 2037 | 1608 | -6732 | -6641 | -6001 | -6450 | -6294 | -217 | 1290 | -5182 | -5137 | 93 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 66 | -1269 | 1372 | -5290 | -4848 | -4047 | -4330 | -4173 | -3617 | -4592 | -1531 | 783 | 233 | 1518 | -4323 | -4625 | 2681 | 1511 | -3381 | -4485 | -4145 | 94 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 24

| | | | | | | | | | | | | | | | | | | | | | |
|---|---|---|---|---|---|---|---|---|---|---|---|---|---|---|---|---|---|---|---|---|---|
| 67 | -1240 | -4199 | -5920 | -6230 | -6753 | -4440 | -5862 | -6474 | -6122 | -6774 | -5889 | -5051 | 4130 | 509 | -5963 | -3825 | -4047 | -1240 | -6953 | -6836 | 95 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 68 | 108 | -4065 | -7124 | -6741 | 434 | -6661 | -6322 | 2424 | -6592 | -3617 | -3454 | -6403 | 2571 | -6423 | -6620 | -5945 | -4483 | 1900 | -5951 | -5492 | 96 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 69 | -1405 | -2708 | -5187 | -4553 | 2792 | -4420 | -3289 | -775 | -4156 | -639 | -1911 | 1332 | -4470 | 618 | -3968 | -303 | -28 | 526 | 1665 | 2169 | 97 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 70 | -662 | -4092 | 1024 | 2245 | -4413 | -3593 | 326 | -4164 | 1661 | -2213 | -44 | -601 | -352 | 799 | -152 | -1385 | -537 | -1818 | -4276 | -3593 | 98 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1356 | -10485 | -717 | -894 | -1115 | -701 | -1378 | * | * | | | | | | | | | | | | |
| 71 | -1559 | 1519 | 384 | -879 | -3251 | -285 | 1083 | -2981 | -803 | -2964 | -2060 | 2667 | -2633 | 2129 | -1307 | -1453 | 323 | -183 | -3163 | -2498 | 99 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -188 | -9133 | -3052 | -894 | -1115 | -4835 | -51 | * | * | | | | | | | | | | | | |
| 72 | -1792 | -1625 | -3998 | -3375 | 867 | -3348 | -2215 | 1966 | 893 | 1010 | -718 | -2943 | -3380 | 1633 | -2846 | -2432 | -1732 | 1248 | -2099 | -1765 | 100 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -91 | -8949 | -4075 | -894 | -1115 | -4936 | -48 | * | * | | | | | | | | | | | | |
| 73 | -1348 | -2799 | 452 | 558 | -238 | -2321 | 1570 | -2855 | -570 | -2811 | -1891 | 1536 | 1707 | -527 | -1076 | 949 | -90 | -2416 | -2988 | 1085 | 101 |
| - | -147 | -501 | 237 | 42 | -382 | 399 | 104 | -628 | 209 | -467 | -722 | 276 | 392 | 46 | 94 | 362 | 120 | -371 | -296 | -251 | |
| - | -4027 | -346 | -2721 | -162 | -3232 | -4977 | -47 | * | * | | | | | | | | | | | | |
| 74 | -1398 | -1247 | -3568 | -2947 | -1199 | -2933 | -1800 | 360 | -2581 | 643 | -435 | 2323 | -2982 | -2239 | -2446 | -2013 | 1170 | 862 | 3508 | -1367 | 104 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8627 | -9669 | -894 | -1115 | -1469 | -647 | * | * | | | | | | | | | | | | |
| 75 | -455 | -2991 | 765 | -1354 | -3181 | 663 | 2621 | -186 | -1258 | -2950 | 164 | 570 | -190 | -1204 | -1733 | 489 | 1132 | 402 | -3260 | -2668 | 105 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9564 | -10606 | -894 | -1115 | -2824 | -220 | * | * | | | | | | | | | | | | |
| 76 | 1379 | -3225 | -70 | -1368 | -3461 | 700 | -1655 | 437 | -421 | -1745 | -2338 | 952 | -899 | 334 | -1766 | -396 | -801 | 1437 | -3462 | -2835 | 106 |

FIG. 25

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9692 | -10734 | -894 | -1115 | -45 | -5023 | * | * | | | | | | | | | | | | |
| 77 | 448 | -3860 | -1339 | -2058 | -4084 | 78 | -2337 | -3769 | -740 | -3834 | 67 | -2348 | -3755 | 969 | -2452 | 2571 | -322 | -28 | -4106 | 1105 | 107 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 78 | -1625 | -4050 | -839 | -1940 | -4352 | 1882 | 547 | -1615 | -903 | -1959 | -3144 | -540 | 2730 | 248 | -2358 | -326 | 170 | -1532 | -4245 | -3574 | 108 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -305 | -10485 | -2397 | -894 | -1115 | -701 | -1378 | * | * | | | | | | | | | | | | |
| 79 | -1428 | -3831 | 469 | 208 | -4152 | 596 | 99 | -3903 | -325 | -1529 | 1961 | 1724 | -888 | 1738 | -2079 | 479 | -568 | -3453 | -4014 | 648 | 109 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1921 | -10182 | -444 | -894 | -1115 | -3323 | -152 | * | * | | | | | | | | | | | | |
| 80 | 372 | -2330 | -897 | -354 | -2616 | -1985 | 1916 | -2329 | 2146 | -2336 | -1448 | 798 | -2082 | -215 | -725 | 692 | -940 | 578 | -2554 | -1910 | 110 |
| - | -150 | -501 | 239 | 44 | -377 | 400 | 104 | -628 | 209 | -467 | -722 | 274 | 396 | 44 | 95 | 359 | 116 | -371 | -296 | -251 | |
| - | -2157 | -369 | -9309 | -557 | -1643 | -3400 | -144 | * | * | | | | | | | | | | | | |
| 81 | 1078 | -2294 | 1350 | -648 | 300 | -485 | -900 | -2151 | -553 | -2254 | 1556 | 1037 | 572 | -499 | -1029 | 66 | -1123 | -1846 | -2562 | 1044 | 114 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8597 | -9639 | -894 | -1115 | -2793 | -225 | * | * | | | | | | | | | | | | |
| 82 | -1461 | -2933 | 984 | -749 | -3253 | -139 | 1474 | -3003 | -675 | -2949 | -2024 | 1555 | -2523 | 717 | 848 | 1813 | -1401 | -2555 | -3117 | 586 | 115 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9004 | -10046 | -894 | -1115 | -1884 | -456 | * | * | | | | | | | | | | | | |
| 83 | 57 | -3035 | -1842 | 31 | -3246 | -482 | -1560 | -2923 | -1198 | -3004 | 861 | 669 | 892 | 1771 | -1680 | -1806 | 1403 | 888 | -3289 | 1312 | 116 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9540 | -10582 | -894 | -1115 | -40 | -5194 | * | * | | | | | | | | | | | | |
| 84 | 873 | -4137 | 291 | -1124 | -4446 | 1513 | -306 | -4191 | -1910 | -4148 | -3231 | -436 | -3744 | -845 | -2419 | 1681 | -2625 | -971 | 3835 | -3646 | 117 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 85 | -4176 | -4768 | 1829 | -3445 | -3695 | -1300 | -3742 | -4659 | -4308 | -4801 | -4205 | 894 | -5163 | -3872 | -4784 | -4205 | -1573 | -1321 | 3566 | 3879 | 118 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 26

| | | | | | | | | | | | | | | | | | | | | | |
|---|---|---|---|---|---|---|---|---|---|---|---|---|---|---|---|---|---|---|---|---|---|
| - | -1 | -10485 | -11527 | -894 | -1115 | -701 | -1378 | * | * | | | | | | | | | | | | |
| 86 | -1132 | -3799 | -861 | 118 | 612 | -712 | 4033 | -3673 | -2003 | -1593 | 1397 | 819 | -3773 | -477 | -2483 | -2604 | 327 | -3356 | 1896 | -377 | 119 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 87 | -1015 | -4079 | -928 | -1940 | -4392 | 2727 | 230 | -4135 | 1129 | -1785 | -3172 | -2248 | 340 | -1811 | 835 | -221 | -2571 | -1529 | -4268 | -3593 | 120 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 88 | -7416 | -6752 | -7795 | -8171 | -4839 | -302 | -5966 | -8217 | -8274 | -7590 | -7577 | -7492 | -7408 | -7730 | -7762 | -7573 | -7664 | -8017 | -5332 | 4874 | 121 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 89 | -4666 | -5065 | 3020 | -4360 | -296 | -5588 | 143 | -4906 | -4122 | -4709 | 233 | -4314 | -5620 | 2387 | -291 | -4603 | -4588 | -4791 | 3763 | 68 | 122 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 90 | -285 | -2705 | -5216 | -4581 | -2659 | -1500 | -3296 | 1800 | -4177 | 411 | 509 | -4068 | 1915 | -1144 | -3980 | -3509 | 1879 | 303 | 1008 | -2821 | 123 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 91 | 482 | -3709 | -2718 | 364 | -791 | -3717 | 285 | -761 | -549 | -1726 | -2840 | -2438 | -3805 | 801 | 1137 | 431 | 1253 | 665 | -3990 | 1751 | 124 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 92 | -4889 | -6628 | 3602 | -2998 | -7225 | -4711 | -4283 | -7248 | -4767 | -7097 | -6541 | 1976 | -5333 | -3990 | -5802 | 1074 | -5057 | -6580 | -7280 | -6167 | 125 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 93 | -7029 | -5996 | -7530 | -7846 | 2273 | -7404 | -3629 | -269 | -7412 | 804 | -4944 | -6040 | -7227 | -6136 | -6780 | -6653 | -6877 | -5902 | 2046 | 4054 | 126 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 94 | -2620 | 1093 | -168 | 384 | 997 | -129 | -2255 | -4144 | 1727 | -4095 | -563 | 290 | -3689 | -278 | 687 | -2503 | 688 | -1293 | -4268 | 2168 | 127 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -21 | -10485 | -6218 | -894 | -1115 | -701 | -1378 | * | * | | | | | | | | | | | | |

FIG. 27

| | | | | | | | | | | | | | | | | | | | | | |
|---|---|---|---|---|---|---|---|---|---|---|---|---|---|---|---|---|---|---|---|---|---|
| 95 | 371 | -4076 | -317 | 1265 | -4397 | -1729 | 212 | 406 | 1377 | 7 | -3165 | 586 | -3669 | 1009 | -234 | 493 | -1214 | -3698 | -4259 | -3576 | 128 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -63 | -10466 | -4571 | -894 | -1115 | -1141 | -872 | * | * | | | | | | | | | | | | |
| 96 | -843 | 191 | -1277 | -1657 | 1107 | -438 | -3165 | 2635 | -3896 | -389 | -1867 | -690 | -235 | -947 | -3795 | -3381 | -212 | 1299 | -3119 | -2770 | 129 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3167 | -10404 | -172 | -894 | -1115 | -2010 | -412 | * | * | | | | | | | | | | | | |
| 97 | -1053 | -2634 | 1898 | 158 | -2897 | -1582 | 2013 | -2699 | -340 | -2629 | -1777 | 2478 | -1882 | 1472 | -923 | -857 | -1032 | -2240 | -2803 | -2027 | 130 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -320 | -7252 | -2377 | -894 | -1115 | -5364 | -35 | * | * | | | | | | | | | | | | |
| 98 | -2259 | -2673 | -1597 | -1655 | -2974 | -2426 | -1778 | -3343 | -1247 | -3149 | -2741 | -1799 | -2844 | 4302 | -1363 | -2273 | -2358 | -3074 | -2844 | -2538 | 131 |
| - | -149 | -500 | 233 | 43 | -381 | 398 | 105 | -627 | 216 | -466 | -721 | 275 | 393 | 45 | 96 | 359 | 117 | -370 | -295 | -250 | |
| - | -2113 | -387 | -7991 | -68 | -4439 | -5394 | -35 | * | * | | | | | | | | | | | | |
| 99 | -2307 | -2447 | -3004 | -3307 | -4059 | 3719 | -3189 | -4433 | -3631 | -4384 | -3905 | -3019 | -3114 | -3435 | -3496 | -2545 | -2690 | -3694 | -3457 | -3941 | 133 |
| - | -149 | -500 | 233 | 43 | -381 | 398 | 105 | -627 | 210 | -466 | -721 | 275 | 393 | 45 | 96 | 360 | 121 | -370 | -295 | -250 | |
| - | -2113 | -387 | -7991 | -68 | -4439 | -5394 | -35 | * | * | | | | | | | | | | | | |
| 100 | -1622 | -1179 | -4160 | -3786 | -1612 | -3872 | -3506 | 2486 | -3640 | -485 | -405 | -3542 | -3714 | -3484 | -3705 | -3175 | -1613 | 2883 | -3068 | -2632 | 135 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -17 | -6949 | -7991 | -894 | -1115 | -343 | -2240 | * | * | | | | | | | | | | | | |
| 101 | -2365 | -3834 | 2901 | -520 | -4154 | -3339 | 974 | -3903 | -1579 | -3850 | -204 | 1923 | -753 | 415 | 106 | -2246 | -987 | -3455 | 1778 | 207 | 136 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10186 | -11228 | -894 | -1115 | -94 | -3985 | * | * | | | | | | | | | | | | |
| 102 | -1119 | -4113 | -534 | 989 | -4433 | 180 | -2271 | -4184 | -1854 | -4129 | -3203 | -909 | 2651 | -1812 | 111 | 685 | 1324 | -3735 | -4297 | -399 | 137 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 103 | -1031 | -4076 | -2475 | 234 | 131 | -1570 | 2594 | 278 | 1057 | -2352 | -611 | 693 | -914 | 1077 | 1767 | -2504 | -327 | -3694 | -4264 | -398 | 138 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 104 | -3766 | -3535 | -5916 | -5401 | 2942 | -840 | -3425 | -3059 | -4991 | 656 | 248 | -4706 | -5245 | -4509 | -1239 | -972 | -3702 | -2996 | 1011 | 3458 | 139 |

FIG. 28

| | | | | | | | | | | | | | | | | | | | | | |
|---|---|---|---|---|---|---|---|---|---|---|---|---|---|---|---|---|---|---|---|---|---|
| - | -143 | -501 | 232 | 42 | -382 | 399 | 105 | -627 | 212 | -467 | -721 | 277 | 393 | 44 | 95 | 358 | 116 | -370 | -295 | -245 | |
| - | -42 | -5149 | -11527 | -2670 | -247 | -701 | -1378 | * | * | | | | | | | | | | | | |
| 105 | -8252 | -7162 | -8163 | -8550 | -8738 | 3865 | -7830 | -9779 | -8750 | -9145 | -9067 | -8451 | -7614 | -8612 | -8185 | -8693 | -8516 | -9303 | -7448 | -8752 | 147 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 106 | -3611 | 276 | 1704 | -4311 | -6496 | -1350 | -4820 | -6315 | -4922 | -6428 | -5526 | 2043 | -793 | -4557 | -5305 | 512 | 2942 | -5291 | -6593 | -6141 | 148 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 107 | -503 | -4051 | 8 | 1036 | -574 | -2005 | -2265 | -1878 | 1377 | 260 | 2254 | 832 | -3697 | -1811 | 1077 | -1552 | 93 | -3663 | 737 | -3574 | 149 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 108 | 1612 | -4106 | 1904 | 1843 | -4427 | -858 | -2263 | -4178 | -659 | -4122 | -695 | -1031 | -3697 | 1321 | -2354 | -197 | -943 | -3728 | -4289 | -3606 | 150 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 109 | 11 | -4538 | 3047 | 1602 | -4847 | -3855 | -2619 | -4610 | -288 | -1877 | -3642 | -2482 | -4021 | 1329 | -2794 | -2886 | 267 | -4156 | -4718 | -4008 | 151 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 110 | -2036 | 1220 | -7421 | -6835 | 3516 | -6860 | -5376 | -2914 | -6508 | 2094 | 660 | -6481 | -6457 | -5667 | -6141 | -6041 | -5012 | -3551 | 403 | -4244 | 152 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 111 | -851 | -4088 | 921 | 828 | 349 | -3602 | -2260 | -604 | 2159 | -989 | -3179 | -2240 | -3695 | 1839 | 1456 | -2510 | -2566 | -3708 | -4273 | -3595 | 153 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 112 | 564 | -4093 | 406 | 1072 | -4414 | -3593 | 231 | -4165 | 466 | -4109 | -3182 | 1180 | -3687 | 1276 | 947 | 1015 | 790 | -3715 | -4276 | -3593 | 154 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 113 | 251 | -5382 | -8381 | -7805 | -3477 | -8030 | -6821 | -2909 | -7602 | 2757 | 3310 | -7863 | -7137 | -6322 | -7056 | -7412 | -5820 | -1221 | -5316 | -5560 | 155 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 29

| | | | | | | | | | | | | | | | | | | | | | |
|---|---|---|---|---|---|---|---|---|---|---|---|---|---|---|---|---|---|---|---|---|---|
| - | -1 | -10485 | -11527 | -894 | -1115 | -701 | -1378 | * | * | | | | | | | | | | | | |
| 114 | -305 | 1484 | -5265 | -4631 | -2702 | -4472 | -3348 | 2502 | -4229 | -612 | 1448 | -4118 | -4520 | -3853 | -1047 | -966 | -987 | 2286 | -3212 | -2869 | 156 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 115 | 884 | -4092 | 1870 | -634 | -4414 | -786 | 843 | -4164 | 304 | -4108 | -3182 | 505 | -3686 | 896 | 434 | 1104 | 225 | -1701 | -4276 | -3593 | 157 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 116 | 1572 | -4092 | -316 | 1390 | -4413 | -3593 | -2252 | -4164 | 1260 | -1864 | -3181 | -565 | -3686 | -20 | 1256 | -11 | 240 | -709 | -4275 | -3593 | 158 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 117 | 2346 | 3387 | -5358 | -4725 | 741 | -4568 | -3442 | -753 | -4323 | 731 | 1479 | -4215 | -4607 | -3938 | -4122 | -3656 | -120 | -1125 | -3290 | -2956 | 159 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 118 | -2653 | -4128 | -124 | -729 | -778 | -1262 | 4466 | -4200 | 1226 | -4143 | -3218 | 354 | -3715 | 446 | -370 | -1338 | -2593 | -3750 | -4310 | -3626 | 160 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 119 | 1456 | -4094 | 122 | 1669 | -4415 | -398 | -2253 | -4166 | 901 | -4110 | -462 | 905 | -3687 | 1166 | -743 | 607 | -2560 | -3716 | -4277 | -3594 | 161 |
| - | -149 | -500 | 235 | 43 | -381 | 398 | 105 | -626 | 210 | -466 | -721 | 275 | 396 | 45 | 96 | 359 | 117 | -369 | -295 | -250 | |
| - | -35 | -5386 | -11527 | -985 | -1015 | -701 | -1378 | * | * | | | | | | | | | | | | |
| 120 | 905 | -3975 | -3344 | -2721 | -4151 | -4168 | -455 | -3757 | 1571 | 72 | -3119 | 1224 | -4233 | -2376 | 2466 | -3147 | -3042 | -301 | -4211 | 1099 | 164 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 121 | -4722 | -6205 | 1052 | -3086 | -7197 | 3376 | -4350 | -7191 | -4837 | -7077 | -6482 | 1612 | -5315 | -4063 | -5831 | -2007 | -4937 | -6437 | -7269 | -6213 | 165 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 122 | -4922 | -4389 | -7600 | -7267 | -4589 | -7480 | -7387 | 3162 | -7240 | -1180 | 3054 | -7139 | -7096 | -6988 | -7325 | -6879 | -4901 | 1873 | -6437 | -6132 | 166 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 30

| | | | | | | | | | | | | | | | | | | | | | |
|---|---|---|---|---|---|---|---|---|---|---|---|---|---|---|---|---|---|---|---|---|---|
| 123 | 362 | -4119 | -1060 | -1952 | -4444 | -3625 | -196 | -4190 | 3130 | -1561 | -3209 | -437 | -3717 | 274 | 1372 | -1594 | -2591 | -3743 | -4297 | -879 | 167 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 124 | -2157 | 1226 | -6830 | -6365 | -616 | -6361 | -5646 | 2243 | -6139 | 479 | -3205 | -6010 | -6258 | -5902 | -6093 | -5571 | -1543 | 2891 | -5359 | -4952 | 168 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 125 | -4973 | -4556 | -7390 | -6825 | -605 | -6889 | -5739 | 2833 | -6544 | 187 | 2572 | -6548 | -6505 | -5815 | -6253 | -6091 | -4885 | 927 | -4941 | 2516 | 169 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 126 | 790 | -2711 | -5231 | -4595 | 719 | -745 | -3305 | -173 | -4190 | 1545 | 2374 | -4079 | -4482 | -3812 | -3990 | -3518 | -868 | 1788 | -3169 | -178 | 170 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 127 | -8466 | -7310 | 4232 | -7396 | -8700 | -7098 | -7495 | -9750 | -8307 | -9096 | -9042 | -7636 | -7557 | -7951 | -8076 | -8688 | -8607 | -9400 | -7444 | -8581 | 171 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 128 | 1130 | -2705 | -5224 | -4588 | 2004 | -410 | -3297 | 574 | -4183 | 665 | -213 | -4072 | -4476 | -3806 | -3983 | -1769 | -1213 | 2047 | -3163 | -324 | 172 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 129 | -202 | -4206 | -7392 | -7072 | -4907 | -7157 | -7171 | -452 | -7025 | -944 | -3609 | -6853 | -6944 | -6970 | -7177 | -6521 | -1808 | 3649 | -6601 | -6084 | 173 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 130 | -1570 | -2728 | -5251 | -4616 | 2039 | -4455 | -3328 | 1709 | -4212 | -885 | 909 | -4101 | 2203 | -3835 | -4013 | -3541 | -400 | 1465 | -3192 | 427 | 174 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 131 | -8077 | -7138 | -7637 | -8023 | -8516 | -7075 | -7642 | -9658 | -8487 | -9057 | -8951 | 4459 | -7552 | -8282 | -8070 | -8424 | -8336 | -9174 | -7395 | -8424 | 175 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 132 | -8777 | -7286 | -8125 | -8503 | -8089 | -7246 | 5476 | -9783 | -8678 | -9076 | -9078 | -8509 | -7683 | -8576 | -8145 | -9272 | -8931 | -9493 | -7256 | -7887 | 176 |

FIG. 31

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 133 | -2889 | 2001 | -4429 | -3820 | -2867 | -4315 | -3121 | -831 | 117 | -2749 | 3125 | -3660 | -4375 | -3300 | 55 | 996 | 2538 | -2318 | -3326 | -30 | 177 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -82 | -10485 | -4194 | -894 | -1115 | -701 | -1378 | * | * | | | | | | | | | | | | |
| 134 | 1475 | -4014 | -6380 | -6508 | -6579 | 1671 | -5822 | -6377 | -6284 | -6626 | 96 | 230 | -5088 | -5833 | -6089 | 2399 | 828 | -5159 | -6797 | -6703 | 178 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10404 | -11446 | -894 | -1115 | -243 | -2687 | * | * | | | | | | | | | | | | |
| 135 | 293 | 1078 | 1810 | -245 | -4380 | 493 | -2259 | -4123 | -1843 | -4081 | -3161 | -505 | 954 | -1802 | -643 | 621 | 742 | -1825 | 140 | 1492 | 179 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 136 | 1323 | -4092 | 1113 | 1711 | 450 | 746 | -2252 | -4164 | -625 | -4108 | -3181 | 366 | -3686 | -7 | -903 | 74 | -1029 | -1325 | -4275 | -3593 | 180 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 137 | -1452 | -108 | 1337 | -1115 | 89 | 609 | 3017 | -4133 | -691 | -2342 | -3166 | 437 | -3690 | 385 | -2346 | 1029 | -91 | -1321 | -4263 | 560 | 181 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -82 | -10485 | -4194 | -894 | -1115 | -701 | -1378 | * | * | | | | | | | | | | | | |
| 138 | 1341 | -3956 | 208 | 1481 | -1210 | 685 | -2203 | -907 | -923 | -1650 | -3053 | -846 | 1318 | -1753 | -1129 | -287 | -699 | -799 | 949 | -3493 | 182 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -167 | -10404 | -3204 | -894 | -1115 | -2010 | -412 | * | * | | | | | | | | | | | | |
| 139 | 459 | -3868 | -497 | -1713 | -4183 | 180 | -2044 | -3930 | 216 | -3882 | -2959 | 356 | -480 | -1587 | -864 | -328 | 887 | -3487 | 4543 | 1218 | 183 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1744 | -10239 | -513 | -894 | -1115 | -3097 | -179 | * | * | | | | | | | | | | | | |
| 140 | 50 | -2754 | 884 | 2171 | -3064 | 1269 | -892 | -2816 | -510 | -2766 | -1855 | -805 | -2307 | -443 | 864 | -1150 | -1225 | -2372 | -2942 | 750 | 184 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -475 | -8501 | -1848 | -894 | -1115 | -5116 | -42 | * | * | | | | | | | | | | | | |
| 141 | 1353 | -2588 | 1260 | 1130 | -2871 | -1952 | -748 | -2615 | -426 | -2593 | 2728 | 1416 | -2136 | -318 | -960 | -1014 | -1103 | -2193 | -2795 | -2097 | 185 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 32

| | | | | | | | | | | | | | | | | | | | | |
|---|---|---|---|---|---|---|---|---|---|---|---|---|---|---|---|---|---|---|---|---|
| - | -8 | -8034 | -9077 | -894 | -1115 | -5240 | -39 | * | * | | | | | | | | | | | |
| 142 | -863 | -2043 | 1060 | -277 | -2257 | 309 | -555 | 640 | 1106 | -2011 | -1164 | -564 | -1971 | 1549 | -670 | -805 | -803 | 1220 | -2296 | -1686 | 186 |
| - | -149 | -502 | 232 | 43 | -379 | 399 | 103 | -629 | 210 | -462 | -723 | 273 | 391 | 46 | 97 | 359 | 117 | -372 | -297 | -231 | |
| - | -3199 | -370 | -3094 | -1784 | -495 | -825 | -1200 | * | * | | | | | | | | | | | | |
| 143 | 491 | -2153 | 235 | -3609 | 3508 | -3761 | -2613 | -133 | -3285 | -666 | -1354 | -185 | -3816 | -2979 | -3220 | -417 | -141 | -259 | -2606 | -2253 | 195 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9798 | -10840 | -894 | -1115 | -1601 | -577 | * | * | | | | | | | | | | | | |
| 144 | -258 | -3708 | 906 | -613 | -448 | -3216 | -1875 | 93 | 973 | -3723 | -2798 | 436 | -770 | 2002 | -91 | 459 | -72 | 225 | -3893 | 21 | 196 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10042 | -11084 | -894 | -1115 | -2093 | -385 | * | * | | | | | | | | | | | | |
| 145 | -375 | -3789 | 737 | 1980 | -4108 | -251 | -1951 | -293 | 784 | -3804 | -2878 | -1928 | 1280 | -1492 | 1139 | -219 | -2257 | -688 | -3973 | -3291 | 197 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10133 | -11175 | -894 | -1115 | -1106 | -901 | * | * | | | | | | | | | | | | |
| 146 | 480 | -2632 | 527 | -3784 | -431 | 222 | 279 | 180 | -3505 | -2487 | -1830 | -3562 | -4203 | -3244 | -3529 | 1858 | 622 | 1238 | -3077 | 885 | 198 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10298 | -11340 | -894 | -1115 | -135 | -3484 | * | * | | | | | | | | | | | | |
| 147 | 66 | -3328 | -871 | -911 | 814 | 289 | -299 | -672 | -1401 | -140 | -2491 | 1631 | -3976 | -2359 | 959 | -2853 | 603 | 454 | 215 | 1373 | 199 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 148 | 735 | -4092 | -1124 | 486 | -4413 | 652 | -236 | -4164 | 1639 | -1722 | 628 | -242 | -297 | 265 | -727 | 1141 | -898 | -1243 | -4275 | -3593 | 200 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -201 | -10485 | -2953 | -894 | -1115 | -701 | -1378 | * | * | | | | | | | | | | | | |
| 149 | -456 | -3914 | 1012 | 1114 | -706 | -460 | -49 | -3982 | 857 | -788 | -3004 | 1137 | -711 | -1622 | -2170 | 1401 | -2387 | -486 | -4099 | -6 | 201 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10286 | -11328 | -894 | -1115 | -307 | -2384 | * | * | | | | | | | | | | | | |
| 150 | 606 | -4057 | 257 | -1902 | -429 | 1035 | -2233 | -1749 | 1549 | -1180 | -3148 | 924 | -639 | -614 | -1007 | 699 | -297 | -3676 | -4244 | 763 | 202 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10459 | -11501 | -894 | -1115 | -1265 | -776 | * | * | | | | | | | | | | | | |

FIG. 33

| 151 | -673 | -34 | 1484 | 597 | -1161 | 1273 | -2230 | -4136 | 447 | -1755 | -3156 | -5 | -3665 | -1771 | 1407 | -320 | 48 | -3688 | -4251 | 1094 | 203 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -446 | -10459 | -1915 | -894 | -1115 | -1265 | -776 | * | * | | | | | | | | | | | | |
| 152 | 199 | -3692 | 162 | -47 | -4013 | -384 | -1851 | -3764 | -225 | -1337 | -2781 | 2037 | 1163 | 852 | -174 | 975 | 231 | -3314 | -3875 | -3192 | 204 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -105 | -10015 | -3849 | -894 | -1115 | -3799 | -108 | * | * | | | | | | | | | | | | |
| 153 | -2161 | -3339 | -2140 | -79 | 588 | 382 | -1859 | -3229 | 631 | -369 | -110 | -1876 | 1995 | 979 | -841 | 336 | 247 | -452 | -3592 | 151 | 205 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1289 | -9912 | -762 | -894 | -1115 | -4011 | -92 | * | * | | | | | | | | | | | | |
| 154 | 356 | -1278 | -3028 | 1286 | 1786 | -2793 | -1624 | 727 | -2150 | -1132 | -476 | -2208 | -2850 | -1890 | 505 | -1846 | -1269 | 1038 | -1721 | 1996 | 206 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -135 | -8629 | -3521 | -894 | -1115 | -5073 | -44 | * | * | | | | | | | | | | | | |
| 155 | 414 | -1974 | 2293 | -781 | 775 | -2242 | -940 | -179 | -674 | -1901 | -1123 | 861 | -2327 | -605 | 819 | -1181 | 70 | -6 | -2296 | -1766 | 207 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8499 | -9542 | -894 | -1115 | -550 | -1657 | * | * | | | | | | | | | | | | |
| 156 | -2293 | -3722 | -466 | 40 | -4025 | -3274 | -1934 | -10 | 877 | -1250 | -2816 | 1348 | -3366 | 104 | -2026 | 135 | 63 | -3334 | 1226 | 3252 | 208 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10099 | -11141 | -894 | -1115 | -225 | -2793 | * | * | | | | | | | | | | | | |
| 157 | 71 | -4062 | 527 | -350 | -4383 | 1922 | -2221 | -4134 | 492 | -4078 | -3151 | -972 | 457 | -11 | 1582 | 374 | -343 | -3684 | -4245 | -3562 | 209 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10448 | -11490 | -894 | -1115 | -375 | -2128 | * | * | | | | | | | | | | | | |
| 158 | -360 | -4089 | 2756 | -254 | -716 | -1508 | -2253 | -244 | 546 | -4104 | -3178 | 894 | -3687 | 1057 | -2341 | -152 | -92 | -1229 | -4273 | -3591 | 210 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -71 | -10485 | -4400 | -894 | -1115 | -701 | -1378 | * | * | | | | | | | | | | | | |
| 159 | -2856 | 579 | -1074 | -4338 | 1305 | -253 | -623 | 496 | -404 | -2566 | -1920 | -3930 | -4423 | -3647 | -3866 | -3446 | -1205 | -2136 | 3651 | 3644 | 211 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -40 | -10415 | -5247 | -894 | -1115 | -1890 | -454 | * | * | | | | | | | | | | | | |
| 160 | -540 | 1605 | -1061 | -671 | 939 | -3507 | 288 | -4021 | -85 | -3982 | 48 | 107 | -940 | 1070 | -131 | -716 | 374 | -1763 | 392 | 3076 | 212 |

FIG. 34

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10377 | -11419 | -894 | -1115 | -2264 | -337 | * | * | | | | | | | | | | | | |
| 161 | -1573 | 581 | 693 | -3797 | 960 | -1395 | 1129 | 2092 | -3527 | -400 | -1911 | 610 | -839 | -716 | -3570 | 467 | -877 | -22 | -3157 | 799 | 213 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2181 | -10377 | -361 | -894 | -1115 | -2264 | -337 | * | * | | | | | | | | | | | | |
| 162 | 591 | -2360 | -791 | 1402 | 867 | 352 | -568 | -2402 | 1092 | -2368 | -1454 | -551 | 505 | -114 | 1041 | -819 | -870 | -1974 | -2552 | -1882 | 214 |
| - | -144 | -500 | 232 | 44 | -381 | 399 | 105 | -627 | 210 | -467 | -721 | 275 | 393 | 48 | 95 | 358 | 117 | -370 | -295 | -250 | |
| - | -3368 | -539 | -2219 | -33 | -5471 | -1006 | -994 | * | * | | | | | | | | | | | | |
| 163 | -3247 | -3172 | -5235 | -4382 | -2478 | -573 | -3019 | -722 | -2773 | -91 | -2102 | -3944 | -4583 | -3265 | 811 | -3721 | -3190 | -2563 | 5731 | -2477 | 216 |
| - | -150 | -501 | 234 | 42 | -375 | 397 | 110 | -628 | 209 | -467 | -722 | 274 | 392 | 44 | 102 | 358 | 124 | -371 | -296 | -246 | |
| - | -397 | -2618 | -3688 | -1648 | -554 | -2653 | -250 | * | * | | | | | | | | | | | | |
| 164 | -660 | -3339 | -426 | -1266 | 2742 | 387 | 1304 | -3361 | 932 | -1045 | -2437 | -1571 | -720 | -1136 | 1608 | -579 | -1878 | -2946 | -3540 | -2876 | 221 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -288 | -9660 | -2475 | -894 | -1115 | -1807 | -485 | * | * | | | | | | | | | | | | |
| 165 | -2004 | -3480 | 1563 | 403 | -76 | -2959 | 1157 | -3551 | 141 | -3496 | -2571 | -230 | 2752 | 890 | -1730 | -1881 | 209 | -3102 | -3663 | -2978 | 222 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9688 | -10730 | -894 | -1115 | -3554 | -128 | * | * | | | | | | | | | | | | |
| 166 | -569 | -3357 | -1920 | -293 | -3638 | 2536 | -1680 | 736 | -200 | -3361 | -2471 | -1673 | 1374 | -1239 | -101 | -749 | -197 | -2961 | -3580 | -2933 | 223 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -606 | -9729 | -1549 | -894 | -1115 | -4297 | -75 | * | * | | | | | | | | | | | | |
| 167 | -1580 | -2399 | 277 | -1234 | -82 | -690 | -1385 | -367 | 1980 | -2323 | -1548 | -1474 | -2771 | -1054 | 1463 | 326 | -1519 | 559 | 2038 | 396 | 224 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -426 | -9127 | -1978 | -894 | -1115 | -4838 | -51 | * | * | | | | | | | | | | | | |
| 168 | -1289 | -1986 | 496 | -1044 | -2072 | 665 | 2322 | 17 | 295 | 441 | -1144 | -1261 | -2512 | -848 | 266 | -18 | -1228 | -39 | 1726 | 583 | 225 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -285 | -8707 | -2500 | -894 | -1115 | -5043 | -44 | * | * | | | | | | | | | | | | |
| 169 | -1243 | -2465 | 528 | -585 | -2734 | 991 | -943 | -2438 | -611 | -2497 | -1644 | 1424 | -2322 | -531 | -1111 | 1631 | -1202 | -44 | -2759 | 1930 | 226 |
| - | -149 | -500 | 233 | 43 | -376 | 400 | 105 | -626 | 210 | -466 | -721 | 275 | 394 | 45 | 96 | 359 | 117 | -369 | -295 | -250 | |

FIG. 35

| | | | | | | | | | | | | | | | | | | | | | |
|---|---|---|---|---|---|---|---|---|---|---|---|---|---|---|---|---|---|---|---|---|---|
| - | -554 | -2243 | -3213 | -87 | -4100 | -5139 | -42 | * | * | | | | | | | | | | | | |
| 170 | -1042 | -2476 | 1476 | 677 | 476 | -1980 | -672 | -2514 | -280 | -2483 | -1575 | 2156 | 304 | -223 | -792 | 578 | -984 | -2086 | -2670 | 878 | 228 |
| - | -147 | -501 | 234 | 47 | -377 | 399 | 105 | -627 | 210 | -467 | -721 | 276 | 393 | 44 | 95 | 358 | 116 | -370 | -295 | -250 | |
| - | -1964 | -430 | -9308 | -29 | -5634 | -2593 | -262 | * | * | | | | | | | | | | | | |
| 171 | -1350 | -2795 | -1208 | 579 | -3104 | -2328 | 1428 | 708 | 253 | -2806 | -1887 | 385 | 1812 | 1242 | -1078 | -146 | 735 | -2411 | -2985 | 934 | 230 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -163 | -8878 | -3259 | -894 | -1115 | -1580 | -587 | * | * | | | | | | | | | | | | |
| 172 | 545 | -3282 | -343 | 277 | -3601 | 2235 | -1448 | -342 | -123 | -1030 | -2372 | 209 | -2882 | 1554 | 84 | -1696 | -1754 | -2903 | -3467 | -2785 | 231 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9510 | -10552 | -894 | -1115 | -729 | -1333 | * | * | | | | | | | | | | | | |
| 173 | 274 | -3822 | 826 | -190 | -796 | 1173 | -1982 | -3893 | 86 | -3838 | -2911 | 2270 | -1235 | -364 | -2070 | -54 | 776 | -604 | -4005 | -3323 | 232 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10171 | -11213 | -894 | -1115 | -804 | -1227 | * | * | | | | | | | | | | | | |
| 174 | -2513 | 1292 | 212 | -964 | 108 | 58 | -204 | -3970 | -813 | 425 | -3029 | 68 | 1475 | -215 | 510 | -1474 | 182 | -1248 | -4130 | 2118 | 233 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10357 | -11399 | -894 | -1115 | -543 | -1673 | * | * | | | | | | | | | | | | |
| 175 | -416 | -4012 | 932 | 231 | 959 | -3576 | 662 | 72 | -267 | -909 | -440 | -720 | -3669 | 396 | -221 | 602 | 685 | -1669 | -4209 | 1883 | 234 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10450 | -11492 | -894 | -1115 | -382 | -2104 | * | * | | | | | | | | | | | | |
| 176 | -1215 | -4092 | 757 | -28 | -512 | -1236 | 1865 | -4163 | -668 | -4107 | -3181 | 1312 | 1610 | 717 | -2340 | 1339 | -277 | -721 | 297 | -3592 | 235 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 177 | 87 | -451 | 1936 | -199 | -4411 | -955 | -2252 | -1208 | 293 | -2357 | -3180 | -74 | 2452 | -319 | -161 | -313 | -2558 | -3713 | 845 | -3592 | 236 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -72 | -10485 | -4386 | -894 | -1115 | -701 | -1378 | * | * | | | | | | | | | | | | |
| 178 | -145 | 1548 | -3360 | -2796 | 1809 | -439 | -2689 | -2692 | -218 | -154 | -2265 | 1208 | -1550 | -985 | -2982 | 856 | 1668 | -2547 | 481 | -4 | 237 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10415 | -11457 | -894 | -1115 | -1898 | -451 | * | * | | | | | | | | | | | | |

FIG. 36

| | | | | | | | | | | | | | | | | | | | | | |
|---|---|---|---|---|---|---|---|---|---|---|---|---|---|---|---|---|---|---|---|---|---|
| 179 | -122 | 1368 | 1509 | -1860 | -4342 | 96 | 52 | -265 | -105 | -4039 | -3114 | 2707 | 94 | -696 | -349 | -2440 | -261 | -3645 | -4209 | -203 | 238 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -42 | -10415 | -5163 | -894 | -1115 | -1898 | -451 | * | * | | | | | | | | | | | | |
| 180 | -2642 | -3153 | -1026 | -1101 | 1324 | -1900 | 32 | -1152 | 677 | -745 | 784 | -410 | -3922 | -2357 | -2825 | -687 | -2582 | -2623 | 4896 | 1322 | 239 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10374 | -11416 | -894 | -1115 | -2289 | -330 | * | * | | | | | | | | | | | | |
| 181 | -2526 | 290 | 89 | 488 | -4278 | 1000 | 1233 | 922 | 665 | -1018 | -3062 | 1359 | -3597 | -1708 | 776 | -30 | -2465 | -805 | -4160 | 232 | 240 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -333 | -10374 | -2283 | -894 | -1115 | -2289 | -330 | * | * | | | | | | | | | | | | |
| 182 | -486 | -3710 | 307 | -1543 | 1206 | 240 | 1404 | -3778 | -220 | -3725 | -2800 | -183 | 954 | -233 | -475 | 1714 | -951 | -3331 | 1938 | -108 | 241 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1263 | -10043 | -780 | -894 | -1115 | -3733 | -113 | * | * | | | | | | | | | | | | |
| 183 | -1728 | -2015 | -2481 | -1929 | 867 | -374 | 3226 | -1618 | 374 | -113 | -1203 | 1516 | -3040 | -1614 | -2041 | -1971 | -1666 | -1490 | 2626 | 1901 | 242 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1036 | -8785 | -971 | -894 | -1115 | -5012 | -45 | * | * | | | | | | | | | | | | |
| 184 | -1792 | 2872 | -2132 | -1434 | -2813 | -2585 | 3935 | -2650 | 2194 | -2624 | -1910 | -1481 | -2710 | -700 | -125 | -1793 | -1706 | -2378 | -2606 | -2177 | 243 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -10 | -7758 | -8800 | -894 | -1115 | -5292 | -37 | * | * | | | | | | | | | | | | |
| 185 | -1177 | 2374 | -3256 | -2703 | 3010 | -2639 | 2355 | -451 | -2327 | -789 | -222 | -2183 | -2704 | -1948 | -2179 | -1740 | -1131 | 1288 | -914 | -197 | 244 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -10 | -7758 | -8800 | -894 | -1115 | -3526 | -131 | * | * | | | | | | | | | | | | |
| 186 | -1135 | -2630 | 1948 | -304 | -2942 | -1997 | 1333 | -2701 | 768 | -2643 | -1732 | 1169 | 818 | -289 | -889 | 1444 | -1083 | -2249 | -2813 | -2111 | 245 |
| - | -150 | -501 | 232 | 43 | -379 | 402 | 105 | -627 | 210 | -467 | -711 | 274 | 393 | 44 | 95 | 360 | 118 | -370 | -295 | -250 | |
| - | -3365 | -343 | -3129 | -29 | -5656 | -4371 | -71 | * | * | | | | | | | | | | | | |
| 187 | 71 | -903 | -3098 | -2485 | -875 | 30 | -1413 | 2394 | -2140 | -763 | -115 | -2097 | 426 | -1816 | -2039 | -1607 | 316 | 695 | 2758 | -1021 | 247 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -8 | -8161 | -9204 | -894 | -1115 | -774 | -1269 | * | * | | | | | | | | | | | | |
| 188 | -1031 | 2075 | 760 | 69 | 17 | -3494 | 1783 | 405 | -184 | 366 | -1824 | -270 | -3569 | -2080 | -2529 | -255 | -721 | 296 | -3039 | 1888 | 248 |

FIG. 37

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9900 | -10942 | -894 | -1115 | -1667 | -545 | * | * | | | | | | | | | | | | |
| 189 | -2286 | 1049 | -894 | -184 | 2378 | 629 | 514 | -3744 | -593 | -1488 | -2803 | 1385 | -3360 | -360 | 377 | -1247 | 34 | -1479 | 2959 | -3234 | 249 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10090 | -11132 | -894 | -1115 | -2048 | -399 | * | * | | | | | | | | | | | | |
| 190 | -1217 | 811 | 2503 | -2484 | -2988 | 1605 | -2436 | 221 | -2347 | -2837 | -106 | -2639 | -3773 | -2242 | 775 | 407 | -339 | -2411 | 1221 | -2875 | 250 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10171 | -11214 | -894 | -1115 | -645 | -1472 | * | * | | | | | | | | | | | | |
| 191 | -2536 | -3936 | 188 | 534 | -4226 | 2096 | -119 | 1393 | -938 | -1731 | -3033 | 462 | -896 | 1150 | -2278 | -2430 | -2475 | -1263 | 881 | 426 | 251 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10381 | -11423 | -894 | -1115 | -558 | -1640 | * | * | | | | | | | | | | | | |
| 192 | -675 | -4067 | -740 | -205 | -4387 | -679 | -2227 | -4138 | -571 | -4083 | -3156 | 998 | 988 | -447 | -2315 | 1892 | 1918 | -1321 | -4250 | -413 | 252 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10456 | -11498 | -894 | -1115 | -414 | -2003 | * | * | | | | | | | | | | | | |
| 193 | 947 | -4090 | 1608 | -1919 | -4410 | -1328 | -2252 | -4160 | -472 | -2033 | 1183 | 1953 | -126 | 1413 | 877 | -571 | -1387 | -1544 | -4274 | -3592 | 253 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 194 | -2997 | -3142 | -128 | -3498 | 1171 | -1186 | -3014 | -2699 | -1015 | -2999 | -2334 | -3482 | -116 | -3116 | -337 | -3351 | -2936 | -285 | 4853 | 2849 | 254 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 195 | -2619 | 1393 | -46 | 1043 | -654 | -353 | 946 | -633 | -686 | -1611 | -3178 | 1221 | -3687 | 419 | -500 | 1339 | 1105 | -3710 | -4273 | -674 | 255 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -61 | -10485 | -4628 | -894 | -1115 | -701 | -1378 | * | * | | | | | | | | | | | | |
| 196 | -2602 | -3745 | 2499 | -2049 | -644 | -3634 | -2309 | -3617 | -204 | -2136 | -2868 | 1352 | -3723 | -1902 | 84 | -179 | 22 | -1164 | 2619 | 2144 | 256 |
| - | -149 | -504 | 231 | 40 | -371 | 404 | 105 | -613 | 215 | -470 | -725 | 273 | 392 | 43 | 102 | 355 | 115 | -373 | -299 | -247 | |
| - | -2772 | -2761 | -502 | -2375 | -309 | -1765 | -503 | * | * | | | | | | | | | | | | |
| 197 | -1540 | -2503 | 1918 | -1033 | -2697 | 1705 | -1283 | -2387 | -937 | -2524 | -1733 | -1285 | -2656 | -925 | 1509 | -1533 | -1505 | 251 | 3157 | -2255 | 269 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 38

| | | | | | | | | | | | | | | | | | | | | | |
|---|---|---|---|---|---|---|---|---|---|---|---|---|---|---|---|---|---|---|---|---|---|
| - | -5 | -8661 | -9703 | -894 | -1115 | -77 | -4268 | * | * | | | | | | | | | | | | |
| 198 | 23 | 1340 | 2073 | -120 | -843 | -3569 | 888 | -636 | -151 | -1214 | -3123 | 1018 | -3662 | -1774 | 392 | 28 | 501 | -3644 | -4222 | 901 | 270 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10448 | -11490 | -894 | -1115 | -375 | -2128 | * | * | | | | | | | | | | | | |
| 199 | -461 | -290 | 619 | 1991 | 117 | 681 | -2279 | -4015 | -1876 | -4007 | -433 | 551 | -352 | -289 | -2376 | -1119 | 342 | -1236 | 2947 | -768 | 271 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 200 | -715 | -4068 | 669 | 1304 | 678 | -3599 | 297 | -1256 | 241 | -1157 | -458 | 1822 | -3692 | 787 | -979 | -1397 | 537 | -1719 | 1920 | -456 | 272 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 201 | 255 | -3362 | -3081 | -2524 | -3437 | 1545 | -2591 | -3036 | -2404 | -2096 | -2524 | -1211 | -915 | -494 | 1309 | 276 | 1032 | 1460 | 1107 | -294 | 273 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -372 | -10485 | -2142 | -894 | -1115 | -701 | -1378 | * | * | | | | | | | | | | | | |
| 202 | -1167 | -3767 | 1430 | -92 | -4085 | 1090 | -1937 | 744 | -370 | -1505 | -2857 | -799 | -3371 | 2171 | -20 | -727 | -2242 | -3387 | 2596 | -82 | 274 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -296 | -10115 | -2438 | -894 | -1115 | -3540 | -130 | * | * | | | | | | | | | | | | |
| 203 | -923 | -3533 | 351 | 1521 | -174 | -647 | 604 | -3605 | -128 | -3549 | -2622 | 1763 | -3126 | 1841 | -106 | -427 | 903 | -3155 | -3716 | -3033 | 275 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -756 | -9821 | -1297 | -894 | -1115 | -2698 | -241 | * | * | | | | | | | | | | | | |
| 204 | -1724 | -2850 | 301 | 742 | 1449 | -339 | -1422 | -2710 | -1096 | -624 | -1979 | 399 | -2828 | -1027 | -1580 | -103 | -1666 | -2402 | -3095 | 3340 | 276 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9215 | -10257 | -894 | -1115 | -2964 | -198 | * | * | | | | | | | | | | | | |
| 205 | -468 | 1610 | -19 | -4425 | 2001 | -4615 | -2413 | -2723 | -4132 | -2869 | -2368 | 895 | -4637 | -3667 | -4029 | -3714 | -3264 | -2664 | 1981 | 3892 | 277 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -190 | -9401 | -3038 | -894 | -1115 | -2877 | -211 | * | * | | | | | | | | | | | | |
| 206 | -2272 | -2368 | -3736 | -3458 | -2327 | 1779 | -2737 | -2113 | -3311 | 2182 | -1785 | 133 | -3786 | -3050 | -3320 | -2695 | 807 | -1983 | -2837 | 1349 | 278 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -181 | -9392 | -3102 | -894 | -1115 | -3606 | -124 | * | * | | | | | | | | | | | | |

FIG. 39

| | | | | | | | | | | | | | | | | | | | | | |
|---|---|---|---|---|---|---|---|---|---|---|---|---|---|---|---|---|---|---|---|---|---|
| 207 | -379 | -3074 | 896 | -979 | -3371 | 379 | 3695 | -3105 | -894 | -3080 | -2170 | 989 | -2735 | -852 | 307 | -1551 | 142 | -2684 | 1764 | 545 | 279 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -3 | -9296 | -10338 | -894 | -1115 | -653 | -1458 | * | * | | | | | | | | | | | | |
| 208 | -98 | 2770 | 198 | -891 | -987 | -15 | 429 | -3536 | -280 | 508 | 404 | -2045 | -758 | 1464 | -285 | -2285 | 18 | -1520 | -3845 | 1525 | 280 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10156 | -11198 | -894 | -1115 | -691 | -1394 | * | * | | | | | | | | | | | | |
| 209 | -494 | -3983 | 1162 | 689 | 2729 | 627 | -2163 | -4043 | -1747 | -3997 | -3075 | 1162 | -3596 | -1705 | -60 | 57 | -512 | -1245 | -4172 | -3493 | 281 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10369 | -11411 | -894 | -1115 | -655 | -1454 | * | * | | | | | | | | | | | | |
| 210 | -190 | -222 | 222 | -1870 | 962 | -1463 | -307 | -641 | -1194 | 1539 | 311 | -3876 | -4392 | -1052 | -3814 | -103 | -586 | 456 | 1616 | 1529 | 282 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10445 | -11487 | -894 | -1115 | -1507 | -626 | * | * | | | | | | | | | | | | |
| 211 | 643 | -3274 | 580 | -1132 | 981 | -423 | -2591 | -1324 | 992 | -154 | -2439 | -659 | -659 | -2344 | -2823 | -138 | -2632 | 1464 | 387 | 933 | 283 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10445 | -11487 | -894 | -1115 | -1507 | -626 | * | * | | | | | | | | | | | | |
| 212 | -19 | -4057 | 510 | 431 | -699 | 1974 | -2216 | -4129 | 639 | -4073 | 757 | -564 | -3651 | 16 | 176 | 1016 | -699 | -3679 | -4240 | -3558 | 284 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10445 | -11487 | -894 | -1115 | -1507 | -626 | * | * | | | | | | | | | | | | |
| 213 | -355 | -3235 | -5099 | -1194 | -2927 | -4831 | -3651 | -2497 | -4185 | 2474 | 2254 | -4298 | -4853 | 2186 | -4129 | -3927 | -3287 | -2567 | -3603 | 423 | 285 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10445 | -11487 | -894 | -1115 | -359 | -2184 | * | * | | | | | | | | | | | | |
| 214 | 1739 | -3082 | -182 | -3038 | -3102 | -1439 | -2838 | -922 | -2878 | -1755 | -2270 | -3124 | 3169 | -2744 | -1266 | -450 | -2728 | -1518 | -3492 | -302 | 286 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 215 | -4651 | 464 | 3855 | -3094 | -6927 | -4683 | -4206 | -6772 | 710 | -6721 | -6082 | 256 | -5270 | -3898 | -4984 | -4424 | -4816 | -1142 | -6886 | -5983 | 287 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 216 | -5461 | -4986 | -7698 | -7163 | 1022 | -7248 | -5463 | 1643 | -6862 | 2782 | -2327 | -6796 | -6720 | -5898 | -6445 | -6466 | -5335 | -654 | 967 | -980 | 288 |

FIG. 40

| | | | | | | | | | | | | | | | | | | | | |
|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 217 | -1455 | -4071 | 2159 | -1938 | -4380 | -1778 | -2266 | -1255 | 495 | -4082 | -440 | 3227 | -3699 | -1810 | -517 | -651 | -2568 | -3687 | 797 | -3587 | 289 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 218 | -2908 | -2760 | -5076 | -4455 | -19 | -4433 | 2308 | -2256 | -4087 | -71 | -193 | -4017 | -955 | 885 | -3946 | -1878 | 2462 | -2176 | 3158 | 2080 | 290 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 219 | -858 | -4092 | 844 | 2089 | -4413 | 396 | -2251 | -1840 | -158 | -116 | -3181 | 619 | -3686 | 723 | 545 | -490 | -536 | -3714 | -4275 | -264 | 291 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -86 | -10485 | -4122 | -894 | -1115 | -701 | -1378 | * | * | | | | | | | | | | | | |
| 220 | -2590 | 432 | -492 | -968 | -4379 | -3554 | 1588 | -4127 | -279 | -4072 | 54 | 3577 | -3651 | -1757 | -653 | 839 | -2529 | -3680 | -4239 | -3559 | 292 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10400 | -11442 | -894 | -1115 | -235 | -2731 | * | * | | | | | | | | | | | | |
| 221 | -1507 | -4130 | 30 | 874 | -4450 | 300 | -2284 | -4201 | -639 | -4146 | -3220 | 971 | 2711 | -1826 | -2379 | -300 | 1292 | -3751 | 880 | -3629 | 293 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 222 | 260 | -4092 | 726 | 1607 | -4412 | -513 | -2252 | -4163 | 92 | -2472 | -413 | -306 | -1618 | 771 | -1255 | -13 | 188 | 257 | -4275 | 1832 | 294 |
| - | -147 | -502 | 234 | 43 | -383 | 397 | 103 | -625 | 209 | -466 | -723 | 280 | 393 | 43 | 93 | 360 | 116 | -366 | -281 | -246 | |
| - | -236 | -3650 | -3805 | -2588 | -262 | -701 | -1378 | * | * | | | | | | | | | | | | |
| 223 | -44 | 1317 | -6066 | -5505 | 1402 | -5405 | -4429 | 230 | -5173 | -839 | -2606 | -5054 | -5394 | -4849 | -5031 | -4538 | -445 | 3184 | -4243 | -3877 | 304 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10378 | -11420 | -894 | -1115 | -623 | -1511 | * | * | | | | | | | | | | | | |
| 224 | 65 | -2865 | -4164 | -3574 | -2846 | -4213 | -3013 | 614 | -1463 | -2725 | 460 | -3487 | -4274 | 2287 | 2202 | -714 | -2751 | 1420 | -3297 | 1201 | 305 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10450 | -11492 | -894 | -1115 | -384 | -2097 | * | * | | | | | | | | | | | | |
| 225 | -651 | -4093 | 1469 | 319 | -4414 | -125 | -2252 | -992 | 1025 | -4109 | -3182 | 1775 | -3686 | 1796 | 695 | 210 | -1255 | -3715 | -4276 | -3593 | 306 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 41

| | | | | | | | | | | | | | | | | | | | | | |
|---|---|---|---|---|---|---|---|---|---|---|---|---|---|---|---|---|---|---|---|---|---|
| - | -1 | -10485 | -11527 | -894 | -1115 | -701 | -1378 | * | * | | | | | | | | | | | | |
| 226 | 338 | -4091 | -1137 | 2053 | -4412 | -1356 | 1269 | -4162 | 366 | -1668 | 113 | 354 | -3686 | 679 | 408 | -2500 | -519 | -587 | -4275 | 1757 | 307 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 227 | -1252 | -2706 | -1848 | -4573 | 971 | -4423 | -3293 | 2094 | -1151 | 939 | 2195 | -273 | -4473 | -626 | -3976 | -3507 | -1544 | 517 | 417 | 1633 | 308 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 228 | 806 | -3111 | -3504 | -1085 | -496 | -4035 | -2787 | -228 | 1468 | 680 | 245 | -1261 | -1626 | -1024 | -237 | -679 | -463 | 149 | -3509 | 2186 | 309 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 229 | -60 | -4091 | 2196 | 907 | -4411 | -1776 | -2252 | -1262 | 1126 | -996 | -3180 | 1611 | -3686 | -1792 | 309 | -1480 | 88 | -3713 | -4275 | -357 | 310 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -601 | -10485 | -1557 | -894 | -1115 | -701 | -1378 | * | * | | | | | | | | | | | | |
| 230 | 130 | -3300 | 320 | 1169 | 473 | -864 | -1863 | -3174 | -1511 | -3265 | -2425 | -1883 | -3276 | -1457 | -1991 | 670 | -325 | -2858 | 4062 | 2148 | 311 |
| - | -147 | -501 | 234 | 44 | -381 | 398 | 111 | -627 | 212 | -467 | -721 | 275 | 393 | 44 | 95 | 360 | 116 | -370 | -295 | -250 | |
| - | -116 | -3705 | -10929 | -1545 | -606 | -55 | -4734 | * | * | | | | | | | | | | | | |
| 231 | 880 | -2705 | -5219 | -1393 | -497 | -146 | -3297 | 1273 | -4179 | 1109 | 2050 | -4070 | -4475 | -3803 | -3981 | -319 | -956 | 1575 | -3163 | -2821 | 315 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 232 | 727 | -57 | -1515 | -3685 | -2832 | -68 | -3067 | 1080 | 799 | 359 | 1459 | 1063 | -4314 | -3227 | -1673 | -82 | -1530 | 871 | -3293 | -301 | 316 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -25 | -10485 | -5900 | -894 | -1115 | -701 | -1378 | * | * | | | | | | | | | | | | |
| 233 | -345 | -4072 | 1466 | 25 | -4393 | -131 | 1146 | -4144 | 1820 | -4088 | -3161 | 77 | -3665 | 415 | 805 | -1371 | -33 | -3694 | 3083 | -3572 | 317 |
| - | -150 | -501 | 234 | 42 | -382 | 399 | 104 | -628 | 209 | -465 | -722 | 274 | 395 | 44 | 97 | 358 | 121 | -371 | -296 | -240 | |
| - | -40 | -5208 | -11503 | -3012 | -191 | -446 | -1911 | * | * | | | | | | | | | | | | |
| 234 | -3098 | 557 | -5412 | -4796 | 2467 | -4633 | 1098 | -2384 | -4390 | 1748 | 408 | -4253 | -4674 | -3991 | -113 | -3721 | -3037 | -908 | -3157 | 2811 | 327 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 42

| | | | | | | | | | | | | | | | | | | | | | |
|---|---|---|---|---|---|---|---|---|---|---|---|---|---|---|---|---|---|---|---|---|---|
| 235 | -440 | -2770 | -4991 | -4354 | -2731 | -4413 | -3255 | 134 | 119 | -429 | -1971 | -3962 | -4464 | -1018 | 73 | -3489 | -1348 | 621 | 5347 | -2874 | 328 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 236 | 518 | -2762 | -8 | -4162 | -1014 | -233 | -3201 | 1185 | -3847 | 1655 | 858 | 446 | -4409 | -1240 | -1731 | 15 | -797 | -383 | -3212 | -256 | 329 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -352 | -10485 | -2213 | -894 | -1115 | -701 | -1378 | * | * | | | | | | | | | | | | |
| 237 | -2321 | -3792 | 2018 | 1012 | -4112 | 4 | -1953 | -3862 | 532 | -740 | 381 | 1728 | -3388 | -1494 | 1351 | -730 | -2260 | -3414 | 841 | -3293 | 330 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -92 | -10135 | -4037 | -894 | -1115 | -1267 | -775 | * | * | | | | | | | | | | | | |
| 238 | -250 | -3844 | 749 | 681 | -4165 | 569 | 1082 | -3915 | 1250 | -2157 | 458 | -1981 | -495 | 607 | 655 | -2252 | 491 | -3466 | 1014 | 1304 | 331 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -500 | -10197 | -1775 | -894 | -1115 | -3266 | -158 | * | * | | | | | | | | | | | | |
| 239 | -2222 | -2815 | -28 | -2116 | 41 | 3002 | -2197 | -2568 | -2074 | -2812 | -2078 | -563 | -315 | -1959 | -2465 | 200 | -2200 | -465 | 1650 | -2767 | 332 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2227 | -9699 | -349 | -894 | -1115 | -4336 | -73 | * | * | | | | | | | | | | | | |
| 240 | -690 | -1030 | -1347 | 667 | -1112 | 1526 | -775 | -536 | -770 | -926 | 2421 | -983 | -2034 | -651 | -1069 | -950 | -658 | 1348 | -1510 | -1082 | 333 |
| - | -149 | -500 | 234 | 45 | -381 | 398 | 105 | -627 | 211 | -465 | -721 | 276 | 393 | 48 | 98 | 359 | 117 | -370 | -295 | -250 | |
| - | -2648 | -650 | -2300 | -749 | -1304 | -3702 | -115 | * | * | | | | | | | | | | | | |
| 241 | -1684 | -3381 | 2298 | 2247 | -3628 | -1975 | -1105 | -3463 | -1067 | -3374 | -2571 | 1229 | -2376 | -724 | -1746 | -1436 | 1284 | -2978 | -3559 | -2700 | 336 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -265 | -7722 | -2618 | -894 | -1115 | -1665 | -547 | * | * | | | | | | | | | | | | |
| 242 | -498 | -1527 | -664 | -3408 | 1644 | -3248 | -2119 | 1205 | -3003 | 1436 | 1589 | -2893 | -3297 | -2626 | -2804 | -2332 | -1641 | 927 | 2073 | 992 | 337 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9095 | -10137 | -894 | -1115 | -3824 | -106 | * | * | | | | | | | | | | | | |
| 243 | -241 | -4561 | 1267 | -1550 | -5048 | 2995 | -2504 | -4899 | -2536 | -4814 | -4030 | 545 | -3695 | 1178 | -3239 | -874 | -3044 | -4358 | -5001 | -4130 | 338 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9182 | -10224 | -894 | -1115 | -89 | -4060 | * | * | | | | | | | | | | | | |
| 244 | 707 | 529 | -5359 | -4732 | 472 | -4578 | 76 | 2402 | -4335 | -790 | 262 | -4224 | -4619 | -3963 | -4141 | -3668 | -2943 | 2418 | -3322 | -2979 | 339 |

FIG. 43

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -36 | -10450 | -5378 | -894 | -1115 | -1420 | -675 | * | * | | | | | | | | | | | | |
| 245 | 108 | -5784 | 3750 | -2898 | -6561 | -553 | -3961 | -6451 | -304 | -6372 | -5641 | -3250 | -5036 | -3629 | -4889 | -171 | -4466 | -5826 | -6560 | -844 | 340 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10415 | -11458 | -894 | -1115 | -267 | -2564 | * | * | | | | | | | | | | | | |
| 246 | -882 | -4791 | -7040 | -7394 | -6930 | 3753 | -6508 | -7307 | -7247 | -7441 | -6597 | -5861 | -5815 | -6771 | -6872 | -4523 | -4737 | -6054 | 933 | -6891 | 341 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 247 | -6543 | -5722 | -7433 | -7597 | 3802 | -7222 | -3668 | 494 | -7173 | 255 | -4495 | -5988 | -7055 | -748 | -6609 | -6447 | -6415 | -5422 | 3771 | 92 | 342 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 248 | -6705 | -6597 | -7597 | -6711 | -7409 | -6618 | -5618 | -7674 | -4419 | -7152 | 33 | -6439 | -6902 | -5393 | 4226 | -6812 | -6659 | -7468 | -6649 | -6845 | 343 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 249 | -5076 | -4650 | -7488 | -6907 | 1609 | -6991 | -5853 | 2609 | -1344 | 1676 | 2141 | -6665 | -6557 | -5839 | -6306 | -6199 | -4979 | 445 | -4988 | -4973 | 344 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 250 | -7293 | -7123 | 4192 | -5905 | -7868 | -6589 | -6618 | -8745 | -7289 | -1940 | -8114 | -6217 | -7106 | -6709 | -7576 | -7234 | -7475 | -8427 | -7251 | -7548 | 345 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 251 | 2483 | -2715 | -5223 | -4589 | 961 | -4433 | 154 | -752 | -4186 | -1198 | -1919 | -4078 | -4484 | -3812 | -3990 | -1105 | 1109 | 1651 | -3176 | -2833 | 346 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 252 | 2379 | -2938 | -5404 | -2004 | -2980 | -1281 | -3615 | 714 | -4438 | -2819 | 193 | -4299 | -4697 | -4079 | -4268 | -903 | -3050 | 2448 | -3509 | -3164 | 347 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 253 | -2633 | -4104 | -1140 | -1930 | -4426 | -1114 | 195 | -4175 | 3070 | -2035 | -3193 | 1385 | 362 | -1802 | 351 | -251 | -866 | -3726 | -4286 | -3605 | 348 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 44

| | | | | | | | | | | | | | | | | | | | | | |
|---|---|---|---|---|---|---|---|---|---|---|---|---|---|---|---|---|---|---|---|---|---|
| - | -1 | -10485 | -11527 | -894 | -1115 | -701 | -1378 | * | * | | | | | | | | | | | | |
| 254 | -2885 | -2752 | -4977 | 201 | 73 | 530 | 4521 | -2250 | -4009 | -482 | 1252 | -3962 | -4455 | -3677 | -3896 | -1731 | -2826 | -727 | -3185 | 141 | 349 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 255 | -2968 | -2788 | -5317 | -4683 | -582 | -1479 | -3399 | 2480 | -4281 | 4 | 2830 | -4171 | -988 | -3900 | -4081 | -3612 | -2908 | 1493 | -3254 | 1837 | 350 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 256 | 502 | -4092 | 1261 | -53 | 263 | -72 | -2252 | -4163 | -166 | -4108 | -3181 | -601 | 1215 | -609 | -740 | 1631 | -2558 | -3714 | 1322 | 641 | 351 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 257 | 411 | -4077 | -106 | 1023 | 584 | -3597 | 1678 | -1191 | 1718 | -390 | 8 | 262 | 1013 | -704 | -2346 | -1133 | -1329 | -3696 | -4265 | -940 | 352 |
| - | -150 | -501 | 236 | 43 | -379 | 398 | 108 | -623 | 209 | -468 | -722 | 274 | 396 | 44 | 96 | 360 | 116 | -366 | -296 | -251 | |
| - | -5649 | -1702 | -572 | -15 | -6554 | -701 | -1378 | * | * | | | | | | | | | | | | |
| 258 | -411 | 1839 | 2192 | 748 | -3114 | -2333 | -996 | -2857 | -582 | -2816 | -1898 | -973 | 1512 | 1354 | 242 | -1244 | -1299 | -445 | -2995 | -2319 | 354 |
| - | -146 | -506 | 264 | 43 | -375 | 397 | 100 | -637 | 194 | -479 | -736 | 283 | 414 | 28 | 89 | 355 | 113 | -372 | -288 | -222 | |
| - | -2874 | -213 | -9917 | -4062 | -89 | -4972 | -47 | * | * | | | | | | | | | | | | |
| 259 | -1416 | -2774 | 1429 | -736 | -3035 | -2386 | 1075 | 242 | -666 | -2768 | -1878 | 2745 | -111 | -622 | 569 | -1317 | -1357 | -2372 | -2977 | 1327 | 382 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8875 | -9917 | -894 | -1115 | -3296 | -155 | * | * | | | | | | | | | | | | |
| 260 | 513 | 1170 | -192 | -1660 | -2115 | 2157 | -1598 | 778 | -1527 | -1967 | -1252 | 1387 | -2915 | -1416 | -1874 | -1807 | -99 | -1536 | -2462 | 897 | 383 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9078 | -10121 | -894 | -1115 | -85 | -4123 | * | * | | | | | | | | | | | | |
| 261 | 557 | -4061 | -56 | 474 | -4382 | 1288 | -175 | -4132 | -1802 | -2004 | -3150 | -494 | 1458 | 382 | -564 | 756 | -301 | -3683 | 796 | 988 | 384 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10450 | -11492 | -894 | -1115 | -384 | -2097 | * | * | | | | | | | | | | | | |
| 262 | -1153 | -2879 | 1150 | -3594 | 2837 | -1439 | -292 | 319 | -1519 | -1069 | -439 | -1257 | -4293 | -3162 | 1061 | -768 | -1281 | -807 | 2822 | -274 | 385 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 45

| | | | | | | | | | | | | | | | | | | | | | |
|---|---|---|---|---|---|---|---|---|---|---|---|---|---|---|---|---|---|---|---|---|---|
| 263 | 122 | -2720 | -1621 | -4453 | -1028 | -539 | -3269 | 1036 | -4078 | 1050 | -1922 | -802 | -4456 | 1084 | -3927 | -838 | -1339 | 403 | 3926 | 595 | 386 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 264 | -233 | -4093 | -707 | -1918 | -4414 | -3594 | 2926 | -4165 | 1899 | -4109 | -3182 | -744 | 114 | 1144 | 1484 | -362 | 548 | -1876 | -4276 | -3593 | 387 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 265 | 499 | -4092 | 580 | 1661 | -4413 | -1745 | 436 | 708 | 417 | -4108 | -3181 | 205 | -1007 | 934 | -2339 | 753 | -672 | -258 | -4275 | -3593 | 388 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 266 | -2891 | -2717 | -5233 | -4599 | 3037 | -4438 | -3300 | 752 | -4194 | 142 | 283 | -889 | -4487 | -1135 | -3994 | -1378 | -2832 | -1132 | 3346 | 2415 | 389 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 267 | -503 | -3183 | -1037 | -1492 | -3218 | -3985 | 813 | 306 | 55 | 370 | 2307 | -1113 | -1033 | -2549 | 1152 | -2960 | 1259 | 340 | 884 | 892 | 390 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 268 | -159 | -4092 | 1289 | 912 | -4413 | -955 | 1047 | -4164 | 313 | -4108 | -431 | -380 | -45 | 1806 | -1132 | 850 | 246 | -1172 | -4276 | -386 | 391 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 269 | 1274 | -4093 | 1238 | 1709 | -4414 | -1956 | 1673 | -4165 | 1186 | -4109 | -3182 | 745 | -3686 | -736 | 397 | -1517 | -2558 | -1728 | -4276 | -674 | 392 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 270 | 407 | -2709 | -5213 | -4578 | -2664 | -4428 | -3299 | 1337 | -4176 | 982 | 2698 | -4069 | -20 | 294 | -3981 | -61 | -775 | 1488 | -3168 | -2826 | 393 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 271 | 85 | -4092 | 262 | -1918 | -4414 | 199 | 975 | -4164 | 1815 | -4108 | -3182 | 2049 | 361 | -319 | 167 | -1030 | -407 | -3714 | -4276 | 1098 | 394 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -144 | -10485 | -3406 | -894 | -1115 | -701 | -1378 | * | * | | | | | | | | | | | | |
| 272 | 1241 | -3970 | 462 | 1296 | -4291 | -189 | -2129 | -4042 | -267 | -3986 | -3059 | 1664 | 178 | 821 | 69 | 334 | -577 | -3592 | -4153 | -3470 | 395 |

FIG. 46

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -284 | -10342 | -2489 | -894 | -1115 | -2532 | -274 | * | * | | | | | | | | | | | | |
| 273 | 625 | -2676 | -1177 | 670 | -171 | 85 | -80 | 494 | 232 | -329 | -1859 | -2778 | -3779 | -2399 | -2817 | -2704 | 1049 | 628 | -3084 | 2108 | 396 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -226 | -10060 | -2793 | -894 | -1115 | -3690 | -116 | * | * | | | | | | | | | | | | |
| 274 | 73 | -2503 | -1066 | -2471 | -21 | -692 | 538 | -115 | 1235 | -326 | 890 | 829 | -3575 | -2174 | -2598 | 443 | 794 | 938 | -2908 | -180 | 397 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -717 | -9836 | -1356 | -894 | -1115 | -4142 | -84 | * | * | | | | | | | | | | | | |
| 275 | -80 | -2978 | 1132 | 1325 | 1194 | -2498 | -1158 | -3038 | 794 | 122 | -2069 | -1136 | -50 | -700 | 870 | -265 | -98 | -2597 | -3166 | -2487 | 398 |
| - | -143 | -506 | 231 | 44 | -380 | 395 | 104 | -628 | 221 | -467 | -713 | 277 | 393 | 41 | 93 | 356 | 114 | -368 | -264 | -255 | |
| - | -1944 | -436 | -10165 | -1835 | -475 | -4841 | -51 | * | * | | | | | | | | | | | | |
| 276 | -356 | -2494 | 1117 | -163 | -2635 | 1340 | -1339 | -366 | -1043 | -2432 | 785 | -1402 | -2734 | -980 | -1496 | 1458 | 735 | 305 | -2800 | -2250 | 410 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9123 | -10165 | -894 | -1115 | -2882 | -210 | * | * | | | | | | | | | | | | |
| 277 | -1905 | -3358 | 239 | -1142 | -3665 | 1869 | 1510 | -3416 | -1072 | -3364 | -2456 | -1452 | 597 | 1163 | 1325 | -1780 | -1846 | -2980 | -3528 | 2375 | 411 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9346 | -10389 | -894 | -1115 | -972 | -1028 | * | * | | | | | | | | | | | | |
| 278 | -1093 | -3703 | 369 | 430 | -4024 | -1118 | 890 | -3775 | 1641 | -3719 | -2792 | -1839 | 1981 | 426 | 570 | 691 | -2169 | -3325 | -3886 | 896 | 412 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10028 | -11070 | -894 | -1115 | -950 | -1052 | * | * | | | | | | | | | | | | |
| 279 | -976 | -3912 | 1701 | 1575 | -1111 | 505 | -2074 | -3981 | 326 | -3927 | -3001 | 430 | 1566 | -1615 | -2163 | 50 | -2380 | -1765 | 2039 | -3413 | 413 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10276 | -11318 | -894 | -1115 | -124 | -3599 | * | * | | | | | | | | | | | | |
| 280 | 429 | 71 | -1863 | -1322 | 834 | -1166 | -3269 | 893 | -4079 | 448 | 1507 | -4006 | 129 | -3728 | 692 | -364 | 215 | 1285 | -3175 | -2830 | 414 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 281 | -781 | -2711 | -348 | -907 | 3229 | -4417 | 185 | -1048 | -4136 | -1108 | 2103 | -4042 | -774 | -3771 | -3958 | -3498 | -2816 | -1046 | 990 | 2512 | 415 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 47

| | | | | | | | | | | | | | | | | | | | | | |
|---|---|---|---|---|---|---|---|---|---|---|---|---|---|---|---|---|---|---|---|---|---|
| - | -31 | -10485 | -5610 | -894 | -1115 | -701 | -1378 | * | * | | | | | | | | | | | | |
| 282 | -561 | 1323 | -5196 | -4560 | 109 | -4398 | -3270 | 1605 | -4155 | 304 | 1757 | -1446 | -4448 | -643 | -3955 | -1828 | 1924 | 1040 | 1341 | -208 | 416 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10455 | -11498 | -894 | -1115 | -412 | -2008 | * | * | | | | | | | | | | | | |
| 283 | -2959 | -2779 | -5308 | -4674 | 2352 | -4516 | -3390 | 290 | -1723 | 239 | 207 | -4162 | -4560 | -3892 | -4072 | -3602 | -218 | 2596 | -3246 | 1386 | 417 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 284 | 968 | -6618 | 158 | -1335 | -6920 | 3180 | -4075 | -6860 | -4391 | -2189 | -6095 | -3269 | -5218 | 1419 | -5293 | -4432 | -4868 | -6301 | -6934 | -5886 | 418 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 285 | -5864 | -7026 | -3549 | 3932 | -7732 | -5502 | -5139 | -8036 | -5596 | -7778 | -7325 | -1213 | -6088 | -4906 | -6414 | -5553 | -6009 | -7450 | -7315 | -6874 | 419 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 286 | -242 | -2704 | -5221 | -4585 | -167 | -4425 | 101 | 1435 | -1866 | -274 | 1375 | -1502 | -862 | -3804 | -3981 | -3509 | -1307 | 2210 | 2926 | 1326 | 420 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 287 | -1781 | -2711 | -1661 | -4530 | 1589 | -1110 | -349 | 1399 | -4138 | -298 | -1913 | -4043 | -1510 | -3772 | -750 | -532 | -2816 | -795 | 4640 | 1422 | 421 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 288 | 162 | -4088 | 1418 | -714 | -4408 | 1367 | 2467 | -1843 | 205 | -758 | -3178 | -1104 | -3687 | 1361 | -2341 | 175 | -841 | -1726 | -4273 | -915 | 422 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2847 | -10485 | -217 | -894 | -1115 | -701 | -1378 | * | * | | | | | | | | | | | | |
| 289 | -732 | -1200 | -2291 | -1892 | -2006 | 1184 | -1642 | 1572 | -1739 | -1880 | -1160 | -1621 | -2261 | -1561 | -1945 | 1858 | 1564 | -1213 | -2374 | -1999 | 423 |
| - | -148 | -503 | 235 | 42 | -383 | 402 | 103 | -627 | 211 | -468 | -718 | 278 | 395 | 44 | 93 | 358 | 115 | -372 | -297 | -237 | |
| - | -518 | -1741 | -8690 | -3476 | -136 | -327 | -2302 | * | * | | | | | | | | | | | | |
| 290 | 588 | -3859 | 1096 | -225 | -4178 | 1819 | -2025 | -3928 | -1606 | -1941 | -166 | 712 | -3459 | 1765 | -1027 | -635 | 580 | -1514 | -4044 | -3362 | 436 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -86 | -10220 | -4136 | -894 | -1115 | -3177 | -169 | * | * | | | | | | | | | | | | |

FIG. 48

| | | | | | | | | | | | | | | | | | | | | | |
|---|---|---|---|---|---|---|---|---|---|---|---|---|---|---|---|---|---|---|---|---|---|
| 291 | 1059 | -3794 | 1830 | -152 | -4111 | 1065 | -1969 | -3859 | -1553 | -1911 | -2887 | 1208 | 141 | -1511 | -2060 | 518 | 446 | -1623 | -3983 | -3302 | 437 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2561 | -10136 | -269 | -894 | -1115 | -3476 | -136 | * | * | | | | | | | | | | | | |
| 292 | 2610 | -1342 | -2763 | -2644 | -3503 | 678 | -2484 | -3255 | -2594 | -3468 | -2570 | -1940 | 1729 | -2326 | -2723 | 888 | -1095 | -2280 | -3694 | -3427 | 438 |
| - | -149 | -500 | 232 | 43 | -381 | 401 | 112 | -627 | 210 | -467 | -721 | 277 | 393 | 46 | 95 | 359 | 117 | -370 | -295 | -250 | |
| - | -2750 | -236 | -8628 | -41 | -5171 | -3546 | -129 | * | * | | | | | | | | | | | | |
| 293 | 136 | -1631 | -1527 | -976 | -1899 | -2091 | -1003 | -1496 | -753 | 473 | -976 | -1123 | -2267 | -730 | 2059 | 773 | 1741 | -1268 | -2155 | -1683 | 440 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -8 | -8080 | -9122 | -894 | -1115 | -68 | -4437 | * | * | | | | | | | | | | | | |
| 294 | -1186 | -4051 | 1864 | -401 | -4367 | 1750 | 1129 | -4115 | -1805 | -1498 | -531 | 719 | -1394 | 238 | -2311 | 105 | 645 | -940 | -4237 | -642 | 441 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -164 | -10448 | -3225 | -894 | -1115 | -375 | -2128 | * | * | | | | | | | | | | | | |
| 295 | 272 | -3956 | 702 | 2234 | -4277 | 227 | -2115 | -4027 | -957 | -1001 | -3045 | -3 | 557 | -604 | -561 | 575 | -12 | -3578 | -4139 | -3456 | 442 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -203 | -10326 | -2940 | -894 | -1115 | -1827 | -478 | * | * | | | | | | | | | | | | |
| 296 | 611 | -2883 | 1048 | -416 | -2916 | -1167 | 1492 | -325 | -2390 | 448 | -2058 | -2673 | 610 | -2278 | 25 | -2681 | -266 | 512 | 2653 | 960 | 443 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10157 | -11199 | -894 | -1115 | -2297 | -328 | * | * | | | | | | | | | | | | |
| 297 | 801 | 1079 | -172 | 312 | -880 | -3954 | -2752 | 341 | 149 | 668 | 538 | -3189 | -4017 | 593 | -3195 | -416 | -86 | 1089 | -3087 | 43 | 444 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10204 | -11246 | -894 | -1115 | -1942 | -435 | * | * | | | | | | | | | | | | |
| 298 | 4 | -3898 | -149 | 88 | -4219 | -1463 | -2058 | -1582 | 892 | -570 | -2987 | 1038 | -689 | 819 | 2246 | 21 | -2365 | -3520 | 981 | -288 | 445 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11303 | -894 | -1115 | -596 | -1564 | * | * | | | | | | | | | | | | |
| 299 | -1397 | -3038 | -928 | -2901 | -504 | 1085 | -2736 | -1186 | 449 | 263 | -2218 | -3006 | 603 | -867 | -554 | 39 | 187 | 1072 | 2048 | 1040 | 446 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10415 | -11457 | -894 | -1115 | -267 | -2567 | * | * | | | | | | | | | | | | |
| 300 | -1177 | -3356 | 1832 | -2532 | -3429 | 237 | -2595 | -1214 | -833 | 294 | -293 | -727 | -137 | 844 | -2813 | -3 | -2659 | 548 | 952 | 2051 | 447 |

FIG. 49

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 301 | 1114 | -4085 | 594 | 798 | -654 | -1917 | -2254 | -1463 | 282 | -1404 | 452 | -505 | -766 | 1139 | -304 | -19 | 1081 | -1324 | -4271 | -341 | 448 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -60 | -10485 | -4636 | -894 | -1115 | -701 | -1378 | * | * | | | | | | | | | | | | |
| 302 | -833 | -4031 | 173 | -1079 | 1188 | -1064 | -2204 | -1235 | -116 | -4045 | -3121 | 191 | 76 | 462 | -1170 | -203 | 439 | -3650 | 963 | 3212 | 449 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10426 | -11468 | -894 | -1115 | -294 | -2438 | * | * | | | | | | | | | | | | |
| 303 | 433 | -3984 | 420 | 767 | -1222 | -3624 | 176 | -318 | -1888 | -905 | -3086 | 906 | 728 | 486 | 104 | -2535 | 1437 | 350 | -4197 | -350 | 450 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 304 | 328 | 1309 | -281 | -282 | -4353 | 1769 | 1890 | -649 | -1024 | -1741 | -3145 | 1134 | -3697 | -1811 | -765 | 556 | -1304 | -1729 | -4245 | 852 | 451 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 305 | -1216 | -4032 | -9 | -1118 | -745 | 942 | -350 | -1689 | 82 | -1244 | -3128 | 691 | -136 | -328 | 962 | -2518 | 133 | 148 | 1628 | 2241 | 452 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 306 | -136 | -3415 | -3012 | -2457 | 1283 | 719 | 1555 | -3109 | -39 | -867 | 1993 | 942 | -900 | -629 | -2757 | 458 | 350 | -1139 | -3759 | 1213 | 453 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 307 | 819 | -4092 | 1457 | 1573 | -4413 | -662 | 414 | -1864 | -1832 | -2123 | -3181 | 760 | -1408 | 664 | -1015 | 939 | 267 | -3714 | -4275 | -3593 | 454 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 308 | 32 | -2705 | -5217 | -4581 | -906 | 41 | -3295 | -1012 | -4178 | 1118 | 251 | 1098 | -4474 | -3801 | -3979 | 460 | -356 | 1357 | 2000 | 1529 | 455 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -71 | -10485 | -4400 | -894 | -1115 | -701 | -1378 | * | * | | | | | | | | | | | | |
| 309 | 142 | -4028 | 108 | 874 | -4348 | -1341 | -2192 | -1403 | -611 | -2296 | 157 | 1235 | 1056 | 1352 | -2280 | 294 | 1338 | -601 | -4212 | -3531 | 456 |
| - | -150 | -501 | 234 | 42 | -382 | 398 | 105 | -627 | 209 | -467 | -721 | 277 | 393 | 48 | 95 | 360 | 119 | -368 | -295 | -245 | |

FIG. 50

| | | | | | | | | | | | | | | | | | | | | | |
|---|---|---|---|---|---|---|---|---|---|---|---|---|---|---|---|---|---|---|---|---|---|
| - | -1126 | -2403 | -1503 | -26 | -5804 | -267 | -2567 | * | * | | | | | | | | | | | | |
| 310 | -734 | -2610 | -2963 | -495 | 1059 | 104 | 638 | -322 | -795 | -1373 | 2904 | -622 | -3585 | -2126 | -392 | 916 | 69 | -154 | -3006 | 1234 | 458 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9894 | -10936 | -894 | -1115 | -3026 | -189 | * | * | | | | | | | | | | | | |
| 311 | -694 | -2235 | -4645 | -4015 | -2191 | 1013 | -2798 | 1221 | -3631 | 1102 | 1518 | -641 | -3982 | -3272 | 851 | -1354 | 282 | 1211 | -2692 | -2347 | 459 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9944 | -10986 | -894 | -1115 | -617 | -1523 | * | * | | | | | | | | | | | | |
| 312 | -1055 | -2651 | -613 | -3810 | 3055 | -4167 | -3000 | -40 | -357 | 532 | 2046 | 142 | -1479 | -3268 | -3551 | -537 | 249 | -2072 | -3096 | -75 | 460 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10321 | -11363 | -894 | -1115 | -149 | -3351 | * | * | | | | | | | | | | | | |
| 313 | -467 | -4167 | 2491 | 1181 | -4487 | -185 | -2314 | -4239 | -1905 | -4183 | -3258 | 1531 | -3743 | 456 | -609 | 712 | 63 | -3789 | -4350 | -3663 | 461 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 314 | -1259 | -2730 | -148 | -4608 | 3644 | -4450 | -3303 | -537 | -4204 | -55 | -1932 | -851 | -4499 | -3826 | -4005 | -3535 | -2845 | 1077 | 1010 | 672 | 462 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 315 | -2622 | -4063 | 394 | -68 | -350 | -1402 | 503 | -985 | 397 | -162 | -3155 | -2242 | 1822 | -427 | 553 | 536 | 286 | -976 | -4254 | 1241 | 463 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 316 | -2746 | -3224 | 1186 | -2730 | 185 | 347 | 2505 | -2850 | -2594 | 1342 | 93 | 441 | -4036 | -2491 | -1349 | -1197 | -6 | -2691 | -3603 | 1960 | 464 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 317 | -203 | -3318 | -3142 | -2584 | 2102 | -381 | 1857 | -1378 | -11 | -870 | 526 | 951 | -3981 | 863 | 548 | -279 | -780 | -1647 | 833 | 1040 | 465 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 318 | 216 | -4079 | 1226 | -6 | 883 | 984 | -2256 | -1835 | 141 | -1227 | -19 | -2234 | -136 | 269 | 384 | -215 | 438 | -3697 | -4266 | 588 | 466 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 51

| | | | | | | | | | | | | | | | | | | | | | |
|---|---|---|---|---|---|---|---|---|---|---|---|---|---|---|---|---|---|---|---|---|---|
| 319 | 388 | -3951 | 165 | -986 | 573 | -3634 | -246 | 1134 | 885 | -125 | -3056 | -396 | -3725 | 158 | -758 | -9 | 727 | 662 | -4172 | -1068 | 467 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 320 | 346 | 551 | 529 | -2498 | -181 | 207 | 603 | 1285 | -574 | 1197 | -542 | -1146 | -3947 | 232 | 341 | -1167 | -2655 | -2869 | -3732 | 493 | 468 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 321 | -41 | -4088 | -2468 | -4 | -4408 | 111 | 1186 | -1261 | 400 | -2211 | -237 | 732 | -883 | 1891 | 1097 | -102 | -291 | -1544 | -4273 | 1406 | 469 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 322 | 507 | -4092 | 449 | 641 | -4414 | 575 | 44 | -4164 | 1050 | -4108 | -3181 | 1550 | 546 | -720 | -205 | 534 | -202 | -1228 | -4276 | -3593 | 470 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 323 | 1505 | -2743 | -4902 | -1789 | 1303 | -1982 | -3231 | -70 | -3946 | 275 | -1944 | -363 | 129 | -1121 | -3855 | 20 | 400 | 1440 | -3195 | -283 | 471 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 324 | -1181 | -3995 | 572 | -1044 | 2076 | 58 | 605 | -1596 | 57 | -562 | -3095 | -2274 | -3713 | 478 | 213 | 1242 | -1331 | 509 | -4205 | -1010 | 472 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -961 | -10485 | -1042 | -894 | -1115 | -701 | -1378 | * | * | | | | | | | | | | | | |
| 325 | 54 | -3258 | 916 | -1144 | -3561 | 794 | -1470 | 532 | -168 | -1378 | -2352 | 55 | -2902 | 791 | 1381 | 518 | -666 | 322 | -3452 | -2781 | 473 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1288 | -9527 | -763 | -894 | -1115 | -4529 | -64 | * | * | | | | | | | | | | | | |
| 326 | -1841 | -2600 | -1835 | -2154 | -4644 | 1586 | -2893 | -4556 | -3135 | -4654 | -3836 | 2243 | 3218 | -2685 | -3520 | -1961 | -2222 | -3536 | -4706 | -4269 | 474 |
| - | -149 | -500 | 232 | 43 | -372 | 398 | 105 | -627 | 210 | -466 | -714 | 277 | 393 | 45 | 95 | 359 | 117 | -370 | -295 | -250 | |
| - | -3410 | -1305 | -996 | -53 | -4787 | -1602 | -576 | * | * | | | | | | | | | | | | |
| 327 | -1431 | 891 | -42 | 1025 | 456 | 1017 | -1064 | -2967 | -646 | -2914 | -1989 | 2083 | -2498 | 1034 | 692 | 218 | -1370 | -2520 | -3084 | -2402 | 476 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -8991 | -10033 | -894 | -1115 | -4118 | -86 | * | * | | | | | | | | | | | | |
| 328 | -355 | -1974 | -2372 | -1796 | 2376 | -2890 | -1625 | -1567 | 1866 | -1854 | 1506 | 675 | -2961 | -1491 | 383 | -1881 | -1570 | 1115 | -2366 | -1940 | 477 |

FIG. 52

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9057 | -10099 | -894 | -1115 | -2560 | -268 | * | * | | | | | | | | | | | | |
| 329 | -1797 | -2342 | -415 | 287 | 2146 | -1027 | -1712 | -51 | -142 | -441 | -1509 | -1885 | -3066 | 709 | -1954 | -458 | 155 | -585 | 3483 | 743 | 478 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9370 | -10413 | -894 | -1115 | -925 | -1079 | * | * | | | | | | | | | | | | |
| 330 | 176 | -3702 | -92 | -245 | -920 | -1338 | -1891 | 146 | 745 | -1033 | -231 | 832 | -3324 | 1918 | 751 | 425 | -935 | -626 | -3891 | 12 | 479 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -41 | -10054 | -5194 | -894 | -1115 | -2687 | -243 | * | * | | | | | | | | | | | | |
| 331 | -2358 | -2946 | 488 | -965 | -3010 | 1948 | 775 | -389 | -803 | 672 | 921 | -883 | -3613 | -2003 | -2483 | -296 | -51 | -1063 | 773 | 1369 | 480 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10061 | -11103 | -894 | -1115 | -1687 | -537 | * | * | | | | | | | | | | | | |
| 332 | -225 | -3817 | 367 | -10 | -624 | 1049 | 412 | -814 | 1051 | -3829 | -2908 | 1912 | -3434 | -1544 | -2091 | 14 | 446 | 5 | -4005 | -591 | 481 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -178 | -10186 | -3115 | -894 | -1115 | -3306 | -154 | * | * | | | | | | | | | | | | |
| 333 | -2215 | -3689 | 592 | -269 | -4010 | -257 | -1848 | -3760 | 469 | -56 | -2778 | 781 | 1787 | -206 | -283 | 1184 | 857 | -3311 | -3872 | -3189 | 482 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -157 | -10010 | -3296 | -894 | -1115 | -3810 | -107 | * | * | | | | | | | | | | | | |
| 334 | -1053 | 451 | -173 | 368 | 985 | -582 | -1891 | 623 | -1580 | -3052 | -2247 | -1944 | -988 | 2031 | 471 | 86 | -2075 | -1017 | 2776 | 1210 | 483 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9856 | -10898 | -894 | -1115 | -3279 | -157 | * | * | | | | | | | | | | | | |
| 335 | -2120 | -3592 | 1872 | -676 | -3913 | -343 | -1752 | -3664 | 159 | -823 | 613 | 947 | -3187 | 752 | 658 | 1133 | 969 | -3214 | -3776 | -3093 | 484 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2547 | -9895 | -273 | -894 | -1115 | -4043 | -90 | * | * | | | | | | | | | | | | |
| 336 | -796 | -2121 | -552 | -63 | -2376 | -1691 | -301 | -2144 | 1349 | -2097 | -1233 | 2085 | -1798 | 2049 | -91 | -685 | -720 | -1755 | -2222 | 1482 | 485 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -697 | -7361 | -1408 | -894 | -1115 | -4530 | -64 | * | * | | | | | | | | | | | | |

FIG. 53

| | | | | | | | | | | | | | | | | | | | | | |
|---|---|---|---|---|---|---|---|---|---|---|---|---|---|---|---|---|---|---|---|---|---|
| 337 | 997 | -1241 | -578 | -133 | -1517 | -1399 | -332 | -1234 | -83 | -1405 | -619 | 1518 | -1603 | -5 | -515 | 1020 | -399 | -944 | -1722 | 1779 | 486 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -17 | -6997 | -8039 | -894 | -1115 | -4345 | -73 | * | * | | | | | | | | | | | | |
| 338 | -813 | -1193 | -2517 | -2345 | -1917 | -1837 | -1987 | 1819 | -2146 | -1614 | -1167 | -1892 | -2390 | -2008 | -2230 | 2830 | -1076 | -631 | -2498 | -2045 | 487 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -13 | -7341 | -8383 | -894 | -1115 | -3330 | -151 | * | * | | | | | | | | | | | | |
| 339 | -927 | 2366 | 1639 | -228 | -2602 | -1871 | -568 | -2325 | 861 | -2315 | -1422 | -531 | -1988 | 1344 | -650 | -823 | 1925 | -1917 | -2518 | -1861 | 488 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -8 | -8030 | -9072 | -894 | -1115 | -177 | -3112 | * | * | | | | | | | | | | | | |
| 340 | 1374 | -2592 | -5077 | -4443 | -124 | -1761 | -3175 | -215 | -4045 | 926 | 3415 | -659 | -1379 | -3673 | 15 | -988 | -784 | -456 | 1250 | -2707 | 489 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -2 | -10357 | -11399 | -894 | -1115 | -179 | -3103 | * | * | | | | | | | | | | | | |
| 341 | 669 | -4072 | -1127 | -1928 | -4384 | 267 | -2258 | 64 | 1359 | -759 | -3164 | 775 | -1426 | 250 | 1455 | 313 | -2560 | -1811 | -4261 | 1229 | 490 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 342 | -60 | -4092 | 1793 | 555 | -4413 | -721 | 591 | -4164 | 866 | -942 | -3181 | 766 | -3686 | 1529 | 137 | -1018 | 189 | -3714 | 415 | 58 | 491 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 343 | -2877 | 521 | -228 | -4579 | 1897 | -1418 | -3294 | 630 | -1972 | 2065 | 336 | -4067 | -1693 | -1394 | -3978 | -1988 | -1133 | -260 | 984 | 733 | 492 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 344 | 1114 | -3970 | 600 | -1986 | -1332 | -3628 | -2293 | -3951 | 1865 | -1722 | 14 | 1176 | -3720 | -798 | -921 | -102 | -163 | 500 | -4186 | 1177 | 493 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 345 | 152 | -4092 | 1011 | 793 | -4413 | 428 | 44 | -1477 | 194 | -2362 | -3181 | 1669 | -3686 | 1065 | -2339 | 509 | 905 | -2008 | -4275 | -3593 | 494 |
| . | -149 | -500 | 233 | 43 | -381 | 399 | 106 | -626 | 210 | -466 | -720 | 275 | 394 | 45 | 96 | 359 | 117 | -369 | -294 | -249 | |
| . | -1 | -10485 | -11527 | -894 | -1115 | -701 | -1378 | * | * | | | | | | | | | | | | |
| 346 | -218 | -2875 | -4193 | -3609 | -142 | -1211 | -323 | 115 | -123 | -219 | 2818 | 279 | -949 | -1143 | 504 | 97 | -293 | -61 | 2641 | 338 | 495 |

FIG. 54

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 347 | 71 | -2705 | -5213 | -4578 | 495 | 657 | -3294 | 1948 | -1135 | 616 | 1591 | -4067 | -1693 | -3799 | -1274 | -1209 | 587 | -343 | 990 | 585 | 496 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -63 | -10485 | -4576 | -894 | -1115 | -701 | -1378 | * | * | | | | | | | | | | | | |
| 348 | 388 | -4039 | 1017 | 598 | -4360 | -547 | 971 | -1236 | -306 | -1981 | 871 | 1250 | 108 | 791 | -1067 | 631 | 642 | -3661 | -4222 | -3539 | 497 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10423 | -11466 | -894 | -1115 | -1793 | -491 | * | * | | | | | | | | | | | | |
| 349 | -1398 | -4039 | 1347 | -135 | -4360 | 1020 | 1623 | -1212 | 777 | -371 | -3128 | 55 | -3633 | 489 | -321 | 861 | -557 | -3661 | -4222 | 379 | 498 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10423 | -11466 | -894 | -1115 | -287 | -2470 | * | * | | | | | | | | | | | | |
| 350 | -2724 | -3331 | -141 | -323 | 272 | -574 | -2612 | -786 | -1221 | -688 | 1421 | -1323 | -3974 | 125 | -182 | -1029 | 643 | 802 | 4091 | 546 | 499 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 351 | 623 | -3456 | -2964 | -82 | -57 | 615 | -2532 | 245 | -308 | 327 | 533 | -572 | -3911 | 2001 | -57 | -1306 | -932 | -531 | -3791 | 661 | 500 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 352 | -156 | -4088 | 25 | 301 | 1032 | 748 | 486 | -4157 | 319 | -991 | 690 | -11 | -3687 | -39 | -1267 | 1019 | 341 | -3709 | 258 | 879 | 501 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 353 | 386 | -4061 | 421 | -302 | 231 | 438 | -2261 | -4109 | 188 | -549 | 1388 | 60 | -3694 | -71 | 552 | 426 | -337 | -783 | 1504 | 789 | 502 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 354 | -879 | 1409 | -4984 | -1583 | -578 | -465 | 1302 | -627 | -886 | 449 | 1708 | -3959 | 1019 | -3674 | -391 | -214 | -226 | -420 | 139 | 2373 | 503 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -25 | -10485 | -5900 | -894 | -1115 | -701 | -1378 | * | * | | | | | | | | | | | | |
| 355 | -1603 | -4071 | 789 | -90 | -4392 | -438 | 525 | -4142 | -667 | -4087 | 1182 | 151 | 2162 | -213 | -573 | 1170 | 360 | -1328 | 353 | -654 | 504 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 55

| | | | | | | | | | | | | | | | | | | | | | |
|---|---|---|---|---|---|---|---|---|---|---|---|---|---|---|---|---|---|---|---|---|---|
| - | -78 | -10461 | -4264 | -894 | -1115 | -1234 | -799 | * | * | | | | | | | | | | | | |
| 356 | 164 | -4006 | 1385 | 874 | -4327 | 15 | 930 | -4077 | -92 | -633 | -3095 | 1912 | -795 | -668 | -2253 | 633 | -2472 | -3628 | -4189 | 918 | 505 |
| - | -148 | -501 | 232 | 42 | -382 | 398 | 105 | -627 | 211 | -467 | -721 | 276 | 395 | 51 | 95 | 359 | 120 | -370 | -295 | -250 | |
| - | -2406 | -2237 | -739 | -24 | -5935 | -502 | -1768 | * | * | | | | | | | | | | | | |
| 357 | 1136 | -3077 | 193 | 959 | -3392 | -16 | -1254 | -3138 | -838 | -3090 | -2168 | -1232 | -210 | 698 | 362 | -1502 | 1125 | 1299 | -3264 | -2585 | 507 |
| - | -149 | -500 | 235 | 43 | -381 | 398 | 105 | -627 | 210 | -466 | -721 | 278 | 393 | 45 | 96 | 359 | 117 | -370 | -280 | -250 | |
| - | -285 | -2486 | -10292 | -60 | -4624 | -1155 | -860 | * | * | | | | | | | | | | | | |
| 358 | -701 | -3609 | 1115 | -1443 | -88 | -14 | 299 | -1392 | 895 | -3624 | -2699 | 1357 | 799 | 704 | -164 | -915 | 153 | 837 | -3794 | -3113 | 509 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9922 | -10964 | -894 | -1115 | -1613 | -571 | * | * | | | | | | | | | | | | |
| 359 | -1231 | 884 | 947 | 1343 | 1375 | 199 | -1959 | -1477 | -501 | -939 | -2788 | -729 | -3388 | 932 | -61 | -647 | -291 | -1379 | 1301 | 949 | 510 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10112 | -11154 | -894 | -1115 | -79 | -4227 | * | * | | | | | | | | | | | | |
| 360 | -422 | -4082 | -177 | -744 | -4399 | -3596 | 812 | -1474 | 1670 | -1007 | -3172 | 1163 | -3689 | -635 | 940 | -409 | -349 | 259 | 3343 | -879 | 511 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 361 | 2063 | -3835 | -284 | -2073 | -4049 | -3672 | -2345 | -3729 | -1980 | 256 | 1615 | 1147 | -3762 | 1155 | -721 | 539 | -297 | -1175 | -4086 | -3475 | 512 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 362 | -83 | -2706 | -5208 | -4573 | 1133 | 57 | -3293 | 500 | -4171 | -12 | 480 | 508 | -4473 | -3797 | -1508 | -985 | 358 | 2404 | -3163 | -2821 | 513 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 363 | -2922 | -2751 | -5249 | -4619 | -2714 | -4471 | -3353 | 366 | -4221 | -66 | -1957 | 1891 | -4523 | -3850 | -4031 | -463 | 2587 | 1278 | 2337 | -2881 | 514 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 364 | -6591 | -5749 | -7397 | -7594 | 3911 | -7189 | -3596 | -5428 | -7161 | 426 | -4871 | -5931 | -7055 | -729 | -6595 | -6411 | -6467 | 69 | 2012 | 1759 | 515 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 56

| | | | | | | | | | | | | | | | | | | | | | |
|---|---|---|---|---|---|---|---|---|---|---|---|---|---|---|---|---|---|---|---|---|---|
| 365 | -1388 | -3732 | -6389 | -5783 | -175 | -5697 | -4594 | 1828 | -5425 | 1541 | 186 | -5350 | -5603 | -4940 | -5204 | -4820 | -3937 | 2430 | 2295 | -3993 | 516 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 366 | -1199 | 728 | 2819 | 1540 | -4376 | 1163 | -2266 | -1160 | -1852 | -4079 | -3161 | -230 | -3698 | -1810 | -909 | -1034 | -1084 | -1474 | -4260 | -3585 | 517 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 367 | -3525 | -4145 | -6117 | -6472 | -6811 | -4397 | -6004 | -6617 | -6593 | -6893 | -5938 | 3991 | -5207 | -6045 | -6340 | 1494 | -990 | -1177 | -7031 | -6952 | 518 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 368 | -8351 | -7039 | -8010 | -8359 | -4914 | -7245 | 5446 | -8380 | -8236 | -7682 | -7739 | -7788 | -7602 | -7853 | -7738 | -8455 | -8411 | -8363 | 437 | -4466 | 519 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 369 | -5713 | -7209 | 4171 | -1139 | -7691 | -5309 | -4876 | -7880 | -5377 | -7635 | -7175 | -4028 | -5899 | -4617 | -6337 | -5333 | -5830 | -7322 | -7358 | -6716 | 520 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 370 | -2724 | -3336 | -3119 | -2562 | -3404 | -1240 | -2610 | -941 | -2438 | -1922 | 2315 | 1570 | -1231 | 2033 | -868 | -637 | 2484 | -1128 | -3694 | -3212 | 521 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -36 | -10485 | -5377 | -894 | -1115 | -701 | -1378 | * | * | | | | | | | | | | | | |
| 371 | -192 | -4062 | -600 | 735 | -4383 | 533 | -2221 | -4133 | -171 | -4078 | 1177 | 830 | 1627 | 1762 | -623 | 64 | -2528 | -849 | -4245 | 550 | 522 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -125 | -10450 | -3599 | -894 | -1115 | -1420 | -675 | * | * | | | | | | | | | | | | |
| 372 | -1141 | -3709 | -4623 | -4041 | -4379 | -4271 | -3670 | -3967 | -3223 | -4210 | 265 | -3864 | 529 | -3489 | 3785 | -1709 | 105 | -3678 | -4619 | -118 | 523 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1658 | -10326 | -551 | -894 | -1115 | -2638 | -253 | * | * | | | | | | | | | | | | |
| 373 | 82 | -2585 | -1301 | 254 | -2969 | 1681 | -1268 | 1213 | -960 | -2739 | -1898 | 2254 | -2584 | -871 | -1448 | 403 | -1457 | -2290 | -3024 | -2414 | 524 |
| - | -149 | -500 | 233 | 43 | -381 | 401 | 105 | -626 | 210 | -466 | -721 | 275 | 394 | 45 | 96 | 359 | 117 | -369 | -295 | -250 | |
| - | -1076 | -2568 | -1486 | -91 | -4030 | -5056 | -44 | * | * | | | | | | | | | | | | |
| 374 | -1367 | -2757 | -684 | 762 | -3061 | -2109 | 3698 | -2796 | -450 | -2756 | -1901 | -755 | -2306 | 1644 | -881 | -1230 | 1816 | -2389 | -2927 | -2269 | 526 |

FIG. 57

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -8 | -8039 | -9081 | -894 | -1115 | -4127 | -85 | * | * | | | | | | | | | | | | |
| 375 | 1394 | -1810 | -3140 | -2842 | 1387 | 2255 | -2607 | -2887 | -2712 | -3150 | -2360 | -2340 | 1262 | -2491 | -2885 | 894 | -1555 | -2316 | -3527 | -3183 | 527 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8232 | -9274 | -894 | -1115 | -3538 | -130 | * | * | | | | | | | | | | | | |
| 376 | 849 | -1609 | -3510 | -3089 | -1549 | 1636 | -2112 | -1290 | -2796 | 2090 | -970 | -2625 | -3110 | -2498 | -2731 | -2012 | -1618 | -1193 | -2101 | 1259 | 528 |
| - | -150 | -501 | 232 | 44 | -382 | 401 | 105 | -627 | 214 | -467 | -721 | 274 | 393 | 48 | 97 | 358 | 116 | -370 | -295 | -250 | |
| - | -1693 | -536 | -9575 | -26 | -5789 | -2879 | -211 | * | * | | | | | | | | | | | | |
| 377 | -226 | -3139 | 1871 | 1010 | -3451 | 1305 | -1240 | -3212 | -871 | -3152 | -2238 | 1334 | 134 | 921 | -1397 | 81 | -1585 | -2757 | -3321 | -2616 | 530 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -8935 | -9977 | -894 | -1115 | -86 | -4118 | * | * | | | | | | | | | | | | |
| 378 | -809 | -2678 | 397 | -4494 | 2346 | 529 | -3251 | 1288 | -4103 | -791 | 89 | -897 | -4434 | -3738 | -3925 | 880 | -2783 | 1385 | -3135 | -2791 | 531 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10447 | -11489 | -894 | -1115 | -369 | -2148 | * | * | | | | | | | | | | | | |
| 379 | 562 | -3868 | -462 | -775 | -69 | -236 | -422 | -464 | -709 | 1303 | 473 | -855 | -1549 | 127 | -937 | 83 | 468 | -107 | -4111 | -249 | 532 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 380 | -743 | -3979 | -1125 | -92 | -111 | -3625 | -2289 | -874 | -1891 | -3974 | -3082 | -613 | -987 | 1020 | -679 | 1753 | 2083 | 394 | 850 | -3542 | 533 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 381 | -962 | 658 | -514 | 224 | 10 | -4134 | 1018 | -475 | -3061 | 495 | -333 | -3271 | -4202 | 431 | 2132 | -150 | -966 | 738 | -3403 | 395 | 534 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 382 | 268 | 2114 | -4241 | 20 | 1894 | -630 | 232 | -2390 | -3421 | 223 | 1430 | 762 | -4307 | 17 | -3539 | -3281 | 1630 | -2291 | 377 | -815 | 535 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 383 | -86 | -3754 | -986 | -2134 | -253 | 2389 | -2380 | -1076 | -705 | -3711 | -2881 | -246 | -3791 | -531 | -2512 | 755 | -2599 | -3301 | 3597 | 561 | 536 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 58

| | | | | | | | | | | | | | | | | | | | | | |
|---|---|---|---|---|---|---|---|---|---|---|---|---|---|---|---|---|---|---|---|---|---|
| - | -1 | -10485 | -11527 | -894 | -1115 | -701 | -1378 | * | * | | | | | | | | | | | | |
| 384 | 237 | -4070 | 1550 | -54 | -92 | 1244 | -2259 | -4124 | 785 | -1746 | 725 | 167 | 902 | -1802 | -59 | -911 | -2560 | -1720 | 353 | -177 | 537 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -72 | -10485 | -4386 | -894 | -1115 | -701 | -1378 | * | * | | | | | | | | | | | | |
| 385 | -63 | -4029 | 2080 | -1002 | 334 | -1340 | -117 | -1612 | 739 | -1661 | -3118 | 1729 | -1558 | 34 | -1142 | 84 | 229 | -611 | -4213 | -3531 | 538 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10415 | -11457 | -894 | -1115 | -1898 | -451 | * | * | | | | | | | | | | | | |
| 386 | -773 | -4031 | -704 | -52 | -4352 | 698 | -2190 | 201 | 967 | -4047 | -3120 | 312 | 1382 | 1007 | 1503 | 529 | -2497 | -1484 | -4214 | -3532 | 539 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -881 | -10415 | -1133 | -894 | -1115 | -1898 | -451 | * | * | | | | | | | | | | | | |
| 387 | 741 | -3304 | 1598 | -1134 | -3623 | -614 | -1467 | -3373 | -107 | -1031 | -2393 | 849 | 1064 | -1008 | 474 | 1233 | -55 | -2925 | -3488 | -2806 | 540 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1176 | -9537 | -847 | -894 | -1115 | -4520 | -64 | * | * | | | | | | | | | | | | |
| 388 | -1675 | -3241 | 2685 | 911 | -3524 | 547 | -1205 | -3308 | -962 | -68 | -2368 | 673 | -2559 | 1497 | -1539 | -1496 | -1645 | -2848 | -3420 | -2662 | 541 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -893 | -8368 | -1126 | -894 | -1115 | -5157 | -41 | * | * | | | | | | | | | | | | |
| 389 | 1055 | -1975 | -432 | 972 | -2289 | -1557 | -243 | -2015 | 1436 | -1999 | -1100 | -219 | 560 | 202 | -320 | -492 | 1175 | -1600 | -2198 | -1539 | 542 |
| - | -151 | -505 | 234 | 40 | -386 | 407 | 100 | -632 | 205 | -471 | -715 | 279 | 393 | 51 | 90 | 364 | 119 | -375 | -269 | -243 | |
| - | -2651 | -632 | -2354 | -3521 | -132 | -4314 | -74 | * | * | | | | | | | | | | | | |
| 390 | 3077 | -1244 | -3035 | -3163 | -3572 | -1512 | -2789 | -3308 | -3117 | -3599 | -2716 | -2079 | -2284 | -2759 | -3042 | 1540 | -1074 | -2263 | -3808 | -3620 | 568 |
| - | -147 | -500 | 232 | 45 | -381 | 398 | 105 | -627 | 212 | -466 | -721 | 277 | 393 | 45 | 95 | 359 | 117 | -370 | -295 | -250 | |
| - | -2640 | -257 | -8518 | -44 | -5048 | -2662 | -248 | * | * | | | | | | | | | | | | |
| 391 | 837 | -2471 | 292 | 1046 | -2759 | -2064 | -726 | -2487 | 1705 | -2473 | 1101 | -712 | -2156 | -277 | 373 | -974 | -1017 | 396 | -2674 | 1075 | 570 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8461 | -9503 | -894 | -1115 | -5129 | -42 | * | * | | | | | | | | | | | | |
| 392 | -3113 | -2830 | 1818 | -4013 | 1528 | -4239 | -1573 | -2480 | -3727 | 986 | -2078 | 186 | -4225 | -3165 | -3598 | -3353 | -3036 | -2449 | 2248 | 3302 | 571 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8461 | -9503 | -894 | -1115 | -3497 | -134 | * | * | | | | | | | | | | | | |

FIG. 59

| | | | | | | | | | | | | | | | | | | | | | |
|---|---|---|---|---|---|---|---|---|---|---|---|---|---|---|---|---|---|---|---|---|---|
| 393 | 1024 | -2812 | 841 | -685 | -3146 | -2343 | -968 | -2875 | 723 | -2815 | 975 | -982 | -2432 | 1215 | 2615 | -1268 | -1317 | -2443 | -2971 | -2324 | 572 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8715 | -9758 | -894 | -1115 | -5040 | -45 | * | * | | | | | | | | | | | | |
| 394 | -1389 | -2365 | -1493 | 1183 | -2536 | -2440 | -1087 | 640 | 869 | -2303 | -1500 | -1174 | -2521 | 995 | 809 | -1382 | -1321 | 1849 | 2205 | -2088 | 573 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8715 | -9758 | -894 | -1115 | -3388 | -145 | * | * | | | | | | | | | | | | |
| 395 | -252 | -2857 | 465 | 727 | -3176 | -2365 | -1023 | 659 | 1621 | -2872 | -1947 | -1002 | 844 | 1191 | 1114 | -1272 | -1330 | -2478 | 2000 | -2361 | 574 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -8936 | -9978 | -894 | -1115 | -533 | -1694 | * | * | | | | | | | | | | | | |
| 396 | 835 | -3773 | 288 | -1664 | -570 | -3328 | -71 | -3812 | 1798 | 672 | 321 | -1971 | -3421 | 504 | 1116 | 821 | -2286 | -3385 | -3968 | -3297 | 575 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10162 | -11204 | -894 | -1115 | -608 | -1540 | * | * | | | | | | | | | | | | |
| 397 | 823 | -3170 | -879 | -864 | -3221 | -1232 | -2575 | 1277 | -838 | 530 | -193 | -665 | -3925 | -2353 | -177 | -750 | -116 | 986 | -3543 | 1959 | 576 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10384 | -11426 | -894 | -1115 | -2206 | -353 | * | * | | | | | | | | | | | | |
| 398 | -2534 | -3999 | 1738 | -525 | -4317 | -3509 | -2167 | -7 | 2491 | -1778 | 797 | -2145 | -29 | -526 | 1325 | -1394 | -495 | -3619 | -4184 | -3503 | 577 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10384 | -11426 | -894 | -1115 | -699 | -1380 | * | * | | | | | | | | | | | | |
| 399 | -258 | -2854 | -4113 | -3531 | -2836 | -1419 | 106 | -1220 | -3309 | 2276 | 2476 | 66 | -4253 | 1410 | -3454 | -795 | -758 | -2284 | -3287 | -2908 | 578 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10447 | -11489 | -894 | -1115 | -369 | -2148 | * | * | | | | | | | | | | | | |
| 400 | 2748 | 75 | -1809 | -4507 | -2673 | 1064 | -3284 | -415 | -4122 | 585 | -1920 | -4034 | -4466 | -750 | -3952 | -3496 | -2818 | -566 | -3175 | -681 | 579 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 401 | 1007 | -2722 | -5068 | -4442 | -260 | -922 | -3266 | -1143 | -4070 | 417 | 924 | 1587 | -4454 | -862 | -171 | -6 | -794 | -314 | 1884 | 2319 | 580 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 402 | 2091 | -2826 | -4410 | -350 | -2798 | -765 | -3108 | 886 | -1305 | -185 | 571 | -1268 | -4343 | -3320 | -3627 | -142 | 257 | 1282 | -3267 | -2900 | 581 |

FIG. 60

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 403 | -316 | -2736 | -5254 | -4620 | 2973 | -4458 | -3317 | 833 | -4215 | 1354 | -1929 | -4102 | -4507 | -3835 | -4014 | -1749 | -2851 | 505 | 890 | 1656 | 582 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 404 | -2877 | -2707 | -5197 | -688 | -2661 | -4422 | -3292 | 2104 | -4164 | 1293 | 2607 | -4060 | -4472 | 1015 | -3972 | -762 | 653 | -558 | 870 | -503 | 583 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 405 | -102 | -249 | -5221 | -4585 | 1419 | -4427 | 1872 | -67 | -4181 | 2348 | 1741 | -1301 | -4477 | -259 | -3983 | -3512 | -2821 | -1289 | -3164 | -2822 | 584 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 406 | 1121 | -2789 | -4966 | -4359 | -2774 | 272 | -3299 | -1241 | -4015 | 817 | 573 | -3967 | -4463 | -3694 | -1461 | 860 | 2532 | -2226 | -3266 | -2918 | 585 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 407 | -1162 | 504 | -5204 | -4569 | 278 | -1169 | 2392 | -705 | -4168 | 978 | 1453 | -1329 | -4472 | -3794 | 1338 | 1072 | -2817 | -857 | 2168 | 578 | 586 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 408 | -197 | -4091 | 834 | 483 | -4411 | -3593 | -2252 | -1792 | -929 | -1839 | -3180 | -524 | 2750 | -56 | 1482 | -663 | -287 | -1727 | -4274 | -3592 | 587 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1579 | -10485 | -590 | -894 | -1115 | -701 | -1378 | * | * | | | | | | | | | | | | |
| 409 | 108 | -1882 | -2115 | -1557 | 277 | 1324 | -1460 | -1493 | -1415 | -235 | -1061 | 540 | -2792 | 356 | -1750 | 116 | -1418 | -1344 | -2264 | 2967 | 588 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -8910 | -9952 | -894 | -1115 | -29 | -5632 | * | * | | | | | | | | | | | | |
| 410 | -1283 | -4239 | -1531 | -5491 | -6763 | 3626 | -5627 | -6578 | -6019 | -6793 | -5871 | -4794 | -5195 | -5548 | -437 | -1285 | -4041 | -1415 | -6951 | -6754 | 589 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 411 | -611 | -2728 | -5019 | -4396 | -875 | -4395 | -346 | 1500 | -4034 | -2578 | 475 | 966 | -4447 | -712 | -1081 | 19 | 2168 | 1067 | 647 | 877 | 590 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 61

| | | | | | | | | | | | | | | | | | | | | | |
|---|---|---|---|---|---|---|---|---|---|---|---|---|---|---|---|---|---|---|---|---|---|
| - | -1 | -10485 | -11527 | -894 | -1115 | -701 | -1378 | * | * | | | | | | | | | | | | |
| 412 | -463 | -3750 | -5545 | -5211 | -4778 | -1375 | -4650 | -4375 | -1470 | -1705 | -3960 | -4554 | 3885 | -4708 | -5002 | -885 | -483 | -587 | -5170 | -4852 | 591 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 413 | -406 | 2352 | -733 | -3127 | 323 | -4097 | -2866 | 504 | -467 | 159 | -2214 | -493 | -1071 | 794 | 174 | -46 | -1390 | 1009 | -3440 | 1877 | 592 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 414 | -4702 | -4203 | -7370 | -7027 | 262 | -7166 | -7004 | 3284 | -6962 | -3594 | 268 | -6819 | -6917 | -6860 | -7081 | -6511 | 232 | 2105 | -6428 | -5951 | 593 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 415 | -7127 | -6045 | -7502 | -7856 | 2309 | -7386 | -309 | -6013 | -7401 | -5320 | 1996 | -5995 | -7240 | -538 | -6768 | -6634 | -6976 | -6169 | -2816 | 4339 | 594 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 416 | -1722 | -4302 | -3604 | -3359 | -4183 | -1214 | -3510 | -4733 | -3410 | -4822 | -4070 | -46 | -4701 | 1972 | -3807 | 1462 | -3584 | -4336 | 1026 | 3906 | 595 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 417 | -1586 | -4606 | 633 | -4189 | -6820 | 3298 | -4973 | -6677 | -5288 | -6784 | -5927 | -4169 | -38 | -4749 | -53 | 525 | -4212 | -5576 | -6941 | -6442 | 596 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 418 | -2645 | -4116 | 2070 | 1526 | -1241 | -3611 | 1940 | -4185 | -1860 | -4131 | -3206 | -2247 | -65 | 1591 | -747 | -2525 | 1067 | -3737 | -4300 | 1627 | 597 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 419 | -2625 | -4031 | -1060 | 3238 | -618 | -1292 | -2271 | -4056 | -681 | -1825 | 1023 | -542 | -3702 | -1821 | -265 | -1370 | -1030 | -1215 | -4231 | -936 | 598 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 420 | -1034 | -2720 | -5079 | -1279 | 1571 | -1417 | 58 | 1638 | -4078 | -417 | 905 | -844 | -4456 | 2001 | -3927 | -491 | -2813 | -331 | 2033 | 1810 | 599 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

FIG. 62

| | | | | | | | | | | | | | | | | | | | | | |
|---|---|---|---|---|---|---|---|---|---|---|---|---|---|---|---|---|---|---|---|---|---|
| 421 | -2907 | -4290 | 618 | -962 | -4563 | 2854 | 664 | -4291 | -2183 | -1667 | -3405 | -2448 | -1378 | -2104 | -2699 | 49 | 404 | -3889 | -4504 | 1570 | 600 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -50 | -10485 | -4914 | -894 | -1115 | -701 | -1378 | * | * | | | | | | | | | | | | |
| 422 | -474 | 598 | -1486 | -1922 | 308 | -114 | -3056 | -1113 | -3495 | -4 | 3600 | -1012 | -4294 | 413 | 445 | -1247 | -830 | -1236 | 2604 | 382 | 601 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10437 | -11479 | -894 | -1115 | -328 | -2299 | * | * | | | | | | | | | | | | |
| 423 | 238 | -4087 | 1128 | -891 | -4406 | -367 | 177 | -1155 | -238 | -2200 | -225 | 301 | 111 | -579 | -2341 | 744 | 2247 | -1726 | -4272 | -3591 | 602 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -125 | -10485 | -3606 | -894 | -1115 | -701 | -1378 | * | * | | | | | | | | | | | | |
| 424 | -1091 | -3993 | 833 | -617 | 75 | 2430 | -131 | -4063 | -51 | -4009 | -3083 | 1846 | -3587 | -162 | -2243 | -2402 | -424 | -3615 | -4177 | 638 | 603 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10362 | -11404 | -894 | -1115 | -2391 | -305 | * | * | | | | | | | | | | | | |
| 425 | -376 | -3984 | 1222 | -100 | 601 | 1631 | -153 | -4054 | 326 | -4000 | -3073 | 48 | -566 | 613 | -2233 | -580 | -473 | 500 | -4168 | 393 | 604 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -30 | -10362 | -5680 | -894 | -1115 | -2391 | -305 | * | * | | | | | | | | | | | | |
| 426 | 127 | -3961 | 870 | -877 | -4283 | 489 | -166 | -4033 | 1214 | -3977 | 113 | 1373 | 475 | -558 | 533 | -106 | -314 | -3583 | 1977 | 258 | 605 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1169 | -10334 | -851 | -894 | -1115 | -2590 | -262 | * | * | | | | | | | | | | | | |
| 427 | -459 | -1653 | -3572 | -408 | 1776 | 1540 | -2061 | 1132 | -2665 | -1506 | 970 | -2687 | -708 | -294 | -2642 | -256 | -1675 | 773 | -2101 | 863 | 606 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -408 | -9169 | -2033 | -894 | -1115 | -3333 | -151 | * | * | | | | | | | | | | | | |
| 428 | -1483 | -2965 | 465 | 1104 | -3283 | 736 | -1106 | -3037 | 263 | -2980 | -2058 | 1862 | 689 | -650 | -1217 | 452 | 1160 | -2586 | -3148 | -2458 | 607 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -309 | -8946 | -2391 | -894 | -1115 | -4938 | -48 | * | * | | | | | | | | | | | | |
| 429 | -1303 | 1409 | 1871 | -648 | -2928 | -2279 | -929 | -2639 | 778 | -2635 | -1750 | -940 | -2373 | -489 | 967 | 834 | -1240 | -2248 | 3918 | -2204 | 608 |
| - | -149 | -501 | 233 | 44 | -378 | 400 | 104 | -628 | 212 | -468 | -722 | 277 | 394 | 47 | 94 | 358 | 117 | -369 | -296 | -251 | |
| - | -1363 | -713 | -9685 | -784 | -1254 | -4263 | -77 | * | * | | | | | | | | | | | | |
| 430 | -1378 | -1464 | 1505 | -149 | -1448 | -383 | -1564 | 2094 | -1845 | 353 | -656 | -2001 | 191 | -1651 | -2009 | -1790 | -1319 | 496 | 1890 | -1511 | 612 |

FIG. 63

| | | | | | | | | | | | | | | | | | | | | | |
|---|---|---|---|---|---|---|---|---|---|---|---|---|---|---|---|---|---|---|---|---|---|
| - | -148 | -501 | 233 | 47 | -382 | 400 | 104 | -628 | 209 | -467 | -722 | 276 | 392 | 44 | 94 | 359 | 122 | -369 | -296 | -251 | |
| - | -3892 | -196 | -4066 | -18 | -6308 | -4205 | -80 | * | * | | | | | | | | | | | | |
| 431 | -1247 | -2712 | 176 | 907 | -3030 | 460 | -881 | -2778 | 772 | -2727 | 930 | -858 | -2315 | 649 | 651 | 1202 | -1186 | 972 | -2898 | -2217 | 614 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8729 | -9771 | -894 | -1115 | -997 | -1003 | * | * | | | | | | | | | | | | |
| 432 | -1003 | -2598 | 3026 | -2324 | -66 | -1180 | -2211 | -860 | -2179 | -1281 | -1775 | -2452 | 1008 | 33 | -2508 | -2445 | -552 | -2055 | -2990 | 1948 | 615 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9851 | -10893 | -894 | -1115 | -2650 | -250 | * | * | | | | | | | | | | | | |
| 433 | -4259 | -6085 | 168 | -389 | -6338 | -1353 | -3437 | -6205 | -1184 | -6026 | -5374 | -2764 | 3905 | -3099 | 443 | -3918 | -4304 | -5704 | -6158 | -5251 | 616 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2578 | -9938 | -266 | -894 | -1115 | -3963 | -96 | * | * | | | | | | | | | | | | |
| 434 | -767 | -1577 | -1043 | -1067 | -3143 | 1519 | -1529 | -2894 | -1441 | -3025 | -2184 | 3091 | -2118 | -1234 | -1831 | -873 | 1385 | -2164 | -3243 | -2736 | 617 |
| - | -150 | -502 | 232 | 42 | -383 | 400 | 112 | -623 | 209 | -468 | -723 | 278 | 394 | 43 | 93 | 358 | 118 | -362 | -297 | -252 | |
| - | -2537 | -712 | -2204 | -2592 | -262 | -5349 | -36 | * | * | | | | | | | | | | | | |
| 435 | -516 | -984 | -1115 | -725 | -1277 | -1618 | -728 | 1389 | -611 | -1043 | -403 | 2411 | -1864 | -536 | -925 | -734 | 1361 | -304 | -1662 | -1201 | 627 |
| - | -149 | -500 | 233 | 43 | -378 | 398 | 105 | -624 | 210 | -466 | -721 | 277 | 394 | 45 | 96 | 359 | 117 | -370 | -295 | -250 | |
| - | -2189 | -746 | -2440 | -82 | -4184 | -3801 | -107 | * | * | | | | | | | | | | | | |
| 436 | -842 | -1512 | -1081 | -942 | -2142 | 956 | -1175 | -1815 | -1029 | -2033 | 3596 | 2383 | -2133 | -939 | -1362 | -970 | -987 | -1484 | -2412 | -1909 | 629 |
| - | -149 | -500 | 232 | 43 | -377 | 398 | 110 | -627 | 210 | -466 | -721 | 277 | 395 | 45 | 95 | 360 | 117 | -370 | -295 | -250 | |
| - | -2587 | -268 | -8465 | -46 | -4987 | -434 | -1945 | * | * | | | | | | | | | | | | |
| 437 | 667 | 22 | 2713 | -265 | 492 | -1542 | -1977 | -915 | -345 | -705 | -2762 | 766 | -3404 | -320 | -2078 | -912 | -2257 | -3252 | -3874 | 750 | 631 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10119 | -11161 | -894 | -1115 | -2057 | -397 | * | * | | | | | | | | | | | | |
| 438 | 163 | 2158 | -139 | 334 | -3981 | -1132 | 428 | 691 | -1645 | -1918 | -2818 | 2472 | -3467 | 59 | -2142 | 214 | -946 | 312 | -3932 | -3284 | 632 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10192 | -11234 | -894 | -1115 | -2369 | -311 | * | * | | | | | | | | | | | | |
| 439 | -2407 | 3398 | -136 | 1040 | -4126 | -1288 | -2049 | -3861 | -1638 | -267 | -2922 | -2032 | -3481 | -62 | 2733 | -1148 | -976 | -3437 | -4023 | -448 | 633 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 64

| | | | | | | | | | | | | | | | | | | | | | |
|---|---|---|---|---|---|---|---|---|---|---|---|---|---|---|---|---|---|---|---|---|---|
| - | -2 | -10227 | -11269 | -894 | -1115 | -2362 | -312 | * | * | | | | | | | | | | | | |
| 440 | -191 | 1100 | -2291 | 1293 | -977 | 303 | -2067 | 945 | 786 | -3856 | -2944 | 291 | -3499 | 486 | 540 | -213 | 700 | -1038 | -4045 | -712 | 634 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10255 | -11297 | -894 | -1115 | -3026 | -189 | * | * | | | | | | | | | | | | |
| 441 | 458 | 1520 | -130 | -1724 | -4201 | 839 | -2056 | -3948 | 280 | 54 | 1209 | 449 | -187 | -122 | 606 | 683 | 410 | -3504 | -4070 | -3390 | 635 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -186 | -10255 | -3060 | -894 | -1115 | -1934 | -438 | * | * | | | | | | | | | | | | |
| 442 | -848 | -3504 | 1165 | -27 | 589 | -713 | -2036 | -749 | -1675 | -434 | 2480 | 2087 | -3452 | -1624 | -577 | 196 | 365 | -3065 | -3759 | -3152 | 636 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10119 | -11162 | -894 | -1115 | -3527 | -131 | * | * | | | | | | | | | | | | |
| 443 | 189 | -3751 | -781 | 227 | -4059 | -151 | -1947 | -1353 | -1532 | -3762 | 1222 | 908 | 1881 | 683 | 871 | -1188 | -1039 | -1510 | 2049 | 1195 | 637 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10119 | -11162 | -894 | -1115 | -1708 | -527 | * | * | | | | | | | | | | | | |
| 444 | -54 | -2472 | -1427 | -4321 | 1165 | 248 | -3054 | -952 | -3923 | 18 | 1178 | -3820 | -823 | -908 | -3734 | -3268 | 33 | -515 | 4459 | 1654 | 638 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10222 | -11264 | -894 | -1115 | -1427 | -671 | * | * | | | | | | | | | | | | |
| 445 | -818 | -3941 | 624 | 13 | 779 | -979 | -146 | -1114 | 967 | -1627 | -3030 | 1286 | -1468 | 599 | 716 | 1074 | -503 | -723 | -4124 | -3442 | 639 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -50 | -10311 | -4899 | -894 | -1115 | -2734 | -235 | * | * | | | | | | | | | | | | |
| 446 | 812 | 2734 | 1602 | 985 | -1033 | 170 | 424 | -1653 | -1827 | -3541 | -2706 | -2203 | 275 | -1774 | -488 | -369 | -2401 | -1049 | 1707 | 227 | 640 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10262 | -11304 | -894 | -1115 | -2217 | -350 | * | * | | | | | | | | | | | | |
| 447 | -1344 | -3417 | 267 | 1427 | 889 | -3595 | -2287 | 749 | -113 | -505 | 855 | -506 | -3681 | -585 | -2447 | -520 | 832 | -1416 | -3725 | 2123 | 641 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10289 | -11331 | -894 | -1115 | -1655 | -551 | * | * | | | | | | | | | | | | |
| 448 | 497 | -3964 | -282 | -89 | 28 | -3465 | 2394 | -4035 | 896 | -3980 | -3053 | 1233 | 744 | 1063 | 609 | -1403 | -812 | -804 | -4147 | 670 | 642 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -117 | -10337 | -3698 | -894 | -1115 | -2571 | -266 | * | * | | | | | | | | | | | | |

FIG. 65

| | | | | | | | | | | | | | | | | | | | | | |
|---|---|---|---|---|---|---|---|---|---|---|---|---|---|---|---|---|---|---|---|---|---|
| 449 | 446 | -3864 | 535 | 716 | -4185 | -1034 | -2025 | -1451 | 913 | -292 | -235 | -738 | -3460 | 1106 | 1382 | -483 | 982 | -3486 | -4048 | -640 | 643 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -618 | -10222 | -1525 | -894 | -1115 | -3170 | -170 | * | * | | | | | | | | | | | | |
| 450 | -1976 | -3458 | 2309 | 892 | -3776 | -61 | -1599 | -3530 | -283 | -3473 | -2550 | 1526 | -3027 | -1143 | 698 | 602 | 739 | -3079 | -3640 | -2951 | 644 |
| - | -147 | -509 | 242 | 49 | -387 | 396 | 105 | -633 | 214 | -473 | -701 | 274 | 385 | 42 | 94 | 360 | 125 | -378 | -261 | -244 | |
| - | -1274 | -1480 | -2132 | -3030 | -188 | -4446 | -68 | * | * | | | | | | | | | | | | |
| 451 | -159 | -1691 | -3708 | -3099 | 1577 | -3286 | -2133 | -73 | 715 | 120 | 910 | -2784 | -3340 | -2483 | -488 | 1106 | 1793 | -78 | -2141 | -1787 | 659 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9234 | -10276 | -894 | -1115 | -3750 | -111 | * | * | | | | | | | | | | | | |
| 452 | 246 | 1159 | 372 | 1702 | 318 | -2656 | -1318 | -3058 | -914 | -648 | 512 | 994 | -26 | -871 | 477 | -444 | 700 | -2651 | -3255 | -2595 | 660 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9312 | -10354 | -894 | -1115 | -981 | -1019 | * | * | | | | | | | | | | | | |
| 453 | 1069 | -2335 | -4412 | 1 | 26 | -3947 | -2797 | 183 | 41 | 1807 | 224 | -3463 | -4001 | -710 | -3406 | -1428 | -885 | -1752 | 2785 | 402 | 661 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10014 | -11056 | -894 | -1115 | -2224 | -347 | * | * | | | | | | | | | | | | |
| 454 | 277 | -3251 | -2499 | -1946 | 1305 | -1730 | 1022 | 590 | 824 | -1777 | -2394 | -2198 | -1131 | 140 | 1402 | -451 | -2290 | -2769 | -3560 | 2663 | 662 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -210 | -10101 | -2891 | -894 | -1115 | -524 | -1716 | * | * | | | | | | | | | | | | |
| 455 | -950 | -3858 | 39 | 480 | -4178 | -1336 | -267 | -277 | 612 | -244 | -4 | 227 | 37 | 2036 | 179 | 175 | 205 | -383 | -4041 | -3359 | 663 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10214 | -11256 | -894 | -1115 | -932 | -1071 | * | * | | | | | | | | | | | | |
| 456 | 728 | -3966 | -624 | 909 | 812 | -1165 | 597 | -542 | 105 | -358 | -3057 | -137 | -831 | 1711 | 170 | -2393 | -962 | -527 | -4154 | 853 | 664 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10357 | -11399 | -894 | -1115 | -2427 | -297 | * | * | | | | | | | | | | | | |
| 457 | 66 | -2591 | -5105 | -4470 | -188 | -1573 | -3183 | 2992 | -1564 | 377 | -1794 | -3956 | -4361 | -3689 | -3867 | -107 | -2705 | 805 | -3049 | 493 | 665 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10357 | -11399 | -894 | -1115 | -2427 | -297 | * | * | | | | | | | | | | | | |
| 458 | 771 | -3980 | 870 | -586 | -4301 | -3482 | -2141 | -250 | 2057 | -2375 | -115 | -992 | -830 | 1327 | -298 | 497 | 102 | -3602 | -4164 | -721 | 666 |

FIG. 66

| | | | | | | | | | | | | | | | | | | | | | |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10357 | -11399 | -894 | -1115 | -2427 | -297 | * | * | | | | | | | | | | | | |
| 459 | 824 | -3981 | -2356 | -648 | -4302 | 961 | -2141 | -4052 | 1359 | -3997 | -3070 | 753 | 459 | -578 | 667 | 926 | 246 | -3603 | 956 | -564 | 667 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10357 | -11399 | -894 | -1115 | -178 | -3104 | * | * | | | | | | | | | | | | |
| 460 | -262 | 504 | -5193 | -4559 | -2662 | -1787 | -3291 | -193 | -4160 | 1812 | 2808 | -4058 | -4471 | -44 | 1634 | -1315 | -2817 | 405 | -3165 | -2822 | 668 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 461 | 608 | -3114 | 1889 | -2942 | -3135 | -1460 | -2791 | 1522 | -2790 | -416 | -2294 | 1311 | -4111 | -449 | -3103 | -610 | -373 | 1203 | -3513 | -3084 | 669 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 462 | 1064 | -4092 | 352 | -287 | -4413 | 692 | 1287 | -4164 | -609 | -518 | -3181 | 810 | 565 | -79 | 69 | 879 | -1440 | -3714 | -4275 | 333 | 670 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 463 | 1044 | -2707 | -5195 | -1784 | 2589 | -2059 | -3291 | 959 | -1193 | 1067 | -1910 | -4058 | -4471 | -3790 | -3971 | -646 | -403 | 212 | 1583 | -2821 | 671 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 464 | -5309 | -5869 | -6219 | -1531 | -6756 | -5764 | 2106 | -1505 | -2098 | -5643 | 8 | -4432 | -5670 | -483 | 3918 | -5184 | -4930 | -5825 | -5467 | -5419 | 672 |
| - | * | * | * | * | * | * | * | * | * | * | * | * | * | * | * | * | * | * | * | * | |
| - | * | * | * | * | * | * | * | * | 0 | | | | | | | | | | | | |

PLANTS WITH REDUCED ACTIVITY OF A CLASS 3 BRANCHING ENZYME

CROSS-REFERENCE TO RELATED APPLICATIONS

This application is a U.S. national stage application of International Application No. PCT/EP2004/010985, filed on Sep. 29, 2004, which claims the benefit of European Patent Application No. 03090325.6, filed Sep. 30, 2003, the disclosures of each of which are herein incorporated by reference in their entireties.

BACKGROUND OF THE INVENTION (i) Field of the Invention

The present invention relates to plant cells and plants, which are genetically modified, wherein the genetic modification leads to the reduction of the activity of a Class 3 vegetable branching enzyme in comparison with corresponding wild type plant cells or wild type plants that have not been genetically modified. Furthermore, the present invention relates to means and methods for the manufacture of such plant cells and plants. Plant cells and plants of this type synthesise a modified starch. The present invention therefore also relates to the starch synthesised by the plant cells and plants according to the invention as well as to methods for the manufacture of the starch and to the manufacture of starch derivatives of this starch. Furthermore, the present invention relates to nucleic acids coding a Class 3 branching enzyme, vectors, host cells, plant cells and plants containing such nucleic acid molecules.

(ii) Description of the Related Art

With regard to the increasing importance currently attributed to vegetable constituents as renewable raw material sources, one of the tasks of biotechnological research is to endeavour to adapt these vegetable raw materials to suit the requirements of the processing industry. Furthermore, in order to enable regenerating raw materials to be used in as many areas of application as possible, it is necessary to achieve a large variety of materials.

Polysaccharide starch is made up of chemically uniform base components, the glucose molecules, but constitutes a complex mixture of different molecule forms, which exhibit differences with regard to the degree of polymerisation and branching, and therefore differ strongly from one another in their physical-chemical characteristics. Discrimination is made between amylose starch, an essentially unbranched polymer made from α-1,4-glycosidically linked glucose units, and the amylopectin starch, a branched polymer, in which the branches come about by the occurrence of additional α-1,6-glycosidic links. A further essential difference between amylose and amylopectin lies in the molecular weight. While amylose, depending on the origin of the starch, has a molecular weight of $5\times10^5$-$10^6$ Da, that of the amylopectin lies between $10^7$ and $10^8$ Da. The two macromolecules can be differentiated by their molecular weight and their different physical-chemical characteristics, which can most easily be made visible by their different iodine bonding characteristics.

Amylose has long been looked upon as a linear polymer, consisting of □-1,4-glycosidically linked □-D-glucose monomers. In more recent studies, however, the presence of □-1,6-glycosidic branching points (ca. 0.1%) has been shown (Hizukuri and Takagi, Carbohydr. Res. 134, (1984), 1-10; Takeda et al., Carbohydr. Res. 132, (1984), 83-92).

Amylopectin constitutes a complex mixture of differently branched glucose chains. In contrast to amylose, amylopectin is more strongly branched. According to textbook information (Voet and Voet, Biochemistry, John Wiley & Sons, 1990), on average, the α-1,6 branches occur every 24 to 30 glucose residues. This is equivalent to a degree of branching of ca. 3%-4%. The figures for the degree of branching are variable and are dependent on the origin (e.g. plant species, plant type etc.) of the appropriate starch. In typical plants used for the industrial production of starch, such as maize, wheat or potato, for example, the synthesised starch consists of ca. 20%-30% amylose starch and ca. 70%-80% amylopectin starch.

The functional characteristics of the starch, along with the amylose/amylopectin ratio and the phosphate content, are strongly affected by the molecular weight, the pattern of the side chain distribution, the ion concentration, the lipid and protein content, the average grain size of the starch and the grain morphology of the starch etc. At the same time, by way of example, the solubility, the retrogradation behaviour, the water bonding capability, the film formation characteristics, the viscosity, the sticking characteristics, the freezing-thawing stability, the acid stability, the gelling strength etc. must be mentioned as important functional characteristics. The grain size of the starch can also be important for different applications.

Branching enzymes, which are also abbreviated by the designation "BE" (from Branching Enzyme; E.C. 2.4.1.18), catalyse the introduction of α-1,6 branches in α-1,4-glucans. Branching enzymes and the nucleic or amino acid sequences that characterise them are known from widely different organisms, such as bacteria, microbial fungi, mammals, algae and higher plants, for example. As only plants synthesise starch, while the above-mentioned non-vegetable organisms (e.g. bacteria, fungi and mammals) synthesise glycogen, the related branching enzymes, which are involved in the synthesis of the appropriate polymer, can also be sub-divided into glycogen branching enzymes and starch branching enzymes. Plants are therefore starch branching enzymes, which are often also referred to as Q-enzymes in older literature.

In all plant species that have been investigated up to now, the branching enzymes described can be associated with two different classes (Burton et al., 1995, Plant Journal 7, 3-15; Mizuno et al., 2001, Plant Cell Physiol. 42(4), 349-357). The association with these classes, sometimes designated in the literature with A or 2 respectively and B or 1 respectively, is based on the comparison of derived protein sequences.

As different nomenclatures have been used in the past for designating and classifying branching enzymes, Smith-White and Preiss (1994, Plant Molecular Biology Reporter 12, 67-71) (1994, Plant Molecular Biology Reporter 12, 67-71) have proposed a system for standardising this nomenclature, in which the association with the two classes of vegetable branching enzymes is also based on the comparison of derived protein sequences (Larsson et al., 1998, Plant Mol. Biol. 37, 505-511). According to this nomenclature, those vegetable branching enzymes, the amino acid sequence of which has a higher degree of identity with that of branching enzyme I of maize (GenBank Acc: D11081), is to be designated as a Class 1 branching enzyme, and those vegetable branching enzymes, the coding amino acid sequence of which has a higher degree of identity with that of branching enzyme II of maize (GenBank Acc: AF072725), is to be designated as a Class 2 branching enzyme. The designation of gene products, which are coding for branching enzymes, are, in accordance with the nomenclature of Smith-White and Preiss, to be incorporated in the already existing nomenclature by means of E.C. numbers. This results in the so-called GPN (Gene Product Number) Codes for the two classes, namely GPN 2.2.4.1.18:1 for Class 1 branching enzymes and GPN 2.2.4.18:2 for Class 2 branching enzymes.

The following vegetable or starch branching enzymes therefore belong to Class 1 (GPN 2.2.1.18:1) according to the nomenclature proposed by Smith-White and Preiss (1994, Plant Molecular Biology Reporter 12, 67-71): BE I from *Aegilops tauschii* (GenBank Acc: AF525746), BE I from barley (GenBank Acc: AY304541), BE from tapioca (GenBank Acc: X77012), BE I (frequently also described as BE 1) from rice (GenBank Acc: D11082, D10752, D10838), BE 3 from bean (GenBank Acc: AB029549), BE II from pea (GenBank Acc: X80010), BE from millet (GenBank Acc: AF169833), BE I from potato (GenBank Acc: Y08786, X69805), BE from wheat (GenBank Acc: Y12320, AF076679, AF002820) and BE I from maize (GenBank Acc: D11081, AAO20100, E03435, AY176762, U17897, AF072724).

At the same time, the amino acid sequences for different Class 1 branching enzymes each have an identity of more than 60% with the amino acid sequence of branching enzyme I from maize (GenBank Acc: D11081).

Branching enzymes, which belong to Class 2 (GPN 2.2.1.18:2) according to the nomenclature proposed by Smith-White and Preiss (1994, Plant Molecular Biology Reporter 12, 67-71) are, for example, BE IIa from *Aegilops tauschii* (GenBank Acc: AF338431, WO 9914314), BE2-1 and BE2-2 from *Arabidosis thaliana* (BE2-1 GenBank Acc: NM_129196 CAA04134; BE2-2 GenBank Acc: CAB82930, NM_120446), BE IIa and BE IIb from barley (BE IIa GenBank Acc: AF064560; BE IIb GenBank Acc: AF064561), BE II from sweet potato (GenBank Acc: AB071286), BE III and BE IV (frequently also described as BE 3 or BE 4 respectively) from rice (BE III GenBank Acc: D16201; BE IV GenBank Acc: AB023498), BE 1 from bean (GenBank Acc: AB029548), BE I from pea (GenBank Acc: X80009), BE IIb from millet (GenBank Acc: AY304540), BE II from potato (GenBank Acc: AJ000004, AJ01885, AJ011888, AJ011889, AJ011890), BE II or BE IIa from wheat (GenBank Acc: Y11282, AF286319, AF338432, U66376) and BE II, or BE IIb from maize (BE II GenBank Acc: AAA18571, T02981; BE IIb GenBank Acc: AF072725, L08065). At the same time, the amino acid sequences for different Class 2 branching enzymes each have an identity of more than 60% with the amino acid sequence of branching enzyme IIb from maize (GenBank Acc: AF072725).

Vegetable or starch branching enzymes belong to the family of alpha-amylolytic enzymes (Svensson, 1994, Plant Molecular Biology 25, 141-157; Jespersen et al., 1991, Biochem J. 280, 51-55) and, with regard to the amino acid sequence, have four conserved domains (Baba et al., 1991, Biochem. Biophys. Res. Commun. 181(1), 87-94; Kuriki et al., 1996, J. of Protein Chemistry 15(3), 305-313).

Structural predictions based on mathematical calculations derived from experimental data such as protein crystal structures show that all previously known branching enzymes from higher plants have two domains: an alpha-amylase domain and an iso-amylase domain. Here, the iso-amylase domain lies closer to the N-terminus of the protein than the alpha-amylase domain.

Plants are known, for example, which have a reduced activity of a Class 2 branching enzyme due to a mutation. These include the so-called "amylose extender" (ae) mutants from maize (Stindard et al., 1993, Plant Cell 5, 1555-1566; Boyer and Preiss, 1978, Biochem. Biophys. Res. Commun. 80, 169-175) and rice (Mizuno et al., 1993, J. Biol. Chem. 268, 19084-19091), as well as the "rugsus" (r) mutation in pea (Smith, 1988, Planta 175, 270-279; Bhattacharyya et al., 1990, Cell 60, 115-122). All these mutants are distinguished by the fact that they synthesise a starch, which has an increased amylose content in comparison with starches from corresponding plants, which do not have this mutation.

Furthermore, genetically modified potato plants are described, in which the activity of a BE I (Class 1) branching enzyme (Kossmann et al., 1991, Mol Gen Genet 230, 39-44; Safford et al., 1998, Carbohydrate Polymers 35, 155-168), or the activity of a BEII (Class 2) branching enzyme (Jobling et al., 1999, The Plant Journal 18), or the activity of a BEI and BEII branching enzyme (Schwall et al., 2000, Nature Biotechnology 18, 551-554, Jobling et al., 2003, Nature Biotechnology 21, 77-80) are reduced.

Previously, it has been possible to associate all vegetable branching enzymes to one or both of the classes described above. Plant cells or plants, which have a reduced activity of a branching enzyme, which cannot be associated with these classes, are unknown.

The object of the present invention is therefore based on providing modified starches, new plant cells and/or plants, which synthesise such a modified starch, as well as means and methods for producing said plants.

This problem is solved by the embodiments described in the claims.

The present invention therefore relates to genetically modified plant cells and genetically modified plants, characterised in that the plant cells or plants have a reduced activity of at least one Class 3 branching enzyme in comparison with corresponding wild type plant cells or wild type plants that have not been genetically modified.

A first aspect of the present invention relates to a plant cell or plant, which is genetically modified, wherein the genetic modification leads to the reduction of the activity of at least one Class 3 branching enzyme in comparison with corresponding wild type plant cells or wild type plants that have not been genetically modified.

At the same time, the genetic modification can be any genetic modification, which leads to a reduction of the activity of at least one Class 3 branching enzyme in comparison with corresponding wild type plant cells or wild type plants that have not been genetically modified.

In conjunction with the present invention, the term "wild type plant cell" means that the plant cells concerned were used as starting material for the manufacture of the plant cells according to the invention, i.e. their genetic information, apart from the introduced genetic modification, corresponds to that of a plant cell according to the invention.

In conjunction with the present invention, the term "wild type plant" means that the plants concerned were used as starting material for the manufacture of the plants according to the invention, i.e. their genetic information, apart from the introduced genetic modification, corresponds to that of a plant according to the invention.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant means that the plant cells or plants, which are compared with one another, have been raised under the same cultivation conditions and that they have the same (cultivation) age.

In an embodiment of the present invention, the genetic modification of the plant cells according to the invention or the plants according to the invention is brought about by mutagenesis of one or more genes. The type of mutation is not important, as long as it leads to a reduction in the activity of a Class 3 branching enzyme.

In conjunction with the present invention, the term "mutagenesis" is to be understood to mean any type of introduced mutation, such as deletions, point mutations (nucleotide exchanges), insertions, inversions, gene conversions or chromosome translocations, for example.

Here, the mutation, which leads to the reduction of the activity of at least one endogenous Class 3 branching enzyme, can be produced by the use of chemical agencies or energy-rich radiation (e.g. x-rays, neutron radiation, gamma radiation or UV radiation).

Agencies, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide ($NaN_3$) is described, for example, in Jauhar and Siddiq (1999, Indian Journal of Genetics, 59 (1), 23-28), in Rao (1977, Cytologica 42, 443-450), Gupta and Sharma (1990, Oryza 27, 217-219) and Satoh and Omura (1981, Japanese Journal of Breeding 31 (3), 316-326). The production of wheat mutants using $NaN_3$ or maleic hydrazide is described in Arora et al. (1992, Annals of Biology 8 (1), 65-69). An overview of the production of wheat mutants using different types of energy-rich radiation and chemical agencies is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutants in triticals. The use of MMS (methyl methane sulphonic acid) and gamma radiation for the production of millet mutants is described in Shashidhara et al. (1990, Journal of Maharashtra Agricultural Universities 15 (1), 20-23).

The manufacture of mutants in plant species, which mainly propagate vegetatively, has been described, for example, for potatoes, which produce a modified starch (Hovenkamp-Hermelink et al. (1987, Theoretical and Applied Genetics 75, 217-221) and for mint with increased oil yield or modified oil quality (Dwivedi et al., 2000, Journal of Medicinal and Aromatic Plant Sciences 22, 460-463). All these methods are basically suitable for manufacturing the plant cells according to the invention and the plants according to the invention.

Mutations in the appropriate genes, in particular in genes coding a Class 3 branching enzyme, can be found with the help of methods known to the person skilled in the art. In particular, analyses based on hybridisations with probes (Southern Blot), amplification by means of polymerase chain reaction (PCR), sequencing of related genomic sequences and the search for individual nucleotide exchanges can be used for this purpose. A method of identifying mutations based on hybridisation patterns is, for example, the search for restriction fragment length differences (Restriction Fragment Length Polymorphism, RFLP) (Nam et al., 1989, The Plant Cell 1, 699-705; Leister and Dean, 1993, The Plant Journal 4 (4), 745-750). A method based on PCR is, for example, the analysis of amplified fragment length differences (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). The use of amplified fragments cut with restriction endonucleases (Cleaved Amplified Polymorphic Sequences, CAPS) can be called upon for the identification of mutations (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753). Methods for the determination of SNPs have been described by Qi et al. (2001, Nucleic Acids Research 29 (22), e116) Drenkard et al. (2000, Plant Physiology 124, 1483-1492) and Cho et al. (1999, Nature Genetics 23, 203-207) amongst others. Methods, which allow several plants to be investigated for mutations in certain genes in a short time, are particularly suitable. Such a method, so-called TILLING (Targeting Induced Local Lesions IN Genomes), has been described by McCallum et al. (2000, Plant Physiology 123, 439-442).

These methods are basically suitable for identifying plant cells according to the invention and plants according to the invention.

Hoogkamp et al. (2000, Potato Research 43, 179-189) have manufactured stable monoploid mutants starting from a potato mutant (amf), which was manufactured by means of chemical mutagens. These plants do not synthesise any more active enzyme for a starch synthesis connected to the starch grain (GBSS I) and therefore produce an amylose-free starch. The monoploid potato plants obtained can be used as starting material for further mutageneses in order to identify plants, which synthesise a starch with modified characteristics. The plant cells according to the invention and plants according to the invention, which produce a starch according to the invention, can be identified and isolated by appropriate methods.

The plant cells according to the invention and the plants according to the invention have a reduction of the activity of at least one Class 3 branching enzyme in comparison with corresponding wild type plant cells that have not been genetically modified.

Here, within the framework of the present invention, the term "reduction of activity" means a reduction in the expression of endogenous genes, which code Class 3 branching enzymes, and/or a reduction in the quantity of protein of a Class 3 branching enzyme in the plant cells and/or a reduction in the enzymatic activity of Class 3 branching enzymes in the plant cells.

The reduction in the expression can, for example, be determined by measuring the quantity of transcripts coding Class 3 branching enzyme, e.g. using Northern blot analysis or RT-PCR. Here, a reduction preferably means a reduction in the amount of transcripts in comparison with corresponding plant cells that have not been genetically modified by at least 50%, in particular by at least 70%, preferably by at least 85% and particularly preferably by at least 95%.

The reduction in the amount of protein of a Class 3 branching enzyme, which results in a reduced activity of this protein in the plant cells concerned, can, for example, be determined by immunological methods such as Western blot analysis, ELISA (Enzyme Linked Immuno Sorbent Assay) or RIA (Radio Immune Assay). Here, a reduction preferably means a reduction in the amount of Class 3 branching enzyme protein in comparison with corresponding plant cells that have not been genetically modified by at least 50%, in particular by at least 70%, preferably by at least 85% and particularly preferably by at least 95%.

Within the framework of the present invention, the term "branching enzyme" ($\alpha$-1,4-glucan: $\alpha$-1,4-glucan 6-glycosyltransferase, E.C. 2.4.1.18) is understood to mean a protein, which catalyses a transglycosylation reaction, in which $\alpha$-1,4 links of an $\alpha$-1,4-glucan donor are hydrolysed and the thereby released $\alpha$-1,4-glucan chains are transferred to an $\alpha$-1,4-glucan acceptor chain and, in doing so, are transformed into $\alpha$-1,6-links. In particular, within the framework of the present invention, the term "branching enzyme" is to be understood to mean a vegetable branching enzyme, i.e. a starch branching enzyme.

The activity of a branching enzyme can be demonstrated, for example, with the help of native acrylamide gel electrophoresis. In doing so, proteins are first separated electrophoretically and, after incubation in buffers containing an activity, which synthesis linear $\alpha$-1,4-glucan chains (e.g. starch phosphorylase a) and its substrate (e.g. glucose-6-phosphate), the corresponding gels are coloured with iodine (Kimihiko et al., 1980, Analytical Biochemistry 108, 16-24). Furthermore, branching enzymes in microbial organisms, such as the *E. coli* strain KV832 for example (Kiel et al., 1987 Mol. Gen. Genet 207: 294-301), which do not synthesise branched $\alpha$-glucans, can be expressed. If an activity of a branching enzyme is introduced into the microbial organism due to the expression of a foreign gene in such strains (e.g. *E. coli* KV832), then the branching enzyme activity can be demonstrated by treating colonies of these organisms with iodine vapour, for example. Colonies, which synthesise linear $\alpha$-1,4-glucans, turn blue in this test, while colonies, which synthesise branched glucans by expressing an additional enzymatic activity of a branching enzyme, turn reddish-brown after treating with iodine vapour. It is also possible to express proteins in phosphoglucomutase mutants of *E. coli* to identify a branching enzyme activity of appropriate proteins (Buettcher et al., 1999, Biochem. Biophys. Acta 1432, 406-412).

A further possibility of demonstrating branching enzyme activity of proteins is the use of a reaction stimulated by phosphorylase a and the subsequent separation of the products by means of thin film chromatography (Almstrupp et al., 2000, Analytical Biochemistry 286, 297-300). Branching enzyme activities can also be demonstrated with the help of the methods described in Guan and Preiss (1993, Plant Physiol. 102. 1269-1273) and Kuriki et al. (1996, J. of Protein Chemistry 15, 305-313).

In conjunction with the present invention, the term "Class 3 branching enzyme" is to be understood as a branching enzyme, which has a higher degree of identity with the amino acid sequence shown in SEQ ID NO 4 than with that of the branching enzyme BE I from maize (GenBank Acc: D11081) or with that of the branching enzyme BE IIb from maize (GenBank Acc: AF072725). Preferably, the Class 3 branching enzyme comes from starch-storing plants, particularly preferably from plant species of the genus *Solanum*, especially preferably from *Solanum tuberosum*.

In a further embodiment of the present invention, amino acid sequences coding Class 3 branching enzymes have an identity of at least 60% with the sequence shown in SEQ ID NO 4, in particular of at least 70%, preferably of at least 80% and particularly preferably of at least 90% and especially preferably of at least 95%.

According to the invention, Class 3 branching enzymes have an iso-amylase domain (Pfam acc.: Pf02922) and an alpha-amylase domain (Pfam acc: Pf00128). According to the invention, the iso-amylase domain and the alpha-amylase domain in amino acid sequences coding branching enzymes are separated from one another by the presence of further amino acids, which do not belong to these two domains.

Class 3 branching enzymes according to the invention are distinguished by the fact that the iso-amylase domain is separated from the alpha-amylase domain by a greater number of amino acids than the iso-amylase domain and the alpha-amylase domain of Class 1 and 2 branching enzymes.

Class 3 branching enzymes according to the invention are preferably distinguished with regard to their amino acid sequence by the fact that they have at least 70, preferably at least 100, particularly preferably at least 130 and especially preferably at least 198 amino acids between the iso-amylase domain and the alpha-amylase domain. In a further embodiment of the present invention, in the case of an amino acid sequence coding a Class 3 branching enzyme, the C-terminal end of the iso-amylase domain is separated from the N-terminal beginning of the alpha-amylase domain by 70 to 198, preferably by 100 to 198, particularly preferably by 130 to 198 and especially particularly preferably by 150 to 198 amino acids.

With the help of the Pfam database (Batemann et. al., 2002, Nucleic Adds Research 30, 276-280; accessible via the Wellcome Trust Sanger Institute website or the Institute National de la Recherche Agronomique website)), it is possible for the person skilled in the art to determine whether amino acid sequences already have known domains (e.g. an iso-amylase domain and/or an alpha-amylase domain). Pfam is a database put together by experts, which classifies amino acid sequences into so-called families. Here, the assignment of an amino acid sequence to a family is carried out on the basis of so-called domains, which are to be looked upon as functional and structural components of proteins. A domain is defined as a structural unit or a repeatedly occurring amino acid sequence unit, which can occur in proteins with widely different functions. Along with information relating to the amino acid sequence of known proteins, further knowledge (e.g. evidence of the enzymatic activity, crystal structure data) is also used for the assignment of a protein to a family. Each family is assigned a name and an "accession" number (e.g. Name: Isoamylase_N, acc: PF02922). A constituent part of each family in the Pfam database is, amongst other things, a so-called "seed alignment". The "seed alignment" contains the amino acid sequences of representative proteins of a family. Starting from "seed alignments", a so-called profile HMM ("profile Hidden Markov Model"; overview article in: Durbin et al., "Biological Sequence Analysis: Probabilistic Models of Proteins and Nucleic Acids", Cambridge University Press, 1998, ISBN 0-521-62041-4) is produced using the HMMER 2 software (freely available on the world wide web). The HMMs produced have names and are stored in the Pfam database specifically for the correspondingly assigned domains. In contrast to classical, multiple "alignments" (e.g. produced using the Clustal W program or the Blossum62 algorithm), HMMs are based on a valid statistical theory (Bayes theory of conditional probability, Markoff chains) and enable an interrogation sequence (query) to be assigned to a family based on the use of position-specific evaluation matrices. This enables an assignment to be made even when there are considerable differences in the amino acid sequences between the interrogation sequence (query) and a comparison sequence (e.g. amino acid sequence entry in a database).

The domain structure of the amino acid sequence concerned can be determined by means of a comparison of the HMMs stored in the Pfam database with amino acid sequences, which are entered as a so-called interrogation sequence (query) (e.g. myhits motif scan, available on the world wide web).

In conjunction with the present invention, the term "iso-amylase domain" is to be understood to mean a Pfam iso-amylase domain (acc: Pf02922). At the same time, the HMM describing this Pfam iso-amylase domain is to be produced with the HMMER 2 [2.3.1] software, starting from a "seed alignment", which contains the amino acid sequences shown in Table 1. In conjunction with the present invention, the "seed alignment" is produced by means of the ClustalW program (Thompson et al., Nucleic Acids Research 22

(1994), 4673-4680; see below). The following settings must be chosen to produce the appropriate HMMs: Build Method of HMM: hmmbuild-F HMM_1s, hmmcalibrate-seed 0 HMM_1s; Gathering cutoff: 2.3 2.3; Trusted cutoff: 2.3 2.2; Noise cutoff: 2.1 2.1). Further information for producing the HMM of the Pfam iso-amylase domain (acc: Pf02922) is given in Table 3.

In conjunction with the present invention, the term "alpha-amylase domain" is to be understood to mean a Pfam alpha-amylase domain (acc: Pf00128). At the same time, the HMM describing this Pfam alpha-amylase domain is to be produced with the HMMER 2 [2.3.1] software, starting from a "seed alignment", which contains the amino acid sequences shown in Table 2. Here, the "seed alignment" is produced by means of HMM_simulated_annealing available on the world wide web). The following settings must be chosen to produce the appropriate HMM: Build Method of HMM: hmmbuild-F HMM_Is, hmmcalibrate-seed 0 HMM_Is; Gathering cutoff: −82.0-82.0; Trusted cutoff: −81.7-81.7; Noise cutoff: −82.7-82.7). Further information for producing the HMM of the Pfam alpha-amylase domain (acc: PF00128) is given in Table 4.

In conjunction with the present invention, the term "Class 3 branching enzyme gene" is to be understood to mean a nucleic acid molecule (cDNA, DNA), which codes a Class 3 branching enzyme, preferably a Class 3 branching enzyme from starch-storing plants, particularly preferably from plant species of the genus *Solanum*, especially preferably from *Solanum tuberosum*.

A preferred embodiment of the present invention relates to a genetically modified plant cell according to the invention or a genetically modified plant according to the invention, wherein the genetic modification consists in the introduction of at least one foreign nucleic acid molecule into the genome of the plant cell or into the genome of the plant.

In this context, the term "genetic modification" means the introduction of homologous and/or heterologous foreign nucleic acid molecules into the genome of a plant cell or into the genome of a plant, wherein said introduction of these molecules leads to a reduction of the activity of a Class 3 branching enzyme.

The plant cells according to the invention or plants according to the invention are modified with regard to their genetic information by the introduction of a foreign nucleic acid molecule. The presence or the expression of the foreign nucleic acid molecule leads to a phenotypic change. Here, "phenotypic" change means preferably a measurable change of one or more functions of the cells. For example, the genetically modified plant cells according to the invention and the genetically modified plants according to the invention exhibit a reduction of the activity of a Class 3 branching enzyme due to the presence or on the expression of the introduced nucleic acid molecule.

In conjunction with the present invention, the term "foreign nucleic acid molecule" is understood to mean such a molecule that either does not occur naturally in the corresponding wild type plant cells that have not been genetically modified, or that does not occur naturally in the concrete spatial arrangement in wild type plant cells that have not been genetically modified, or that is localised at a place in the genome of the wild type plant cell at which it does not occur naturally. Preferably, the foreign nucleic acid molecule is a recombinant molecule, which consists of different elements, the combination or specific spatial arrangement of which does not occur naturally in vegetable cells. In principle, the foreign nucleic acid molecule can be any nucleic acid molecule, which effects a reduction of the activity of a Class 3 branching enzyme in the plant cell or plant.

In conjunction with the present invention, the term "genome" is to be understood to mean the totality of the genetic material present in a vegetable cell. It is known to the person skilled in the art that, as well as the cell nucleus, other compartments (e.g. plastids, mitochondrions) also contain genetic material.

In a further embodiment, the plant cells according to the invention and the plants according to the invention are characterised in that the foreign nucleic acid molecule codes a Class 3 branching enzyme, preferably a Class 3 branching enzyme from starch-storing plants, particularly preferably from plants of a species of the genus *Solanum*, especially preferably from *Solanum tuberosum*.

In a particularly preferred embodiment, the foreign nucleic acid molecule codes a Class 3 branching enzyme with the amino acid sequence specified in SEQ ID NO 4.

A large number of techniques are available for the introduction of DNA into a vegetable host cell. These techniques include the transformation of vegetable cells with T-DNA using *Agrobacterium tumefaciens* or *Agrobacterium rhizogenes* as the transformation medium, the fusion of protoplasts, injection, the electroporation of DNA, the introduction of DNA by means of the biolistic approach as well as other possibilities. The use of agrobacteria-mediated transformation of plant cells has been intensively investigated and adequately described in EP 120516; Hoekema, Ind.: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297). All the above methods are suitable within the framework of the present invention.

Amongst other things, the plant cells according to the invention and the plants according to the invention can be differentiated from wild type plant cells and wild type plants respectively in that they contain a foreign nucleic acid molecule, which does not occur naturally in wild type plant cells or wild type plants, or in that such a molecule is present integrated at a place in the genome of the plant cell according to the invention or in the genome of the plant according to the invention at which it does not occur in wild type plant cells or wild type plants, i.e. in a different genomic environment. Furthermore, plant cells according to the invention and plants according to the invention of this type differ from wild type plant cells and wild type plants respectively in that they contain at least one copy of the foreign nucleic acid molecule stably integrated within their genome, possibly in addition to naturally occurring copies of such a molecule in the wild type plant cells or wild type plants. If the foreign nucleic acid molecule(s) introduced into the plant cells according to the invention or into the plants according to the invention is (are) additional copies of molecules already occurring naturally in the wild type plant cells or wild type plants respectively, then the plant cells according to the invention and the plants according to the invention can be differentiated from wild type plant cells or wild type plants respectively in particular in that this additional copy or these additional copies is (are) localised at places in the genome at which it does not occur (or they do not occur) in wild type plant cells or wild type plants. This can be verified, for example, with the help of a Southern blot analysis.

Furthermore, the plant cells according to the invention and the plants according to the invention can preferably be differentiated from wild type plant cells or wild type plants respectively by at least one of the following characteristics: If the foreign nucleic acid module that has been introduced is heterologous with respect to the plant cell or plant, then the plant cells according to the invention or plants according to the invention have transcripts of the introduced nucleic acid molecules. These can be verified, for example, by Northern blot analysis or by RT-PCR (Reverse Transcription Polymerase Chain Reaction). Plant cells according to the invention and plants according to the invention, which express an antisense and/or an RNAi transcript, can be verified, for example, with the help of specific nucleic acid probes, which are complimentary to the RNA (occurring naturally in the plant cell), which is coding for the protein.

If the foreign nucleic acid module that has been introduced is homologous with respect to the plant cell or plant, the plant cells according to the invention or plants according to the invention can be differentiated from wild type plant cells or wild type plants respectively due to the additional expression of the introduced foreign nucleic acid molecule, for example. The plant cells according to the invention and the plants according to the invention preferably contain (sense and/or antisense) transcripts of the foreign nucleic acid molecules. This can be demonstrated by Northern blot analysis, for example, or with the help of so-called quantitative PCR.

In a special embodiment, the plant cells according to the invention and the plants according to the invention are transgenic plant cells or transgenic plants respectively.

In a further embodiment, the present invention relates to plant cells according to the invention and plants according to the invention wherein the foreign nucleic acid molecule is chosen from the group consisting of a) Nucleic acid molecules, which code a protein with the amino acid sequence given under Seq ID NO 4;

b) Nucleic acid molecules, which code a protein, the amino acid sequence of which has an identity of at least 50% with the amino acid sequence given under SEQ ID NO: 4;

c) Nucleic acid molecules, which include the nucleotide sequence shown under Seq ID NO 3 or a complimentary sequence;

d) Nucleic acid molecules, the nucleic acid sequence of which has an identity of at least 50% with the nucleic acid sequences described under a) or c);

e) Nucleic acid molecules, which hybridise with at least one strand of the nucleic acid molecules described under a) or c) under stringent conditions;

f) Nucleic acid molecules, the nucleotide sequence of which deviates from the sequence of the nucleic acid molecules identified under a), b), c), d), e) or f) due to the degeneration of the genetic code; and g) Nucleic acid molecules, which represent fragments, allelic variants and/or derivatives of the nucleic acid molecules identified under a), b), c), d), e) or f).

A further embodiment of the present invention relates to plant cells according to the invention and plants according to the invention wherein the foreign nucleic acid molecule is chosen from the group consisting of a) Nucleic acid molecules, which code at least one antisense RNA, which effects a reduction in the expression of at least one endogenous gene, which codes a Class 3 branching enzyme;

b) Nucleic acid molecules, which by means of a co-suppression effect lead to the reduction in the expression of at least one endogenous gene, which codes a Class 3 branching enzyme;

c) Nucleic acid molecules, which code at least one ribozyme, which splits specific transcripts of at least one endogenous gene, which codes a Class 3 branching enzyme;

d) Nucleic acid molecules, which simultaneously code at least one antisense RNA and at least one sense RNA, wherein the said antisense RNA and the said sense RNA form a double-stranded RNA molecule, which effects a reduction in the expression of at least one endogenous gene, which codes a Class 3 branching enzyme (RNAi technology);

e) Nucleic acid molecules introduced by means of in vivo mutagenesis, which lead to a mutation or an insertion of a heterologous sequence in at least one endogenous gene coding a Class 3 branching enzyme, wherein the mutation or insertion effects a reduction in the expression of a gene coding a Class 3 branching enzyme or results in the synthesis of inactive Class 3 branching enzymes;

f) Nucleic acid molecules, which code an antibody, wherein the antibody results in a reduction in the activity of a Class 3 branching enzyme due to the bonding to a Class 3 branching enzyme.

g) DNA molecules, which contain transposons, wherein the integration of these transposons leads to a mutation or an insertion in at least one endogenous gene coding a Class 3 branching enzyme, which effects a reduction in the expression of at least one gene coding a Class 3 branching enzyme, or results in the synthesis of inactive Class 3 branching enzymes; and/or h) T-DNA molecules, which, due to insertion in at least one endogenous gene coding a Class 3 branching enzyme, effect a reduction in the expression of at least one gene coding a Class 3 branching enzyme, or result in the synthesis of inactive Class 3 branching enzyme.

The plant cells according to the invention and plants according to the invention can be manufactured by different methods known to the person skilled in the art. These include, for example, the expression of a corresponding antisense RNA or of a double-stranded RNA construct, the provision of molecules or vectors, which impart a cosuppression effect, the expression of a correspondingly constructed ribozyme that splits specific transcripts, which code a Class 3 branching enzyme, or so-called "in vivo mutagenesis". Furthermore, the reduction of the Class 3 branching enzyme activity in plant cells and plants can also be brought about by the simultaneous expression of sense and antisense RNA molecules of the respective target gene to be repressed, preferably of the Class 3 branching enzyme gene. In addition to this, it is known that in planta the formation of double-stranded RNA molecules of promoter sequences can lead in trans to methylation and transcriptional inactivation of homologous copies of this promoter (Mette et al., EMBO J. 19, (2000), 5194-5201).

A further possible way in which to reduce the enzymatic activity of proteins in plant cells or plants is the so-called immunomodulation method. It is known that an in planta expression of antibodies, which specifically recognise a vegetable protein, results in a reduction of the activity of the proteins concerned in appropriate plant cells due to the formation of a protein antibody complex (Conrad and Manteufel, Trends in Plant Science 6, (2001), 399-402; De Jaeger et al., Plant Molecular Biology 43, (2000), 419-428; Jobling et al., Nature Biotechnology 21, (2003), 77-80).

All these methods are based on the introduction of a foreign or of several foreign nucleic acid molecules into the genome of plant cells or plants and are therefore basically suitable for manufacturing plant cells according to the invention and plants according to the invention.

For inhibiting the expression of genes by means of antisense or cosuppression technology, a DNA molecule can be used, for example, which includes the whole coding sequence for a Class 3 branching enzyme, including any existing flanking sequences, as well as DNA molecules, which include only parts of the coding sequence, whereby these parts must be long enough to produce an antisense effect or a cosuppression effect respectively in the cells. In general, sequences up to a minimum length of 21 bp, preferably a minimum length of at least 100 bp, particularly preferably of at least 500 bp are suitable. For example, the DNA molecules have a length of 21-100 bp, preferably of 100-500 bp, particularly preferably over 500 bp.

The use of DNA sequences, which have a high degree of identity with the endogenous sequences occurring in the plant cells and which code Class 3 branching enzymes, is also suitable for antisense or cosuppression approaches. The minimum identity should be greater than ca. 65%, preferably greater than 80%. The use of sequences with identities of at least 90%, in particular between 95% and 100%, is to be preferred. The meaning of the term "identity" will be defined elsewhere.

Furthermore, the use of introns, i.e. of non-coding areas of genes, which code for Class 3 branching enzymes, is also conceivable for achieving an antisense or a cosuppression effect.

The use of intron sequences for inhibiting the gene expression of genes, which code for starch biosynthesis proteins, has been described in the international patent applications WO97/04112, WO97/04113, WO98/37213, WO98/37214.

The person skilled in the art knows how to achieve an antisense and a cosuppression effect. For example, the method of cosuppression inhibition has been described in Jorgensen (Trends Biotechnol. 8 (1990), 340-344), Niebel et al., (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), de Borne et al. (Mol. Gen. Genet. 243 (1994), 613-621).

The expression of ribozymes for reducing the activity of particular enzymes in cells is also known to the person skilled in the art, and is described, for example, in EP-B1 0321201. The expression of ribozymes in vegetable cells has been described, for example, in Feyter et al. (Mol. Gen. Genet. 250, (1996), 329-338).

The reduction of the activity of a Class 3 branching enzyme in plant cells according to the invention and plants according to the invention can also be brought about by the simultaneous expression of sense and antisense RNA molecules (RNAi technology) of the respective target gene to be repressed, preferably of the Class 3 branching enzyme gene. This can be achieved, for example, by the use of chimeric constructs, which contain "inverted repeats" of the respective target gene or parts of the target gene. In this case, the generic constructs code for sense and antisense RNA molecules of the respective target gene. Sense and antisense RNA are synthesised simultaneously in planta as an RNA molecule, wherein sense and antisense RNA are separated from one another by a spacer, and are able to form a double-stranded RNA molecule.

It has been shown that the introduction of inverted repeat DNA constructs into the genome of plant cells or plants is a very effective method of repressing the genes corresponding to the inverted repeat DNA constructs (Waterhouse et al., Proc. Natl. Acad. Sci. USA 95, (1998), 13959-13964; Wang and Waterhouse, Plant Mol. Biol. 43, (2000), 67-82; Singh et al., Biochemical Society Transactions Vol. 28 part 6 (2000), 925-927; Liu et al., Biochemical Society Transactions Vol. 28 part 6 (2000), 927-929); Smith et al., (Nature 407, (2000), 319-320; international patent application WO99/53050 Al). Sense and antisense sequences of the target gene or the target genes can also be expressed separately from one another by means of similar or different promoters (Nap, J-P et al, 6$^{th}$ International Congress of Plant Molecular Biology, Quebec, 18th-24th June, 2000; Poster S7-27, Presentation Session S7).

The reduction of the activity of a Class 3 branching enzyme in plant cells according to the invention or plants according to the invention can therefore also be achieved by producing double-stranded RNA molecules. In this regard, "inverted repeats" of DNA molecules of Class 3 branching enzyme genes or cDNAs are preferably introduced into the genome of plants, wherein the DNA molecules (Class 3 branching enzyme gene or cDNA or fragments of this gene or cDNA) to be transcribed are under the control of a promoter, which controls the expression of said DNA molecules. In addition to this, it is known that the formation of double-stranded RNA molecules from promoter DNA molecules in plants in trans can lead to methylation and transcriptional inactivation of homologous copies of these promoters, which are to be referred to in the following as target promoters (Mette et al., EMBO J. 19, (2000), 5194-5201). It is therefore possible to reduce the gene expression of a particular target gene (e.g. branching enzyme Class 3 gene), which is naturally under the control of this target promoter, by deactivating the target promoter. This means that, in this case, the DNA molecules, which include the target promoters of the genes to be repressed (target genes), in contrast to the original function of promoters in plants, are not used as control elements for the expression of genes or cDNAs, but are themselves used as transcribable DNA molecules.

For the production of double-stranded target promoter RNA molecules in planta, which can occur there as RNA hairpin molecules, constructs are preferably used, which contain the "inverted repeats" of the target promoter DNA molecules, wherein the target promoter DNA molecules are under the control of a promoter, which controls the gene expression of said target promoter DNA molecules. These constructs are subsequently introduced into the genome of plants. The expression of the "inverted repeats" of said target promoter DNA molecules in planta leads to the formation of double-stranded target promoter RNA molecules (Mette et al., EMBO J. 19, (2000), 5194-5201). The target promoter can be inactivated by this means.

The reduction of the activity of a Class 3 branching enzyme in plant cells according to the invention and plants according to the invention can therefore also be achieved by the production of double-stranded RNA molecules of promoter sequences of Class 3 branching enzyme genes. In this regard, "inverted repeats" of promoter DNA molecules of Class 3 branching enzyme genes are preferably introduced into the genome of plants, wherein the target promoter DNA molecules (promoter of a Class 3 branching enzyme gene) to be transcribed are under the control of a promoter, which controls the expression of said target promoter DNA molecules.

For inhibiting the expression of genes by means of the simultaneous expression of sense and antisense RNA molecules (RNAi technology), a DNA molecule can be used, for example, which includes the whole coding sequence for a Class 3 branching enzyme, including any existing flanking sequences, as well as DNA molecules, which include only parts of the coding sequence, whereby these parts must be long enough to produce a so-called RNAi effect in the cells. In general, sequences with a minimum length of 40 bp, preferably a minimum length of at least 100 bp, particularly preferably of at least 500 bp are suitable. For example, the DNA molecules have a length of 21-100 bp, preferably of 100-500 bp.

The use of DNA sequences, which have a high degree of identity with the endogenous sequences occurring in the plant cells and which code Class 3 branching enzymes, is also suitable for the simultaneous expression of sense and antisense RNA molecules (RNAi technology). The minimum identity should be greater than ca. 65%, preferably greater than 80%. The use of sequences with identities of at least 90%, in particular between 95% and 100%, is to be particularly preferred.

Furthermore, the reduction of the activity of a Class 3 branching enzyme in plant cells according to the invention and plants according to the invention can also be achieved by so-called "in vivo mutagenesis", in which a hybrid RNA-DNA oligonucleotide ("Chimeroplast") is introduced into plant cells (Kipp, P. B. et al., Poster Session at the "5$^{th}$ International Congress of Plant Molecular Biology, 21-27 Sep. 1997, Singapore; R. A. Dixon and C. J. Arntzen, meeting report on "Metabolic Engineering in Transgenic Plants", Keystone Symposia, Copper Mountain, Co., USA, TIBTECH 15, (1997), 441-447; international patent application WO 9515972; Kren et al., Hepatology 25, (1997), 1462-1468; Cole-Strauss et al., Science 273, (1996), 1386-1389; Beetham et al., 1999, PNAS 96, 8774-8778). A part of the DNA components of the RNA-DNA oligonucleotide is homologous to a nucleic acid sequence of an endogenous Class 3 branching enzyme gene, but, in comparison with the nucleic acid sequence of a Class 3 branching enzyme gene, it has a mutation or contains a heterologous region, which is surrounded by the homologous regions. By base pairing of the homologous regions of the RNA-DNA oligonucleotide and the endogenous nucleic acid molecule followed by homologous recombination, the mutation or heterologous region contained in the DNA components of the RNA-DNA oligonucleotide can be transferred into the genome of a plant cell. This leads to the reduction of the activity of one or more Class 3 branching enzymes.

The person skilled in the art knows that he can achieve the activity of Class 3 branching enzymes by the expression of non-functional derivatives, in particular transdominant mutants, of such proteins, and/or by the expression of antagonists/inhibitors of such proteins.

Antagonist/inhibitors of such proteins include, for example, antibodies, antibody fragments or molecules with similar bonding characteristics. For example, a cytoplasmatic scFv antibody has been used to modulate the activity of the phytochrome A protein in genetically modified tobacco plants (Owen, Bio/Technology 10 (1992), 790-4; Review: Franken, E, Teuschel, U. and Hain, R., Current Opinion in Biotechnology 8, (1997), 411-416; Whitelam, Trends Plant Sci. 1 (1996), 268-272; Conrad and Manteufel, Trends in Plant Science 6, (2001), 399-402; De Jaeger et al., Plant Molecular Biology 43, (2000), 419-428). The reduction of the activity of a branching enzyme in potato plants by expressing a specific antibody has been described by Jobling et al. (Nature Biotechnology 21, (2003), 77-80). Here, the antibody was provided with a plastidiary target sequence so that the inhibition of proteins localised in plastids was guaranteed.

In conjunction with the present invention, plant cells and plants according to the invention can also be manufactured by the use of so-called insertion mutagenesis (overview article: Thorneycroft et al., 2001, Journal of experimental Botany 52 (361), 1593-1601). Insertion mutagenesis is to be understood to mean particularly the insertion of transposons or so-called transfer DNA (T-DNA) into a gene coding for a Class 3 branching enzyme, whereby, as a result of which, the activity of a Class 3 branching enzyme in the cell concerned is reduced.

The transposons can be both those that occur naturally in the cell (endogenous transposons) and also those that do not occur naturally in said cell but are introduced into the cell (heterologous transposons) by means of genetic engineering methods, such as transformation of the cell, for example. Changing the expression of genes by means of transposons is known to the person skilled in the art. An overview of the use of endogenous and heterologous transposons as tools in plant biotechnology is presented in Ramachandran and Sundaresan (2001, Plant Physiology and Biochemistry 39, 234-252). The possibility of identifying mutants in which specific genes have been inactivated by transposon insertion mutagenesis is presented in an overview by Maes et al. (1999, Trends in Plant Science 4 (3), 90-96). The production of rice mutants with the help of endogenous transposons is described by Hirochika (2001, Current Opinion in Plant Biology 4, 118-122). The identification of maize genes with the help of endogenous retrotransposons is presented, for example, by Hanley et al. (2000, The Plant Journal 22 (4), 557-566). The possibility of manufacturing mutants with the help of retrotransposons and methods of identifying mutants are described by Kumar and Hirochika (2001, Trends in Plant Science 6 (3), 127-134). The activity of technological transposons in different species has been described both for dicotyledonous and for monocotyledonous plants: e.g. for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon und Gynheung, 2001, Plant Science 161, 211-219), barley (2000, Koprek et al., The Plant Journal 24 (2), 253-263) *Arabidopsis thaliana* (Aarts et al., 1993, Nature 363, 715-717, Schmidt und Willmitzer, 1989, Molecular and General Genetics 220, 17-24; Altmann et al., 1992, Theoretical and Applied Gentics 84, 371-383; Tissier et al., 1999, The Plant Cell 11, 1841-1852), tomato (Belzile und Yoder, 1992, The Plant Journal 2 (2), 173-179) and potato (Frey et al., 1989, Molecular and General Genetics 217, 172-177; Knapp et al., 1988, Molecular and General Genetics 213, 285-290).

Basically, the plant cells according to the invention and the plants according to the invention can be manufactured both with the help of homologous and heterologous transposons, whereby the use of homologous transposons is also to be understood to mean those, which are naturally present in the corresponding wild type plant genome.

T-DNA insertion mutagenesis is based on the fact that certain sections (T-DNA) of Ti plasmids from *Agrobacterium* can integrate into the genome of vegetable cells. The place of integration in the vegetable chromosome is not defined, but can take place at any point. If the T-DNA integrates into a part of the chromosome, which constitutes a gene function, then this can lead to a change in the gene expression and thus also to a change in the activity of a protein coded by the gene concerned. In particular, the integration of a T-DNA into the coded area of a protein often leads to the corresponding protein no longer being able to be synthesised at all, or no longer synthesised in active form, by the cell concerned. The use of T-DNA insertions for producing mutants is described, for example, for *Arabidopsis thaliana* (Krysan et al., 1999, The Plant Cell 11, 2283-2290; Atipiroz-Leehan and Feldmann, 1997, Trends in genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants, which have been produced with the help of T-DNA insertion mutagenesis, are described, amongst others, by Young et al., (2001, Plant Physiology 125, 513-518), Parinov et al. (1999, The Plant cell 11, 2263-2270), Thorneycroft et al. (2001, Journal of Experimental Botany 52, 1593-1601), and McKinney et al. (1995, The Plant Journal 8 (4), 613-622).

T-DNA mutagenesis is basically suitable for the production of the plant cells and plants according to the invention, which have a reduced activity of a Class 3 branching enzyme.

Surprisingly, it has been found that plant cells according to the invention and plants according to the invention synthesise a modified starch in comparison with starch of corresponding wild type plant cells or wild type plants that have not been genetically modified.

The plant cells according to the invention and plants according to the invention synthesise a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

It was surprisingly found that plant cells or plants of the invention synthesize a modified starch having decreased phosphate content. So far known plants with a reduced activity of a branching enzyme (Class 1 and/or Class 2) did show an increased phosphate content.

The present invention therefore also includes plant cells according to the invention and plants according to the invention, which synthesise a modified starch.

In a preferred embodiment of the invention, the plant cells according to the invention or the plant according to the invention synthesize a starch with a decreased phosphate content in comparison with corresponding starch isolated from wild type plant cells or wild type plants that have not been genetically modified. Preferably the plant cells according to the invention or the plants according to the invention synthesize a starch having a total phosphate content that is decreased by at least 10%, more preferably by at least 15% and particular preferably by at least 20% in comparison with starch isolated from corresponding wild type plant cells or wild type plants that have not been genetically modified. Especially preferably the total phosphate content of starch isolated from plant cells of the invention or plants of the invention is decreased by 14% to 22% in comparison with starch isolated from corresponding wild type plant cells or wild type plants that have not been genetically modified.

In respect with C-6-phosphate content the plant cells according to the invention or the plants according to the invention synthesize a starch having a C-6-phosphate content that is decreased by at least 15%, more preferably by at least 19% and particular preferably by at least 25% in comparison with starch isolated from corresponding wild type plant cells or wild type plants that have not been genetically modified. Especially preferably the C-6-phoaphate content of starch isolated from plant cells of the invention or plants of the invention is decreased by 15%% to 27% in comparison with starch isolated from corresponding wild type plant cells or wild type plants that have not been-genetically modified.

Methods for the determination of total phosphate or C-6-phosphate content in starches are well known by a person skilled in the art. Preferred methods for the determination of total or C-6-phosphate content in starches to be used in combination with the present invention are described below in the section "general methods" (Starch analysis, e) Analysis of the side-chain distribution of the amylopectin by means of ion-exchange chromatography).

In a further preferred embodiment of the invention, the plant cells according to the invention or the plants according to the invention synthesize a starch which has has an altered viscosity behaviour in comparison with starch isolated from corresponding wild type plant cells or wild type plants that have not been genetically modified. Plant cells of the invention or plants of the invention synthesize a starch which has a decreased maximum viscosity, a decreased minimum viscosity and/or a decreased final viscosity in comparison with starch isolated from corresponding wild type plant cells or wild type plants that have not been genetically modified.

The maximum viscosity of starch isolated from plant cells of the invention or plants of the invention is preferably decreased by at least 8% and more preferably by at least 16% in comparison with starch isolated from corresponding wild type plant cells or wild type plants that have not been genetically modified. Especially preferably the maximum viscosity of starch isolated from plant cells of the invention or plants of the invention is decreased by 8% to 16% in comparison with starch isolated from corresponding wild type plant cells or wild type plants that have not been genetically modified.

The minimum viscosity of starch isolated from plant cells of the invention or plants of the invention is preferably decreased by at least 10%, more preferably by at least 15% and particularly preferably by at lest 25% in comparison with starch isolated from corresponding wild type plant cells or wild type plants that have not been genetically modified. Especially preferably the minimum viscosity of starch isolated from plant cells of the invention or plants of the invention is decreased by 15% to 25% in comparison with starch isolated from corresponding wild type plant cells or wild type plants that have not been genetically modified.

The final viscosity of starch isolated from plant cells of the invention or plants of the invention is preferably decreased by at least 5% and more preferably by at least 10% in comparison with starch isolated from corresponding wild type plant cells or wild type plants that have not been genetically modified. Particularly preferably the minimum viscosity of starch isolated from plant cells of the invention or plants of the invention is decreased by 5% to 10% in comparison with starch isolated from corresponding wild type plant cells or wild type plants that have not been genetically modified.

It has further been found, that starch isolated from plant cells of the invention or plants of the invention shows an increased gelling strength in comparison with starch isolated from corresponding wild type plant cells or wild type plants that have not been genetically modified.

The present invention therefore also comprises plant cells of the invention or plants of the invention that synthesize a starch with an increased gel strength in comparison with starch isolated from corresponding wild type plant cells or wild type plants that have not been genetically modified. Preferably plant cells of the invention or plants of the invention synthesize a starch which shows a gel strength which is increased by at least 20%, more preferably by at least 30% and particular preferably by at least 35% in comparison with starch isolated from corresponding wild type plant cells or wild type plants that have not been genetically modified. Especially preferably the gel strength of starch isolated from plant cells of the invention or plants of the invention is increased by 27% to 38% in comparison with starch isolated from corresponding wild type plant cells or wild type plants that have not been genetically modified.

Methods for the determination of viscosity behaviour or gelling properties of starches are well known by a person skilled in the art. Preferred methods for the determination of viscosity behaviour or gelling properties of starches to be used in combination with the present invention are described below in the section “general methods”.

Furthermore it was surprisingly found that starch, isolated from plant cells of the invention or plants of the invention shows an altered side chain distribution pattern in the amylopectin fraction in comparison with the amylopectin fraction from starch isolated from corresponding wild type plant cells or wild type plants that have not been genetically modified.

In a further embodiment of the invention, plant cells according to the invention or the plants according to the invention synthesize a starch with an altered short-side-chain distribution pattern in the amylopectin fraction in comparison with the amylopectin fraction from starch isolated from corresponding wild type plant cells or wild type plants that have not been genetically modified. Preferably plant cells according to the invention or the plants according to the invention synthesize a starch wherein the short-side-chains in the amylopectin fraction having a degree of polymerization (DP) of 6 and/or a DP of 7 is increased in comparison with the amylopectin fraction from starch isolated from corresponding wild type plant cells or wild type plants that have not been genetically modified. More preferably the amylopectin fraction of starch isolated form plant cells according to the invention or plants according to the invention synthesize a starch wherein short-side-chains with a DP 6 is increased by at least 15%, particularly preferably by at least 20%, especially particularly by at least 25% and/or the short-side-chains with a DP 7 are increased by at least 2%, particularly preferably by at least 4%, especially preferably by at least 8% in comparison with the amylopectin fraction from starch isolated from corresponding wild type plant cells or wild type plants that have not been genetically modified.

In a further preferred embodiment of the invention the plant cells according to the invention or the plants according to the invention synthesize a starch wherein the short-side-chains of DP 6 in the amylopectin fraction is increased by 17% to 29% and/or the side chains of DP 7 in the amylopectin fraction is increased by 2% to 9% in comparison with the amylopectin fraction from starch isolated from corresponding wild type plant cells or wild type plants that have not been genetically modified.

In conjunction with the present invention, the term “short-side-chain” shall mean alpha-1,6-linked side-chains in the starch molecule having a degree of polymerization between DP 6 and DP 34.

Methods for the quantification of short-side-chains having a specified DP in the amylopectin fraction are well known by the person skilled in the art. Preferred methods for the quantification of side-chains having a specified DP, suitable to be used in combination with the present invention are described below in the section “general methods (Analysis of the side-chain distribution of the amylopectin by means of ion-exchange chromatography).

Furthermore it was found that the amylopectin fraction of starch, isolated from the plant cells according to the invention or the plants according to the invention shows an altered total-side-chain distribution.

Therefore, further embodiments of the present invention are the plant cells according to the invention or the plants according to the invention which synthesize a starch wherein the groups of total-side-chains in the amylopectin fraction characterized by the following ranges:

a) DP up to 1,
b) DP 12 to DP 19,
c) DP 20 to Dp 25 and/or
d) DP 26 to DP 31 is/are increased and/or the groups of total-side- chains in the amylopectin fraction characterized by the following ranges:

a) DP 38 to DP 43
b) DP 44 to DP 49
c) DP 50 to DP 56
d) DP 57 to DP 62 and/or
e) DP 63 to DP 123

Is/are decreased in comparison with the amylopectin fraction from starch isolated from corresponding wild type plant cells or wild type plants that have not been genetically modified.

In conjunction with the present invention, the term “total-side-chains” shall mean alpha-1,6-linked side-chains in the starch molecule having a degree of polymerization up to DP 123. A group of total-side-chains consists of all side-chains spanning a defined DP range (e.g. DP up to 11,DP 12 to DP 19, DP 20to Dp 25,DP 26to DP 31,DP 38 to DP 43,DP 44to DP 49, DP 50 to DP 56, DP 57 to DP 62, DP 63 to DP 123).

Methods for the quantification of groups of total-side-chains spanning ranges of side-chains with a specified DP in the amylopectin fraction are well known by the person skilled in the art. Preferred methods for the quantification groups of total-side-chains, suitable to be used in combination with the present invention are described below in example 5d).

Further embodiments of the invention are the plant cells according to the invention or the plants according to the invention which synthesize a starch having a decreased peak onset Temperature ($T_0$), a decreased peak temperature (T Peak) and an increased delta H (dH) when analyzed by differential scanning calorimetrie (DSC) in comparison to starch isolated from corresponding wild type plant cells or wild type plants that have not been genetically modified.

Methods for the analysis of starch by DSC are well known by a person skilled in the art. Preferred Methods for DSC analysis suitable to be used in combination with the present invention are described below in the section “general methods” (DSC-analysis (“Differential Scanning Calorimetry”).

Furthermore, genetically modified plants, which contain the plant cells according to the invention, are also the subject matter of the invention. Plants of this type can be produced from plant cells according to the invention by regeneration.

In principle, the plants according to the invention can be plants of any plant species, i.e. both monocotyledonous and dicotyledonous plants. Preferably they are useful plants, i.e. plants, which are cultivated by people for the purposes of food or for technical, in particular industrial purposes.

In a further preferred embodiment, the plant according to the invention is a starch-storing plant.

In a further preferred embodiment, the present invention relates to starch-storing plants according to the invention of the genus *Solanum*, in particular *Solanum tuberosum.*

The term "starch-storing plants" includes all plants with starch-storing plant parts such as, for example, maize, rice, wheat, rye, oat, barley, cassava, potato, sago, mung bean, pea or sorghum. Preferred starch-storing plant parts are, for example, tubers, storage roots and grains containing an endosperm; tubers are particularly preferred.

In conjunction with the present invention, the term "potato plant" or "potato" means plant species of the genus *Solanum*, in particular tuber-producing species of the genus *Solanum* and especially *Solanum tuberosum.*

The present invention also relates to propagation material of plants according to the invention containing a plant cell according to the invention.

Here, the term "propagation material" includes those constituents of the plant that are suitable for producing offspring by vegetative or sexual means. Cuttings, callus cultures, rhizomes or tubers, for example, are suitable for vegetative propagation. Other propagation material includes, for example, fruits, seeds, seedlings, protoplasts, cell cultures, etc. Preferably, the propagation material is seeds and particularly preferably tubers.

In a further embodiment, the present invention relates to harvestable plant parts of plants according to the invention such as fruits, storage roots, roots, blooms, buds, shoots or stems, preferably seeds or tubers, wherein these harvestable parts contain at least one plant cell according to the invention.

Furthermore, the present invention also relates to a method for the manufacture of a plant according to the invention, wherein a) a plant cell is genetically modified, whereby the genetic modification leads to the reduction of the activity of a Class 3 vegetable branching enzyme in comparison with corresponding wild type plant cells that have not been genetically modified;

b) a plant is regenerated from plant cells from Step a); and c) if necessary, further plants are produced with the help of the plants according to Step b).

The genetic modification introduced into the plant cell according to Step a) can basically be any type of genetic modification, which leads to the reduction of the activity of a Class 3 branching enzyme.

The regeneration of the plants according to Step (b) can be carried out using methods known to the person skilled in the art (e.g. described in "Plant Cell Culture Protocols", 1999, edt. by R. D. Hall, Humana Press, ISBN 0-89603-549-2).

The production of further plants according to Step (c) of the method according to the invention can be carried out, for example, by vegetative propagation (for example using cuttings, tubers or by means of callus culture and regeneration of whole plants) or by sexual propagation. Here, sexual propagation preferably takes place under controlled conditions, i.e. selected plants with particular characteristics are crossed and propagated with one another.

In a preferred embodiment of the method according to the invention, the genetic modification consists in the introduction of a foreign nucleic acid molecule into the genome of the plant cell, wherein the presence or the expression of said foreign nucleic acid molecule leads to a reduced activity of a Class 3 branching enzyme in the cell.

The statements made in conjunction with plant cells according to the invention and plants according to the invention apply with regard to the "introduction of a foreign nucleic acid molecule".

In a further preferred embodiment, the method according to the invention is used for producing potato plants according to the invention.

In a further preferred embodiment of the method according to the invention, the foreign nucleic acid molecule is chosen from the group consisting of a) Nucleic acid molecules, which code a protein with the amino acid sequence given under Seq ID NO 4;

b) Nucleic acid molecules, which code a protein, the amino acid sequence of which has an identity of at least 50% with the amino acid sequence given under SEQ ID NO: 4;

c) Nucleic acid molecules, which include the nucleotide sequence shown under Seq ID NO. 3 or a complimentary sequence;

d) Nucleic acid molecules, the nucleic acid sequence of which has an identity of at least 50% with the nucleic acid sequences described under a) or c);

e) Nucleic acid molecules, which hybridise with at least one strand of the nucleic acid molecules described under a) or c) under stringent conditions;

f) Nucleic acid molecules, the nucleotide sequence of which deviates from the sequence of the nucleic acid molecules identified under a), b), c), d), e) or f) due to the degeneration of the genetic code; and g) Nucleic acid molecules, which represent fragments, allelic variants and/or derivatives of the nucleic acid molecules identified under a), b), c), d), e) or f).

In a further preferred embodiment of the method according to the invention, the foreign nucleic acid molecule is chosen from the group consisting of a) Nucleic acid molecules, which code at least one antisense RNA, which effects a reduction in the expression of at least one endogenous gene, which codes a Class 3 branching enzyme;

b) Nucleic acid molecules, which by means of a co-suppression effect lead to the reduction in the expression of at least one endogenous gene, which codes a Class 3 branching enzyme;

c) Nucleic acid molecules, which code at least one ribozyme, which splits specific transcripts of at least one endogenous gene, which codes a Class 3 branching enzyme;

d) Nucleic acid molecules, which simultaneously code at least one antisense RNA and at least one sense RNA, wherein the said antisense RNA and the said sense RNA form a double-stranded RNA molecule, which effects a reduction in the expression of at least one endogenous gene, which codes a Class 3 branching enzyme (RNAi technology);

e) Nucleic acid molecules introduced by means of in vivo mutagenesis, which lead to a mutation or an insertion of a heterologous sequence in at least one endogenous gene coding a Class 3 branching enzyme, wherein the mutation or insertion effects a reduction in the expression of a gene coding a Class 3 branching enzyme or results in the synthesis of inactive Class 3 branching enzymes;

f) Nucleic acid molecules, which code an antibody, wherein the antibody results in a reduction in the activity of a Class 3 branching enzyme due to the bonding to a Class 3 branching enzyme.

g) Nucleic acid molecules, which contain transposons, wherein the integration of these transposons leads to a mutation or an insertion in at least one endogenous gene coding a Class 3 branching enzyme, which effects a reduction in the expression of at least one gene coding a Class 3 branching enzyme, or results in the synthesis of inactive Class 3 branching enzymes; and/or h) T-DNA molecules, which, due to insertion in at least one endogenous gene coding a Class 3 branching enzyme, effect a reduction in the expression of at least one gene coding a Class 3 branching enzyme, or result in the synthesis of inactive Class 3 branching enzyme.

In a further embodiment of the method according to the invention, the genetically modified plants according to the invention synthesise a modified starch in comparison with corresponding wild type plants that have not been genetically modified.

In a further embodiment of the method according to the invention, the method according to the invention is used to manufacture plants according to the invention.

The present invention also relates to the plants obtainable by the method according to the invention.

It is also an object of the present invention to provide means such as DNA molecules, for example, for the production of plant cells according to the invention and plants according to the invention, which synthesise a modified starch in comparison with modified wild type plant cells or wild type plants that have not been genetically modified.

The present invention therefore also relates to nucleic acid molecules coding for a protein with the enzymatic activity of a Class 3 branching enzyme, chosen from the group consisting of a) Nucleic acid molecules, which code a protein with the amino acid sequence given under Seq ID NO 4;

b) Nucleic acid molecules, which code a protein, which includes the amino acid sequence, which is coded by the insertion in plasmid DSM 15926;

c) Nucleic acid molecules, which code a protein, the sequence of which has an identity of at least 70% with the amino acid sequence given under SEQ ID NO 4;

d) Nucleic acid molecules, which code a protein, the sequence of which has an identity of at least 70% with the amino acid sequence, which is coded by the insertion in plasmid DSM 15926;

e) Nucleic acid molecules, which include the nucleotide sequence shown under Seq ID NO 3 or a complimentary sequence;

f) Nucleic acid molecules, which include the nucleotide sequence of the insertion contained in plasmid DSM 15926;

g) Nucleic acid molecules, which have an identity of at least 70% with the nucleic acid sequences described under a), b), d) or e);

h) Nucleic acid molecules, which hybridise with at least one strand of the nucleic acid molecules described under a), b), d), e) or f) under stringent conditions;

i) Nucleic acid molecules, the nucleotide sequence of which deviates from the sequence of the nucleic acid molecules identified under a), b), e) or f) due to the degeneration of the genetic code; and j) Nucleic acid molecules, which represent fragments, allelic variants and/or derivatives of the nucleic acid molecules identified under a), b), c), d), e), f), g), h) or i).

The amino acid sequence shown in SEQ ID NO 4 codes a protein with the activity of a Class 3 branching enzyme from *Solanum tuberosum.*

The proteins coded from the different varieties of nucleic acid molecules according to the invention have certain common characteristics. These can include, for example, biological activity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc.

The molecular weight of the Class 3 branching enzyme from *Solanum tuberosum* derived from the amino acid sequence shown under SEQ ID NO 4 is ca. 103 kDa. The derived molecular weight of a protein according to the invention therefore preferably lies in the range from 85 kDa to 120 kDa, preferably in the range from 95 kDa to 110 kDa and particularly preferably from ca. kDa 100 to 105 kDa.

The present invention relates to nucleic acid molecules, which code a protein with the enzymatic activity of a Class 3 branching enzyme, wherein the coded protein has an identity of at least 70%, preferably of at least 80%, particularly preferably of at least 90% and especially preferably of 95% with the amino acid sequence specified under SEQ ID NO 4.

A plasmid containing a cDNA, which codes a Class 3 branching enzyme from *Solanum tuberosum*, was deposited with the Deutsche Sammlung von Mikroorganismen und Zellkulturen GmbH, Mascheroder Weg 1b, 38124 Braunschweig, Germany, in accordance with the Budapest Treaty on 15 Sep. 2003 under the number DSM 15926. The amino acid sequence shown SEQ ID NO 4 can be derived from the coding region of the cDNA sequence integrated in plasmid DSM 15926 and codes for a Class 3 branching enzyme from *Solanum tuberosum*. The present invention therefore also relates to nucleic acid molecules, which code a protein with the enzymatic activity of a Class 3 branching enzyme, which includes the amino acid sequence, which is coded by the insertion in plasmid DSM 15926, wherein the coded protein has an identity of at least 70%, preferably of at least 80%, particularly preferably of at least 90% and especially preferably of 95% with the amino acid sequence, which can be derived from the insertion in DSM 15926.

The nucleic acid sequence shown SEQ ID NO 3 is a cDNA sequence, which includes the coding region for a Class 3 branching enzyme from *Solanum tuberosum.*

The present invention therefore also relates to nucleic acid molecules, which code a Class 3 branching enzyme and the coding region of the nucleotide sequence shown under Seq ID NO 3 or a complimentary sequence, nucleic acid molecules, which include the coding region of the nucleotide sequence of the insertion contained in plasmid DSM 15926 and nucleic acid molecules, which have an identity of at least 70%, preferably of at least 80%, particularly preferably of at least 90% and especially preferably of at least 95% with the said nucleic acid molecules.

With the help of the sequence information of the nucleic acid molecule according to the invention or with the help of the nucleic acid molecule according to the invention, it is now possible for the person skilled in the art to isolate homologous sequences from other plant species, preferably from starch-storing plants, preferably from plant species of the genus *Solanum*, particularly preferably from *Solanum tuberosum*. This can be carried out, for example, with the help of conventional methods such as the examination of cDNA or genomic banks with suitable hybridisation samples. The person skilled in the art knows that homologous sequences can also be isolated with the help of (degenerated) oligonucleotides and the use of PCR-based methods.

The examination of databases, such as are made available, for example, by EMBL or NCBI National Center for Biotechnology Information, can also be used for identifying homologous sequences, which code for a Class 3 branching enzyme. In this case, one or more sequences are specified as a so-called query. This query sequence is then compared by means of statistical computer programs with sequences, which are contained in the selected databases. Such database queries (e.g. blast or fasta searches) are known to the person skilled in the art and can be carried out by various providers. If such a database query is carried out, e.g. at the NCBI (National Center for Biotechnology Information website, then the standard settings, which are specified for the particular comparison inquiry, should be used. For protein sequence comparisons (blastp), these are the following settings: Limit entrez=not activated; Filter=low complexity activated; Expect value=10; word size=3; Matrix=BLOSUM62; Gap costs: Existence=11, Extension=1.

For nucleic acid sequence comparisons (blastn), the following parameters must be set: Limit entrez=not activated; Filter=low complexity activated; Expect value=10; word size=11.

With such a database search, the sequences described in the present invention can be used as a query sequence in order to identify further nucleic acid molecules and/or proteins, which code a Class 3 branching enzyme.

With the help of the described methods, it is also possible to identify and/or isolate nucleic acid molecules according to the invention, which hybridise with the sequence specified under SEQ ID NO 3 and which code a Class 3 branching enzyme.

Within the framework of the present invention, the term "hybridising" means hybridisation under conventional hybridisation conditions, preferably under stringent conditions such as, for example, are described in Sambrock et al., Molecular Cloning, A Laboratory Manual, 2nd Ed. (1989) Cold Spring Harbor Laboratory Press, Cold Spring Harbor, N.Y.). Particularly preferably, "hybridising" means hybridisation under the following conditions:

Hybridisation buffer: 2×SSC; 10×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS Hybridisation temperature: T=65 to 68° C.

Wash buffer: 0.2×SSC; 0.1% SDS

Wash temperature: T=65 to 68° C.

In principle, nucleic acid molecules, which hybridise with the nucleic acid molecules according to the invention, can originate from any plant species, which expresses an appropriate protein, preferably they originate from starch-storing plants, preferably from species of the genus *Solanum*, particularly preferably from *Solanum tuberosum*. Nucleic acid molecules, which hybridise with the molecules according to the invention, can, for example, be isolated from genomic or from cDNA libraries. The identification and isolation of nuclear acid molecules of this type can be carried out using the nucleic acid molecules according to the invention or parts of these molecules or the reverse complements of these molecules, e.g. by means of hybridisation according to standard methods (see, for example, Sambrook et al., 1989, Molecular Cloning, A Laboratory Manual, 2nd Ed. Cold Spring Harbor Laboratory Press, Cold Spring Harbor, N.Y.) or by amplification using PCR.

Nucleic acid molecules, which exactly or essentially have the nucleotide sequence specified under SEQ ID NO 3 or parts of this sequence, can be used as hybridisation samples. The fragments used as hybridisation samples can also be synthetic fragments or oligonucleotides, which have been manufactured using established synthesising techniques and the sequence of which corresponds essentially with that of a nucleic acid molecule according to the invention. If genes have been identified and isolated, which hybridise with the nucleic acid sequences according to the invention, then a determination of this sequence and an analysis of the characteristics of the proteins coded by this sequence should be carried out in order to establish whether a Class 3 branching enzyme is involved. Homology comparisons on the level of the nucleic acid or amino acid sequence and a determination of the enzymatic activity are particularly suitable for this purpose. As described above, the activity of a Class 3 branching enzyme can take place by expression in *E. coli* strains, which themselves do not express an active branching enzyme (Kiel et al., 1987 Mol. Gen. Genet. 207: 294-301); Guan et al., 1995, Proc. Natl. Acad. Sci. 92, 964-967).

The molecules hybridising with the nucleic acid molecules according to the invention particularly include fragments, derivatives and allelic variants of the nucleic acid molecules according to the invention, which code a Class 3 branching enzyme from plants, preferably from starch-storing plants, preferably from plant species of the genus *Solanum*, particularly preferably from *Solanum tuberosum*. In conjunction with the present invention, the term "derivative" means that the sequences of these molecules differ at one or more positions from the sequences of the nucleic acid molecules described above and have a high degree of identity with these sequences.

Here, the deviation from the nucleic acid molecules described above can have come about, for example, due to deletion, addition, substitution, insertion or recombination.

Furthermore, identity means that functional and/or structural equivalence exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations can occur naturally, for example they can be sequences from other plant species, or they can be mutations, wherein these mutations may have occurred in a natural manner or have been introduced by objective mutagenesis. The variations can also be synthetically manufactured sequences. The allelic variants can be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

The proteins coded from the different derivatives of nucleic acid molecules according to the invention have certain common characteristics. These can include, for example, biological activity, substrate specificity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc.

The nucleic acid molecules according to the invention can be any nucleic acid molecules, in particular DNA or RNA molecules, for example cDNA, genomic DNA, mRNA etc. They can be naturally occurring molecules or molecules manufactured by genetic or chemical synthesis methods. They can be single-stranded molecules, which either contain the coding or the non-coding strand, or double-stranded molecules.

Furthermore, the present invention relates to nucleic acid molecules of at least 21, preferably more than 50 and particularly preferably more than 200 nucleotides length, which specifically hybridise with at least one nucleic acid molecule according to the invention. Here, specifically hybridise means that these molecules hybridise with nucleic acid molecules, which code a protein according to the invention, but not with nucleic acid molecules, which code other proteins. In particular, the invention relates to such nucleic acid molecules, which hybridise with transcripts of nucleic acid molecules according to the invention and, as a result, can hinder their translation. Such nucleic acid molecules, which specifically hybridise with the nucleic acid molecules according to the invention, can, for example, be constituents of antisense, RNAi or cosuppression constructs or ribozymes, or can be used as primers for PCR amplification.

In conjunction with the present invention, the term "identity" means a sequence identity over the whole length of the coding region of at least 60%, in particular an identity of at least 70%, preferably greater than 80%, particularly preferably greater than 90% and especially of at least 95%. In conjunction with the present invention, the term "identity" is to be understood to mean the number of amino acids/nucleotides (identity) corresponding with other proteins/nucleic acids, expressed as a percentage. Identity is preferably determined by comparing the Seq. ID NO 4 or SEQ ID NO 3 with other proteins/nucleic acids with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Génétique et de Biologie Moléculaire et Cellulaire, B.P.163, 67404 Illkirch Cedex, France; and the EBI as well as from all mirrored Internet sites of the EBI (European Bioinformatics Institute, Wellcome Trust Genome Campus, Hinxton, Cambridge CB10 1SD, UK).

Preferably, Version 1.8 of the ClustalW computer program is used to determine the identity between proteins according to the invention and other proteins. In doing so, the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, Version 1.8 of the ClustalW computer program is used to determine the identity between the nucleotide sequence of the nucleic acid molecules according to the invention, for example, and the nucleotide sequence of other nucleic acid molecules. In doing so, the following parameters must be set: KTUPLE=2, TOPDIAGS=4, PAIRGAP=5, DNAMATRIX:IUB, GAPOPEN=10, GAPEXT=5, MAXDIV=40, TRANSITIONS: unweighted.

Basically, nucleic acid molecules according to the invention, can originate from any plant, preferably they originate from starch-storing plants, preferably from plant species of the genus *Solanum*, particularly preferably from *Solanum tuberosum*.

Furthermore, the invention relates to vectors, in particular plasmids, cosmids, viruses, bacteriophages and other common vectors in genetic engineering, which contain the nucleic acid molecules according to the invention described above.

In a preferred embodiment, the nucleic acid molecules according to the invention contained in the vectors are linked with regulatory sequences, which guarantee expression in prokarygntic or eukaryontic cells. Here, the term "expression" can mean both transcription as well as transcription and translation. In this case, the nucleic acid molecules according to the invention can be present in "sense" orientation and/or in "antisense" orientation to the regulatory sequences.

Regulatory sequences for expression in prokaryontic organisms, e.g. *E. coli*, and in eukaryontic organisms are adequately described in the literature, in particular those for expression in yeast such as *Saccharomyces cerevisiae*, for example. An overview of different expression systems for proteins in different host organisms can be found, for example, in Methods in Enzymology 153 (1987), 383-516 and in Bitter et al. (Methods in Enzymology 153 (1987), 516-544).

For expressing the nucleic acid molecules, which code a Class 3 branching enzyme, in sense and/or antisense orientation in vegetable cells, these are preferably linked with regulatory DNA sequences, which guarantee transcription in vegetable cells. In particular, these include promoters. In general, any promoter that is active in vegetable cells is eligible for expression. At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule.

Suitable promoters are, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-i promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Bäumlein et al., Mol. Gen. Genet. 225 (1991), 459-467).

Furthermore, a termination sequence (polyadenylation signal) can be present, which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

In a further embodiment, the present invention relates to vectors, which contain DNA molecules, which code at least one antisense RNA, which effects a reduction in the expression of at least one endogenous gene, which codes a Class 3 branching enzyme.

In a further special embodiment, the present invention relates to vectors, which contain DNA molecules, which by means of a cosuppression effect lead to a reduction in the expression of at least one endogenous gene, which codes a Class 3 branching enzyme.

In a further embodiment, the present invention relates to vectors, which contain DNA molecules, which code at least one ribozyme, which splits specific transcripts of at least one endogenous gene, which codes a Class 3 branching enzyme.

In a further embodiment, the present invention relates to vectors, which contain DNA molecules, which simultaneously code at least one antisense RNA and at least one sense RNA, wherein the said antisense RNA and the said sense RNA form a double-stranded RNA molecule, which effects a reduction in the expression of at least one endogenous gene, which codes a Class 3 branching enzyme (RNAi technology).

A further subject of the present invention is a host cell, in particular a prokaryontic or eukaryontic cell, which is genetically modified with a nucleic acid molecule according to the invention and/or with a vector according to the invention, as well as cells, which originate from host cells of this type and which contain the genetic modification according to the invention.

In a preferred embodiment, the invention relates to host cells, in particular prokaryontic or eukaryontic cells, which have been transformed using the nucleic acid molecule according to the invention or a vector according to the invention, as well as host cells, which originate from host cells of this type and which contain the described nucleic acid molecules or vectors according to the invention.

The host cells can be bacteria (e.g. *E. coli*) or fungus cells (e.g. yeast, in particular *S. cerevisiae, Agaricus*, in particular *Agaricus bisporus*), as well as vegetable or animal cells. Here, the term "transforms" means that the cells according to the invention are genetically modified with a nucleic acid molecule according to the invention inasmuch as they contain at least one nucleic acid molecule according to the invention in addition to their natural genome. This can be freely present in the cell, possibly as a self-replicating molecule, or it can be stably integrated in the genome of the host cell.

The host cells are preferably microorganisms. Within the framework of the present application, these are understood to mean all bacteria and all protista (e.g. fungi, in particular yeast and algae), as defined, for example, in Schlegel "Allgemeine Mikrobiologie" (Georg Thieme Verlag (1985), 1-2).

It is especially preferred if the host cells according to the invention are plant cells. In principle, these can be plant cells from any plant species, i.e. both monocotyledonous and dicotyledonous plants. Preferably, these will be plant cells from useful agricultural plants, i.e. from plants, which are cultivated by people for the purposes of food or for technical, in particular industrial purposes. The invention relates preferably to plant cells and plants from starch-storing plants (maize, rice, wheat, rye, oat, barley, cassava, potato, sago, mung bean, pea or sorghum); in particular, plant cells from maize, rice, wheat or potato plants are particularly preferred.

A further subject of the present invention are proteins with the enzymatic activity of a Class 3 branching enzyme, chosen from the group consisting of a) Proteins, which include the amino acid sequence specified under SEQ ID NO 4;

b) Proteins, which are coded by the coding region of the DNA inserted in the plasmid DSM 15926; or c) Proteins, which have an identity of at least 70% with the amino acid sequence of the proteins identified under a) or b).

In a further embodiment, the present invention relates to proteins with the enzymatic activity of a Class 3 branching enzyme, wherein the coded protein has an identity of at least 70%, preferably of at least 80%, particularly preferably of at least 90% and especially preferably of 95% with the amino acid sequence specified under SEQ ID NO 4 or with the amino acid sequence of a Class 3 branching enzyme coded by the insertion in plasmid DSM 15926.

In a further embodiment, the invention also relates to proteins, which are coded by nucleic acid molecules according to the invention.

In a preferred embodiment, the present invention relates to a protein with the enzymatic activity of a Class 3 branching enzyme, wherein the Class 3 branching enzyme originates from a potato plant.

Surprisingly, it has been found that plant cells and plants, which have a reduced activity of a Class 3 branching enzyme, synthesise a starch, which is modified in comparison with starch from wild type plant cells or wild type plants.

In conjunction with the present invention, the term "modified starch" means that the starch has changed physical-chemical characteristics compared with non-modified starch obtainable from corresponding wild type plant cells or wild type plants that have not been genetically modified.

In a preferred embodiment of the present invention, the modified starch is native starch.

In conjunction with the present invention, the term "native starch" means that the starch is isolated from plants according to the invention, harvestable plant plants according to the invention or propagation material of plants according to the invention by methods known to the person skilled in the art.

Starch is a classical additive for many foodstuffs in which it essentially takes over the function of binding aqueous additives or increasing the viscosity, or brings about an increased formation of gel. Important characteristic features are the flow and sorption behaviour, the source and sticking temperature, the viscosity and thickening performance, the solubility of the starch, the transparency and paste structure, the heat, shearing and acidic stability, the tendency to retrogradation, the ability to form a film, the freezing/thawing stability, the digestibility as well as the ability to form complexes with, for example, inorganic or organic ions.

In the area of the non-foodstuffs industry, starch can be used, for example, as an auxiliary substance for different manufacturing processes or as an additive in technical products. Particular mention must be made here of the paper and cardboard industry where starch is used as an auxiliary substance. Here, the starch is primarily used for retardation (holding back of solids), the bonding of filler and fine material particles, as a consolidation material and for dehydration. In addition to this, the favourable characteristics of starch with regard to stiffness, hardness, sound, grip, shine, smoothness and resistance to splitting as well as the surfaces are also fully utilised.

A further major area of use of starches is in the adhesive industry, where the possible applications are divided into four sub-areas. Use as a pure starch adhesive, use with starch adhesives prepared with special chemicals, use of starch as an additive to synthetic resins and polymer dispersions, and the use of starches as a stretching medium for synthetic adhesives.

Furthermore, starches can be used as additives for building materials (e.g. plasterboard sheets, ready-mixed concrete, plaster and mineral fibres), for the manufacture of media for stabilising soil, as a functional aid in plant protection media or fertilisers, as a functional aid in the pharmaceutical industry (e.g. as a bonding medium, tablet dispersal medium, in lubricating and vulnerary powders) and the cosmetic industry (as a carrier of additives), as a strengthening additive for coal and briquettes, as a flocculation medium (e.g. in the preparation of carbon sludge) and as a bonding medium, e.g. in Betonit.

Plant cells according to the invention and plants according to the invention synthesise a modified starch in comparison with starch of corresponding wild type plant cells or wild type plants that have not been genetically modified. In its physical-chemical characteristics, e.g. the amylopectin/amylose ratio, the degree of branching, the phosphate content, the average chain length, the viscosity behaviour, the starch grain size, the side chain distribution and/or the starch grain form, the modified starch is changed in comparison with the synthesised starch in wild type plant cells or plants so that it is better suited for use in particular application areas, for example.

The present invention therefore also relates to modified starches obtainable or isolated from plant cells according to the invention or plants according to the invention, from propagation material according to the invention or from harvestable plant parts according to the invention.

In a particularly preferred embodiment, the present invention relates to modified potato starch.

Furthermore the present invention relates to a method for the manufacture of a modified starch including the step of extracting the starch from a plant cell according to the invention or from a plant according to the invention, from propagation material according to the invention of such a plant and/or from harvestable plant parts according to the invention of such a plant, preferably from starch-storing parts according to the invention of a plant. Preferably, such a method also includes the step of harvesting the cultivated plants or plant parts and/or the propagation material of these plants before the extraction of the starch and, further, particularly preferably the step of cultivating plants according to the invention before harvesting.

Methods for extracting starches from plants or from starch-storing parts of plants are known to the person skilled in the art. Furthermore, methods for extracting starch from different starch-storing plants are described, e.g. in Starch: Chemistry and Technology (Publisher: Whistler, BeMiller and Paschall (1994), 2nd Edition, Academic Press Inc. London Ltd; ISBN 0-12-746270-8; see e.g. Chapter XII, Page 412-468: Maize and *Sorghum* Starches: Manufacture; by Watson; Chapter XIII, Page 469-479: Tapioca, Arrowroot and Sago Starches: Manufacture; by Corbishley and Miller; Chapter XIV, Page 479-490: Potato starch: Manufacture and Uses; by Mitch; Chapter XV, Page 491 to 506: Wheat starch: Manufacture, Modification and Uses; by Knight and Oson; and Chapter XVI, Page 507 to 528: Rice starch: Manufacture and Uses; by Rohmer and Klem; Maize starch: Eckhoff et al., Cereal Chem. 73 (1996), 54-57, the extraction of maize starch on an industrial scale is generally achieved by so-called "wet milling".). Devices, which are in common use in methods for extracting starch from plant material are separators, decanters, hydrocyclones, spray dryers and fluid bed dryers.

In conjunction with the present invention, the term "starch-storing parts" is to be understood to mean such parts of a plant in which, in contrast to transitory leaf starch, starch is stored as a deposit for surviving for longer periods. Preferred starch-storing parts are tubers, storage roots, seeds or endosperm; particularly preferred are potato tubers or the endosperm of maize, wheat or rice plants.

Modified starch obtainable by the method according to the invention is also the subject matter of the present invention.

Furthermore, the use of plant cells according to the invention or plants according to the invention for manufacturing a modified starch are the subject matter of the present invention.

The person skilled in the art knows that the characteristics of starch can be changed by thermal, chemical, enzymatic or mechanical derivation, for example. Derived starches are particularly suitable for different applications in the foodstuffs and/or non-foodstuffs sector. The starches according to the invention are better suited as a starting substance for the manufacture of derived starches than conventional starches. In the manufacture of derived starch, they are distinguished by better processing capability and lead to new products, as a modified starch is used as a new starting material for the derivation process.

The present invention therefore also relates to the manufacture of a derived starch, wherein modified starch according to the invention is derived retrospectively.

In conjunction with the present invention, the term "derived starch" is to be understood to mean a modified starch according to the invention, the characteristics of which have been retrospectively changed after isolation from vegetable cells with the help of chemical, enzymatic, thermal or mechanical methods.

In a preferred embodiment of the present invention, the derived starch according to the invention is starch that has been heat-treated and/or acid-treated.

In a further preferred embodiment, the derived starches are starch ethers, in particular starch alkyl ethers, O-allyl ethers, hydroxylalkyl ethers, O-carboxylmethyl ethers, nitrogen-containing starch ethers, phosphate-containing starch ethers or sulphur-containing starch ethers.

In a further preferred embodiment, the derived starches are cross-linked starches.

In a further preferred embodiment, the derived starches are starch graft polymers.

In a further preferred embodiment, the derived starches are oxidised starches.

In a further preferred embodiment, the derived starches are starch esters, in particular starch esters, which have been introduced into the starch using organic acids. Particularly preferably these are phosphate, nitrate, sulphate, xanthate, acetate or citrate starches.

The derived starches according to the invention are suitable for different applications in the foodstuffs and/or non-foodstuffs sector. Methods for manufacturing derived starches according to the invention are known to the person skilled in the art and are adequately described in the general literature. An overview on the manufacture of derived starches can be found, for example, in Orthoefer (in Corn, Chemistry and Technology, 1987, eds. Watson und Ramstad, Chapter 16, 479-499).

Derived starch obtainable by the method according to the invention for manufacturing a derived starch is also the subject matter of the present invention.

Furthermore, the use of modified starches according to the invention for manufacturing derived starch is the subject matter of the present invention.

DESCRIPTION OF SEQUENCES

SEQ ID NO 1: Nucleic acid sequence containing the coding region of the 3'-area of a Class 3 branching enzyme from *Solanum tuberosum* (cv Désirée). This sequence is inserted in plasmid AN 46-196.

SEQ ID NO 2: Nucleic acid sequence containing the coding region of the 5'-area of a Class 3 branching enzyme from *Solanum tuberosum* (cv Désirée). This sequence is inserted in plasmid AN 47-196.

SEQ ID NO 3: Nucleic acid sequence containing the full coding region of a Class 3 branching enzyme from *Solanum*

*tuberosum* (cv Désirée). This sequence is inserted in plasmid AN 49 and was deposited with the Deutsche Sammlung von Mikroorganismen und Zellkulturen GmbH, Mascheroder Weg 1b, 38124 Braunschweig, Germany, in accordance with the Budapest Treaty on 15 Sep. 2003 under the number DSM 15926.

SEQ ID NO 4: Amino acid sequence coding a Class 3 branching enzyme from *Solanum tuberosum* (cv Désirée ). This sequence can be derived from the nucleic acid sequence inserted in plasmid AN 49 or from the nucleic acid sequence described under SEQ ID NO 3.

SEQ ID NO 5: Nucleic acid sequence containing the full coding region of a Class 3 branching enzyme from *Solanum tuberosum* (cv Désirée ). This sequence has been obtained by combining the nucleic acid sequences described under SEQ ID NO 1 and SEQ ID NO 2. This nucleic acid sequence constitutes an allelic variant of the nucleic acid sequence described under SEQ ID NO 3 coding a Class 3 branching enzyme.

SEQ ID NO 6: Amino acid sequence coding a Class 3 branching enzyme from *Solanum tuberosum* (cv Désirée ). This sequence can be derived from the nucleic acid sequence described under SEQ ID NO 5 and constitutes an allelic variant of the amino acid sequence described under SEQ ID NO 4 coding a Class 3 branching enzyme

DESCRIPTION OF THE FIGURES

FIG. 1 shows the amino acid sequences, contained in the "seed alignment," that are used for producing the HMM describing for the Pfam isoamylase domain (PF 02922).

FIG. 2 shows the amino acid sequences, contained in the "seed alignment," that are used for producing the HMM describing for the Pfam alpha-amylase domain (PF 00128).

FIGS. 3-16 show information for producing the HMM for the Pfam isoamylase domain (PF 02922).

FIGS. 17-67 show information for producing the HMM for the Pfam alpha-amylase domain (PF 00128).

GENERAL METHODS

Figure 11:
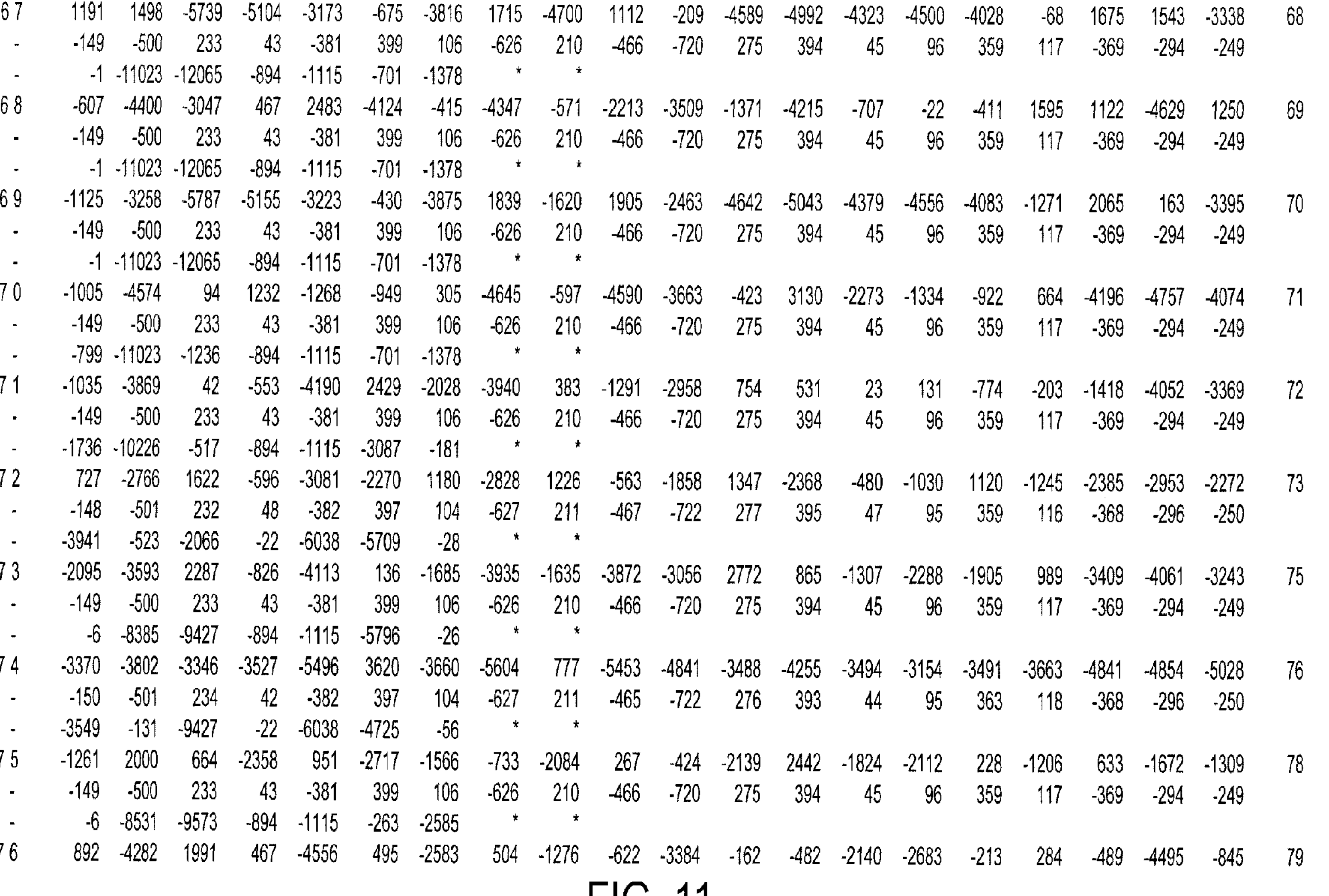
Figure 15:
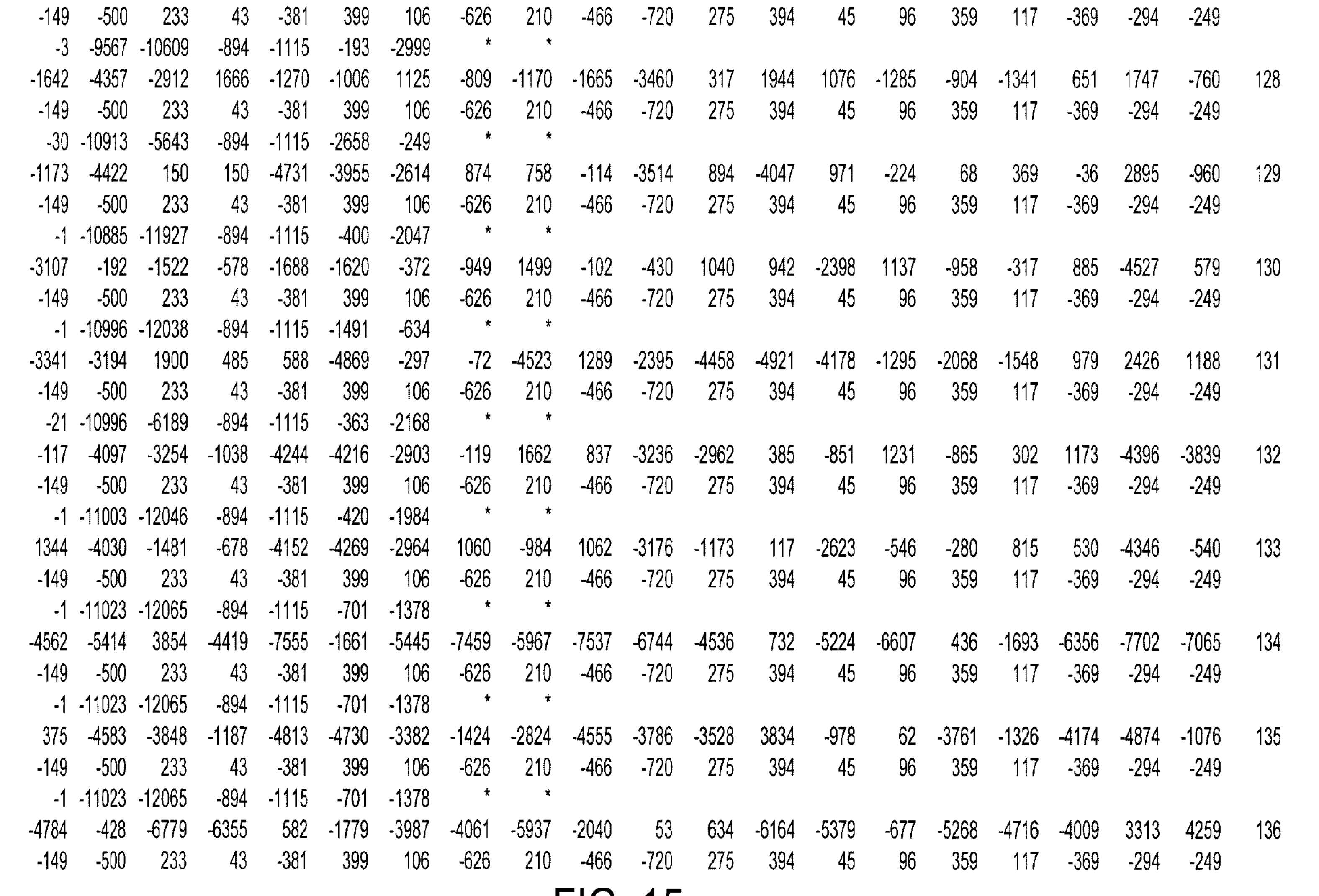

The following methods were used in the examples:

Demonstration of the Activity of a Class 3 Branching Enzyme

The activity of a Class 3 branching enzyme was demonstrated with the help of non-denaturing gel electrophoresis as follows:

To isolate proteins from plants, the test material was ground with a pestle in liquid nitrogen, absorbed into an extraction buffer (50 mM Na citrate, pH 6.5; 1 mM EDTA, 4 mM DTT) and, after centrifugation (10 min, 14.000g, 4° C.), was used directly for measurement of the protein content according to, Bradford. Subsequently, 5g to 20 μg total protein extract was mixed with 4×loading buffer (20% glycerol, 125 mM Tris HCl, pH 6.8) and loaded onto a BE activity gel. The BE activity gel was made up as follows: 2.5 ml 30% acrylamide: 0.8% bisacrylamide, 0.1 ml running buffer, 7.4 ml $H_2O$, 10% ammonium persulphate solution and 5 μl N,N, N',N'-tetramethylethylenediamine (TEMED). The running buffer (RB) was made up as follows: RB=30.2 g Tris base, pH 8.0, 144g glycine on 1 L $H_2O$. On completion of the gel run, each of the gels was incubated overnight at 37° C. in 25 ml "phosphorylase buffer" (25 ml 1M Na citrate pH 7.0, 0.47 g glucose-1-phosphate, 12.5 mg AMP, 2.5 mg phosphorylase a/b from "rabbit"). The gels were coloured with Lugol's solution.

Starch Analysis a) Determination of the Amylose Content and of the Amylose/Amylopectin Ratio Starch was isolated from potato plants by standard methods, and the amylose content and the amylose:amylopectin ratio was determined by the method described by Hovenkamp-Hermelink et al. (Potato Research 31, (1988), 241-246).

b) Determination of the Phosphate Content

In starch, the positions C2, C3 and C6 of the glucose units can be phosphorylated. To determine the C6-P content of starch, 50 mg of starch are hydrolysed for 4 h at 95° C. in 500 μl of 0.7 M HCl. The samples are then centrifuged for 10 minutes at 15500×g and the supernatants are removed. 7 μl of the supernatants are mixed with 193 μl of imidazole buffer (100 mM imidazole, pH 7.4; 5 mM $MgCl_2$, 1 mM EDTA and 0.4 mM NAD). The measurement was carried out in a photometer at 340 nm. After the base absorption had been established, the enzyme reaction was started by addition of 2 units glucose-6-phosphate dehydrogenase (from Leuconostoc mesenteroides, Boehringer Mannheim). The change in absorption is directly proportional to the concentration of the G-6-P content of the starch.

The total phosphate content was determined by the method of Ames (Methods in Enzymology VIII, (1966), 115-118).

Approximately 50 mg of starch are treated with 30 μl of ethanolic magnesium nitrate solution and ashed for 3 hours at 500° C. in a muffle oven. The residue is treated with 300 μl of 0.5 M hydrochloric acid and incubated for 30 minutes at 60° C. One aliquot is subsequently made up to 300 μl 0.5 M hydrochloric acid and this is added to a mixture of 100 μl of 10% ascorbic acid and 600 μl of 0.42% ammonium molybdate in 2 M sulphuric acid and incubated for 20 minutes at 45° C.

This is followed by a photometric determination at 820 nm with a phosphate calibration series as standard.

c) Determination of the Viscosity Characteristics by Means of a Rapid Visco Analyser (RVA)

2g of starch (DM) are taken up in 25 ml of $H_2O$ (VE-type water, conductivity of at least 15 mega ohm) and used for the analysis in a Rapid Visco Analyser Super3 (Newport Scientific Pty Ltd., Investmet Support Group, Warriewod NSW 2102, Australia). The apparatus is operated following the manufacturer's instructions. The viscosity values are indicated in Centipoise (cP) in accordance with the manufacturer's operating manual, which is incorporated into the description herewith by reference. To determine the viscosity of the aqueous starch solution, the starch suspension is first stirred for 10 seconds at 960 rpm and subsequently heated at 50° C. at a stirring speed of 160 rpm, initially for a minute (step 1). The temperature was then raised from 50° C. to 95° C. at a heating rate of 12° C. per minute (step 2). The temperature is held for 2.5 minutes at 95° C. (step 3) and then cooled from 95° C. to 50° C. at 12° C. per minute (step 4). In the last step (step 5), the temperature of 50° C. is held for 2 minutes. The viscosity is determined during the entire duration.

After the programme has ended, the stirrer is removed and the beaker covered. The gelatinized starch is now available for the texture analysis after 24 hours incubation at room temperature.

The profile of the RVA analysis contains parameters which are shown for the comparison of different measurements and substances. In the context of the present invention, the following terms are to be understood as follows:

1. Maximum Viscosity (RVA Max)

The maximum viscosity is understood as meaning the highest viscosity value, measured in cP, obtained in step 2 or 3 of the temperature profile.

2. Minimum Viscosity (RVA Min)

The minimum viscosity is understood as meaning the lowest viscosity value, measured in cP, observed in the temperature profile after the maximum viscosity. Normally, this takes place in step 3 of the temperature profile.

3. Final Viscosity (RVA Fin)

The final viscosity is understood as meaning the viscosity value, measured in cP, observed at the end of the measurement.

4. Setback (RVA Set)

What is known as the "setback" is calculated by subtracting the value of the final viscosity from that of the minimum occurring after the maximum viscosity in the curve.

5. Gelatinization Temperature (RVA PT)

The gelatinization temperature is understood as meaning the point in time of the temperature profile where, for the first time, the viscosity increases drastically for a brief period.

d) Determination of the Gel Strength (Texture Analyser)

2g of starch (DM) are gelatinized in the RVA apparatus in 25 ml of an aqueous suspension (temperature programme: see item d) "Determination of the viscosity characteristics by means of a Rapid Visco Analyser (RVA)") and subsequently stored for 24 hours at room temperature in a sealed container. The samples are fixed under the probe (round piston with planar surface) of a Texture Analyser TA-XT2 from Stable Micro Systems (Surrey, UK) and the gel strength was determined using the following parameters:

| | |
|---|---|
| Test speed | 0.5 mm/s |
| Depth of penetration | 7 mm |
| Contact surface | 113 $mm^2$ |
| Pressure | 2 g |

e) Analysis of the Side-Chain Distribution of the Amylopectin by Means of Ion-Exchange Chromatography To separate amylose and amylopectin, 200 mg of starch are dissolved in 50 ml reaction vessels, using 12 ml of 90% (v/v) DMSO in $H_20$. After addition of 3 volumes of ethanol, the precipitate is separated by centrifugation for 10 minutes at about 1800×g at room temperature (RT). The pellet is then washed with 30 ml of ethanol, dried and dissolved in 40 ml of 1% (w/v) NaCl solution at 75° C. After the solution has cooled to 30° C., approximately 90 mg of thymol are added slowly, and this solution is incubated for at least 60 h at 30° C. The solution is then centrifuged for 30 minutes at 2000×g (RT). The supernatant is then treated with 3 volumes of ethanol, and the amylopectin which settles out is separated by centrifugation for 5 minutes at 2000×g (RT). The pellet (amylopectin) is then washed with ethanol and dried using acetone. By addition of DMSO to the pellet, one obtains a 1% solution, of which 200 µl are treated with 345 µl of water, 10 µl of 0.5 M sodium acetate (pH 3.5) and 5 µl of isoamylase (dilution 1:10; Megazyme) and incubated for about 16 hours at 37° C. A 1:5 aqueous dilution of this digest is subsequently filtered through a 0.2 µm filter, and 10011 of the filtrate are analysed by ion chromatography (HPAEC-PAD, Dionex). Separation was performed using a PA-100 column (with suitable precolumn), while detection was performed amperometrically. The elution conditions were as follows:

Solution A -0.1 SM NaOH

Solution B -1 M sodium acetate in 0.1 SM NaOH

TABLE A

Composition of the elution buffer for the side chain analysis of the amylopectin at different times during the HPEAC-PAD Dionex analysis. Between the times stated, the composition of the elution buffer changes in each case linearly.

| t (min) | Solution A (%) | Solution B (%) |
|---|---|---|
| 5 | 0 | 100 |
| 35 | 30 | 70 |
| 45 | 32 | 68 |
| 60 | 100 | 0 |
| 70 | 100 | 0 |
| 72 | 0 | 100 |
| 80 | 0 | 100 |
| Stop | | |

The determination of the relative amount of short side chains in the total of all side chains is carried out via the determination of the percentage of a particular side chain in the total of all side chains. The total of all side chains is determined via the determination of the total area under the peaks which represent the polymerization degrees of DP 6 to 34 in the HPCL chromatogram.

The percentage of a particular side chain in the total of all side chains is determined via the determination of the ratio of the area under the peak which represents this side chain in the HPLC chromatogram to the total area. The programme Chromelion 6.20 Version 6.20 from Dionex, USA, was used for determining the peak areas.

f) Determination of the Activity of the BEIII Protein

This was carried out as specified in the example.

g) DSC-Analysis ("Differential Scanning Calorimetry")

Investigations with the aid of DSC-analysis have been done by the method described by WO 01/19975. 10 mg starch treated with 30 µl $H_20$ (VE-type water, conductivity of at least 15 mega ohm) were sealed in stainless steal pans (volume 50 µl). The pan is heated from 20° C. to 150° C. at a rate of 10° C. per minute in a Diamond DSC-instrument (Perkin Elmer). The programme Pyres from Perkin Elmer was used for determining the data.

EXAMPLES

Example 1

Cloning of a Full-Length Sequence Coding a Class 3 Branching Enzyme from *Solanum tuberosum*

The gene sequence coding for this Class 3 branching enzyme in *Solanum tuberosum* has not previously been described.

By sequence comparisons with different branching enzymes, a domain was identified, with the help of which EST databases were examined. In doing so, the EST TC73137 (TIGR database) from potato was identified.

With the help of the primers B1_Asp (GAT GGG TAC CAG CAC TTC TAC TTG GCA GAG G) and B2_Sal (TCA AGT CGA CCA CAA CCA GTC CAT TTC TGG), a sequence from a tuber-specific cDNA bank from *Solanum tuberosum* (cv. Désirée ) corresponding to this EST sequence was amplified. Attempts to use leaf-specific, "sink"-tissue-specific or "source"-tissue-specific cDNA banks as a template for the PCR reaction led to no amplification.

In order to amplify the whole coding sequence of the branching enzyme concerned, which up to now had also included unknown sequences, primers were manufactured, which were complimentary to the ends of the previously known sequence and vector sequences of the cDNA banks concerned. With all the primer combinations for the amplification of a full-length sequence of a Class 3 branching enzyme used in this approach, it was not possible to amplify any further area. Hereupon, EST databases of tomato were examined again.

In this case, two ESTs from tomato were identified (TIGR database; BG127920 and TC130382), which either had a high homology to the amplification of the Class 3 branching enzyme from potato described above (TC130382) and (BG127920) respectively, or to the putative branching enzyme gene from *arabidopsis* (GenBank: GP|9294564|dbj|BAB02827.1).

Primers were now manufactured again in order to also amplify previously unknown sequences of the Class 3 branching enzyme. By means of PCR, the 3'-area of the Class 3 branching enzyme was amplified from a cDNA bank, made from tubers of *Solanum tuberosum* (cv. Désirée), with the primers KM2_Spe (5'-TCAAACTAGTCACAACCAGTCCATTTCTGG-3') and So_putE (5'-CACTTTAGAAGGTATCAGAGC-3'). The fragment with a size of ca. 1 kb that was obtained was cloned undirectedly in the pCR4-TOPO vector from Invitrogen (product number: 45-0030). The plasmid produced was designated as AN 46-196. The sequence of the inserted fragments in the plasmid AN 46-196 is shown under SEQ ID NO 1.

The 5'-area was likewise amplified by means of PCR technology and using the primers So_put5' (5'-GTATTTCTGCGAAGGAACGACC-3') and So_putA (5'-AACAATGCTCTCTCTGTCGG-3') from the same cDNA bank. The fragment with a size of ca. 2 kb that was obtained was cloned undirectedly in the pCR4-TOPO vector from Invitrogen (product number: 45-0030). The plasmid produced was designated as AN 47-196. The sequence of the inserted fragments in the plasmid AN 47-196 is shown under SEQ ID NO 2.

Primers were now manufactured again in order to amplify a full-length sequence.

The following primers were used: SO_putA (AACAATGCTCTCTCTGTCGG) and SO_putE (CACTTTAGAAGGTATCAGAGC). A PCR product with an approximate size of 3.2 kb was obtained and was cloned in the pCR2.1 vector from Invitrogen (product number: 45-0030). The plasmid obtained (filed under DSM 15926) was designated as AN 49. The sequence of the inserted fragments in the plasmid AN 49 is shown under SEQ ID NO 3.

Example 2

Information on Vectors and Plasmids

Information on Vector AN 54-196

AN 54-196 is a derivative of the plasmid pBinB33-Hyg, to which was added a part sequence of the Class 3 branching enzyme gene as an "inverted repeat, (RNAi technology) under the control of the promoters of the patatin gene B33 from *Solanum tuberosum* (Rocha-Sosa et al., 1989). For this purpose, first of all, a PCR product with the primers B1_Asp (GAT GGG TAC CAG CAC TTC TAC TTG GCA GAG G) and B2_Sal (TCA AGT CGA CCA CAA CCA GTC CAT TTC TGG) from a tuber-specific cDNA bank from *Solanum tuberosum* (cv. Désirée ) was amplified, as a result of which the sites Asp718 and SalI were added. The PCR product obtained (625 bp) was cloned in "antisense" orientation to the B33 promoter via these two sites. A second PCR fragment, which was amplified with the primers B3_Sal (GCT TGT CGA CGG GAG AAT TTT GTC CAG AGG) and B4_Sal (GAT CGT CGA CAG CAC TTC TAC TTG GCA GAG G) from a tuber-specific cDNA bank from *Solanum tuberosum* (cv. Désirée ) and which is identical to the 301 bp of the first fragment, was cloned via the SalI site behind the first fragment, but in "sense" orientation to the B33 promoter. This arrangement is described as "inverted repeat" (RNAi technology).

Information on Vector pBbinB33-Hyg

Starting from the plasmid pBinB33, the EcoRI-HindIII fragment including the B33 promoter, a part of the polylinker, and the ocs terminator were cut out and spliced into the correspondingly cut vector pBIB-Hyg (Becker, 1990).

The plasmid pBinB33 was obtained by splicing the promoter of the patatin gene B33 from *Solanum tuberosum* (Rocha-Sosa et al., 1989) as a DraI fragment (nucleotide −1512-+14) into the vector pUC19 cut with SstI, the ends of which had been smoothed with the help of the T4 DNA polymerase. This resulted in the plasmid pUC19-B33. The B33 promoter was cut out from this plasmid with EcoRI and SmaI and spliced into the correspondingly cut vector pBinAR. This resulted in the vegetable expression vector pBinB33.

The plasmid pBinAR is a derivative of the vector plasmid pBin19 (Bevan, 1984) and was constructed as follows:

A fragment of length 529 Bp, which included the nucleotides 6909-7437 of the 35S RNA promoter of the cauliflower mosaic virus (Pietrzak et al., 1986, Nucleic Acids Research 14, 5857-5868), was isolated as an EcoRI/KpnI fragment from the plasmid pDH51 (Pietrzak et al., 1986) and spliced between the EcoRI and KpnI sites of the polylinker from pUC18. This resulted in the plasmid pUC18-35S.

With the help of the restriction endonucleases HindIII und PvuII, a fragment of length 192 Bp, which included the polyadenylation signal (3'-end) of the octopin synthase gene (gene 3) of the T-DNA of the Ti plasmid pTiACH5 (Gielen et al., 1984) (nucleotides 11749-11939) was isolated from the plasmid pAGV40 (Herrera-Estrella et al., 1983). After the addition of SspI linkers to the PvuII site, the fragment was spliced between the SphI and HindIII site from pUC18-35S. This resulted in the plasmid pA7.

The whole polylinker containing the 35S promoter and the ocs terminator with EcoRI and HindIII was cut out of pA7 and spliced into the correspondingly cut pBin19. This resulted in the vegetable expression vector pBinAR(Höfgen and Willmitzer, 1990).

Example 3

Genetically Modified Plants with Reduced Class 3 Branching Enzyme Activity

In order to produce transgenic potato plants, which have a reduced expression of a Class 3 branching enzyme gene, the T-DNA of the plasmid AN 54-196 was transferred into potato plants of the variety Désirée with the help of agrobacteria, as described in Rocha-Sosa et al. (EMBO J. 8, (1989), 23-29). The plants of the variety Désirée obtained by transformation with the plasmid AN 53-196 were designated as 369SO.

Analysis with the help of non-denaturising gel electrophoresis of protein extracts from tubers of wild type plant cells and/or protein extracts from genetically modified plants (396SO), showed that the genetically modified plant cells have a reduced activity of a Class 3 branching enzyme in comparison with protein extracts from tubers of wild type plant cells.

Additionally mRNA of tuber material was extracted with standard methods and applied to quantitative RT-PCR analysis. The analysis were performed with a PCR-instrument ABI Prism 7700 form Applied Biosystems using the primer St_BE-f2 (5'-TCA GGT CTA CAA GTT GAC CCG A-3'), St_BE-r2 (5'-GTA GAA CCT TCC CTT TTG TGT GA-3') and St_BE-Fam (5'-Fam-CAT GAT CAC TCT AGC AAT CAA AGT GCC-Tamra-3'). It could be shown that given plants showed reduced transcript in comparison with the corresponding wild type.

Example 4

Potato Starch Extraction Process

All tubers of one line (0.3 to 0.7 kg) are processed jointly in a commercially available juice extractor (Multipress automatic MP80, Braun). The starch-containing fruit water is collected in a 1-1 bucket (ratio bucket height:bucket diameter=approx. 1.1) containing 20 ml of tap water together with a spoon-tipful (approx. 0.3-0.4 g) of sodium disulphite. The bucket is subsequently filled completely with tap water. After the starch has been allowed to settle for 2 hours (h), the supernatant is decanted off, the starch is resuspended in 1 l of tap water and poured over a sieve with a mesh size of 125 μm. After 2 h (starch has again settled at the bottom of the bucket), the aqueous supernatant is again decanted off. This wash step is repeated 3 more times so that the starch is resuspended a total of 5 times in fresh tap water. Thereafter, the starches are dried at 37° C. to a water content of 12-17% and homogenized using a pestle and mortar. The starches are now available for analyses.

Example 5

Analysis of the Starch from Plants with Reduced BEIII Gene Expression

The starch from various independent lines of plants named 369SO were isolated from potato tubers. The physico-chemical properties of this starch were subsequently analysed. The results of the characterization of the modified starches are shown in the following for an example of a selection of certain plant lines. The analyses were carried out by the methods described hereinabove.

a) RVA Analysis

TABLE 2

Parameters of the RVA analysis of starch isolated from wild-type plants (cv. Desiree), plants with a reduced activity of a BEIII protein (369SO) in percent based on data of starch of the wild type. The RVA analysis was carried out as described in general methods.

| | RVA Max (%) | RVA Min (%) | RVA Fin (%) | RVA Set (%) | RVA PT (%) | Gel strength |
|---|---|---|---|---|---|---|
| cv. Desiree | 100 | 100 | 100 | 100 | 100 | 100 |
| 369SO048 | 91 | 64 | 90 | N.d. | 98 | 128 |
| 369SO050 | 84 | 84 | 89 | 112 | 98 | 127 |
| 369SO052 | 94 | 85 | 88 | 101 | 98 | N.d. |
| 369SO106 | 91 | 87 | 89 | 99 | 98 | N.d. |
| 369SO129 | 87 | 88 | 93 | 114 | 99 | 138 |

N.d. = not determined.

b) Analysis of the Phosphate and Amylose Content

TABLE 3

Phosphate and amylose contents of starch isolated from wild-type plants (cv. Desiree), plants with a reduced activity of BEIII protein (369SO). The phosphate contents in the C6 position of the glucose monomers and the total phosphate content of the starch are indicated in percent based on starch from wild-type plants; amylose contents are indicated in percent amylose based on the total amount of the starch, or in percent based on the amylose content of starch from wild-type plants.

| No. | Genotype | Phosphate in C6 (%) | Total phosphate in (%) | Amylose (%) | Amylose (% WT) |
|---|---|---|---|---|---|
| 1 | cv. Desiree | 100.0 | 100.0 | 21.3 | 100.0 |
| 2 | 369SO048 | 72.8 | 84.8 | 20.8 | 97.7 |
| 3 | 369SO050 | 79.2 | 78.0 | 20.1 | 94.4 |
| 4 | 369SO052 | 84.8 | 83.2 | 19.6 | 92.0 |
| 5 | 369SO106 | 84.8 | 85.9 | 20.1 | 94.4 |
| 6 | 369SO129 | 80.8 | 81.2 | 20.2 | 94.8 |

c) Analysis of Side-Chain Distribution

The analysis of the side-chain distribution of the amylopectin was carried out as described above. The table which follows is a summary of the contributions of the individual peak areas:

TABLE 4

The table shows a summary of the contributions of the individual peak areas of the HPAEC chromatogram to the total peak area of wild-type plants (cv. Desiree) and of 369SO plants (potato plants with reduced activity of a BEIII protein). The number of glucose monomers in the individual side chains is shown as dp.

| Glucose units | cv. Desiree | 369SO 048 | 369SO 050 | 369SO 052 | 369SO 106 | 369SO 129 |
|---|---|---|---|---|---|---|
| dp 6 | 2.19 | 2.57 | 2.83 | 2.78 | 2.59 | 2.59 |
| dp 7 | 1.69 | 1.76 | 1.84 | 1.85 | 1.85 | 1.73 |
| dp 8 | 1.35 | 1.34 | 1.37 | 1.38 | 1.44 | 1.36 |
| dp 9 | 2.26 | 2.27 | 2.31 | 2.32 | 2.42 | 2.31 |
| dp 10 | 3.74 | 3.81 | 3.86 | 3.94 | 4.00 | 3.85 |
| dp 11 | 5.13 | 5.23 | 5.30 | 5.45 | 5.37 | 5.30 |
| dp 12 | 5.99 | 6.14 | 6.18 | 6.32 | 6.17 | 6.17 |
| dp 13 | 6.40 | 6.53 | 6.54 | 6.63 | 6.48 | 6.63 |
| dp 14 | 6.39 | 6.45 | 6.44 | 6.49 | 6.37 | 6.52 |
| dp 15 | 6.11 | 6.14 | 6.12 | 6.15 | 6.05 | 6.09 |
| dp 16 | 5.74 | 5.75 | 5.72 | 5.75 | 5.68 | 5.72 |
| dp 17 | 5.37 | 5.35 | 5.35 | 5.35 | 5.30 | 5.35 |

TABLE 4-continued

The table shows a summary of the contributions of the individual peak areas of the HPAEC chromatogram to the total peak area of wild-type plants (cv. Desiree) and of 369SO plants (potato plants with reduced activity of a BEIII protein). The number of glucose monomers in the individual side chains is shown as dp.

| Glucose units | cv. Desiree | 369SO 048 | 369SO 050 | 369SO 052 | 369SO 106 | 369SO 129 |
|---|---|---|---|---|---|---|
| dp 18 | 5.08 | 5.04 | 5.06 | 5.05 | 5.01 | 5.06 |
| dp 19 | 4.89 | 4.86 | 4.88 | 4.84 | 4.83 | 4.86 |
| dp 20 | 4.68 | 4.59 | 4.65 | 4.60 | 4.60 | 4.62 |
| dp 21 | 4.41 | 4.39 | 4.37 | 4.32 | 4.34 | 4.35 |
| dp 22 | 4.10 | 4.05 | 4.06 | 4.00 | 4.02 | 4.02 |
| dp 23 | 3.78 | 3.73 | 3.69 | 3.63 | 3.71 | 3.73 |
| dp 24 | 3.40 | 3.34 | 3.29 | 3.26 | 3.33 | 3.29 |
| dp 25 | 3.07 | 2.97 | 2.94 | 2.88 | 2.96 | 2.98 |
| dp 26 | 2.75 | 2.67 | 2.59 | 2.57 | 2.65 | 2.63 |
| dp 27 | 2.40 | 2.30 | 2.25 | 2.20 | 2.28 | 2.28 |
| dp 28 | 2.07 | 1.99 | 1.91 | 1.89 | 1.97 | 1.94 |
| dp 29 | 1.76 | 1.71 | 1.62 | 1.59 | 1.68 | 1.67 |
| dp 30 | 1.51 | 1.42 | 1.38 | 1.35 | 1.41 | 1.41 |
| dp 31 | 1.26 | 1.20 | 1.14 | 1.12 | 1.16 | 1.18 |
| dp 32 | 1.03 | 0.97 | 0.92 | 0.92 | 0.95 | 0.95 |
| dp 33 | 0.84 | 0.77 | 0.75 | 0.76 | 0.78 | 0.78 |
| dp 34 | 0.68 | 0.62 | 0.60 | 0.61 | 0.63 | 0.62 |
| Total | 100.00 | 99.96 | 99.96 | 100.00 | 100.03 | 99.99 |

TABLE 5

The table shows a summary of the contributions of the individual peak areas of the HPAEC chromatogram in percent based on starch from wild-type plants.

| Glucose units | cv. Desiree | 369SO 048 | 369SO 050 | 369SO 052 | 369SO 106 | 369SO 129 |
|---|---|---|---|---|---|---|
| dp 6 | 100 | 117.4 | 129.2 | 126.9 | 118.3 | 118.3 |
| dp 7 | 100 | 104.1 | 108.9 | 109.5 | 109.5 | 102.4 |
| dp 8 | 100 | 99.3 | 101.5 | 102.2 | 106.7 | 100.7 |
| dp 9 | 100 | 100.7 | 102.4 | 102.9 | 107.3 | 102.4 |
| dp 10 | 100 | 102.0 | 103.3 | 105.5 | 107.1 | 103.1 |
| dp 11 | 100 | 102.0 | 103.4 | 106.3 | 104.8 | 103.4 |
| dp 12 | 100 | 102.5 | 103.2 | 105.5 | 103.0 | 103.0 |
| dp 13 | 100 | 102.1 | 102.3 | 103.7 | 101.3 | 103.7 |
| dp 14 | 100 | 100.9 | 100.8 | 101.6 | 99.7 | 102.0 |
| dp 15 | 100 | 100.5 | 100.2 | 100.7 | 99.0 | 99.7 |
| dp 16 | 100 | 100.3 | 99.7 | 100.3 | 99.0 | 99.7 |
| dp 17 | 100 | 99.7 | 99.7 | 99.7 | 98.8 | 99.7 |
| dp 18 | 100 | 99.3 | 99.7 | 99.5 | 98.7 | 99.7 |
| dp 19 | 100 | 99.5 | 99.9 | 99.1 | 98.9 | 99.5 |
| dp 20 | 100 | 98.1 | 99.4 | 98.3 | 98.3 | 98.7 |
| dp 21 | 100 | 99.5 | 99.1 | 98.0 | 98.4 | 98.6 |
| dp 22 | 100 | 98.8 | 99.0 | 97.6 | 98.0 | 98.0 |
| dp 23 | 100 | 98.8 | 97.7 | 96.2 | 98.3 | 98.8 |
| dp 24 | 100 | 98.4 | 96.9 | 96.0 | 98.1 | 96.9 |
| dp 25 | 100 | 96.9 | 95.9 | 94.0 | 96.6 | 97.2 |
| dp 26 | 100 | 97.1 | 94.2 | 93.5 | 96.4 | 95.6 |
| dp 27 | 100 | 95.8 | 93.8 | 91.7 | 95.0 | 95.0 |
| dp 28 | 100 | 96.1 | 92.3 | 91.3 | 95.2 | 93.7 |
| dp 29 | 100 | 97.2 | 92.0 | 90.3 | 95.5 | 94.9 |
| dp 30 | 100 | 94.0 | 91.4 | 89.4 | 93.4 | 93.4 |
| dp 31 | 100 | 95.6 | 90.8 | 89.2 | 92.4 | 94.0 |
| dp 32 | 100 | 94.2 | 89.3 | 89.3 | 92.2 | 92.2 |
| dp 33 | 100 | 92.2 | 89.8 | 91.0 | 93.4 | 93.4 |
| dp 34 | 100 | 91.9 | 88.9 | 90.4 | 93.3 | 91.9 |

d) Analysis of the Amylopectin Side Chain Distribution by Means of Gel Permeation Chromatography Analysis of the amylopectin side chain distribution by means of gel permeation chromatography were additionally performed.

TO separate amylose and amylopectin, 100 mg of starch are dissolved in 6 ml of 90% strength (v/v) DMSO with constant stirring. After addition of 3 volumes of ethanol, the precipitate is separated off by centrifugation for 10 minutes at 1800×g at room temperature. The pellet is subsequently washed with 30 ml of ethanol, dried and dissolved in 10 ml of 1% strength (w/v) NaCl solution at 60° C. After cooling the solution to 30° C., approximately 50 mg of thymol are added slowly, and this solution is incubated for 2 to 3 days at 30° C. The solution is subsequently centrifuged for 30 minutes at 2000×g at room temperature. The supernatant is treated with three volumes of ethanol, and the amylopectin which precipitates is separated off by centrifugation for 5 minutes at 2000×g at room temperature. The pellet (amylopectin) is washed with 10 ml of 70% strength (v/v) ethanol, centrifuged for 10 minutes at 2000×g at room temperature and then dried using acetone.

10 mg of amylopectin are subsequently stirred for 10 minutes at 70° C. in 250 µl of 90% strength (v/v) DMSO. 375 µl of water at a temperature of 80° C. are added to the solution until dissolution is complete.

200 µl of this solution are treated with 300 µl of a 16.6 mM sodium acetate solution pH 3.5 and 2 µl of isoamylase (0.24 u/µl, Megazyme, Sydney, Australia) and the mixture is incubated for 15 hours at 37° C.

A 1:4 dilution of this aqueous isoamylase reaction mixture with DMSO, comprising 90 mM sodium nitrate, is subsequently filtered through a 0.2 µm filter, and 24 µl of the filtrate is analysed chromatographically. Separation was carried out with two columns connected in series, first a Gram PSS3000 (Polymer Standards Service, with suitable precolumn), followed by a Gram PSS100. Detection was by means of refraction index detector (RI 71, Shodex). The column was equilibrated with DMSO comprising 90 mM sodium nitrate. It was eluted with DMSO comprising 90 mM sodium nitrate at a flow rate of 0.7 ml/min over a period of 1 hour.

To correlate the elution volume with the molecular mass, the column used was calibrated with dextran standards. The dextrans used, their molecular mass and the elution volumes are shown in Table 6. Using the resulting calibration graph, the elution diagram was pictured as a molecular weight distribution.

The chromatograms obtained were further evaluated using the program Wingpc Version 6 from Polymer Standards Service GmbH, Mainz, Germany.

The total area under the line of the GPC chromatogram was divided into individual segments, each of which represent groups of side chains of different lengths. The chosen segments contained glucan chains with the following degree of polymerization (DP=number of glucose monomers within one side chain): DP<12, DP12-18, DP19-24, DP25-30, DP31-36, DP37-42, DP43-48, DP49-55, DP56-61 and DP62-123. To determine the molecular weight of the individual side chains, a molecular weight of 162 was assumed for glucose. The total area under the line in the GPC chromatogram was then set as 100%, and the percentage of the areas of the individual segments was calculated based on the percentage of the total area. Results obtained from this analysis are shown in Table 7.

TABLE 6

| Calibration table. | | |
|---|---|---|
| elution volume [ml] | molar mass [D] | sample |
| 18.76 | 401300 | Dextran T670 |
| 19.41 | 276500 | Dextran T410 |
| 20.49 | 196300 | Dextran T270 |
| 21.35 | 123600 | Dextran T150 |
| 22.45 | 66700 | Dextran T80 |
| 23.52 | 43500 | Dextran T50 |
| 25.15 | 21400 | Dextran T25 |
| 26.92 | 9890 | Dextran T12 |
| 28.38 | 4440 | Dextran T5 |
| 30.77 | 1080 | Dextran T1 |

TABLE 7

Side chain profiles DP < 12, DP 12 to 18, DP 19 to 24, DP 25 to 30, DP 31 to 36, DP 37 to 42, DP 43-48, DP 49 to 55, DP 56 to 61 and DP 62 to 123 for amylopectin isolated from wild-type plants (cv. Desiree) and from plants with a reduced activity of a BEIII protein (369SO).

| degree of | % total area | | | | | |
|---|---|---|---|---|---|---|
| polymerisation | cv. Desiree | 369 SO 48 | 369 SO 50 | 369 SO 52 | 369 SO 106 | 369 SO 129 |
| <dp12 | 16.49 | 16.57 | 17.07 | 17.73 | 17.59 | 17.64 |
| dp12-19 | 13.89 | 14.47 | 14.22 | 14.82 | 14.16 | 14.23 |
| dp20-25 | 15.74 | 16.54 | 16.15 | 16.74 | 16.32 | 16.51 |
| dp26-31 | 9.41 | 9.73 | 9.57 | 9.80 | 9.86 | 9.88 |
| dp32-37 | 8.53 | 8.53 | 8.45 | 8.56 | 8.59 | 8.45 |
| dp38-43 | 6.82 | 6.67 | 6.57 | 6.63 | 6.58 | 6.44 |
| dp44-49 | 6.05 | 5.91 | 5.81 | 5.83 | 5.79 | 5.72 |
| dp50-56 | 4.88 | 4.78 | 4.71 | 4.66 | 4.70 | 4.67 |
| dp57-62 | 4.26 | 4.15 | 4.10 | 3.98 | 4.09 | 4.10 |
| dp63-123 | 13.92 | 12.66 | 13.35 | 11.25 | 12.31 | 12.38 |

TABLE 8

Side chain profiles DP < 12, DP 12 to 18, DP 19 to 24, DP 25 to 30, DP 31 to 36, DP 37 to 42, DP 43-48, DP 49 to 55, DP 56 to 61 and DP 62 to 123 for amylopectin isolated from wild-type plants (cv. Desiree) and from plants with a reduced activity of a BEIII protein (369SO). The percentages indicate the modification of the individual side chain profiles based on amylopectin isolated from wild-type plants.

| degree of | % WT | | | | | |
|---|---|---|---|---|---|---|
| polymerisation | cv. Desiree | 369 SO 48 | 369 SO 50 | 369 SO 52 | 369 SO 106 | 369 SO 129 |
| <dp12 | 100.00 | 100.47 | 103.53 | 107.53 | 106.69 | 106.96 |
| dp12-19 | 100.00 | 104.13 | 102.37 | 106.68 | 101.90 | 102.40 |
| dp20-25 | 100.00 | 105.11 | 102.62 | 106.32 | 103.69 | 104.87 |
| dp26-31 | 100.00 | 103.34 | 101.67 | 104.09 | 104.81 | 104.92 |
| dp32-37 | 100.00 | 100.01 | 99.05 | 100.38 | 100.73 | 99.04 |
| dp38-43 | 100.00 | 97.74 | 96.40 | 97.23 | 96.54 | 94.48 |
| dp44-49 | 100.00 | 97.68 | 96.00 | 96.27 | 95.76 | 94.48 |
| dp50-56 | 100.00 | 97.90 | 96.45 | 95.57 | 96.26 | 95.78 |
| dp57-62 | 100.00 | 97.36 | 96.07 | 93.44 | 95.91 | 96.13 |
| dp63-123 | 100.00 | 90.95 | 95.89 | 80.82 | 88.41 | 88.89 |

e) DSC-Analysis ("Differential Scanning Calorimetry")

Investigations with the aid of DSC-analysis ("Differential Scanning Calorimetry") have been done by the method described by WO 01/19975. Results obtained from this analysis are shown in-Table 9.

TABLE 9

Parameters of the DSC analysis of starch isolated from wild-type plants (cv. Desiree), plants with a reduced activity of a BEIII protein (369SO) indicated in ° C. respectively J/g and in percent based on data of starch of the wild type. The DSC analysis was carried out as described in general methods. T0 [° C.] = peak onset, T Peak [° C.] = Peak temperature, dH [J/g] = heat of_melting.

| | TO (° C.) | TO (%) | T Peak (° C.) | T Peak (%) | dH (J/g) | dH (J/g) |
|---|---|---|---|---|---|---|
| cv. Desiree | 64.84 | 100 | 68.09 | 100 | 20.31 | 100 |
| 369SO048 | 64.32 | 99.2 | 67.16 | 98.6 | 20.33 | 100.1 |
| 369SO050 | 63.35 | 97.7 | 66.75 | 98.0 | 20.63 | 101.6 |
| 369SO052 | 63.27 | 97.6 | 66.46 | 97.6 | 21.23 | 104.5 |
| 369SO106 | 63.77 | 98.3 | 66.96 | 98.3 | 21.42 | 105.5 |
| 369SO129 | 63.75 | 98.3 | 67.41 | 99.0 | 20.57 | 101.3 |

What is claimed is:

1. A nucleic acid molecule encoding a protein with the enzymatic activity of a class 3 branching enzyme, wherein the class 3 branching enzyme comprises an iso-amylase domain and an alpha-amylase domain, and wherein the C-terminal end of the iso-amylase domain is separated from the N-terminal beginning of the alpha-amylase domain by at least 198 amino acids, and wherein said protein catalyses a transglycosylation reaction, in which α-1,4 links of an α-1,4-glucan donor are hydrolysed and released, and wherein the α-1,4-glucan chains are transformed into α-1,6-links.

2. A nucleic acid molecule encoding a protein with the enzymatic activity of a class 3 branching enzyme, wherein the class 3 branching enzyme comprises an iso-amylase domain and an alpha-amylase domain, and wherein the C-terminal end of the iso-amylase domain is separated from the N-terminal beginning of the alpha-amylase domain by 150 to 198 amino acids, and wherein said protein catalyses a transglycosylation reaction, in which α-1,4 links of an α-1,4-glucan donor are hydrolysed and released, and wherein the α-1,4-glucan chains are transformed into α-1,6-links.

3. The nucleic acid molecule of claim 1, wherein the nucleic acid molecule comprises (a) a nucleic acid sequence encoding an amino acid sequence of SEQ ID NO: 4;

(b) a nucleic acid sequence encoding an amino acid sequence with an identity of at least 95% with SEQ ID NO: 4;

(c) a nucleic acid sequence comprising SEQ ID NO: 3 or the complementary sequence thereof;

(d) a nucleic acid sequence with an identity of at least 95% with the nucleic acid sequences of a) or c);

(e) a nucleic acid sequence that hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 pg/ml tRNA; or 25 M sodium phosphate buffer pH 7.2; 1 mM EDTA; 7% SDS, and washing at 65° C.-68° C. in a solution comprising 0.2×SSC and 0.1% SDS; or (f) a nucleic acid sequence which deviates from the sequence of the nucleic acid molecules identified under (a), (b), (c), (d) or (e) due to the degeneration of the genetic code.

4. The nucleic acid molecule of claim 3, wherein the nucleic acid sequence encodes an amino acid sequence of SEQ ID NO: 4.

5. The nucleic acid molecule of claim 3, wherein the nucleic acid sequence encodes an ammo acid sequence with an identity of at least 95% with the amino acid sequence of SEQ ID NO: 4.

6. The nucleic acid molecule of claim 3, wherein the nucleic acid sequence comprises SEQ ID NO: 3 or the complementary sequence thereof.

7. The nucleic acid molecule of claim 3, wherein the nucleic acid molecule comprises a nucleic acid sequence with an identity of at least 95% with the nucleic acid sequences of (a) or (c).

8. The nucleic acid molecule of claim 3, wherein the nucleic acid sequence hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS, and washing at 65° C.-68° C. in a solution comprising 0.2×SSC and 0.1% SDS.

9. The nucleic acid molecule of claim 3, wherein the nucleic acid sequence deviates from the sequence of the nucleic acid sequences of (a), (b), (c), (d) or (e) due to the degeneration of the genetic code.

10. The nucleic acid molecule of claim 3, wherein the nucleic acid molecule encodes a class 3 branching enzyme of potato.

11. A vector comprising the nucleic acid molecule of claim 3.

12. The vector of claim 6, wherein the nucleic acid molecule is linked with regulatory sequences for transcription into prokaryotic or eukaryotic cells.

13. A genetically modified host cell comprising the nucleic acid molecule of claim 3.

14. A genetically modified plant cell comprising a foreign nucleic acid molecule, wherein said foreign nucleic acid comprises (a) a nucleic acid sequence encoding an amino acid sequence of SEQ ID NO: 4;

(b) a nucleic acid sequence encoding an amino acid sequence with an identity of at least 95% with SEQ ID NO: 4;

(c) a nucleic acid sequence comprising SEQ ID NO: 3 or the complementary sequence thereof;

(d) a nucleic acid sequence with an identity of at least 95% with the nucleic acid sequences of a) or c);

(e) a nucleic acid sequence that hybridizes with at least one strand of the nucleic acid molecule of (a) or (c) under stringent conditions, wherein said stringent conditions are conducting the hybridization reaction at 65° C.-68° C. in a solution comprising 2×SSC 1×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS, and washing at 65° C.-68° C. in a solution comprising 0.2×SSC and 0.1% SDS;

(f) a nucleic acid sequence which deviates from the sequence of the nucleic acid molecules identified under (a), (b), (c), (d) or (e) due to the degeneration of the genetic code; or (g) a nucleic acid sequence comprising at least 100 nucleotides of SEQ ID NO: 3, wherein said genetically modified plant cell has a reduced activity of at least one class 3 branching enzyme and synthesizes a starch with a decreased phosphate content in comparison with starch synthesized from a corresponding wild type plant cell that has not been genetically modified.

15. The genetically modified plant cell of claim 14, wherein the starch has a total phosphate content decreased by at least 10% in comparison with starch synthesized from a corresponding wild type plant cell that has not been genetically modified.

16. The genetically modified plant cell of claim 14, wherein the starch has a C-6 phosphate content decreased by at least 15% in comparison with starch synthesized from a corresponding wild type plant cell that has not been genetically modified.

17. The genetically modified plant cell of claim 14, wherein the nucleic acid sequence encodes an amino acid sequence of SEQ ID NO: 4.

18. The genetically modified plant cell of claim 14, wherein the nucleic acid sequence encodes an ammo acid sequence with an identity of at least 95% with the amino acid sequence of SEQ ID NO: 4.

19. The genetically modified plant cell of claim 14, wherein the nucleic acid sequence comprises SEQ ID NO: 3 or a complementary sequence thereof.

20. The genetically modified plant cell of claim 14, wherein the nucleic acid molecule comprises a nucleic acid sequence with an identity of at least 95% with the nucleic acid sequences of (a) or (c).

21. The genetically modified plant cell of claim 14, wherein the nucleic add sequence hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS, and washing at 65° C.-68° C. in a solution comprising 0.2×SSC and 0.1% SDS.

22. The genetically modified plant cell of claim 14, wherein the nucleic acid sequence deviates from the sequence of the nucleic acid sequences of (a), (b), (c), (d) or (e) due to the degeneration of the genetic code.

23. The genetically modified plant cell of claim 14, wherein the nucleic acid sequence comprises at least 100 nucleotides of SEQ ID NO: 3.

24. The genetically modified plant cell of claim 14, wherein the nucleic acid sequence comprises 100-500 nucleotides of SEQ ID NO: 3.

25. The genetically modified plant cell of claim 14, wherein the nucleic acid sequence comprises at least 500 nucleotides of SEQ ID NO: 3.

26. The genetically modified plant cell of claim 14, wherein said foreign nucleic add molecule is a) a DNA molecule, which codes at least one antisense RNA, which effects a reduction in the expression of at least one endogenous gene encoding a class 3 branching enzyme;

b) a DNA molecule, which by means of a co-suppression effect leads to the reduction in the expression of at least one endogenous gene encoding a class 3 branching enzyme;

c) a DNA molecule, which codes at least one ribozyme, which splits specific transcripts of at least one endogenous gene encoding a class 3 branching enzyme;

d) a DNA molecule, which simultaneously codes at least one antisense RNA and at least one sense RNA, wherein said antisense RNA and said sense RNA form a double-stranded RNA molecule, which effects a reduction in the expression of at least one endogenous gene encoding a class 3 branching enzyme; or e) a nucleic acid molecule introduced by means of in vivo mutagenesis, which leads to a mutation or an insertion of a heterologous sequence in at least one endogenous gene encoding a class 3 branching enzyme, wherein the mutation or insertion effects a reduction in the expression of said gene or results in the synthesis of an inactive class 3 branching enzyme.

27. The genetically modified plant cell of claim 14, wherein the plant cell is a potato plant cell.

28. A plant comprising the genetically modified plant cell of claim 14.

29. The plant of claim 28, wherein said plant is a starch-storing plant.

30. The plant of claim 29, wherein said plant is a maize, rice, wheat, rye, oat, barley, cassava, potato, sago, mung bean, pea or sorghum plant.

31. The plant of claim 30, wherein said plant is a potato plant.

32. Propagation material comprising the genetically modified plant cell of claim 14.

33. Harvestable plant parts comprising the genetically modified plant cell of claim 14.

34. A method for manufacturing a genetically modified plant, comprising;

a) introducing at least one foreign nucleic acid molecule into the genome of a plant cell to obtain a genetically modified plant cell, wherein the foreign nucleic acid molecule comprises (i) a nucleic acid sequence encoding an amino acid sequence of SEQ ID NO: 4;

(ii) a nucleic acid sequence encoding an amino acid sequence with an identity of at least 95% with SEQ ID NO: 4;

(iii) a nucleic acid sequence comprising SEQ ID NO: 3 or the complementary sequence thereof, (iv) a nucleic acid sequence with an identity of at least 95% with the nucleic acid sequences of (i) or (iii);

(v) a nucleic acid sequence that hybridizes with at least one strand of the nucleic acid molecule of (i) or (iii) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS, and washing at 65° C.-68° C. in a solution comprising 0.2×SSC and 0.1% SDS;

(vi) a nucleic acid sequence which deviates from the sequence of the nucleic acid molecules identified under (i), (ii), (iii), (iv), or (v) due to the degeneration of the genetic code; or (vii) a nucleic acid sequence comprising at least 100 nucleotides of SEQ ID NO: 3, wherein said genetically modified plant cell has a reduced activity of at least one class 3 branching enzyme and synthesizes a starch with a decreased phosphate content in comparison with starch synthesized from a corresponding wild type plant cell that has not been genetically modified;

b) regenerating a plant from the genetically modified plant cell from Step a); and c) optionally, producing further plants with the plants of Step b).

35. The method of claim 34, wherein the starch has a total phosphate content decreased by at least 10% in comparison with starch synthesized from a corresponding wild type plant cell that has not been genetically modified.

36. The method of claim 34, wherein the starch has a C-6 phosphate content decreased by at least 15% in comparison with starch synthesized from a corresponding wild type plant cell that has not been genetically modified.

37. The method of claim 34, wherein the nucleic acid sequence encodes an amino acid sequence of SEQ ID NO: 4.

38. The method of claim 34, wherein the nucleic acid sequence encodes an amino acid sequence with an identity of at least 95% with the amino acid sequence of SEQ ID NO: 4.

39. The method of claim 34, wherein the nucleic acid sequence comprises SEQ ID NO: 3 or the complementary sequence thereof.

40. The method of claim 34, wherein the nucleic acid molecule comprises a nucleic acid sequence with an identity of at least 95% with the nucleic acid sequences of (i) or (iii).

41. The method of claim 34, wherein the nucleic acid sequence hybridizes with at least one strand of the nucleic acid molecule of (i) or (iii) under stringent conditions, wherein said stringent conditions are conducting the hybridization reaction at 65° C.-68° C. in a solution comprising 2×SSC 10×Denhardt solution Ficoll 400+PEG+BSA; Ratio 1:1:1); 0.1% SDS; 5 mM EDTA; 50 mM $Na_2HPO_4$; 250 μg/ml herring sperm DNA; 50 μg/ml tRNA; or 25 M sodium phosphate buffer pH 7.2; 1 mM EDTA; 7% SDS, and washing at 65° C.-68° C. in a solution comprising 0.2×SSC and 0.1% SDS.

42. The method of claim 34, wherein the nucleic acid sequence deviates from the sequence of the nucleic acid sequences of (i), (ii), (iii), (iv), or (v) due to the degeneration of the genetic code.

43. The method of claim 34, wherein the nucleic acid sequence comprises at least 100 nucleotides of SEQ ID NO: 3.

44. The method of claim 34, wherein the nucleic acid sequence comprises 100-500 nucleotides of SEQ ID NO: 3.

45. The method of claim 34, wherein the nucleic acid sequence comprises at least 500 nucleotides of SEQ ID NO: 3.

46. The method of claim 34, wherein said foreign nucleic acid molecule is (a) a DNA molecule, which codes at least one antisense RNA, which effects a reduction in the expression of at least one endogenous gene encoding a class 3 branching enzyme;

(b) a DNA molecule, which by means of a co-suppression effect leads to the reduction in the expression of at least one endogenous gene encoding a class 3 branching enzyme;

(c) a DNA molecule, which codes at least one ribozyme, which splits specific transcripts of at least one endogenous gene encoding a class 3 branching enzyme;

(d) a DNA molecule, which simultaneously codes at least one antisense RNA and at least one sense RNA, wherein said antisense RNA and said sense RNA form a double-stranded RNA molecule, which effects a reduction in the expression of at least one endogenous gene encoding a class 3 branching enzyme; or (e) a nucleic acid molecule introduced by means of in vivo mutagenesis, which leads to a mutation or an insertion of a heterologous sequence in at least one endogenous gene encoding a class 3 branching enzyme, wherein the mutation or insertion effects a reduction in the expression of said gene or results in the synthesis of an inactive class 3 branching enzyme.

47. The method of claim 34, wherein the plant is a potato plant.

48. A genetically modified plant cell comprising a foreign nucleic acid molecule comprising a nucleic acid molecule encoding a protein with the enzymatic activity of a class 3 branching enzyme, wherein the class 3 branching enzyme comprises an iso-amylase domain and an alpha-amylase domain, wherein the C-terminal end of the iso-amylase domain is separated from the N-terminal beginning of the alpha-amylase domain by at least 198 amino adds, and wherein said genetically modified plant cell has a reduced activity of at least one class 3 branching enzyme and synthesizes a starch with a decreased phosphate content in comparison with starch synthesized from a corresponding wild type plant cell that has not been genetically modified.

49. A genetically modified plant cell comprising a foreign nucleic acid molecule comprising a nucleic acid molecule encoding a protein with the enzymatic activity of a class 3 branching enzyme, wherein the class 3 branching enzyme comprises an iso-amylase domain and an alpha-amylase domain, wherein the C-terminal end of the iso-amylase domain is separated from the N-terminal beginning of the alpha-amylase domain by 150 to 198 amino acids, and wherein said genetically modified plant cell has a reduced activity of at least one class 3 branching enzyme and synthesizes a starch with a decreased phosphate content in comparison with starch synthesized from a corresponding wild type plant cell that has not been genetically modified.

50. The genetically modified plant cell of claim 48, wherein the starch has a total phosphate content decreased by at least 10% in comparison with starch synthesized from a corresponding wild type plant cell that has not been genetically modified.

51. The genetically modified plant cell of claim 48, wherein the starch has a C-6 phosphate content decreased by at least 15% in comparison with starch synthesized from a corresponding wild type plant cell that has not been genetically modified.

52. The genetically modified plant cell of claim 48, wherein the plant cell is a potato plant cell.

* * * * *

UNITED STATES PATENT AND TRADEMARK OFFICE

CERTIFICATE OF CORRECTION

PATENT NO. : 7,626,080 B2
APPLICATION NO. : 10/573998
DATED : December 1, 2009
INVENTOR(S) : Claus Frohberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 81 days.

Signed and Sealed this

Second Day of November, 2010

David J. Kappos

*Director of the United States Patent and Trademark Office*

SEQUENCE LISTING

```
<160> NUMBER OF SEQ ID NOS: 6

<210> SEQ ID NO 1
<211> LENGTH: 1004
<212> TYPE: DNA
<213> ORGANISM: Solanum tuberosum

<400> SEQUENCE: 1

tcaaactagt cacaaccagt ccatttctgg aggtcgttcc ttcgcagaaa tactgattgg      60

taactccttg gggaaatcct ccatatcaca agagtcatta cttagaggct gctcgttaca     120

caagatgatc agattaatta catctacaat tggtggtcat gcatacctca acttcatggg     180

caatgaattt ggtcacccaa agagagtaga gtttccaatg tcaagcaaca atttctcctt     240

ttcactggct aaccgtcgct gggatctatt ggaagatgtt gtacattatc aattgttctc     300

atttgataag ggtatgatgg acttggataa aaatgggaga attttgtcca gaggtcttgc     360

caacattcac catgtcaatg atactaccat ggtgatttct tacttgagag gtcccaatct     420

ctttgtgttc aactttcatc ctgtcaattc atatgaaaga tacattatag gtgtggaaga     480

agctggagag tatcaagtca cattaaatac agatgaaaac aagtatggtg gtagaggact     540

acttggccat gatcagaata ttcaaagaac cattagtaga agagctgatg gaatgagatt     600

ttgcttggaa gtgcctctgc caagtagaag tgctcaggtc tacaagttga cccgaattct     660

aagagcatga tcactctagt aatcaaagtg cctcatatga tgacacaaaa ggaaaggttc     720

tacattgccc ttacactgat caatattgac acctttccga ggtgagtttc tgtgattctt     780

gagcagactg ttggctagtc aattatcatg aacttttgcc ttcagcatcc ggatagtcgc     840

ttctcctgtg caatgagggc atggacgaat tttttttgg cttgtcatgg gggtcataag     900

catccgccag attaagattt cacaggcctc gagtaaaacc atcacttact ttaaggatac     960

acaaacacac caacggggtg caggctctga taccttctaa agtg                     1004

<210> SEQ ID NO 2
<211> LENGTH: 2096
<212> TYPE: DNA
<213> ORGANISM: Solanum tuberosum

<400> SEQUENCE: 2

aacaatgctc tctctgtcgg attcaattcg aatttcttca ccattgagcg attctcgtct      60

tagttttcta tctcaaaccg gaagcagaac cagtcgccag cttaaatttg ttcgcagccg     120
```

-continued

```
ccgggctcga gtttcgaggt gtagatgctc agcaacggag caaccgccac cgcaacgacg    180

gaagcaacga ccggagaagt acaaacagtc ggaggaaggg aaaggaatcg atcctgttgg    240

atttctcagc aaatacggca ttactcataa agcgtttgct caatttcttc gtgaaagata    300

taaatcattg aaggacttga aggatgaaat attgactcgt catttcagtc tcaaggagat    360

gtctactggg tatgaattaa tgggtatgca tcgcaacata caacatcgag tggatttctt    420

ggaatgggct ccaggtgctc gctactgtgc tctgattggt gacttcaatg ggtggtcaac    480

aactggtaac tgtgccagag agggtcattt tggtcatgac gattatgggt attggtttat    540

tattcttgaa gataaattac gtgaaggaga agaacctgat aaattgtatt ttcaacagta    600

caattatgcg gaggactatg gtaaaggtga cacgggtatt accgtcgagg aaatctttaa    660

aaaagcaaat gatgagtatt gggaacctgg agaagatcgc ttcattaaat cacgttatga    720

ggtggcagca aagttatatg aggaaatgtt cggaccaaat ggacctcaaa cagaagagga    780

actagaagca atgcctgatg cagctacacg atacaaaact tggaaagagc aacaaaaaga    840

ggatccggca agcaatttgc catcgtatga tgtggtagat agtggaaaag aatatgatat    900

ttacaatatt ataggtgatc ctgaatcgtt taagaaattt cgtatgaaac agcctcctat    960

tgcttactgg ttagaaacta aaaagggaag gaaaggctgg ttacagaaat atatgcctgc   1020

tttacctcat ggaagcaaat acagggtgta ttttaacaca ccaaatgggc ctcttgaacg   1080

agttcctgcg tgggccaatt ttgtcattcc agatgcaggc gggatggcat tagcagtcca   1140

ttgggaacca cctcctgaat atgcttataa atggaaacac aagctaccag tcaagcctaa   1200

gtccttgcgc atatatgaat gtcatgttgg catctctggc caggaaccaa aagtttcatc   1260

tttcaatgat tttattagca aggtccttcc gcatgtaaaa gaagctggat acaatgcaat   1320

acaaattatt ggagttgttg agcacaagga ttatttcact gttggatata gagtgaccaa   1380

tttttatgct gttagtagcc gttatggcac accggatgac ttcaagcgct tggttgatga   1440

agcacatggg cttggactgc ttgtcttttt ggagattgtg cactcttatg cagcagcaga   1500

tgaaatggtt gggttatctc tttttgatgg agcaaatgat tgctatttcc acactggtaa   1560

acgtggacac cacaaattct ggggcacacg gatgttcaaa tatggagatc ttgatgttct   1620

gcactttctt ctttcaaatc tgaactggtg ggtggaggag tatcatgtcg atggcttcca   1680

ttttcattcg ctctcgtcca tgttgtatac gcataatgga tttgcttcat ttactggtga   1740

catggatgaa tactgtaacc aatatgttga caaggaggcc ttattgtacc tcatattagc   1800

aaatgaagta ttacatgctc ttcatcctaa tgtgatcacg attgctgagg atgcaactct   1860

gtatcctgga ctctgcgatc caacatctca aggtggactg ggctttgatt attttgccaa   1920

tctttctgcc tcagagatgt ggcttgcatt acttgaaaat actcctgatc atgaatggtg   1980

catgagtaag attgttagca cattagtggg cgatagacaa aatactgata aaatgctttt   2040

gtatgcagaa aatcacaacc agtccatttc tggaggtcgt tccttcgcag aaatac       2096
```

<210> SEQ ID NO 3
<211> LENGTH: 3204
<212> TYPE: DNA
<213> ORGANISM: Solanum tuberosum
<220> FEATURE:
<221> NAME/KEY: CDS
<222> LOCATION: (99)..(2804)

<400> SEQUENCE: 3

```
gaattgtaat acgactcact atagggcgaa ttgggccctc tagatgcatg ctcgagcggc     60
```

-continued

```
cgccagtgtg atggatatct gcagaattcg gcttaaca atg ctc tct ctg tcg gat    116
                                          Met Leu Ser Leu Ser Asp
                                          1               5

tca att cga att tct tca cca ttg agc gat tct cgt ctt agt ttt cta      164
Ser Ile Arg Ile Ser Ser Pro Leu Ser Asp Ser Arg Leu Ser Phe Leu
            10                  15                  20

tct caa acc gga agc aga acc agt cgc cag ctt aaa ttt gtt cgc agc      212
Ser Gln Thr Gly Ser Arg Thr Ser Arg Gln Leu Lys Phe Val Arg Ser
        25                  30                  35

cgc cgg gct cga gtt tcg agg tgt aga tgc tca gca acg gag caa ccg      260
Arg Arg Ala Arg Val Ser Arg Cys Arg Cys Ser Ala Thr Glu Gln Pro
    40                  45                  50

cca ccg caa cga cgg aag caa cga ccg gag aag tac aaa cag tcg gag      308
Pro Pro Gln Arg Arg Lys Gln Arg Pro Glu Lys Tyr Lys Gln Ser Glu
55                  60                  65                  70

gaa gag aaa gga atc gat cct gtt gga ttt ctc agc aaa tac ggc att      356
Glu Glu Lys Gly Ile Asp Pro Val Gly Phe Leu Ser Lys Tyr Gly Ile
                75                  80                  85

act cat aaa gcg ttt gct caa ttt ctt cgt gaa aga tat aaa tca ttg      404
Thr His Lys Ala Phe Ala Gln Phe Leu Arg Glu Arg Tyr Lys Ser Leu
            90                  95                  100

aag gac ttg aag gat gaa ata ttg act cgt cat ttc agt ctc aag gag      452
Lys Asp Leu Lys Asp Glu Ile Leu Thr Arg His Phe Ser Leu Lys Glu
        105                 110                 115

atg tct act ggg tat gaa tta atg ggt atg cat cgc aac ata caa cat      500
Met Ser Thr Gly Tyr Glu Leu Met Gly Met His Arg Asn Ile Gln His
    120                 125                 130

cga gtg gat ttc ttg gaa tgg gct cca ggt gct cgc tac tgt gct ctg      548
Arg Val Asp Phe Leu Glu Trp Ala Pro Gly Ala Arg Tyr Cys Ala Leu
135                 140                 145                 150

att ggt gac ttc aat ggg tgg tca aca act ggt aac tgt gcc aga gag      596
Ile Gly Asp Phe Asn Gly Trp Ser Thr Thr Gly Asn Cys Ala Arg Glu
                155                 160                 165

ggt cat ttt ggt cat gac gat tat ggg tat tgg ttt att att ctt gaa      644
Gly His Phe Gly His Asp Asp Tyr Gly Tyr Trp Phe Ile Ile Leu Glu
            170                 175                 180

gat aaa tta cgt gaa gga gaa gaa cct gat aaa ttg tat ttt caa cag      692
Asp Lys Leu Arg Glu Gly Glu Glu Pro Asp Lys Leu Tyr Phe Gln Gln
        185                 190                 195

tac aat tat gcg gag gac tat gat aaa ggt gac acg ggt att acc gtc      740
Tyr Asn Tyr Ala Glu Asp Tyr Asp Lys Gly Asp Thr Gly Ile Thr Val
    200                 205                 210

gag gaa atc ttt aaa aaa gca aat gat gag tat tgg gaa cct gga gaa      788
Glu Glu Ile Phe Lys Lys Ala Asn Asp Glu Tyr Trp Glu Pro Gly Glu
215                 220                 225                 230

gat cgc ttc att aaa tca cgt tat gag gtg gca gca aag tta tat gag      836
Asp Arg Phe Ile Lys Ser Arg Tyr Glu Val Ala Ala Lys Leu Tyr Glu
                235                 240                 245

gaa atg ttc gga cca aat gga cct caa aca gaa gag gaa cta gaa gca      884
Glu Met Phe Gly Pro Asn Gly Pro Gln Thr Glu Glu Glu Leu Glu Ala
            250                 255                 260

atg cct gat gca gct aca cga tac aaa act tgg aaa gag caa caa aaa      932
Met Pro Asp Ala Ala Thr Arg Tyr Lys Thr Trp Lys Glu Gln Gln Lys
        265                 270                 275

aag gat ccg gca agc aat ttg cca tcg tat gat gtg gta gat agt gga      980
Lys Asp Pro Ala Ser Asn Leu Pro Ser Tyr Asp Val Val Asp Ser Gly
    280                 285                 290

aaa gaa tat gat att tac aat att ata ggt gat cct gaa tcg ttt aag     1028
Lys Glu Tyr Asp Ile Tyr Asn Ile Ile Gly Asp Pro Glu Ser Phe Lys
295                 300                 305                 310
```

-continued

```
aaa ttt cgt atg aaa cag cct cct att gct tac tgg tta gaa act aaa     1076
Lys Phe Arg Met Lys Gln Pro Pro Ile Ala Tyr Trp Leu Glu Thr Lys
            315                 320                 325

aag gga agg aaa ggc tgg tta cag aaa tat atg cct gct tta cct cat     1124
Lys Gly Arg Lys Gly Trp Leu Gln Lys Tyr Met Pro Ala Leu Pro His
            330                 335                 340

gga agc aaa cac agg gtg tat ttt aac aca cca aat ggg cct ctt gaa     1172
Gly Ser Lys His Arg Val Tyr Phe Asn Thr Pro Asn Gly Pro Leu Glu
        345                 350                 355

cga gtt cct gcg tgg gcc aat ttt gtc att cca gat gca gac ggg atg     1220
Arg Val Pro Ala Trp Ala Asn Phe Val Ile Pro Asp Ala Asp Gly Met
    360                 365                 370

gca tta gca gtc cat tgg gaa cca cct cct gaa tat gct tat aaa tgg     1268
Ala Leu Ala Val His Trp Glu Pro Pro Pro Glu Tyr Ala Tyr Lys Trp
375                 380                 385                 390

aaa cac aag cta cca gtc aag cct aag tcc ttg cgc ata tat gaa tgt     1316
Lys His Lys Leu Pro Val Lys Pro Lys Ser Leu Arg Ile Tyr Glu Cys
            395                 400                 405

cat gtt ggc atc tct ggc cag gaa cca aaa gtt tca tct ttc aat gat     1364
His Val Gly Ile Ser Gly Gln Glu Pro Lys Val Ser Ser Phe Asn Asp
            410                 415                 420

ttt att agc aag gtc ctt ccg cat gta aaa gaa gct gga tac aat gca     1412
Phe Ile Ser Lys Val Leu Pro His Val Lys Glu Ala Gly Tyr Asn Ala
        425                 430                 435

acg caa att att gga gtt gtt gag cac aag gat tat ttc act gtt gga     1460
Thr Gln Ile Ile Gly Val Val Glu His Lys Asp Tyr Phe Thr Val Gly
    440                 445                 450

tat aga gtg acc aat ttt tat gct gtt agt agc cgt tat ggc aca ccg     1508
Tyr Arg Val Thr Asn Phe Tyr Ala Val Ser Ser Arg Tyr Gly Thr Pro
455                 460                 465                 470

gat gac ttc aag cgc ttg gtt gat gaa gca cat ggg ctt gga ctg ctt     1556
Asp Asp Phe Lys Arg Leu Val Asp Glu Ala His Gly Leu Gly Leu Leu
            475                 480                 485

gtc ttt ttg gag att gtg cac tcc tat gca gca gca gat gaa atg gtt     1604
Val Phe Leu Glu Ile Val His Ser Tyr Ala Ala Ala Asp Glu Met Val
            490                 495                 500

ggg tta tct ctt ttt gat gga gca aat gat tgc tat ttc cac act ggt     1652
Gly Leu Ser Leu Phe Asp Gly Ala Asn Asp Cys Tyr Phe His Thr Gly
        505                 510                 515

aaa cgt gga cac cac aaa ttc tgg ggc aca cgg atg ttc aaa tat gga     1700
Lys Arg Gly His His Lys Phe Trp Gly Thr Arg Met Phe Lys Tyr Gly
    520                 525                 530

gat cct gat gtt ctg cac ttt ctt ctt tca aat ctg aac tgg tgg gtg     1748
Asp Pro Asp Val Leu His Phe Leu Leu Ser Asn Leu Asn Trp Trp Val
535                 540                 545                 550

gag gag tat cat gtc gat ggc ttc cat ttt cat tcg ctc tcg tcc atg     1796
Glu Glu Tyr His Val Asp Gly Phe His Phe His Ser Leu Ser Ser Met
                555                 560                 565

ttg tat acg cat aat gga ttt gct tca ttt act ggt gac atg gat gaa     1844
Leu Tyr Thr His Asn Gly Phe Ala Ser Phe Thr Gly Asp Met Asp Glu
            570                 575                 580

tac tgt aac caa tat gtt gac aag gag gcc tta ttg tac ctc ata tta     1892
Tyr Cys Asn Gln Tyr Val Asp Lys Glu Ala Leu Leu Tyr Leu Ile Leu
        585                 590                 595

gca aat gaa gta tta cat gct ctt cat cct aat gtg atc acg att gct     1940
Ala Asn Glu Val Leu His Ala Leu His Pro Asn Val Ile Thr Ile Ala
    600                 605                 610

gtg gat gca act ctg tat cct gga ctc tgc gat cca aca tct caa ggt     1988
Val Asp Ala Thr Leu Tyr Pro Gly Leu Cys Asp Pro Thr Ser Gln Gly
```

-continued

```
615                 620                 625                 630

gga ctg ggc ttt gat tat ttt gcc aat ctt tct gcc tca gag atg tgg      2036
Gly Leu Gly Phe Asp Tyr Phe Ala Asn Leu Ser Ala Ser Glu Met Trp
                635                 640                 645

ctt gca tta ctt gaa aat act cct gat cat gaa tgg tgc atg agt aag      2084
Leu Ala Leu Leu Glu Asn Thr Pro Asp His Glu Trp Cys Met Ser Lys
            650                 655                 660

att gtt agc aca tta gtg ggc gat aga caa aat act gat aaa atg ctt      2132
Ile Val Ser Thr Leu Val Gly Asp Arg Gln Asn Thr Asp Lys Met Leu
        665                 670                 675

ttg tat gca gaa aat cac aac cag tcc att tct gga ggt cgt tcc ttc      2180
Leu Tyr Ala Glu Asn His Asn Gln Ser Ile Ser Gly Gly Arg Ser Phe
    680                 685                 690

gca gaa ata ctg att ggt aac tcc ttg ggg aaa tct tcc ata tca caa      2228
Ala Glu Ile Leu Ile Gly Asn Ser Leu Gly Lys Ser Ser Ile Ser Gln
695                 700                 705                 710

gag tca tta ctt aga ggc tgc tcg tta cac aag atg atc aga tta att      2276
Glu Ser Leu Leu Arg Gly Cys Ser Leu His Lys Met Ile Arg Leu Ile
                715                 720                 725

aca tct aca att ggt ggt cat gca tac ctc aac ttc atg ggc aat gaa      2324
Thr Ser Thr Ile Gly Gly His Ala Tyr Leu Asn Phe Met Gly Asn Glu
            730                 735                 740

ttt ggt cac cca aag aga gta gag ttt cca atg tca agc aac aat ttc      2372
Phe Gly His Pro Lys Arg Val Glu Phe Pro Met Ser Ser Asn Asn Phe
        745                 750                 755

tcc ttt tca ctg gct aac cgt cgc tgg gat cta ttg gaa gat gtt gta      2420
Ser Phe Ser Leu Ala Asn Arg Arg Trp Asp Leu Leu Glu Asp Val Val
    760                 765                 770

cat tat caa tta ttc tca ttt gat aag gat atg atg gac ttg gat aaa      2468
His Tyr Gln Leu Phe Ser Phe Asp Lys Asp Met Met Asp Leu Asp Lys
775                 780                 785                 790

aat ggg aga att ttg tcc aga ggt ctt gcc aac att cac cat gtc aat      2516
Asn Gly Arg Ile Leu Ser Arg Gly Leu Ala Asn Ile His His Val Asn
                795                 800                 805

gat act acc atg gtg att tct tac ttg aga ggt ccc aat ctc ttt gtg      2564
Asp Thr Thr Met Val Ile Ser Tyr Leu Arg Gly Pro Asn Leu Phe Val
            810                 815                 820

ttc aac ttt cat cct gtc aat tca tat gaa aga tac att ata ggt gtg      2612
Phe Asn Phe His Pro Val Asn Ser Tyr Glu Arg Tyr Ile Ile Gly Val
        825                 830                 835

gaa gaa gct gga gag tat caa gtc aca tta aat aca gat gaa aac aag      2660
Glu Glu Ala Gly Glu Tyr Gln Val Thr Leu Asn Thr Asp Glu Asn Lys
    840                 845                 850

tat ggt ggt aga gga cta ctt ggc cat gat cag aat act caa aga acc      2708
Tyr Gly Gly Arg Gly Leu Leu Gly His Asp Gln Asn Thr Gln Arg Thr
855                 860                 865                 870

att agt aga aga gct gat gga atg aga ttt tgc ttg gaa gta cct ctg      2756
Ile Ser Arg Arg Ala Asp Gly Met Arg Phe Cys Leu Glu Val Pro Leu
                875                 880                 885

cca agt aga agt gct cag gtc tac aag ttg acc cga att cta aga gca      2804
Pro Ser Arg Ser Ala Gln Val Tyr Lys Leu Thr Arg Ile Leu Arg Ala
            890                 895                 900

tgatcactct agcaatcaaa gtgcctcata tgatcacaca aaagggaagg ttctacattg   2864

cccttatact gaccaatatt gtggcctttc cgaggtgagt ttctgtgatt cttgagcaca   2924

ggctgttggc tagtcagtta tcatgaactt ttgccttcag catctggata agcgcttctc   2984

ctgtgcaatg agggcatgga cgaaattttt ttggttcgtc atgggagtca aaagcatctg   3044

ccagattaag atttcacagg cctcgagtaa aaccatcact tacttaggat acacaaacac   3104
```

-continued

```
atcaacgggg tgcaggctct gataccttct aaagtgaagc cgaattccag cacactggcg   3164

gccgttacta gtggatccga gctcggtacc aagcttggcg                         3204


<210> SEQ ID NO 4
<211> LENGTH: 902
<212> TYPE: PRT
<213> ORGANISM: Solanum tuberosum

<400> SEQUENCE: 4

Met Leu Ser Leu Ser Asp Ser Ile Arg Ile Ser Ser Pro Leu Ser Asp
1               5                   10                  15

Ser Arg Leu Ser Phe Leu Ser Gln Thr Gly Ser Arg Thr Ser Arg Gln
            20                  25                  30

Leu Lys Phe Val Arg Ser Arg Arg Ala Arg Val Ser Arg Cys Arg Cys
        35                  40                  45

Ser Ala Thr Glu Gln Pro Pro Pro Gln Arg Arg Lys Gln Arg Pro Glu
    50                  55                  60

Lys Tyr Lys Gln Ser Glu Glu Glu Lys Gly Ile Asp Pro Val Gly Phe
65                  70                  75                  80

Leu Ser Lys Tyr Gly Ile Thr His Lys Ala Phe Ala Gln Phe Leu Arg
                85                  90                  95

Glu Arg Tyr Lys Ser Leu Lys Asp Leu Lys Asp Glu Ile Leu Thr Arg
            100                 105                 110

His Phe Ser Leu Lys Glu Met Ser Thr Gly Tyr Glu Leu Met Gly Met
        115                 120                 125

His Arg Asn Ile Gln His Arg Val Asp Phe Leu Glu Trp Ala Pro Gly
    130                 135                 140

Ala Arg Tyr Cys Ala Leu Ile Gly Asp Phe Asn Gly Trp Ser Thr Thr
145                 150                 155                 160

Gly Asn Cys Ala Arg Glu Gly His Phe Gly His Asp Asp Tyr Gly Tyr
                165                 170                 175

Trp Phe Ile Ile Leu Glu Asp Lys Leu Arg Glu Gly Glu Glu Pro Asp
            180                 185                 190

Lys Leu Tyr Phe Gln Gln Tyr Asn Tyr Ala Glu Asp Tyr Asp Lys Gly
        195                 200                 205

Asp Thr Gly Ile Thr Val Glu Glu Ile Phe Lys Lys Ala Asn Asp Glu
    210                 215                 220

Tyr Trp Glu Pro Gly Glu Asp Arg Phe Ile Lys Ser Arg Tyr Glu Val
225                 230                 235                 240

Ala Ala Lys Leu Tyr Glu Glu Met Phe Gly Pro Asn Gly Pro Gln Thr
                245                 250                 255

Glu Glu Glu Leu Glu Ala Met Pro Asp Ala Ala Thr Arg Tyr Lys Thr
            260                 265                 270

Trp Lys Glu Gln Gln Lys Lys Asp Pro Ala Ser Asn Leu Pro Ser Tyr
        275                 280                 285

Asp Val Val Asp Ser Gly Lys Glu Tyr Asp Ile Tyr Asn Ile Ile Gly
    290                 295                 300

Asp Pro Glu Ser Phe Lys Lys Phe Arg Met Lys Gln Pro Pro Ile Ala
305                 310                 315                 320

Tyr Trp Leu Glu Thr Lys Lys Gly Arg Lys Gly Trp Leu Gln Lys Tyr
                325                 330                 335

Met Pro Ala Leu Pro His Gly Ser Lys His Arg Val Tyr Phe Asn Thr
            340                 345                 350
```

-continued

```
Pro Asn Gly Pro Leu Glu Arg Val Pro Ala Trp Ala Asn Phe Val Ile
        355                 360                 365

Pro Asp Ala Asp Gly Met Ala Leu Ala Val His Trp Glu Pro Pro Pro
    370                 375                 380

Glu Tyr Ala Tyr Lys Trp Lys His Lys Leu Pro Val Lys Pro Lys Ser
385                 390                 395                 400

Leu Arg Ile Tyr Glu Cys His Val Gly Ile Ser Gly Gln Glu Pro Lys
                405                 410                 415

Val Ser Ser Phe Asn Asp Phe Ile Ser Lys Val Leu Pro His Val Lys
            420                 425                 430

Glu Ala Gly Tyr Asn Ala Thr Gln Ile Ile Gly Val Val Glu His Lys
        435                 440                 445

Asp Tyr Phe Thr Val Gly Tyr Arg Val Thr Asn Phe Tyr Ala Val Ser
    450                 455                 460

Ser Arg Tyr Gly Thr Pro Asp Asp Phe Lys Arg Leu Val Asp Glu Ala
465                 470                 475                 480

His Gly Leu Gly Leu Leu Val Phe Leu Glu Ile Val His Ser Tyr Ala
                485                 490                 495

Ala Ala Asp Glu Met Val Gly Leu Ser Leu Phe Asp Gly Ala Asn Asp
            500                 505                 510

Cys Tyr Phe His Thr Gly Lys Arg Gly His His Lys Phe Trp Gly Thr
        515                 520                 525

Arg Met Phe Lys Tyr Gly Asp Pro Asp Val Leu His Phe Leu Leu Ser
    530                 535                 540

Asn Leu Asn Trp Trp Val Glu Glu Tyr His Val Asp Gly Phe His Phe
545                 550                 555                 560

His Ser Leu Ser Ser Met Leu Tyr Thr His Asn Gly Phe Ala Ser Phe
                565                 570                 575

Thr Gly Asp Met Asp Glu Tyr Cys Asn Gln Tyr Val Asp Lys Glu Ala
            580                 585                 590

Leu Leu Tyr Leu Ile Leu Ala Asn Glu Val Leu His Ala Leu His Pro
        595                 600                 605

Asn Val Ile Thr Ile Ala Val Asp Ala Thr Leu Tyr Pro Gly Leu Cys
    610                 615                 620

Asp Pro Thr Ser Gln Gly Gly Leu Gly Phe Asp Tyr Phe Ala Asn Leu
625                 630                 635                 640

Ser Ala Ser Glu Met Trp Leu Ala Leu Leu Glu Asn Thr Pro Asp His
                645                 650                 655

Glu Trp Cys Met Ser Lys Ile Val Ser Thr Leu Val Gly Asp Arg Gln
            660                 665                 670

Asn Thr Asp Lys Met Leu Leu Tyr Ala Glu Asn His Asn Gln Ser Ile
        675                 680                 685

Ser Gly Gly Arg Ser Phe Ala Glu Ile Leu Ile Gly Asn Ser Leu Gly
    690                 695                 700

Lys Ser Ser Ile Ser Gln Glu Ser Leu Leu Arg Gly Cys Ser Leu His
705                 710                 715                 720

Lys Met Ile Arg Leu Ile Thr Ser Thr Ile Gly Gly His Ala Tyr Leu
                725                 730                 735

Asn Phe Met Gly Asn Glu Phe Gly His Pro Lys Arg Val Glu Phe Pro
            740                 745                 750

Met Ser Ser Asn Asn Phe Ser Phe Ser Leu Ala Asn Arg Arg Trp Asp
        755                 760                 765

Leu Leu Glu Asp Val Val His Tyr Gln Leu Phe Ser Phe Asp Lys Asp
```

-continued

```
    770                 775                 780

Met Met Asp Leu Asp Lys Asn Gly Arg Ile Leu Ser Arg Gly Leu Ala
785                 790                 795                 800

Asn Ile His His Val Asn Asp Thr Thr Met Val Ile Ser Tyr Leu Arg
                805                 810                 815

Gly Pro Asn Leu Phe Val Phe Asn Phe His Pro Val Asn Ser Tyr Glu
            820                 825                 830

Arg Tyr Ile Ile Gly Val Glu Glu Ala Gly Glu Tyr Gln Val Thr Leu
        835                 840                 845

Asn Thr Asp Glu Asn Lys Tyr Gly Gly Arg Gly Leu Leu Gly His Asp
    850                 855                 860

Gln Asn Thr Gln Arg Thr Ile Ser Arg Arg Ala Asp Gly Met Arg Phe
865                 870                 875                 880

Cys Leu Glu Val Pro Leu Pro Ser Arg Ser Ala Gln Val Tyr Lys Leu
                885                 890                 895

Thr Arg Ile Leu Arg Ala
            900


<210> SEQ ID NO 5
<211> LENGTH: 3047
<212> TYPE: DNA
<213> ORGANISM: Solanum tuberosum
<220> FEATURE:
<221> NAME/KEY: CDS
<222> LOCATION: (5)..(2710)

<400> SEQUENCE: 5

aaca atg ctc tct ctg tcg gat tca att cga att tct tca cca ttg agc      49
     Met Leu Ser Leu Ser Asp Ser Ile Arg Ile Ser Ser Pro Leu Ser
     1               5                   10                  15

gat tct cgt ctt agt ttt cta tct caa acc gga agc aga acc agt cgc       97
Asp Ser Arg Leu Ser Phe Leu Ser Gln Thr Gly Ser Arg Thr Ser Arg
                20                  25                  30

cag ctt aaa ttt gtt cgc agc cgc cgg gct cga gtt tcg agg tgt aga      145
Gln Leu Lys Phe Val Arg Ser Arg Arg Ala Arg Val Ser Arg Cys Arg
            35                  40                  45

tgc tca gca acg gag caa ccg cca ccg caa cga cgg aag caa cga ccg      193
Cys Ser Ala Thr Glu Gln Pro Pro Pro Gln Arg Arg Lys Gln Arg Pro
        50                  55                  60

gag aag tac aaa cag tcg gag gaa ggg aaa gga atc gat cct gtt gga      241
Glu Lys Tyr Lys Gln Ser Glu Glu Gly Lys Gly Ile Asp Pro Val Gly
    65                  70                  75

ttt ctc agc aaa tac ggc att act cat aaa gcg ttt gct caa ttt ctt      289
Phe Leu Ser Lys Tyr Gly Ile Thr His Lys Ala Phe Ala Gln Phe Leu
80                  85                  90                  95

cgt gaa aga tat aaa tca ttg aag gac ttg aag gat gaa ata ttg act      337
Arg Glu Arg Tyr Lys Ser Leu Lys Asp Leu Lys Asp Glu Ile Leu Thr
                100                 105                 110

cgt cat ttc agt ctc aag gag atg tct act ggg tat gaa tta atg ggt      385
Arg His Phe Ser Leu Lys Glu Met Ser Thr Gly Tyr Glu Leu Met Gly
            115                 120                 125

atg cat cgc aac ata caa cat cga gtg gat ttc ttg gaa tgg gct cca      433
Met His Arg Asn Ile Gln His Arg Val Asp Phe Leu Glu Trp Ala Pro
        130                 135                 140

ggt gct cgc tac tgt gct ctg att ggt gac ttc aat ggg tgg tca aca      481
Gly Ala Arg Tyr Cys Ala Leu Ile Gly Asp Phe Asn Gly Trp Ser Thr
    145                 150                 155

act ggt aac tgt gcc aga gag ggt cat ttt ggt cat gac gat tat ggg      529
Thr Gly Asn Cys Ala Arg Glu Gly His Phe Gly His Asp Asp Tyr Gly
```

-continued

```
160                 165                 170                 175

tat tgg ttt att att ctt gaa gat aaa tta cgt gaa gga gaa gaa cct      577
Tyr Trp Phe Ile Ile Leu Glu Asp Lys Leu Arg Glu Gly Glu Glu Pro
                180                 185                 190

gat aaa ttg tat ttt caa cag tac aat tat gcg gag gac tat ggt aaa      625
Asp Lys Leu Tyr Phe Gln Gln Tyr Asn Tyr Ala Glu Asp Tyr Gly Lys
            195                 200                 205

ggt gac acg ggt att acc gtc gag gaa atc ttt aaa aaa gca aat gat      673
Gly Asp Thr Gly Ile Thr Val Glu Glu Ile Phe Lys Lys Ala Asn Asp
        210                 215                 220

gag tat tgg gaa cct gga gaa gat cgc ttc att aaa tca cgt tat gag      721
Glu Tyr Trp Glu Pro Gly Glu Asp Arg Phe Ile Lys Ser Arg Tyr Glu
    225                 230                 235

gtg gca gca aag tta tat gag gaa atg ttc gga cca aat gga cct caa      769
Val Ala Ala Lys Leu Tyr Glu Glu Met Phe Gly Pro Asn Gly Pro Gln
240                 245                 250                 255

aca gaa gag gaa cta gaa gca atg cct gat gca gct aca cga tac aaa      817
Thr Glu Glu Glu Leu Glu Ala Met Pro Asp Ala Ala Thr Arg Tyr Lys
                260                 265                 270

act tgg aaa gag caa caa aaa gag gat ccg gca agc aat ttg cca tcg      865
Thr Trp Lys Glu Gln Gln Lys Glu Asp Pro Ala Ser Asn Leu Pro Ser
            275                 280                 285

tat gat gtg gta gat agt gga aaa gaa tat gat att tac aat att ata      913
Tyr Asp Val Val Asp Ser Gly Lys Glu Tyr Asp Ile Tyr Asn Ile Ile
        290                 295                 300

ggt gat cct gaa tcg ttt aag aaa ttt cgt atg aaa cag cct cct att      961
Gly Asp Pro Glu Ser Phe Lys Lys Phe Arg Met Lys Gln Pro Pro Ile
    305                 310                 315

gct tac tgg tta gaa act aaa aag gga agg aaa ggc tgg tta cag aaa     1009
Ala Tyr Trp Leu Glu Thr Lys Lys Gly Arg Lys Gly Trp Leu Gln Lys
320                 325                 330                 335

tat atg cct gct tta cct cat gga agc aaa tac agg gtg tat ttt aac     1057
Tyr Met Pro Ala Leu Pro His Gly Ser Lys Tyr Arg Val Tyr Phe Asn
                340                 345                 350

aca cca aat ggg cct ctt gaa cga gtt cct gcg tgg gcc aat ttt gtc     1105
Thr Pro Asn Gly Pro Leu Glu Arg Val Pro Ala Trp Ala Asn Phe Val
            355                 360                 365

att cca gat gca ggc ggg atg gca tta gca gtc cat tgg gaa cca cct     1153
Ile Pro Asp Ala Gly Gly Met Ala Leu Ala Val His Trp Glu Pro Pro
        370                 375                 380

cct gaa tat gct tat aaa tgg aaa cac aag cta cca gtc aag cct aag     1201
Pro Glu Tyr Ala Tyr Lys Trp Lys His Lys Leu Pro Val Lys Pro Lys
    385                 390                 395

tcc ttg cgc ata tat gaa tgt cat gtt ggc atc tct ggc cag gaa cca     1249
Ser Leu Arg Ile Tyr Glu Cys His Val Gly Ile Ser Gly Gln Glu Pro
400                 405                 410                 415

aaa gtt tca tct ttc aat gat ttt att agc aag gtc ctt ccg cat gta     1297
Lys Val Ser Ser Phe Asn Asp Phe Ile Ser Lys Val Leu Pro His Val
                420                 425                 430

aaa gaa gct gga tac aat gca ata caa att att gga gtt gtt gag cac     1345
Lys Glu Ala Gly Tyr Asn Ala Ile Gln Ile Ile Gly Val Val Glu His
            435                 440                 445

aag gat tat ttc act gtt gga tat aga gtg acc aat ttt tat gct gtt     1393
Lys Asp Tyr Phe Thr Val Gly Tyr Arg Val Thr Asn Phe Tyr Ala Val
        450                 455                 460

agt agc cgt tat ggc aca ccg gat gac ttc aag cgc ttg gtt gat gaa     1441
Ser Ser Arg Tyr Gly Thr Pro Asp Asp Phe Lys Arg Leu Val Asp Glu
    465                 470                 475

gca cat ggg ctt gga ctg ctt gtc ttt ttg gag att gtg cac tct tat     1489
```

-continued

```
Ala His Gly Leu Gly Leu Leu Val Phe Leu Glu Ile Val His Ser Tyr
480                 485                 490                 495

gca gca gca gat gaa atg gtt ggg tta tct ctt ttt gat gga gca aat     1537
Ala Ala Ala Asp Glu Met Val Gly Leu Ser Leu Phe Asp Gly Ala Asn
                500                 505                 510

gat tgc tat ttc cac act ggt aaa cgt gga cac cac aaa ttc tgg ggc     1585
Asp Cys Tyr Phe His Thr Gly Lys Arg Gly His His Lys Phe Trp Gly
            515                 520                 525

aca cgg atg ttc aaa tat gga gat ctt gat gtt ctg cac ttt ctt ctt     1633
Thr Arg Met Phe Lys Tyr Gly Asp Leu Asp Val Leu His Phe Leu Leu
        530                 535                 540

tca aat ctg aac tgg tgg gtg gag gag tat cat gtc gat ggc ttc cat     1681
Ser Asn Leu Asn Trp Trp Val Glu Glu Tyr His Val Asp Gly Phe His
    545                 550                 555

ttt cat tcg ctc tcg tcc atg ttg tat acg cat aat gga ttt gct tca     1729
Phe His Ser Leu Ser Ser Met Leu Tyr Thr His Asn Gly Phe Ala Ser
560                 565                 570                 575

ttt act ggt gac atg gat gaa tac tgt aac caa tat gtt gac aag gag     1777
Phe Thr Gly Asp Met Asp Glu Tyr Cys Asn Gln Tyr Val Asp Lys Glu
                580                 585                 590

gcc tta ttg tac ctc ata tta gca aat gaa gta tta cat gct ctt cat     1825
Ala Leu Leu Tyr Leu Ile Leu Ala Asn Glu Val Leu His Ala Leu His
            595                 600                 605

cct aat gtg atc acg att gct gag gat gca act ctg tat cct gga ctc     1873
Pro Asn Val Ile Thr Ile Ala Glu Asp Ala Thr Leu Tyr Pro Gly Leu
        610                 615                 620

tgc gat cca aca tct caa ggt gga ctg ggc ttt gat tat ttt gcc aat     1921
Cys Asp Pro Thr Ser Gln Gly Gly Leu Gly Phe Asp Tyr Phe Ala Asn
    625                 630                 635

ctt tct gcc tca gag atg tgg ctt gca tta ctt gaa aat act cct gat     1969
Leu Ser Ala Ser Glu Met Trp Leu Ala Leu Leu Glu Asn Thr Pro Asp
640                 645                 650                 655

cat gaa tgg tgc atg agt aag att gtt agc aca tta gtg ggc gat aga     2017
His Glu Trp Cys Met Ser Lys Ile Val Ser Thr Leu Val Gly Asp Arg
                660                 665                 670

caa aat act gat aaa atg ctt ttg tat gca gaa aat cac aac cag tcc     2065
Gln Asn Thr Asp Lys Met Leu Leu Tyr Ala Glu Asn His Asn Gln Ser
            675                 680                 685

att tct gga ggt cgt tcc ttc gca gaa ata ctg att ggt aac tcc ttg     2113
Ile Ser Gly Gly Arg Ser Phe Ala Glu Ile Leu Ile Gly Asn Ser Leu
        690                 695                 700

ggg aaa tcc tcc ata tca caa gag tca tta ctt aga ggc tgc tcg tta     2161
Gly Lys Ser Ser Ile Ser Gln Glu Ser Leu Leu Arg Gly Cys Ser Leu
    705                 710                 715

cac aag atg atc aga tta att aca tct aca att ggt ggt cat gca tac     2209
His Lys Met Ile Arg Leu Ile Thr Ser Thr Ile Gly Gly His Ala Tyr
720                 725                 730                 735

ctc aac ttc atg ggc aat gaa ttt ggt cac cca aag aga gta gag ttt     2257
Leu Asn Phe Met Gly Asn Glu Phe Gly His Pro Lys Arg Val Glu Phe
                740                 745                 750

cca atg tca agc aac aat ttc tcc ttt tca ctg gct aac cgt cgc tgg     2305
Pro Met Ser Ser Asn Asn Phe Ser Phe Ser Leu Ala Asn Arg Arg Trp
            755                 760                 765

gat cta ttg gaa gat gtt gta cat tat caa ttg ttc tca ttt gat aag     2353
Asp Leu Leu Glu Asp Val Val His Tyr Gln Leu Phe Ser Phe Asp Lys
        770                 775                 780

ggt atg atg gac ttg gat aaa aat ggg aga att ttg tcc aga ggt ctt     2401
Gly Met Met Asp Leu Asp Lys Asn Gly Arg Ile Leu Ser Arg Gly Leu
    785                 790                 795
```

-continued

```
gcc aac att cac cat gtc aat gat act acc atg gtg att tct tac ttg     2449
Ala Asn Ile His His Val Asn Asp Thr Thr Met Val Ile Ser Tyr Leu
800                 805                 810                 815

aga ggt ccc aat ctc ttt gtg ttc aac ttt cat cct gtc aat tca tat     2497
Arg Gly Pro Asn Leu Phe Val Phe Asn Phe His Pro Val Asn Ser Tyr
                820                 825                 830

gaa aga tac att ata ggt gtg gaa gaa gct gga gag tat caa gtc aca     2545
Glu Arg Tyr Ile Ile Gly Val Glu Glu Ala Gly Glu Tyr Gln Val Thr
            835                 840                 845

tta aat aca gat gaa aac aag tat ggt ggt aga gga cta ctt ggc cat     2593
Leu Asn Thr Asp Glu Asn Lys Tyr Gly Gly Arg Gly Leu Leu Gly His
        850                 855                 860

gat cag aat att caa aga acc att agt aga aga gct gat gga atg aga     2641
Asp Gln Asn Ile Gln Arg Thr Ile Ser Arg Arg Ala Asp Gly Met Arg
    865                 870                 875

ttt tgc ttg gaa gtg cct ctg cca agt aga agt gct cag gtc tac aag     2689
Phe Cys Leu Glu Val Pro Leu Pro Ser Arg Ser Ala Gln Val Tyr Lys
880                 885                 890                 895

ttg acc cga att cta aga gca tgatcactct agtaatcaaa gtgcctcata        2740
Leu Thr Arg Ile Leu Arg Ala
                900

tgatgacaca aaaggaaagg ttctacattg cccttacact gatcaatatt gacacctttc   2800

cgaggtgagt ttctgtgatt cttgagcaga ctgttggcta gtcaattatc atgaactttt   2860

gccttcagca tccggatagt cgcttctcct gtgcaatgag ggcatggacg aatttttttt   2920

tggcttgtca tgggggtcat aagcatccgc cagattaaga tttcacaggc ctcgagtaaa   2980

accatcactt actttaagga tacacaaaca caccaacggg gtgcaggctc tgataccttc   3040

taaagtg                                                             3047
```

<210> SEQ ID NO 6
<211> LENGTH: 902
<212> TYPE: PRT
<213> ORGANISM: Solanum tuberosum

<400> SEQUENCE: 6

```
Met Leu Ser Leu Ser Asp Ser Ile Arg Ile Ser Ser Pro Leu Ser Asp
1               5                   10                  15

Ser Arg Leu Ser Phe Leu Ser Gln Thr Gly Ser Arg Thr Ser Arg Gln
            20                  25                  30

Leu Lys Phe Val Arg Ser Arg Arg Ala Arg Val Ser Arg Cys Arg Cys
        35                  40                  45

Ser Ala Thr Glu Gln Pro Pro Pro Gln Arg Arg Lys Gln Arg Pro Glu
    50                  55                  60

Lys Tyr Lys Gln Ser Glu Glu Gly Lys Gly Ile Asp Pro Val Gly Phe
65                  70                  75                  80

Leu Ser Lys Tyr Gly Ile Thr His Lys Ala Phe Ala Gln Phe Leu Arg
                85                  90                  95

Glu Arg Tyr Lys Ser Leu Lys Asp Leu Lys Asp Glu Ile Leu Thr Arg
            100                 105                 110

His Phe Ser Leu Lys Glu Met Ser Thr Gly Tyr Glu Leu Met Gly Met
        115                 120                 125

His Arg Asn Ile Gln His Arg Val Asp Phe Leu Glu Trp Ala Pro Gly
    130                 135                 140

Ala Arg Tyr Cys Ala Leu Ile Gly Asp Phe Asn Gly Trp Ser Thr Thr
145                 150                 155                 160

Gly Asn Cys Ala Arg Glu Gly His Phe Gly His Asp Asp Tyr Gly Tyr
```

-continued

```
            165                 170                 175

Trp Phe Ile Ile Leu Glu Asp Lys Leu Arg Glu Gly Glu Glu Pro Asp
        180                 185                 190

Lys Leu Tyr Phe Gln Gln Tyr Asn Tyr Ala Glu Asp Tyr Gly Lys Gly
    195                 200                 205

Asp Thr Gly Ile Thr Val Glu Glu Ile Phe Lys Lys Ala Asn Asp Glu
    210                 215                 220

Tyr Trp Glu Pro Gly Glu Asp Arg Phe Ile Lys Ser Arg Tyr Glu Val
225                 230                 235                 240

Ala Ala Lys Leu Tyr Glu Glu Met Phe Gly Pro Asn Gly Pro Gln Thr
            245                 250                 255

Glu Glu Glu Leu Glu Ala Met Pro Asp Ala Ala Thr Arg Tyr Lys Thr
        260                 265                 270

Trp Lys Glu Gln Gln Lys Glu Asp Pro Ala Ser Asn Leu Pro Ser Tyr
    275                 280                 285

Asp Val Val Asp Ser Gly Lys Glu Tyr Asp Ile Tyr Asn Ile Ile Gly
    290                 295                 300

Asp Pro Glu Ser Phe Lys Lys Phe Arg Met Lys Gln Pro Pro Ile Ala
305                 310                 315                 320

Tyr Trp Leu Glu Thr Lys Lys Gly Arg Lys Gly Trp Leu Gln Lys Tyr
            325                 330                 335

Met Pro Ala Leu Pro His Gly Ser Lys Tyr Arg Val Tyr Phe Asn Thr
        340                 345                 350

Pro Asn Gly Pro Leu Glu Arg Val Pro Ala Trp Ala Asn Phe Val Ile
    355                 360                 365

Pro Asp Ala Gly Gly Met Ala Leu Ala Val His Trp Glu Pro Pro Pro
    370                 375                 380

Glu Tyr Ala Tyr Lys Trp Lys His Lys Leu Pro Val Lys Pro Lys Ser
385                 390                 395                 400

Leu Arg Ile Tyr Glu Cys His Val Gly Ile Ser Gly Gln Glu Pro Lys
            405                 410                 415

Val Ser Ser Phe Asn Asp Phe Ile Ser Lys Val Leu Pro His Val Lys
        420                 425                 430

Glu Ala Gly Tyr Asn Ala Ile Gln Ile Ile Gly Val Val Glu His Lys
    435                 440                 445

Asp Tyr Phe Thr Val Gly Tyr Arg Val Thr Asn Phe Tyr Ala Val Ser
    450                 455                 460

Ser Arg Tyr Gly Thr Pro Asp Asp Phe Lys Arg Leu Val Asp Glu Ala
465                 470                 475                 480

His Gly Leu Gly Leu Leu Val Phe Leu Glu Ile Val His Ser Tyr Ala
            485                 490                 495

Ala Ala Asp Glu Met Val Gly Leu Ser Leu Phe Asp Gly Ala Asn Asp
        500                 505                 510

Cys Tyr Phe His Thr Gly Lys Arg Gly His His Lys Phe Trp Gly Thr
    515                 520                 525

Arg Met Phe Lys Tyr Gly Asp Leu Asp Val Leu His Phe Leu Leu Ser
    530                 535                 540

Asn Leu Asn Trp Trp Val Glu Glu Tyr His Val Asp Gly Phe His Phe
545                 550                 555                 560

His Ser Leu Ser Ser Met Leu Tyr Thr His Asn Gly Phe Ala Ser Phe
            565                 570                 575

Thr Gly Asp Met Asp Glu Tyr Cys Asn Gln Tyr Val Asp Lys Glu Ala
        580                 585                 590
```

-continued

```
Leu Leu Tyr Leu Ile Leu Ala Asn Glu Val Leu His Ala Leu His Pro
        595                 600                 605

Asn Val Ile Thr Ile Ala Glu Asp Ala Thr Leu Tyr Pro Gly Leu Cys
    610                 615                 620

Asp Pro Thr Ser Gln Gly Gly Leu Gly Phe Asp Tyr Phe Ala Asn Leu
625                 630                 635                 640

Ser Ala Ser Glu Met Trp Leu Ala Leu Leu Glu Asn Thr Pro Asp His
                645                 650                 655

Glu Trp Cys Met Ser Lys Ile Val Ser Thr Leu Val Gly Asp Arg Gln
            660                 665                 670

Asn Thr Asp Lys Met Leu Leu Tyr Ala Glu Asn His Asn Gln Ser Ile
        675                 680                 685

Ser Gly Gly Arg Ser Phe Ala Glu Ile Leu Ile Gly Asn Ser Leu Gly
    690                 695                 700

Lys Ser Ser Ile Ser Gln Glu Ser Leu Leu Arg Gly Cys Ser Leu His
705                 710                 715                 720

Lys Met Ile Arg Leu Ile Thr Ser Thr Ile Gly Gly His Ala Tyr Leu
                725                 730                 735

Asn Phe Met Gly Asn Glu Phe Gly His Pro Lys Arg Val Glu Phe Pro
            740                 745                 750

Met Ser Ser Asn Asn Phe Ser Phe Ser Leu Ala Asn Arg Arg Trp Asp
        755                 760                 765

Leu Leu Glu Asp Val Val His Tyr Gln Leu Phe Ser Phe Asp Lys Gly
    770                 775                 780

Met Met Asp Leu Asp Lys Asn Gly Arg Ile Leu Ser Arg Gly Leu Ala
785                 790                 795                 800

Asn Ile His His Val Asn Asp Thr Thr Met Val Ile Ser Tyr Leu Arg
                805                 810                 815

Gly Pro Asn Leu Phe Val Phe Asn Phe His Pro Val Asn Ser Tyr Glu
            820                 825                 830

Arg Tyr Ile Ile Gly Val Glu Glu Ala Gly Glu Tyr Gln Val Thr Leu
        835                 840                 845

Asn Thr Asp Glu Asn Lys Tyr Gly Gly Arg Gly Leu Leu Gly His Asp
    850                 855                 860

Gln Asn Ile Gln Arg Thr Ile Ser Arg Arg Ala Asp Gly Met Arg Phe
865                 870                 875                 880

Cys Leu Glu Val Pro Leu Pro Ser Arg Ser Ala Gln Val Tyr Lys Leu
                885                 890                 895

Thr Arg Ile Leu Arg Ala
            900
```